US008211643B2

(12) United States Patent
Tsao et al.

(10) Patent No.: US 8,211,643 B2
(45) Date of Patent: Jul. 3, 2012

(54) PROGNOSTIC AND PREDICTIVE GENE SIGNATURE FOR NON-SMALL CELL LUNG CANCER AND ADJUVANT CHEMOTHERAPY

(75) Inventors: Ming-Sound Tsao, Toronto (CA);
Frances A. Shepherd, Toronto (CA);
Igor Jurisica, Toronto (CA); Sandy D. Der, Toronto (CA); Chang-Qi Zhu, Thornhill (CA); Dan Strumpf, Toronto (CA); Lesley Seymour, Kingston (CA);
Keyue Ding, Kingston (CA)

(73) Assignee: University Health Network, Toronto, Ontario (CA)

( * ) Notice: Subject to any disclaimer, the term of this patent is extended or adjusted under 35 U.S.C. 154(b) by 331 days.

(21) Appl. No.: 12/465,954

(22) Filed: May 14, 2009

(65) Prior Publication Data

US 2009/0291448 A1    Nov. 26, 2009

Related U.S. Application Data

(60) Provisional application No. 61/071,728, filed on May 14, 2008.

(51) Int. Cl.
*C12Q 1/70*  (2006.01)
*C12P 19/34*  (2006.01)
*C07H 21/04*  (2006.01)
*C07H 1/04*  (2006.01)

(52) U.S. Cl. .................. 435/6.12; 435/91.2; 536/24.31; 536/24.33

(58) Field of Classification Search .................. None
See application file for complete search history.

(56) References Cited

U.S. PATENT DOCUMENTS

| 2004/0241725 A1 | 12/2004 | Xiao et al. | |
| 2010/0184063 A1* | 7/2010 | Tsao et al. | 435/6 |

FOREIGN PATENT DOCUMENTS

| WO | 03/015613 | 2/2003 |
| WO | PCT/CA2009/000650 | 11/2009 |

OTHER PUBLICATIONS

AFFYMETRIX, GeneChip® Human Genome Arrays, © 2003-2004 AFFYMETRIX, Inc., four pages.*
AFFYMETRIX, Fifteen + Probe Set IDS for AFFYMetrix U133 chip, pp. 1-3, retrieved online on Jul. 26, 2011 from: https://www.affymetrix.com.*
Talantov et al., Novel Genes Associated with Malignant Melanoma but not Benign Melanocytic Lesions, Clin Cancer Res 2005;11(20) Oct. 15, 2005, pp. 7234-7242.*
Xu et al., Survival analysis of microarray expression data by transformation models, Computational Biology and Chemistry 29 (2005) 91-94.*
Ooi et al., Genetic algorithms applied to multi-class prediction for the analysis of gene expression data, Bioinformatics vol. 19 No. 1 2003 pp. 37-44.*

Raychaudhuri et al., Principal Components Analysis to Summarize Microarray Experiments: Application to Sporulation Time Series,Pac Symp Biocomput. Author manuscript; available in PMC Apr. 17, 2009, Published in final edited form as: Pac Symp Biocomput. 2000 455-466.*
Tsao, M.S., et al., "A 15-gene expression signature prognostic for survival and predictive for adjuvant chemotherapy benefit in JBR.10 patients", Journal of Clinical Oncology, May 20, 2008, vol. 26, No. 15S, Abstract No. 7510.
Tanney, A., et al., "Generation of non-small cell lung cancer transcriptome microarray", BMC Medical Genomics, May 30, 2008, pp. 1-12, vol. 1, No. 20.
Chen, H-Y., et al., "A five-gene signature and clinical outcome in non-small-cell lung cancer", The New England Journal of Medicine, Jan. 4, 2007, pp. 11-20, vol. 356, No. 1.
Lau, S.K., et al., "Three-gene prognostic classifier for early-stage non-small-cell lung cancer", Journal of Clinical Oncology, Dec. 10, 2007, pp. 5562-5569, vol. 25, No. 35.
Lu, Y., et al., "A gene expression signature predicts survival of patients with stage 1 non-small cell lung cancer", PLOS Medicine, Dec. 2006, pp. 2229-2243, vol. 3, No. 12.
Jemal, A., et al., "Cancer statistics, 2007", CA: A Cancer Journal for Clinicians, May 6, 2010, pp. 43-67, vol. 57, No. 1.
Arriagada, R., et al., "Cisplatin-based adjuvant chemotherapy in patients with completely resected non-small-cell lung cancer", The New England Journal of Medicine, Jan. 22, 2004, pp. 351-360, vol. 350.
Winton, T., et al., "Vinorelbine plus cisplatin vs. observation in resected non-small-cell lung cancer", The New England Journal of Medicine, Jun. 23, 2005, pp. 2589-2597, vol. 352, Issue 25.
Douillard, J.Y., et al., "Adjuvant vinorelbine plus cisplatin versus observation in patients with completely resected stage IB-IIIA non-small-cell lung cancer (Adjuvant Navelbine International Trialist Association [ANITA]): a randomised controlled trial", The Lancet Oncology, Sep. 2006, pp. 719-727, vol. 7, No. 9.
Strauss, G.M., et al., "Adjuvant paclitaxel plus carboplatin compared with observation in stage IB non-small-cell lung cancer: CALGB 9633 with the cancer and leukemia group B, radiation therapy oncology group, and north central cancer treatment group study groups", Journal of Clinical Oncology, Nov. 1, 2008, pp. 5043-5051, vol. 26, No. 31. Pignon, J.P., et al., "Lung adjuvant cisplatin evaluation (LACE): a pooled analysis of five randomized clinical trials including 4,584 patients", Journal of Clinical Oncology, 2006 ASCO Annual Meeting Proceedings (Post-Meeting Edition), Jun. 2006, vol. 24, No. 18S.
Scagliotti, G.V., et al., "Randomized study of adjuvant chemotherapy for completely resected stage I, II, IIIA non-small-cell lung cancer", Journal of the National Cancer Institute, Oct. 1, 2003, pp. 1453-1461, vol. 95, No. 19.
Waller, D., et al., "Chemotherapy for patients with non-small cell lung cancer: the surgical setting of the Big Lung Trial", European Journal of Cardio-Thoracic Surgery, 2004, pp. 173-182, vol. 26, No. 1.

(Continued)

*Primary Examiner* — Mark Staples
(74) *Attorney, Agent, or Firm* — Bereskin & Parr LLP; Melanie Szweras

(57) ABSTRACT

The application provides methods of prognosing and classifying lung cancer patients into poor survival groups or good survival groups and for determining the benefit of adjuvant chemotherapy by way of a multigene signature. The application also includes kits and computer products for use in the methods of the application.

13 Claims, 10 Drawing Sheets

OTHER PUBLICATIONS

Douillard, J., et al., "ANITA: Phase III adjuvant vinorelbine (N) and cisplatin (P)", Journal of Clinical Oncology, 2005 ASCO Annual Meeting, Jun. 2005, vol. 23, No. 16S.

Hoffman, P.C., et al., "Lung cancer", The Lancet, Feb. 5, 2000, pp. 479-485, vol. 355.

Nesbitt, J.C., et al., "Survival in early-stage non-small cell lung cancer", The Annals of Thoracic Surgery, 1995, pp. 466-472, vol. 60.

Beer, D.G., et al., "Gene-expression profiles predict survival of patients with lung adenocarcinoma", Nature Medicine, Aug. 2002, pp. 816-824, vol. 8, No. 8.

Potti, A., et al., "A genomic strategy to refine prognosis in early-stage non-small-cell lung cancer", The New England Journal of Medicine, Aug. 10, 2006, pp. 570-582, vol. 355, Issue 6.

Raponi, M., et al., "Gene expression signatures for predicting prognosis of squamous cell and adenocarcinomas of the lung", Cancer Research (American Association of Cancer Research Journals), Aug. 1, 2006, pp. 7466-7472, vol. 66, No. 15.

Wigle, D.A., et al., "Molecular profiling of non-small cell lung cancer and correlation with disease-free survival", Cancer Research (American Association of Cancer Research Journals), Jun. 1, 2002, pp. 3005-3008, vol. 62.

Bianchi, F., et al., "Survival prediction of stage I lung adenocarcinomas by expression of 10 genes", The Journal of Clinical Investigation, Nov. 2007, pp. 3436-3444, vol. 117, No. 11.

Sun, Z., et al., "Non-overlapping and non-cell-type-specific gene expression signatures predict lung cancer survival", Journal of Clinical Oncology, Feb. 20, 2008, pp. 877-883, vol. 26, No. 6.

Bolstad, B.M., et al., "A comparison of normalization methods for high density oligonucleotide array data based on variance and bias", Bioinformatics, 2003, pp. 185-193, vol. 19, No. 2.

Transcript Assignment for Netaffx Annotations, revision date: Mar. 24, 2006, Revision Version 2.3, affymetrix GeneChip IVT Array Whitepaper Collection.

Dworakowska, D., et al., "Clinical significance of apoptotic index in non-small cell lung cancer: correlation with p53, mdm2, pRb and p21WAF1/CIP1 protein expression", Journal of Cancer Research & Clinical Oncology, May 2005, pp. 617-623, vol. 131.

Allory, Y., et al., "The L1 cell adhesion molecule is induced in renal cancer cells and correlates with metastasis in clear cell carcinomas", Clinical Cancer Research, Feb. 1, 2005, pp. 1190-1197, vol. 11.

Boo, Y.J., et al., "L1 expression as a marker for poor prognosis, tumor progression, and short survival in patients with colorectal cancer", Annals of Surgical Oncology, Jan. 9, 2007, pp. 1703-1711, vol. 14, No. 5.

Gast, D., et al., "L1 augments cell migration and tumor growth but not B3 integrin expression in ovarian carcinomas", International Journal of Cancer, Feb. 9, 2005, pp. 658-665, vol. 115, Issue 4.

Thies, A., et al., "Overexpression of the cell adhesion molecule L1 is associated with metastasis in cutaneous malignant melanoma", European Journal of Cancer, Mar. 19, 2002, pp. 1708-1716, vol. 38, Issue 13.

Ouellet, V., et al., "Discrimination between serous low malignant potential and invasive epithelial ovarian tumors using molecular profiling", Oncogene, May 30, 2005, pp. 4672-4687, vol. 24, Issue 29.

Oshita, F., et al., "Genomic-wide cDNA microarray screening to correlate gene expression profile with chemoresistance in patients with advanced lung cancer", Journal of Experimental Therapeutic and Oncology, 2004, pp. 155-160, vol. 4.

Raponi Mitch et al: "Supplementary Information: Gene expression signatures for predicting prognosis of squamous cell and adenocarcinomas of the lung", Cancer Research, American Association for Cancer Rerearch, US, vol. 66, No. 15, 2006, pp. 1-17.

Tomida S et al: "Gene expression-based, individualized outcome prediction for surgically treated lung cancer patients", Oncogene, Nature Publishing Group, GB, vol. 23, No. 31, 2004, pp. 5360-5370.

"Affymetrix GeneChip Human Genome U133 Array Set HG-U133A", GEO, Mar. 2002.

Jiunn-Liang Ko et al: "MDM2 mRNA expression is a favorable prognostic factor in non-small-cell lung cancer", International Journal of Cancer, vol. 89, No. 3, 2000, pp. 265-270.

Higashiyama M et al: "MDM2 gene amplification and expression in non-small-cell lung cancer: immunohistochemical expression of its protein is a favourable prognostic marker in patients without p53 protein accumulation", British Journal of Cancer, vol. 75, No. 9, 1997, pp. 1302-1308.

Weaver David A et al: "ABCC5, ERCC2, XPA and XRCC1 transcript abundance levels correlate with cisplatin chemoresistance in non-small cell lung cancer cell lines", Molecular Cancer, Biomed Central, London, GB, 4:18, 2005, pp. 1-8.

\* cited by examiner

A. Data-mining flowchart

B. Signature optimization

A

B

C

D

E

F

C

D

E

F

G

H

| Cluster | January 2004(%) | June 2005 (%) |
|---|---|---|
| 1 | 103 (93) | 6 (27) |
| 2 | 6 (5) | 16 (73) |
| Outlier | 2 (2) | |
| Total | 111 | 22 |

PROGNOSTIC AND PREDICTIVE GENE SIGNATURE FOR NON-SMALL CELL LUNG CANCER AND ADJUVANT CHEMOTHERAPY

CROSS-REFERENCE TO RELATED APPLICATION

This application claims benefit under 35 U.S.C. §119(e) to U.S. provisional application Ser. No. 61/071,728, filed 14 May 2008, incorporated herein by reference in its entirety.

FIELD

The application relates to compositions and methods for prognosing and classifying non-small cell lung cancer and for determining the benefit of adjuvant chemotherapy.

BACKGROUND OF THE INVENTION

In North America, lung cancer is the leading cancer in males and the leading cause of cancer deaths in both males and females[1]. Non-small cell lung cancer (NSCLC) represents 80% of all lung cancers and has an overall 5-year survival rate of only 16%[1]. Tumor stage is the primary determinant for treatment selection for NSCLC patients. Recent clinical trials have led to the adoption of adjuvant cisplatin-based chemotherapy in early stage NSCLC patients (Stages IB-IIIA).

The 5-year survival advantage conferred by adjuvant chemotherapy in recent trials are 4% in the International Adjuvant Lung Trial (IALT) involving 1,867 stage I-III patients[2], 15% in the National Cancer Institute of Canada Clinical Trials Group (NCIC CTG) BR.10 Trial involving 483 stage IB-II patients[3], and 9% in the Adjuvant Navelbine International Trialist Association (ANITA) trial involving 840 stage IB-IIIA patients[4]. Pre-planned stratification analysis in the later two trials showed no significant survival benefit for stage IB patients[3,4]. This was also demonstrated in the Cancer and Leukemia Group (CALGB) Trial 9633 that tested the benefit of chemotherapy on 344 stage IB patients receiving carboplatin and paclitaxel or observation[5]. Although initially presented in 2004 as a positive trial, recent survival analyses show no significant survival advantage with chemotherapy for either disease-free survival (HR=0.80, p=0.065) or overall survival (HR=0.83, p=0.12)[5]. In an attempt to draw an overall conclusion regarding the effectiveness of adjuvant cisplatin-based chemotherapy, the Lung Adjuvant Cisplatin Evaluation (LACE) meta-analysis was conducted which synthesized information from the 5 largest published, cisplatin-based trials that did not administer concurrent thoracic radiation [Adjuvant Lung Project Italy (ALPI)[7], Big Lung Trial (BLT)[8], IALT[2], BR.10[3], and ANITA[9]]. The study found a 5.3% absolute survival advantage at 5-year (HR=0.89, 95% CI 0.82-0.96, p=0.004). However, stratified analysis by stage showed that the stage IB patients did not benefit significantly from cisplatin treatment (HR=0.92, 95% CI 0.78-1.10). Moreover, a detriment for chemotherapy was suggested in stage IA patients (HR=1.41, 95% CI 0.96-2.09)[6]. Therefore, the current standard of treatment for patients with stage I NSCLC remains surgical resection alone. However, 30 to 40 percent of these stage I patients are expected to relapse after the initial surgery[10,11], indicating that a subgroup of these patients might benefit from adjuvant chemotherapy.

The lack of consistent prognostic molecular markers for early stage NSCLC patients led to attempts to identify novel gene expression signatures using genome wide microarray platforms. Such multi-gene signatures might be stronger than individual genes to predict poor prognosis and poor prognostic patients could potentially benefit from adjuvant therapies. Previous microarray studies have identified prognostic signatures that demonstrated minimal overlaps in the gene sets.[12-20] While only one of the early studies involved secondary signature validation in independent datasets[12], all recently reported signatures were tested for validation[13-16,20]. Nevertheless, lack of direct overlaps between signatures remains. One of the potential confounding factors is that signatures were derived from patients operated at single institutions, which may introduce biases.

SUMMARY OF THE INVENTION

As discussed in the Background section, certain patients suffering from NSCLC benefit from adjuvant chemotherapy. Attempts to identify systematically patient subpopulations in which adjuvant therapy would lead to increased survival or improve patient prognosis have generally failed. Efforts to assemble prognostic molecular markers have yielded various non-overlapping gene sets but have fallen short of establishing a gene signature with a minimal set of genes that is predictive regardless of the form of NSCLC (eg. adenocarcinoma or squamous cell carcinoma) or stage, and serves as a reliable classifier for adjuvant therapy benefit.

As will be discussed in more detail below, Applicants have identified from historical patient data a minimal set of fifteen genes whose expression levels, either alone or in combination with that of one to 3 additional genes, is prognostic of survival outcome and diagnostic of adjuvant therapy benefit. The fifteen genes are provided in Table 4. Optional additional genes may be selected from those provided in Table 3. The prognostic and diagnostic value of the gene sets identified by Applicants was verified by validation against independent data sets, as set forth in the Examples below. The present disclosure provides methods and kits useful for obtaining and utilizing expression information for the fifteen, and optionally one to 3 additional genes, to obtain prognostic and diagnostic information for patient with NSCLC.

The methods of the present disclosure generally involve obtaining from a patient relative expression data, at the DNA, mRNA, or protein level, for each of the fifteen, and optional additional, genes, processing the data and comparing the resulting information to one or more reference values. Relative expression levels are expression data normalized according to techniques known to those skilled in the art.

Expression data may be normalized with respect to one or more genes with invariant expression, such as "housekeeping" genes. In some embodiments, expression data may be processed using standard techniques, such as transformation to a z-score, and/or software tools, such as RMAexpress v0.3.

In one aspect, a multi-gene signature is provided for prognosing or classifying patients with lung cancer. In some embodiments, a fifteen-gene signature is provided, comprising reference values for each of fifteen different genes based on relative expression data for each gene from a historical data set with a known outcome, such as good or poor survival, and/or known treatment, such as adjuvant chemotherapy. In one embodiment, four reference values are provided for each of the fifteen genes listed in Table 4. In one embodiment, the reference values for each of the fifteen genes are principal component values set forth in Table 10.

In some embodiments, a sixteen-, seventeen-, or eighteen-gene signature comprises reference values for each of sixteen, seventeen, or eighteen different genes based on relative expression data for each gene from a historical data set with a known outcome and/or known treatment. In some embodiments, reference values are provided for one, two, three genes in addition to those listed in Table 4, and the genes are selected from those listed in Table 3. In some embodiments, a single reference value for each gene is provided.

In one aspect, relative expression data from a patient are combined with the gene-specific reference values on a gene-by-gene basis for each of the fifteen, and optional additional, genes, to generate a test value which allows prognosis or therapy recommendation. In some embodiments, relative expression data are subjected to an algorithm that yields a single test value, or combined score, which is then compared to a control value obtained from the historical expression data for a patient or pool of patients. In some embodiments, the control value is a numerical threshold for predicting outcomes, for example good and poor outcome, or making therapy recommendations, for example adjuvant therapy in addition to surgical resection or surgical resection alone. In some embodiments, a test value or combined score greater than the control value is predictive, for example, of high risk (poor outcome) or benefit from adjuvant therapy, whereas a combined score falling below the control value is predictive, for example, of low risk (good outcome) or lack of benefit from adjuvant therapy.

In one embodiment, the combined score is calculated from relative expression data multiplied by reference values, determined from historical data, for each gene. Accordingly, the combined score may be calculated using the algorithm of Formula I below:

$$\text{Combined score} = 0.557 \times PC1 + 0.328 \times PC2 + 0.43 \times PC3 + 0.335 \times PC4$$

Where PC1 is the sum of the relative expression level for each gene in a multi-gene signature multiplied by a first principal component for each gene in the multi-gene signature, PC2 is the sum of the relative expression level for each gene multiplied by a second principal component for each gene, PC3 is the sum of the relative expression level for each gene multiplied by a third principal component for each gene, and PC4 is the sum of the relative expression level for each gene multiplied by a fourth principal component for each gene. In some embodiments, the combined score is referred to as a risk score. A risk score for a subject can be calculated by applying Formula I to relative expression data from a test sample obtained from the subject.

In some embodiments, PC1 is the sum of the relative expression level for each gene provided in Table 4 multiplied by a first principal component for each gene, respectively, as set forth in Table 10; PC2 is the sum of the relative expression level for each gene provided in Table 4 multiplied by a second principal component for each gene, respectively, as set forth in Table 10; PC3 is the sum of the relative expression level for each gene provided in Table 4 multiplied by a third principal component for each gene, respectively, as set forth in Table 10; and PC4 is the sum of the relative expression level for each gene provided in Table 4 multiplied by a fourth principal component for each gene, respectively, as set forth in Table 10.

The present inventors have identified a gene signature that is prognostic for survival as well as predictive for benefit from adjuvant chemotherapy.

Accordingly in one embodiment, the application provides a method of prognosing or classifying a subject with non-small cell lung cancer comprising the steps:
    a. determining the expression of fifteen biomarkers in a test sample from the subject, wherein the biomarkers correspond to genes in Table 4, and
    b. comparing the expression of the fifteen biomarkers in the test sample with expression of the fifteen biomarkers in a control sample,
wherein a difference or a similarity in the expression of the fifteen biomarkers between the control and the test sample is used to prognose or classify the subject with NSCLC into a poor survival group or a good survival group.

In an aspect, the application provides a method of predicting prognosis in a subject with non-small cell lung cancer comprising the steps:
    a. obtaining a subject biomarker expression profile in a sample of the subject;
    b. obtaining a biomarker reference expression profile associated with a prognosis, wherein the subject biomarker expression profile and the biomarker reference expression profile each have fifteen values, each value representing the expression level of a biomarker, wherein each biomarker corresponds to one gene in Table 4; and
    c. selecting the biomarker reference expression profile most similar to the subject biomarker expression profile, to thereby predict a prognosis for the subject.

In another aspect, the prognoses and classifying methods of the application can be used to select treatment. For example, the methods can be used to select or identify subjects who might benefit from adjuvant chemotherapy.

Accordingly, in one embodiment, the application provides a method of selecting a therapy for a subject with NSCLC, comprising the steps:
    a. classifying the subject with NSCLC into a poor survival group or a good survival group according to the method of the application; and
    b. selecting adjuvant chemotherapy for the poor survival group or no adjuvant chemotherapy for the good survival group.

In another embodiment, the application provides a method of selecting a therapy for a subject with NSCLC, comprising the steps:
    a. determining the expression of fifteen biomarkers in a test sample from the subject, wherein the fifteen biomarkers correspond to the fifteen genes in Table 4;
    b. comparing the expression of the fifteen biomarkers in the test sample with the fifteen biomarkers in a control sample;
    c. classifying the subject in a poor survival group or a good survival group, wherein a difference or a similarity in the expression of the fifteen biomarkers between the control sample and the test sample is used to classify the subject into a poor survival group or a good survival group;
    d. selecting adjuvant chemotherapy if the subject is classified in the poor survival group and selecting no adjuvant chemotherapy if the subject is classified in the good survival group.

Another aspect of the application provides compositions useful for use with the methods described herein.

The application also provides for kits used to prognose or classify a subject with NSCLC into a good survival group or a poor survival group or for selecting therapy for a subject with NSCLC that includes detection agents that can detect the expression products of the biomarkers.

In one aspect, the present disclosure provides kits useful for carrying out the diagnostic and prognostic tests described herein. The kits generally comprise reagents and compositions for obtaining relative expression data for the fifteen, and optional additional, genes described in Tables 3 and 4. As will be recognized by the skilled artisans, the contents of the kits will depend upon the means used to obtain the relative expression information.

Kits may comprise a labeled compound or agent capable of detecting protein product(s) or nucleic acid sequence(s) in a sample and means for determining the amount of the protein or mRNA in the sample (e.g., an antibody which binds the protein or a fragment thereof, or an oligonucleotide probe which binds to DNA or mRNA encoding the protein). Kits can also include instructions for interpreting the results obtained using the kit.

In some embodiments, the kits are oligonucleotide-based kits, which may comprise, for example: (1) an oligonucleotide, e.g., a detectably labeled oligonucleotide, which hybridizes to a nucleic acid sequence encoding a marker protein or (2) a pair of primers useful for amplifying a marker nucleic acid molecule. Kits may also comprise, e.g., a buffering agent, a preservative, or a protein stabilizing agent. The kits can further comprise components necessary for detecting the detectable label (e.g., an enzyme or a substrate). The kits can also contain a control sample or a series of control samples which can be assayed and compared to the test sample. Each component of a kit can be enclosed within an individual container and all of the various containers can be within a single package, along with instructions for interpreting the results of the assays performed using the kit.

In some embodiments, the kits are antibody-based kits, which may comprise, for example: (1) a first antibody (e.g., attached to a solid support) which binds to a marker protein; and, optionally, (2) a second, different antibody which binds to either the protein or the first antibody and is conjugated to a detectable label.

A further aspect provides computer implemented products, computer readable mediums and computer systems that are useful for the methods described herein.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

Figure 1:
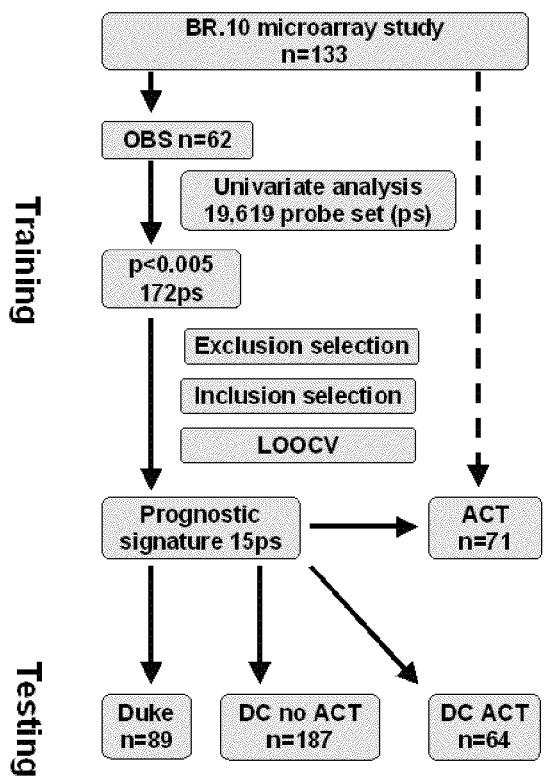
FIG. 1 shows the derivation and testing of the prognostic signature.
Figure 1:
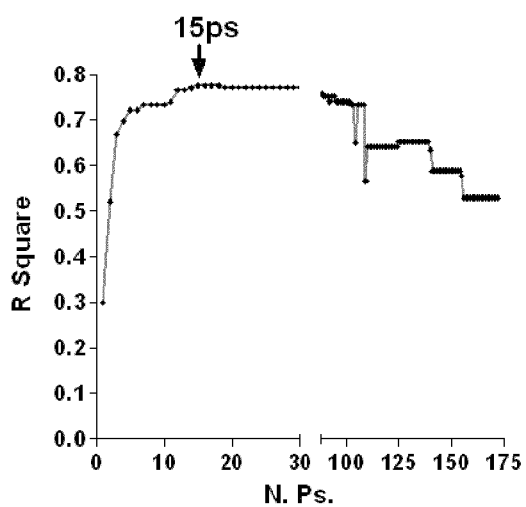

The application relates to 15 biomarkers that form a 15-gene signature, and provides methods, compositions, computer implemented products, detection agents and kits for prognosing or classifying a subject with non-small cell lung cancer (NSCLC) and for determining the benefit of adjuvant chemotherapy.

The term "biomarker" as used herein refers to a gene that is differentially expressed in individuals with non-small cell lung cancer (NSCLC) according to prognosis and is predictive of different survival outcomes and of the benefit of adjuvant chemotherapy. In some embodiments, a 15-gene signature comprises 15 biomarker genes listed in Table 4. Optional additional biomarkers for a 16-, 17-, or 18-gene signature may be selected from the genes listed in Table 3.

Accordingly, one aspect of the invention is a method of prognosing or classifying a subject with non-small cell lung cancer, comprising the steps:
  a. determining the expression of fifteen biomarkers in a test sample from the subject, wherein the biomarkers correspond to genes in Table 4, and
  b. comparing the expression of the fifteen biomarkers in the test sample with expression of the fifteen biomarkers in a control sample,
wherein a difference or a similarity in the expression of the fifteen biomarkers between the control and the test sample is used to prognose or classify the subject with NSCLC into a poor survival group or a good survival group.

In another aspect, the application provides a method of predicting prognosis in a subject with non-small cell lung cancer (NSCLC) comprising the steps:
  a. obtaining a subject biomarker expression profile in a sample of the subject;
  b. obtaining a biomarker reference expression profile associated with a prognosis, wherein the subject biomarker expression profile and the biomarker reference expression profile each have fifteen values, each value representing the expression level of a biomarker, wherein each biomarker corresponds to a gene in Table 4; and
  c. selecting the biomarker reference expression profile most similar to the subject biomarker expression profile, to thereby predict a prognosis for the subject.

The term "reference expression profile" as used herein refers to the expression of the 15 biomarkers or genes listed in Table 4 associated with a clinical outcome in a NSCLC patient. The reference expression profile comprises 15 values, each value representing the expression level of a biomarker, wherein each biomarker corresponds to one gene in Table 4. The reference expression profile is identified using one or more samples comprising tumor wherein the expression is similar between related samples defining an outcome class or group such as poor survival or good survival and is different to unrelated samples defining a different outcome class such that the reference expression profile is associated with a particular clinical outcome. The reference expression profile is accordingly a reference profile of the expression of the 15 genes in Table 4, to which the subject expression levels of the corresponding genes in a patient sample are compared in methods for determining or predicting clinical outcome.

As used herein, the term "control" refers to a specific value or dataset that can be used to prognose or classify the value e.g expression level or reference expression profile obtained from the test sample associated with an outcome class.

In one embodiment, a dataset may be obtained from samples from a group of subjects known to have NSCLC and good survival outcome or known to have NSCLC and have poor survival outcome or known to have NSCLC and benefited from adjuvant chemotherapy or known to have NSCLC and not have benefited from adjuvant chemotherapy. The expression data of the biomarkers in the dataset can be used to create a "control value" that is used in testing samples from new patients. A control value is obtained from the historical expression data for a patient or pool of patients with a known outcome. In some embodiments, the control value is a numerical threshold for predicting outcomes, for example good and poor outcome, or making therapy recommendations, for example adjuvant therapy in addition to surgical resection or surgical resection alone.

In some embodiments, the "control" is a predetermined value for the set of 15 biomarkers obtained from NSCLC patients whose biomarker expression values and survival times are known. Alternatively, the "control" is a predetermined reference profile for the set of fifteen biomarkers obtained from NSCLC patients whose survival times are known. Using values from known samples allows one to develop an algorithm for classifying new patient samples into good and poor survival groups as described in the Example.

Accordingly, in one embodiment, the control is a sample from a subject known to have NSCLC and good survival outcome. In another embodiment, the control is a sample from a subject known to have NSCLC and poor survival outcome.

A person skilled in the art will appreciate that the comparison between the expression of the biomarkers in the test sample and the expression of the biomarkers in the control will depend on the control used. For example, if the control is from a subject known to have NSCLC and poor survival, and there is a difference in expression of the biomarkers between the control and test sample, then the subject can be prognosed or classified in a good survival group. If the control is from a subject known to have NSCLC and good survival, and there is a difference in expression of the biomarkers between the control and test sample, then the subject can be prognosed or classified in a poor survival group. For example, if the control is from a subject known to have NSCLC and good survival, and there is a similarity in expression of the biomarkers between the control and test sample, then the subject can be prognosed or classified in a good survival group. For example, if the control is from a subject known to have NSCLC and poor survival, and there is a similarity in expression of the biomarkers between the control and test sample, then the subject can be prognosed or classified in a poor survival group.

As used herein, a "reference value" refers to a gene-specific coefficient derived from historical expression data. The multi-gene signatures of the present disclosure comprise gene-specific reference values. In some embodiments, the multi-gene signature comprises one reference value for each gene in the signature.

In some embodiments, the multi-gene signature comprises four reference values for each gene in the signature. In some embodiments, the reference values are the first four components derived from principal component analysis for each gene in the signature.

The term "differentially expressed" or "differential expression" as used herein refers to a difference in the level of expression of the biomarkers that can be assayed by measuring the level of expression of the products of the biomarkers, such as the difference in level of messenger RNA transcript expressed or proteins expressed of the biomarkers. In a preferred embodiment, the difference is statistically significant. The term "difference in the level of expression" refers to an increase or decrease in the measurable expression level of a given biomarker as measured by the amount of messenger RNA transcript and/or the amount of protein in a sample as compared with the measurable expression level of a given biomarker in a control. In one embodiment, the differential expression can be compared using the ratio of the level of expression of a given biomarker or biomarkers as compared with the expression level of the given biomarker or biomarkers of a control, wherein the ratio is not equal to 1.0. For example, an RNA or protein is differentially expressed if the ratio of the level of expression in a first sample as compared with a second sample is greater than or less than 1.0. For example, a ratio of greater than 1, 1.2, 1.5, 1.7, 2, 3, 3, 5, 10, 15, 20 or more, or a ratio less than 1, 0.8, 0.6, 0.4, 0.2, 0.1, 0.05, 0.001 or less. In another embodiment the differential expression is measured using p-value. For instance, when using p-value, a biomarker is identified as being differentially expressed as between a first sample and a second sample when the p-value is less than 0.1, preferably less than 0.05, more preferably less than 0.01, even more preferably less than 0.005, the most preferably less than 0.001.

The term "similarity in expression" as used herein means that there is no or little difference in the level of expression of the biomarkers between the test sample and the control or reference profile. For example, similarity can refer to a fold difference compared to a control. In a preferred embodiment, there is no statistically significant difference in the level of expression of the biomarkers.

The term "most similar" in the context of a reference profile refers to a reference profile that is associated with a clinical outcome that shows the greatest number of identities and/or degree of changes with the subject profile.

The term "prognosis" as used herein refers to a clinical outcome group such as a poor survival group or a good survival group associated with a disease subtype which is reflected by a reference profile such as a biomarker reference expression profile or reflected by an expression level of the fifteen biomarkers disclosed herein. The prognosis provides an indication of disease progression and includes an indication of likelihood of death due to lung cancer. In one embodiment the clinical outcome class includes a good survival group and a poor survival group.

The term "prognosing or classifying" as used herein means predicting or identifying the clinical outcome group that a subject belongs to according to the subject's similarity to a reference profile or biomarker expression level associated with the prognosis. For example, prognosing or classifying comprises a method or process of determining whether an individual with NSCLC has a good or poor survival outcome, or grouping an individual with NSCLC into a good survival group or a poor survival group.

The term "good survival" as used herein refers to an increased chance of survival as compared to patients in the "poor survival" group. For example, the biomarkers of the application can prognose or classify patients into a "good survival group". These patients are at a lower risk of death after surgery.

The term "poor survival" as used herein refers to an increased risk of death as compared to patients in the "good survival" group. For example, biomarkers or genes of the application can prognose or classify patients into a "poor survival group". These patients are at greater risk of death from surgery.

Accordingly, in one embodiment, the biomarker reference expression profile comprises a poor survival group. In another embodiment, the biomarker reference expression profile comprises a good survival group.

The term "subject" as used herein refers to any member of the animal kingdom, preferably a human being that has NSCLC or that is suspected of having NSCLC.

NSCLC patients are classified into stages, which are used to determine therapy. Staging classification testing may include any or all of history, physical examination, routine laboratory evaluations, chest x-rays, and chest computed tomography scans or positron emission tomography scans with infusion of contrast materials. For example, stage I includes cancer in the lung, but has not spread to adjacent lymph nodes or outside the chest. Stage I is divided into two categories based on the size of the tumor (IA and IB). Stage II includes cancer located in the lung and proximal lymph nodes. Stage II is divided into 2 categories based on the size of tumor and nodal status (IIA and IIB). Stage III includes cancer located in the lung and the lymph nodes. Stage III is divided into 2 categories based on the size of tumor and nodal status (IIIA and IIIB). Stage 1V includes cancer that has metastasized to distant locations. The term "early stage NSCLC" includes patients with Stage I to IIIA NSCLC. These patients are treated primarily by complete surgical resection.

In an aspect, a multi-gene signature is prognostic of patient outcome and/or response to adjuvant chemotherapy. In some embodiments, a minimal signature for 15 genes is provided. In one embodiment, the signature comprises reference values for each of the 15 genes listed in Table 4. In some embodiments, the 15-gene signature is associated with the early stages of NSCLC. Accordingly, in one embodiment, the subject has stage I NSCLC. In another embodiment, the subject has stage II NSCLC. In some embodiments, a 16-, 17-, 18-gene signature is prognostic of patient outcome and/or response to adjuvant chemotherapy. In some embodiments, the signature comprises reference values for one, two or three genes selected from those listed in Table 3, in addition to reference values for each of the genes listed in Table 4. In some embodiments, the additional one, two, or three genes are selected from RGS4, UGT2B4, and MCF2 listed in Table 3.

In some embodiments, the multi-gene signature comprises four coefficients, or reference values, for each gene in the signature. In one embodiment, the four coefficients are the first four principal components derived from principal component analysis described in Example 1 below. In one embodiment, the 15-gene signature comprises the principal component values listed in Table 10 below. In some embodiments, a 16-, 17-, 18-gene signature comprises coefficients for a sixteenth, seventeenth, and eighteenth gene, respectively, derived from principal component analysis as described in Example 1 below. In some embodiments, the coefficients for a sixteenth, seventeenth, and eighteenth gene, respectively, are the first four principal components derived according to Example 1. In some embodiments, the additional one, two, or three genes are selected from RGS4, UGT2B4, and MCF2 listed in Table 3.

The term "test sample" as used herein refers to any cancer-affected fluid, cell or tissue sample from a subject which can be assayed for biomarker expression products and/or a reference expression profile, e.g. genes differentially expressed in subjects with NSCLC according to survival outcome.

The phrase "determining the expression of biomarkers" as used herein refers to determining or quantifying RNA or proteins expressed by the biomarkers. The term "RNA" includes mRNA transcripts, and/or specific spliced variants of mRNA. The terms "RNA product of the biomarker," "biomarker RNA," or "target RNA" as used herein refers to RNA transcripts transcribed from the biomarkers and/or specific spliced variants. In the case of "protein", it refers to proteins translated from the RNA transcripts transcribed from the biomarkers. The term "protein product of the biomarker" or "biomarker protein" refers to proteins translated from RNA products of the biomarkers.

A person skilled in the art will appreciate that a number of methods can be used to detect or quantify the level of RNA products of the biomarkers within a sample, including arrays, such as microarrays, RT-PCR (including quantitative PCR), nuclease protection assays and Northern blot analyses. Any analytical procedure capable of permitting specific and quantifiable (or semi-quantifiable) detection of the 15 and, optionally, additional biomarkers may be used in the methods herein presented, such as the microarray methods set forth herein, and methods known to those skilled in the art.

Accordingly, in one embodiment, the biomarker expression levels are determined using arrays, optionally microarrays, RT-PCR, optionally quantitative RT-PCR, nuclease protection assays or Northern blot analyses.

In some embodiments, the biomarker expression levels are determined by using an array. cDNA microarrays consist of multiple (usually thousands) of different cDNAs spotted (usually using a robotic spotting device) onto known locations on a solid support, such as a glass microscope slide. Microarrays for use in the methods described herein comprise a solid substrate onto which the probes are covalently or non-covalently attached. The cDNAs are typically obtained by PCR amplification of plasmid library inserts using primers complementary to the vector backbone portion of the plasmid or to the gene itself for genes where sequence is known. PCR products suitable for production of microarrays are typically between 0.5 and 2.5 kB in length. In a typical microarray experiment, RNA (either total RNA or poly A RNA) is isolated from cells or tissues of interest and is reverse transcribed to yield cDNA. Labeling is usually performed during reverse transcription by incorporating a labeled nucleotide in the reaction mixture. A microarray is then hybridized with labeled RNA, and relative expression levels calculated based on the relative concentrations of cDNA molecules that hybridized to the cDNAs represented on the microarray. Microarray analysis can be performed by commercially available equipment, following manufacturer's protocols, such as by using Affymetrix GeneChip® technology, Agilent Technologies cDNA microarrays, Illumina Whole-Genome DASL® array assays, or any other comparable microarray technology.

In some embodiments, probes capable of hybridizing to one or more biomarker RNAs or cDNAs are attached to the substrate at a defined location ("addressable array"). Probes can be attached to the substrate in a wide variety of ways, as will be appreciated by those in the art. In some embodiments, the probes are synthesized first and subsequently attached to the substrate. In other embodiments, the probes are synthesized on the substrate. In some embodiments, probes are synthesized on the substrate surface using techniques such as photopolymerization and photolithography.

In some embodiments, microarrays are utilized in a RNA-primed, Array-based Klenow Enzyme ("RAKE") assay. See Nelson, P. T. et al. (2004) *Nature Methods* 1(2):1-7; Nelson, P. T. et al. (2006) *RNA* 12(2):1-5, each of which is incorporated herein by reference in its entirety. In these embodiments, total RNA is isolated from a sample. Optionally, small RNAs can be further purified from the total RNA sample. The RNA sample is then hybridized to DNA probes immobilized at the 5'-end on an addressable array. The DNA probes comprise a base sequence that is complementary to a target RNA of interest, such as one or more biomarker RNAs capable of specifically hybridizing to a nucleic acid comprising a sequence that is identically present in one of the genes listed in Table 4 under standard hybridization conditions.

In some embodiments, the addressable array comprises DNA probes for no more than the 15 genes listed in Table 4.

In some embodiments, the addressable array comprises DNA probes for each of the 15 genes listed in Table 4 and optionally, no more than one, two, or three additional genes selected from those listed in Table 3. In one embodiment, the addressable array comprises DNA probes for each of the 15 genes listed in Table 4 and DNA probes for one, two, or all three of RGS4, UGT2B4, and MCF2 listed in Table 3.

In some embodiments, quantitation of biomarker RNA expression levels requires assumptions to be made about the total RNA per cell and the extent of sample loss during sample preparation. In some embodiments, the addressable array comprises DNA probes for each of the 15 genes listed in Table 4 and, optionally, one, two, three, or four housekeeping genes. In one embodiment, the addressable array comprises DNA probes for each of the 15 genes listed in Table 4, one, two, three, or four housekeeping genes, and, additionally, no more than one, two, three or four additional genes selected from those listed in Table 3.

In some embodiments, expression data are pre-processed to correct for variations in sample preparation or other non-experimental variables affecting expression measurements. For example, background adjustment, quantile adjustment, and summarization may be performed on microarray data, using standard software programs such as RMAexpress v0.3, followed by centering of the data to the mean and scaling to the standard deviation.

After the sample is hybridized to the array, it is exposed to exonuclease I to digest any unhybridized probes. The Klenow fragment of DNA polymerase I is then applied along with biotinylated dATP, allowing the hybridized biomarker RNAs to act as primers for the enzyme with the DNA probe as template. The slide is then washed and a streptavidin-conjugated fluorophore is applied to detect and quantitate the spots on the array containing hybridized and Klenow-extended biomarker RNAs from the sample.

In some embodiments, the RNA sample is reverse transcribed using a biotin/poly-dA random octamer primer. The RNA template is digested and the biotin-containing cDNA is hybridized to an addressable microarray with bound probes that permit specific detection of biomarker RNAs. In typical embodiments, the microarray includes at least one probe comprising at least 8, at least 9, at least 10, at least 11, at least 12, at least 13, at least 14, at least 15, at least 16, at least 17, at least 18, at least 19, even at least 20, 21, 22, 23, or 24 contiguous nucleotides identically present in each of the genes listed in Table 4. After hybridization of the cDNA to the microarray, the microarray is exposed to a streptavidin-bound detectable marker, such as a fluorescent dye, and the bound cDNA is detected. See Liu C. G. et al. (2008) Methods 44:22-30, which is incorporated herein by reference in its entirety.

In one embodiment, the array is a U133A chip from Affymetrix. In another embodiment, a plurality of nucleic acid probes that are complementary or hybridizable to an expression product of the genes listed in Table 4 are used on the array. In a particular embodiment, the probe target sequences are listed in Table 9. In some embodiments, the probe target sequences are selected from SEQ ID NO: 3, 11-15, 22, 26, 35, 49, 78, 85, 130, 133, and 169. In one embodiment, fifteen probes are used, each probe hybridizable to a different target sequence selected from SEQ ID NO: 3, 11-15, 22, 26, 35, 49, 78, 85, 130, 133, and 169. In some embodiments, a plurality of nucleic acid probes that are complementary or hybridizable to an expression product of some or all the genes listed in Table 3 are used on the array. In some embodiments, the probe target sequences are selected from those listed in Table 11. In some embodiments, the probe target sequences are selected from SEQ ID NO:1-172.

The term "nucleic acid" includes DNA and RNA and can be either double stranded or single stranded.

The term "hybridize" or "hybridizable" refers to the sequence specific non-covalent binding interaction with a complementary nucleic acid. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. For example, 6.0× sodium chloride/sodium citrate (SSC) at about 45° C., followed by a wash of 2.0×SSC at 50° C. may be employed.

The term "probe" as used herein refers to a nucleic acid sequence that will hybridize to a nucleic acid target sequence. In one example, the probe hybridizes to an RNA product of the biomarker or a nucleic acid sequence complementary thereof. The length of probe depends on the hybridization conditions and the sequences of the probe and nucleic acid target sequence. In one embodiment, the probe is at least 8, 10, 15, 20, 25, 50, 75, 100, 150, 200, 250, 400, 500 or more nucleotides in length.

In some embodiments, compositions are provided that comprise at least one biomarker or target RNA-specific probe. The term "target RNA-specific probe" encompasses probes that have a region of contiguous nucleotides having a sequence that is either (I) identically present in one of the genes listed in Tables 3 or 4, or (ii) complementary to the sequence of a region of contiguous nucleotides found in one of the genes listed in Tables 3 or 4, where "region" can comprise the full length sequence of any one of the genes listed in Tables 3 or 4, a complementary sequence of the full length sequence of any one of the genes listed in Tables 3 or 4, or a subsequence thereof.

In some embodiments, target RNA-specific probes consist of deoxyribonucleotides. In other embodiments, target RNA-specific probes consist of both deoxyribonucleotides and nucleotide analogs. In some embodiments, biomarker RNA-specific probes comprise at least one nucleotide analog which increases the hybridization binding energy. In some embodiments, a target RNA-specific probe in the compositions described herein binds to one biomarker RNA in the sample.

In some embodiments, more than one probe specific for a single biomarker RNA is present in the compositions, the probes capable of binding to overlapping or spatially separated regions of the biomarker RNA.

It will be understood that in some embodiments in which the compositions described herein are designed to hybridize to cDNAs reverse transcribed from biomarker RNAs, the composition comprises at least one target RNA-specific probe comprising a sequence that is identically present in a biomarker RNA (or a subsequence thereof).

In some embodiments, a biomarker RNA is capable of specifically hybridizing to at least one probe comprising a base sequence that is identically present in one of the genes listed in Table 4. In some embodiments, a biomarker RNA is capable of specifically hybridizing to at least one nucleic acid probe comprising a sequence that is identically present in one of the genes listed in Table 3. In some embodiments, a target RNA is capable of specifically hybridizing to at least one nucleic acid probe, and comprises a sequence that is identical to a sequence selected from SEQ ID NO:1-172, or a sequence listed in Table 11. In some embodiments, a target RNA is capable of specifically hybridizing to at least one nucleic acid probe, and comprises a sequence that is identical to a sequence listed in Table 9. In some embodiments, a target RNA is capable of specifically hybridizing to at least one nucleic acid probe, and comprises a sequence that is identical to a sequence selected from SEQ ID NO: 3, 11-15, 22, 26, 35, 49, 78, 85, 130, 133, and 169. In some embodiments, a biomarker RNA is capable of specifically hybridizing to at least one probe comprising a base sequence that is identically present in one of the genes listed in Table 4.

In some embodiments, the composition comprises a plurality of target or biomarker RNA-specific probes each comprising a region of contiguous nucleotides comprising a base sequence that is identically present in one or more of the genes listed in Table 4, or in a subsequence thereof. In some embodiments, the composition comprises a plurality of target or biomarker RNA-specific probes each comprising a region of contiguous nucleotides comprising a base sequence that is complementary to a sequence listed in Table 9. In some embodiments, the composition comprises a plurality of target RNA-specific probes each comprising a region of contiguous nucleotides comprising a base sequence that is complementary to a sequence selected from SEQ ID NO: 3, 11-15, 22, 26, 35, 49, 78, 85, 130, 133, and 169.

As used herein, the terms "complementary" or "partially complementary" to a biomarker or target RNA (or target region thereof, and the percentage of "complementarity" of the probe sequence to that of the biomarker RNA sequence is the percentage "identity" to the reverse complement of the sequence of the biomarker RNA. In determining the degree of "complementarity" between probes used in the compositions described herein (or regions thereof) and a biomarker RNA, such as those disclosed herein, the degree of "complementarity" is expressed as the percentage identity between the sequence of the probe (or region thereof and the reverse complement of the sequence of the biomarker RNA that best aligns therewith. The percentage is calculated by counting the number of aligned bases that are identical as between the 2 sequences, dividing by the total number of contiguous nucleotides in the probe, and multiplying by 100.

In some embodiments, the microarray comprises probes comprising a region with a base sequence that is fully complementary to a target region of a biomarker RNA. In other embodiments, the microarray comprises probes comprising a region with a base sequence that comprises one or more base mismatches when compared to the sequence of the best-aligned target region of a biomarker RNA.

As noted above, a "region" of a probe or biomarker RNA, as used herein, may comprise or consist of 8, 9, 10, 11, 12, 13, 14, 15, 16, 17, 18, 19, 20, 21, 22, 23, 24, 25, 26, 27, 28, 29 or more contiguous nucleotides from a particular gene or a complementary sequence thereof. In some embodiments, the region is of the same length as the probe or the biomarker RNA. In other embodiments, the region is shorter than the length of the probe or the biomarker RNA.

In some embodiments, the microarray comprises fifteen probes each comprising a region of at least 10 contiguous nucleotides, such as at least 11 contiguous nucleotides, such as at least 13 contiguous nucleotides, such as at least 14 contiguous nucleotides, such as at least 15 contiguous nucleotides, such as at least 16 contiguous nucleotides, such as at least 17 contiguous nucleotides, such as at least 18 contiguous nucleotides, such as at least 19 contiguous nucleotides, such as at least 20 contiguous nucleotides, such as at least 21 contiguous nucleotides, such as at least 22 contiguous nucleotides, such as at least 23 contiguous nucleotides, such as at least 24 contiguous nucleotides, such as at least 25 contiguous nucleotides with a base sequence that is identically present in one of the genes listed in Table 4.

In some embodiments, the microarray component comprises fifteen probes each comprising a region with a base sequence that is identically present in each of the genes listed in Table 4. In some embodiments, the microarray comprises sixteen, seventeen, eighteen probes, each of which comprises a region with a base sequence that is identically present in each of the genes listed in Table 4 and, optionally, one, two, or three of the genes listed in Table 3. In one embodiment, the one, two, or three genes from Table 3 are selected from RGS4, UGT2B4, and MCF2.

In another embodiment, the biomarker expression levels are determined by using quantitative RT-PCR. RT-PCR is one of the most sensitive, flexible, and quantitative methods for measuring expression levels. The first step is the isolation of mRNA from a target sample. The starting material is typically total RNA isolated from human tumors or tumor cell lines. General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al., BioTechniques 18:42044(1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy® mini-columns. Numerous RNA isolation kits are commercially available.

In some embodiments, the primers used for quantitative RT-PCR comprise a forward and reverse primer for each gene listed in Table 4. In one embodiment, the primers used for quantitative RT-PCR are listed in Table 7. In one embodiment, primers comprising sequences identical to the sequences of SEQ ID NO: 173-202 are used for quantitative RT-PCR, wherein primers with sequences identical to SEQ ID NO:173-187 are forward primers and primers with sequences identical to SEQ ID NO:188-202 are reverse primers.

In some embodiments the analytical method used for detecting at least one biomarker RNA in the methods set forth herein includes real-time quantitative RT-PCR. See Chen, C. et al. (2005) *Nucl. Acids Res.* 33:e179, which is incorporated herein by reference in its entirety. Although PCR can use a variety of thermostable DNA-dependent DNA polymerases, it typically employs the Taq DNA polymerase, which has a 5'-3' nuclease activity but lacks a 3'-5' proofreading endonuclease activity. In some embodiments, RT-PCR is done using a TaqMan® assay sold by Applied Biosystems, Inc. In a first step, total RNA is isolated from the sample. In some embodiments, the assay can be used to analyze about 10 ng of total RNA input sample, such as about 9 ng of input sample, such as about 8 ng of input sample, such as about 7 ng of input sample, such as about 6 ng of input sample, such as about 5 ng of input sample, such as about 4 ng of input sample, such as about 3 ng of input sample, such as about 2 ng of input sample, and even as little as about 1 ng of input sample containing RNA.

The TaqMan® assay utilizes a stem-loop primer that is specifically complementary to the 3'-end of a biomarker RNA. The step of hybridizing the stem-loop primer to the biomarker RNA is followed by reverse transcription of the biomarker RNA template, resulting in extension of the 3' end of the primer. The result of the reverse transcription step is a chimeric (DNA) amplicon with the step-loop primer sequence at the 5' end of the amplicon and the cDNA of the biomarker RNA at the 3' end. Quantitation of the biomarker RNA is achieved by RT-PCR using a universal reverse primer comprising a sequence that is complementary to a sequence at the 5' end of all stem-loop biomarker RNA primers, a biomarker RNA-specific forward primer, and a biomarker RNA sequence-specific TaqMan® probe.

The assay uses fluorescence resonance energy transfer ("FRET") to detect and quantitate the synthesized PCR product. Typically, the TaqMan® probe comprises a fluorescent dye molecule coupled to the 5'-end and a quencher molecule coupled to the 3'-end, such that the dye and the quencher are in close proximity, allowing the quencher to suppress the fluorescence signal of the dye via FRET. When the polymerase replicates the chimeric amplicon template to which the TaqMan® probe is bound, the 5'-nuclease of the polymerase cleaves the probe, decoupling the dye and the quencher so that FRET is abolished and a fluorescence signal is generated. Fluorescence increases with each RT-PCR cycle proportionally to the amount of probe that is cleaved.

In some embodiments, quantitation of the results of RT-PCR assays is done by constructing a standard curve from a nucleic acid of known concentration and then extrapolating quantitative information for biomarker RNAs of unknown concentration. In some embodiments, the nucleic acid used for generating a standard curve is an RNA of known concentration. In some embodiments, the nucleic acid used for generating a standard curve is a purified double-stranded plasmid DNA or a single-stranded DNA generated in vitro.

In some embodiments, where the amplification efficiencies of the biomarker nucleic acids and the endogenous reference are approximately equal, quantitation is accomplished by the comparative $C_t$ (cycle threshold, e.g., the number of PCR cycles required for the fluorescence signal to rise above background) method. $C_t$ values are inversely proportional to the amount of nucleic acid target in a sample. In some embodiments, $C_t$ values of the target RNA of interest can be compared with a control or calibrator, such as RNA from normal tissue. In some embodiments, the $C_t$ values of the calibrator and the target RNA samples of interest are normalized to an appropriate endogenous housekeeping gene (see above).

In addition to the TaqMan® assays, other RT-PCR chemistries useful for detecting and quantitating PCR products in the methods presented herein include, but are not limited to, Molecular Beacons™, Scorpion™ probes and SYBR® Green detection.

In some embodiments, Molecular Beacons™ can be used to detect and quantitate PCR products. Like TaqMan® probes, Molecular Beacons™ use FRET to detect and quantitate a PCR product via a probe comprising a fluorescent dye and a quencher attached at the ends of the probe. Unlike TaqMan® probes, Molecular Beacons™ remain intact during the PCR cycles. Molecular Beacon™ probes form a stem-loop structure when free in solution, thereby allowing the dye and quencher to be in close enough proximity to cause fluorescence quenching. When the Molecular Beacon™ hybridizes to a target, the stem-loop structure is abolished so that the dye and the quencher become separated in space and the dye fluoresces. Molecular Beacons™ are available, e.g., from Gene Link™ (see world wide web at genelink.com/newsite/products/mbintro.asp).

In some embodiments, Scorpion™ probes can be used as both sequence-specific primers and for PCR product detection and quantitation. Like Molecular Beacons™, Scorpion™ probes form a stem-loop structure when not hybridized to a target nucleic acid. However, unlike Molecular Beacons™, a Scorpion™ probe achieves both sequence-specific priming and PCR product detection. A fluorescent dye molecule is attached to the 5'-end of the Scorpion ™ probe, and a quencher is attached to the 3'-end. The 3' portion of the probe is complementary to the extension product of the PCR primer, and this complementary portion is linked to the 5'-end of the probe by a non-amplifiable moiety. After the Scorpion™ primer is extended, the target-specific sequence of the probe binds to its complement within the extended amplicon, thus opening up the stem-loop structure and allowing the dye on the 5'-end to fluoresce and generate a signal. Scorpion™ probes are available from, e.g, Premier Biosoft International (see world wide web at premierbiosoft.com/tech_notes/Scorpion.html).

In some embodiments, RT-PCR detection is performed specifically to detect and quantify the expression of a single biomarker RNA. The biomarker RNA, in typical embodiments, is selected from a biomarker RNA capable of specifically hybridizing to a nucleic acid comprising a sequence that is identically present in one of the genes set forth in Table 4. In some embodiments, the biomarker RNA specifically hybridizes to a nucleic acid comprising a sequence that is identically present in at least one of the genes in Table 3.

In various other embodiments, RT-PCR detection is utilized to detect, in a single multiplex reaction, each of 15, each of 16, each of 17, even each of 18 biomarker RNAs. The biomarker RNAs, in some embodiments, are capable of specifically hybridizing to a nucleic acid comprising a sequence that is identically present in one of the fifteen genes listed in Table 4 and optionally one, two, or three additional genes listed in Table 3.

In some multiplex embodiments, a plurality of probes, such as TaqMan® probes, each specific for a different RNA target, is used. In typical embodiments, each target RNA-specific probe is spectrally distinguishable from the other probes used in the same multiplex reaction.

In some embodiments, quantitation of RT-PCR products is accomplished using a dye that binds to double-stranded DNA products, such as SYBR® Green. In some embodiments, the assay is the QuaniTect™ SYBR® Green PCR assay from Qiagen. In this assay, total RNA is first isolated from a sample. Total RNA is subsequently poly-adenylated at the 3'-end and reverse transcribed using a universal primer with poly-dT at the 5'-end. In some embodiments, a single reverse transcription reaction is sufficient to assay multiple biomarker RNAs. RT-PCR is then accomplished using biomarker RNA-specific primers and an miScript™ Universal Primer, which comprises a poly-dT sequence at the 5'-end. SYBR® Green dye binds non-specifically to double-stranded DNA and upon excitation, emits light. In some embodiments, buffer conditions that promote highly-specific annealing of primers to the PCR template (e.g., available in the QuaniTec™ SYBR® Green PCR Kit from Qiagen) can be used to avoid the formation of non-specific DNA duplexes and primer dimers that will bind SYBR® Green and negatively affect quantitation. Thus, as PCR product accumulates, the signal from SYBR® green increases, allowing quantitation of specific products.

RT-PCR is performed using any RT-PCR instrumentation available in the art. Typically, instrumentation used in real-time RT-PCR data collection and analysis comprises a thermal cycler, optics for fluorescence excitation and emission collection, and optionally a computer and data acquisition and analysis software.

In some embodiments, the method of detectably quantifying one or more biomarker RNAs includes the steps of: (a) isolating total RNA; (b) reverse transcribing a biomarker RNA to produce a cDNA that is complementary to the biomarker RNA; (c) amplifying the cDNA from step (b); and (d) detecting the amount of a biomarker RNA with RT-PCR.

As described above, in some embodiments, the RT-PCR detection is performed using a FRET probe, which includes, but is not limited to, a TaqMan® probe, a Molecular Beacon™ probe and a Scorpion™ probe. In some embodiments, the RT-PCR detection and quantification is performed with a TaqMan® probe, i.e., a linear probe that typically has a fluorescent dye covalently bound at one end of the DNA and a quencher molecule covalently bound at the other end of the DNA. The FRET probe comprises a base sequence that is complementary to a region of the cDNA such that, when the FRET probe is hybridized to the cDNA, the dye fluorescence is quenched, and when the probe is digested during amplification of the cDNA, the dye is released from the probe and produces a fluorescence signal. In such embodiments, the amount of biomarker RNA in the sample is proportional to the amount of fluorescence measured during cDNA amplification.

The TaqMan® probe typically comprises a region of contiguous nucleotides comprising a base sequence that is complementary to a region of a biomarker RNA or its complementary cDNA that is reverse transcribed from the biomarker RNA template (i.e., the sequence of the probe region is complementary to or identically present in the biomarker RNA to be detected) such that the probe is specifically hybridizable to the resulting PCR amplicon. In some embodiments, the probe comprises a region of at least 6 contiguous nucleotides having a base sequence that is fully complementary to or identically present in a region of a cDNA that has been reverse transcribed from a biomarker RNA template, such as comprising a region of at least 8 contiguous nucleotides, or comprising a region of at least 10 contiguous nucleotides, or comprising a region of at least 12 contiguous nucleotides, or comprising a region of at least 14 contiguous nucleotides, or even comprising a region of at least 16 contiguous nucleotides having a base sequence that is complementary to or identically present in a region of a cDNA reverse transcribed from a biomarker RNA to be detected.

Preferably, the region of the cDNA that has a sequence that is complementary to the TaqMan® probe sequence is at or near the center of the cDNA molecule. In some embodiments, there are independently at least 2 nucleotides, such as at least 3 nucleotides, such as at least 4 nucleotides, such as at least 5 nucleotides of the cDNA at the 5'-end and at the 3'-end of the region of complementarity.

In typical embodiments, all biomarker RNAs are detected in a single multiplex reaction. In these embodiments, each TaqMan® probe that is targeted to a unique cDNA is spectrally distinguishable when released from the probe. Thus, each biomarker RNA is detected by a unique fluorescence signal.

In some embodiments, expression levels may be represented by gene transcript numbers per nanogram of cDNA. To control for variability in cDNA quantity, integrity and the overall transcriptional efficiency of individual primers, RT-PCR data can be subjected to standardization and normalization against one or more housekeeping genes as has been previously described. See e.g., Rubie et al., Mol. Cell. Probes 19(2):101-9 (2005).

Appropriate genes for normalization in the methods described herein include those as to which the quantity of the product does not vary between different cell types, cell lines or under different growth and sample preparation conditions. In some embodiments, endogenous housekeeping genes useful as normalization controls in the methods described herein include, but are not limited to, ACTB, BAT1, B2M, TBP, U6 snRNA, RNU44, RNU 48, and U47. In typical embodiments, the at least one endogenous housekeeping gene for use in normalizing the measured quantity of RNA is selected from ACTB, BAT1, B2M, TBP, U6 snRNA, U6 snRNA, RNU44, RNU 48, and U47. In some embodiments, normalization to the geometric mean of two, three, four or more housekeeping genes is performed. In some embodiments, one housekeeping gene is used for normalization. In some embodiments, two, three, four or more housekeeping genes are used for normalization.

In some embodiments, labels that can be used on the FRET probes include colorimetric and fluorescent labels such as Alexa Fluor® dyes, BODIPY® dyes, such as BODIPY® FL; Cascade® Blue; Cascade® Yellow; coumarin and its derivatives, such as 7-amino-4-methylcoumarin, aminocoumarin and hydroxycoumarin; cyanine dyes, such as Cy3™ and Cy5™; eosins and erythrosins; fluorescein and its derivatives, such as fluorescein isothiocyanate; macrocyclic chelates of lanthanide ions, such as Quantum Dye™; Marina Blue®; Oregon Green®; rhodamine dyes, such as Rhodamine Red™ Tetramethylrhodamine and rhodamine 6G; Texas Red®; fluorescent energy transfer dyes, such as thiazole orange-ethidium heterodimer; and, TOTAB.

Specific examples of dyes include, but are not limited to, those identified above and the following: Alexa Fluor® 350, Alexa Fluor® 405, Alexa Fluor® 430, Alexa Fluor® 488, Alexa Fluor® 500. Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 647, Alexa Fluor® 660, Alexa Fluor® 680, Alexa Fluor® 700, and, Alexa Fluor® 750; amine-reactive BODIPY® dyes, such as BODIPY® 493/503, BODIPY® 530/550, BODIPY® 558/568, BODIPY® 564/570, BODIPY® 576/589, BODIPY® 581/591, BODIPY® 630/650, BODIPY® 650/655, BODIPY® FL, BODIPY® R6G, BODIPY® TMR, and, BODIPY®-TR; Cy3™, Cy5™, 6-FAM™, Fluorescein Isothiocyanate, HEX™, 6-JOE™, Oregon Green® 488, Oregon Green® 500, Oregon Green® 514, Pacific Blue™, REG, Rhodamine Green™, Rhodamine Red™, Renographin®, ROX™, SYPRO®, TAMRA™, 2',4',5',7'-Tetrabromosulfonefluorescein, and TET™.

Specific examples of fluorescently labeled ribonucleotides useful in the preparation of RT-PCR probes for use in some embodiments of the methods described herein are available from Molecular Probes® (Invitrogen), and these include, Alexa Fluor® 488-5-UTP, Fluorescein-12-UTP, BODIPY® FL-14-UTP, BODIPY® TMR-14-UTP, Tetramethyl-rhodamina-6-UTP, Alexa Fluor® 546-14-UTP, Texas Red™-5-UTP, and BODIPY® TR-14-UTP. Other fluorescent ribonucleotides are available from Amersham Biosciences (GE Healthcare), such as Cy3™-UTP and Cy5™-UTP.

Examples of fluorescently labeled deoxyribonucleotides useful in the preparation of RT-PCR probes for use in the methods described herein include Dinitrophenyl (DNP)-1'-dUTP, Cascade® Blue -7-dUTP, Alexa Fluor® 488-5-dUTP, Fluorescein-12-dUTP, Oregon Greene® 488-5-dUTP, BODIPY® FL-14-dUTP, Rhodamine Green™-5-dUTP, Alexa Fluor® 532-5-dUTP, BODIPY® TMR-14-dUTP, Tetramethylrhodamine-6-dUTP, Alexa Fluor® 546-14-dUTP, Alexa Fluor® 568-5-dUTP, Texas Red®-12-dUTP, Texas Red®-5-dUTP, BODIPY® TR-14-dUTP, Alexa Fluor® 594-5-dUTP, BODIPY® 630/650-14-dUTP, BODIPY® 650/665-14-dUTP; Alexa Fluor® 488-7-OBEA-dCTP, Alexa Fluor® 546-16-OBEA-dCTP, Alexa Fluor® 594-7-OBEA-dCTP, Alexa Fluor® 647-12-OBEA-dCTP. Fluorescently labeled nucleotides are commercially available and can be purchased from, e.g., Invitrogen.

In some embodiments, dyes and other moieties, such as quenchers, are introduced into nucleic acids used in the methods described herein, such as FRET probes, via modified nucleotides. A "modified nucleotide" refers to a nucleotide that has been chemically modified, but still functions as a nucleotide. In some embodiments, the modified nucleotide has a chemical moiety, such as a dye or quencher, covalently attached, and can be introduced into an oligonucleotide, for example, by way of solid phase synthesis of the oligonucleotide. In other embodiments, the modified nucleotide includes one or more reactive groups that can react with a dye or quencher before, during, or after incorporation of the modified nucleotide into the nucleic acid. In specific embodiments, the modified nucleotide is an amine-modified nucleotide, i.e., a nucleotide that has been modified to have a reactive amine group. In some embodiments, the modified nucleotide comprises a modified base moiety, such as uridine, adenosine, guanosine, and/or cytosine. In specific embodiments, the amine-modified nucleotide is selected from 5-(3-aminoallyl)-UTP; 8-[(4-amino)butyl]-amino-ATP and 8-[(6-amino)butyl]-amino-ATP; N6-(4-amino)butyl-ATP, N6-(6-amino)butyl-ATP, N4-[2,2-oxy-bis-(ethylamine)]-CTP; N6-(6-Amino)hexyl-ATP; 8-[(6-Amino)hexyl]-amino-ATP; 5-propargylamino-CTP, 5-propargylamino-UTP. In some embodiments, nucleotides with different nucleobase moieties are similarly modified, for example, 5-(3-aminoallyl)-GTP instead of 5-(3-aminoallyl)-UTP. Many amine modified nucleotides are commercially available from, e.g., Applied Biosystems, Sigma, Jena Bioscience and TriLink.

In some embodiments, the methods of detecting at least one biomarker RNA described herein employ one or more modified oligonucleotides, such as oligonucleotides comprising one or more affinity-enhancing nucleotides. Modified oligonucleotides useful in the methods described herein include primers for reverse transcription, PCR amplification primers, and probes. In some embodiments, the incorporation of affinity-enhancing nucleotides increases the binding affinity and specificity of an oligonucleotide for its target nucleic acid as compared to oligonucleotides that contain only deoxyribonucleotides, and allows for the use of shorter oligonucleotides or for shorter regions of complementarity between the oligonucleotide and the target nucleic acid.

In some embodiments, affinity-enhancing nucleotides include nucleotides comprising one or more base modifications, sugar modifications and/or backbone modifications.

In some embodiments, modified bases for use in affinity-enhancing nucleotides include 5-methylcytosine, isocytosine, pseudoisocytosine, 5-bromouracil, 5-propynyluracil, 6-aminopurine, 2-aminopurine, inosine, diaminopurine, 2-chloro-6-aminopurine, xanthine and hypoxanthine.

In some embodiments, affinity-enhancing modifications include nucleotides having modified sugars such as 2'-substituted sugars, such as 2'-O-alkyl-ribose sugars, 2'-aminodeoxyribose sugars, 2'-fluoro-deoxyribose sugars, 2'-fluoro-arabinose sugars, and 2'-O-methoxyethyl-ribose (2'MOE) sugars. In some embodiments, modified sugars are arabinose sugars, or d-arabino-hexitol sugars.

In some embodiments, affinity-enhancing modifications include backbone modifications such as the use of peptide nucleic acids (e.g., an oligomer including nucleobases linked together by an amino acid backbone). Other backbone modifications include phosphorothioate linkages, phosphodiester modified nucleic acids, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof.

In some embodiments, the oligomer includes at least one affinity-enhancing nucleotide that has a modified base, at least nucleotide (which may be the same nucleotide) that has a modified sugar, and at least one internucleotide linkage that is non-naturally occurring.

In some embodiments, the affinity-enhancing nucleotide contains a locked nucleic acid ("LNA") sugar, which is a bicyclic sugar. In some embodiments, an oligonucleotide for use in the methods described herein comprises one or more nucleotides having an LNA sugar. In some embodiments, the oligonucleotide contains one or more regions consisting of nucleotides with LNA sugars. In other embodiments, the oligonucleotide contains nucleotides with LNA sugars interspersed with deoxyribonucleotides. See, e.g., Frieden, M. et al. (2008) Curr. Pharm. Des. 14(11):1138-1142.

The term "primer" as used herein refers to a nucleic acid sequence, whether occurring naturally as in a purified restriction digest or produced synthetically, which is capable of acting as a point of synthesis when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less. The factors involved in determining the appropriate length of primer are readily known to one of ordinary skill in the art. In one embodiment, primer sets for the 15 genes are those listed in Table 7.

In addition, a person skilled in the art will appreciate that a number of methods can be used to determine the amount of a protein product of the biomarker of the invention, including immunoassays such as Western blots, ELISA, and immunoprecipitation followed by SDS-PAGE and immunocytochemistry.

Accordingly, in another embodiment, an antibody is used to detect the polypeptide products of the fifteen biomarkers listed in Table 4. In another embodiment, the sample comprises a tissue sample. In a further embodiment, the tissue sample is suitable for immunohistochemistry.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include Fab, Fab', F(ab')2, scFv, dsFv, ds-scFv, dimers, minibodies, diabodies, and multimers thereof and bispecific antibody fragments. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques.

Conventional techniques of molecular biology, microbiology and recombinant DNA techniques are within the skill of the art. Such techniques are explained fully in the literature. See, e.g., Sambrook, Fritsch & Maniatis, 1989, Molecular Cloning: A Laboratory Manual, Second Edition; Oligonucleotide Synthesis (M. J. Gait, ed., 1984); Nucleic Acid Hybridization (B. D. Harnes & S. J. Higgins, eds., 1984); A Practical Guide to Molecular Cloning (B. Perbal, 1984); and a series, Methods in Enzymology (Academic Press, Inc.); Short Protocols In Molecular Biology, (Ausubel et al., ed., 1995).

For example, antibodies having specificity for a specific protein, such as the protein product of a biomarker, may be prepared by conventional methods. A mammal, (e.g. a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g. the hybridoma technique originally developed by Kohler and Milstein (Nature 256:495-497 (1975)) as well as other techniques such as the human B-cell hybridoma technique (Kozbor et al., Immunol. Today 4:72 (1983)), the EBV-hybridoma technique to produce human monoclonal antibodies (Cole et al., Methods Enzymol, 121:140-67 (1986)), and screening of combinatorial antibody libraries (Huse et al., Science 246:1275 (1989)). Hybridoma cells can be screened immunochemically for production of antibodies specifically reactive with the peptide and the monoclonal antibodies can be isolated.

In some embodiments, recombinant antibodies are provided that specifically bind protein products of the fifteen genes listed in Table 4, and optionally expression products of one or more genes listed in Table 3. Recombinant antibodies include, but are not limited to, chimeric and humanized monoclonal antibodies, comprising both human and non-human portions, single-chain antibodies and multi-specific antibodies. A chimeric antibody is a molecule in which different portions are derived from different animal species, such as those having a variable region derived from a murine monoclonal antibody (mAb) and a human immunoglobulin constant region. (See, e.g., Cabilly et al., U.S. Pat. No. 4,816, 567; and Boss et al., U.S. Pat. No. 4,816,397, which are incorporated herein by reference in their entirety.) Single-chain antibodies have an antigen binding site and consist of single polypeptides. They can be produced by techniques known in the art, for example using methods described in Ladner et. al U.S. Pat. No. 4,946,778 (which is incorporated herein by reference in its entirety); Bird et al., (1988) Science 242:423-426; Whitlow et al., (1991) Methods in Enzymology 2:1-9; Whitlow et al., (1991) Methods in Enzymology 2:97-105; and Huston et al., (1991) Methods in Enzymology Molecular Design and Modeling: Concepts and Applications 203:46-88. Multi-specific antibodies are antibody molecules having at least two antigen-binding sites that specifically bind different antigens. Such molecules can be produced by techniques known in the art, for example using methods described in Segal, U.S. Pat. No. 4,676,980 (the disclosure of which is incorporated herein by reference in its entirety); Holliger et al., (1993) Proc. Natl. Acad. Sci. USA 90:6444-6448; Whitlow et al., (1994) Protein Eng 7:1017-1026 and U.S. Pat. No. 6,121,424.

Monoclonal antibodies directed against any of the expression products of the genes listed in Table 4 and, optionally, against expression products of one or more genes listed in Table 3, can be identified and isolated by screening a recombinant combinatorial immunoglobulin library (e.g., an antibody phage display library) with the polypeptide(s) of interest. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology 9:1370-1372; Hay et al. (1992) Hum. Antibod. Hybridomas 3:81-85; Huse et al. (1989) Science 246:1275-1281; Griffiths et al. (1993) EMBO J. 12:725-734.

Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Cancer Res. 47:999-1005; Wood et al. (1985) Nature 314:446-449; and Shaw et al. (1988) J. Natl. Cancer Inst. 80:1553-1559); Morrison (1985) Science 229:1202-1207; Oi et al. (1986) Bio/Techniques 4:214; U.S. Pat. No. 5,225,539; Jones et al. (1986) Nature 321:552-525; Verhoeyan et al. (1988) Science 239:1534; and Beidler et al. (1988) J. Immunol. 141:4053-4060.

In some embodiments, humanized antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide corresponding to a protein product. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995) Int. Rev. Immunol. 13:65-93). For a detailed discussion of this technology for producing human antibodies and human monoclonal antibodies and protocols for producing such antibodies, see, e.g., U.S. Pat. Nos. 5,625,126; 5,633, 425; 5,569,825; 5,661,016; and 5,545,806. In addition, companies such as Abgenix, Inc. (Fremont, Calif.), can be engaged to provide human antibodies directed against a selected antigen using technology similar to that described above.

Antibodies may be isolated after production (e.g., from the blood or serum of the subject) or synthesis and further purified by well-known techniques. For example, IgG antibodies can be purified using protein A chromatography. Antibodies specific for a protein can be selected or (e.g., partially purified) or purified by, e.g., affinity chromatography. For example, a recombinantly expressed and purified (or partially purified) expression product may be produced, and covalently or non-covalently coupled to a solid support such as, for example, a chromatography column. The column can then be used to affinity purify antibodies specific for the protein products of the genes listed in Tables 3 and 4 from a sample containing antibodies directed against a large number of different epitopes, thereby generating a substantially purified antibody composition, i.e., one that is substantially free of contaminating antibodies. By a substantially purified antibody composition it is meant, in this context, that the antibody sample contains at most only 30% (by dry weight) of contaminating antibodies directed against epitopes other than those of the protein products of the genes listed in Tables 3 and 4, and preferably at most 20%, yet more preferably at most 10%, and most preferably at most 5% (by dry weight) of the sample is contaminating antibodies. A purified antibody composition means that at least 99% of the antibodies in the composition are directed against the desired protein.

In some embodiments, substantially purified antibodies may specifically bind to a signal peptide, a secreted sequence, an extracellular domain, a transmembrane or a cytoplasmic domain or cytoplasmic membrane of a protein product of one of the genes listed in Tables 3 and 4. In an embodiment, substantially purified antibodies specifically bind to a secreted sequence or an extracellular domain of the amino acid sequences of a protein product of one of the genes listed in Tables 3 and 4.

In some embodiments, antibodies directed against a protein product of one of the genes listed in Tables 3 and 4 can be used to detect the protein products or fragment thereof (e.g., in a cellular lysate or cell supernatant) in order to evaluate the level and pattern of expression of the protein. Detection can be facilitated by the use of an antibody derivative, which comprises an antibody coupled to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, .beta.-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, 131I, 35S or 3H.

A variety of techniques can be employed to measure expression levels of each of the fifteen, and optional additional, genes given a sample that contains protein products that bind to a given antibody. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining protein expression levels of the fifteen, and optional additional products of the genes listed in Tables 4 and 3.

In one embodiment, antibodies, or antibody fragments or derivatives, can be used in methods such as Western blots or immunofluorescence techniques to detect the expressed proteins. In some embodiments, either the antibodies or proteins are immobilized on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present disclosure. The support can then be washed with suitable buffers followed by treatment with the detectably labeled antibody. The solid phase support can then be washed with the buffer a second time to remove unbound antibody. The amount of bound label on the solid support can then be detected by conventional means.

Immunohistochemistry methods are also suitable for detecting the expression levels of the prognostic markers. In some embodiments, antibodies or antisera, including polyclonal antisera, and monoclonal antibodies specific for each marker may be used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

Immunological methods for detecting and measuring complex formation as a measure of protein expression using either specific polyclonal or monoclonal antibodies are known in the art. Examples of such techniques include enzyme-linked immunosorbent assays (ELISAs), radioimmunoassays (RIAs), fluorescence-activated cell sorting (FACS) and antibody arrays. Such immunoassays typically involve the measurement of complex formation between the protein and its specific antibody. These assays and their quantitation against purified, labeled standards are well known in the art (Ausubel, supra, unit 10.1-10.6). A two-site, monoclonal-based immunoassay utilizing antibodies reactive to two non-interfering epitopes is preferred, but a competitive binding assay may be employed (Pound (1998) Immunochemical Protocols, Humana Press, Totowa N.J.).

Numerous labels are available which can be generally grouped into the following categories:
(a) Radioisotopes, such as $^{36}S$, $^{14}C$, $^{125}I$, $^{3}H$, and $^{131}I$. The antibody variant can be labeled with the radioisotope using the techniques described in Current Protocols in Immunology, vol 1-2, Coligen et al., Ed., Wiley-Interscience, New York, Pubs. (1991) for example and radioactivity can be measured using scintillation counting.
(b) Fluorescent labels such as rare earth chelates (europium chelates) or fluorescein and its derivatives, rhodamine and its derivatives, dansyl, Lissamine™, phycoerythrin and Texas Red® are available. The fluorescent labels can be conjugated to the antibody variant using the techniques disclosed in Current Protocols in Immunology, supra, for example. Fluorescence can be quantified using a fluorimeter.
(c) Various enzyme-substrate labels are available and U.S. Pat. Nos. 4,275,149, 4,318,980 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for Use in Enzyme Immunoassay, in Methods in Enzyme. (Ed. J. Langone & H. Van Vunakis), Academic press, New York, 73: 147-166 (1981).

In some embodiments, a detection label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g. digoxin) and one of the different types of labels mentioned above is conjugated with an anti-hapten antibody (e.g. anti-digoxin antibody). In some embodiments, the antibody need not be labeled, and the presence thereof can be detected using a labeled antibody, which binds to the antibody.

The 15-gene signature described herein can be used to select treatment for NCSLC patients. As explained herein, the biomarkers can classify patients with NSCLC into a poor survival group or a good survival group and into groups that might benefit from adjuvant chemotherapy or not.

Accordingly, in one embodiment, the application provides a method of selecting a therapy for a subject with NSCLC, comprising the steps:

(a) classifying the subject with NSCLC into a poor survival group or a good survival group according to the methods described herein; and (b) selecting adjuvant chemotherapy for the subject classified as being in the poor survival group or no adjuvant chemotherapy for the subject classified as being in the good survival group.

In another embodiment, the application provides a method of selecting a therapy for a subject with NSCLC, comprising the steps:

(a) determining the expression of fifteen biomarkers in a test sample from the subject, wherein the fifteen biomarkers correspond to the fifteen genes in Table 4;

(b) comparing the expression of the fifteen biomarkers in the test sample with the fifteen biomarkers in a control sample;

(c) classifying the subject in a poor survival group or a good survival group, wherein a difference or a similarity in the expression of the fifteen biomarkers between the control sample and the test sample is used to classify the subject into a poor survival group or a good survival group; and (d) selecting adjuvant chemotherapy if the subject is classified in the poor survival group and selecting no adjuvant chemotherapy if the subject is classified in the good survival group.

The term "adjuvant chemotherapy" as used herein means treatment of cancer with chemotherapeutic agents after surgery where all detectable disease has been removed, but where there still remains a risk of small amounts of remaining cancer. Typical chemotherapeutic agents include cisplatin, carboplatin, vinorelbine, gemcitabine, doccetaxel, paclitaxel and navelbine.

In another aspect, the application provides compositions useful in detecting changes in the expression levels of the 15 genes listed in Table 4. Accordingly in one embodiment, the application provides a composition comprising a plurality of isolated nucleic acid sequences wherein each isolated nucleic acid sequence hybridizes to:

(a) a RNA product of one of the 15 genes listed in Table 4; and/or (b) a nucleic acid complementary to a), wherein the composition is used to measure the level of RNA expression of the 15 genes. In a particular embodiment, the plurality of isolated nucleic acid sequences comprise isolated nucleic acids hybridizable to the 15 probe target sequences as set out in Table 9. In one embodiment, the plurality of isolated nucleic acid sequences comprise isolated nucleic acids hybridizable to SEQ ID NO: 3, 11-15, 22, 26, 35, 49, 78, 85, 130, 133, and 169.

In another embodiment, the application provides a composition comprising 15 forward and 15 reverse primers for amplifying a region of each gene listed in Table 4. In particular embodiment, the 30 primers are as set out in Table 7. In one embodiment, the 30 primers each comprise a sequence that is identical to the sequence of one of SEQ ID NO: 173-202.

In a further aspect, the application also provides an array that is useful in detecting the expression levels of the 15 genes set out in Table 4. Accordingly, in one embodiment, the application provides an array comprising for each gene shown in Table 4 one or more nucleic acid probes complementary and hybridizable to an expression product of the gene. In a particular embodiment, the array comprises the nucleic acid probes hybridizable to the probe target sequences listed in Table 9. In one embodiment, the array comprises the nucleic acid probes hybridizable to sequences identical to each of SEQ ID NO: 3, 11-15, 22, 26, 35, 49, 78, 85, 130, 133, and 169.

In yet another aspect, the application also provides for kits used to prognose or classify a subject with NSCLC into a good survival group or a poor survival group or to select a therapy for a subject with NSCLC that includes detection agents that can detect the expression products of the biomarkers. Accordingly, in one embodiment, the application provides a kit to prognose or classify a subject with early stage NSCLC comprising detection agents that can detect the expression products of 15 biomarkers, wherein the 15 biomarkers comprise 15 genes in Table 4. In another embodiment, kits for classifying a subject comprise detection agents that can detect the expression of 16, 17, or 18 biomarkers, wherein 15 biomarkers comprise the 15 genes in Table 4, and the additional biomarkers are selected from the genes listed in Table 3. In one embodiment, the additional sixteenth, seventeenth, and eighteenth biomarkers may be selected from RGS4, UGT2B4, and MCF2 listed in Table 3.

In one embodiment, the application provides a kit to select a therapy for a subject with NSCLC, comprising detection agents that can detect the expression products of 15 biomarkers, wherein the 15 biomarkers comprise 15 genes in Table 4.

In some embodiments, kits for selecting therapy for a subject comprise detection agents that can detect the expression of 16, 17, or 18 biomarkers, wherein 15 biomarkers comprise the 15 genes in Table 4, and the additional biomarkers are selected from the genes listed in Table 3. In one embodiment, the additional sixteenth, seventeenth, and eighteenth biomarkers may be selected from RGS4, UGT2B4, and MCF2 listed in Table 3.

The materials and methods of the present disclosure are ideally suited for preparation of kits produced in accordance with well known procedures. In some embodiments, kits comprise agents (like the polynucleotides and/or antibodies described herein as non-limiting examples) for the detection of expression of the disclosed sequences, such as for example, SEQ ID NO: 3, 11-15, 22, 26, 35, 49, 78, 85, 130, 133, and 169, the target sequences listed in Table 9, or the target sequences listed in Table 11. Kits, may comprise containers, each with one or more of the various reagents (sometimes in concentrated form), for example, pre-fabricated microarrays, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more primer complexes (e.g., appropriate length poly(T) or random primers linked to a promoter reactive with the RNA polymerase). A set of instructions will also typically be included.

In some embodiments, a kit may comprise a plurality of reagents, each of which is capable of binding specifically with a target nucleic acid or protein. Suitable reagents for binding with a target protein include antibodies, antibody derivatives, antibody fragments, and the like. Suitable reagents for binding with a target nucleic acid (e.g. a genomic DNA, an mRNA, a spliced mRNA, a cDNA, or the like) include complementary nucleic acids. For example, nucleic acid reagents may include oligonucleotides (labeled or non-labeled) fixed to a substrate, labeled oligonucleotides not bound with a substrate, pairs of PCR primers, molecular beacon probes, and the like.

In some embodiments, kits may comprise additional components useful for detecting gene expression levels. By way of example, kits may comprise fluids (e.g. SSC buffer) suitable for annealing complementary nucleic acids or for binding an antibody with a protein with which it specifically binds, one or more sample compartments, a material which provides instruction for detecting expression levels, and the like.

In some embodiments, kits for use in the RT-PCR methods described herein comprise one or more target RNA-specific FRET probes and one or more primers for reverse transcription of target RNAs or amplification of cDNA reverse transcribed therefrom.

In some embodiments, one or more of the primers is "linear". A "linear" primer refers to an oligonucleotide that is a single stranded molecule, and typically does not comprise a short region of, for example, at least 3, 4 or 5 contiguous nucleotides, which are complementary to another region within the same oligonucleotide such that the primer forms an internal duplex. In some embodiments, the primers for use in reverse transcription comprise a region of at least 4, such as at least 5, such as at least 6, such as at least 7 or more contiguous nucleotides at the 3'-end that has a base sequence that is complementary to region of at least 4, such as at least 5, such as at least 6, such as at least 7 or more contiguous nucleotides at the 5'-end of a target RNA.

In some embodiments, the kit further comprises one or more pairs of linear primers (a "forward primer" and a "reverse primer") for amplification of a cDNA reverse transcribed from a target RNA. Accordingly, in some embodiments, the forward primer comprises a region of at least 4, such as at least 5, such as at least 6, such as at least 7, such as at least 8, such as at least 9, such as at least 10 contiguous nucleotides having a base sequence that is complementary to the base sequence of a region of at least 4, such as at least 5, such as at least 6, such as at least 7, such as at least 8, such as at least 9, such as at least 10 contiguous nucleotides at the 5'-end of a target RNA. Furthermore, in some embodiments, the reverse primer comprises a region of at least 4, such as at least 5, such as at least 6, such as at least 7, such as at least 8, such as at least 9, such as at least 10 contiguous nucleotides having a base sequence that is complementary to the base sequence of a region of at least 4, such as at least 5, such as at least 6, such as at least 7, such as at least 8, such as at least 9, such as at least 10 contiguous nucleotides at the 3'-end of a target RNA.

In some embodiments, the kit comprises at least a first set of primers for amplification of a cDNA that is reverse transcribed from a target RNA capable of specifically hybridizing to a nucleic acid comprising a sequence identically present in one of the genes listed in Table 4. In some embodiments, the kit comprises at least fifteen sets of primers, each of which is for amplification of a different target RNA capable of specifically hybridizing to a nucleic acid comprising a sequence identically present in a different gene listed in Table 4. In one embodiment, the kit comprises fifteen forward and fifteen reverse primers described in Table 7, comprising sequences identical to SEQ ID NOs 173-202. In some embodiments, the kit comprises one, two, or three more sets of primers, in addition to the fifteen sets of primers, each of the additional sets being for amplification of a different target RNA capable of specifically hybridizing to a nucleic acid comprising a sequence identically present in a different gene listed in Table 3. In some embodiments, the kit comprises one, two, or three more sets of primers, in addition to the fifteen sets of primers, each of the additional sets being for amplification of a different target RNA capable of specifically hybridizing to a nucleic acid comprising a sequence identically present in RGS4, UGT2B4, or MCF2 listed in Table 3. In some embodiments, the kit comprises at least one set of primers that is capable of amplifying more than one cDNA reverse transcribed from a target RNA in a sample.

In some embodiments, probes and/or primers for use in the compositions described herein comprise deoxyribonucleotides. In some embodiments, probes and/or primers for use in the compositions described herein comprise deoxyribonucleotides and one or more nucleotide analogs, such as LNA analogs or other duplex-stabilizing nucleotide analogs described above. In some embodiments, probes and/or primers for use in the compositions described herein comprise all nucleotide analogs. In some embodiments, the probes and/or primers comprise one or more duplex-stabilizing nucleotide analogs, such as LNA analogs, in the region of complementarity.

In some embodiments, the compositions described herein also comprise probes, and in the case of RT-PCR, primers, that are specific to one or more housekeeping genes for use in normalizing the quantities of target RNAs. Such probes (and primers) include those that are specific for one or more products of housekeeping genes selected from ACTB, BAT1, B2M, TBP, U6 snRNA, RNU44, RNU 48, and U47.

In some embodiments, the kits for use in real time RT-PCR methods described herein further comprise reagents for use in the reverse transcription and amplification reactions. In some embodiments, the kits comprise enzymes such as reverse transcriptase, and a heat stable DNA polymerase, such as Taq polymerase. In some embodiments, the kits further comprise deoxyribonucleotide triphosphates (dNTP) for use in reverse transcription and amplification. In further embodiments, the kits comprise buffers optimized for specific hybridization of the probes and primers.

In some embodiments, kits are provided containing antibodies to each of the protein products of the genes listed in Table 4, conjugated to a detectable substance, and instructions for use. In some embodiments, the kits comprise antibodies to one, two, or three protein products of the genes listed in Table 3, in addition to antibodies to each of the protein products of the genes listed in Table 4. In some embodiments, the kit comprises antibodies to the protein product of one, two, or all three of RGS4, UGT2B4, or MCF2 listed in Table 3, in addition to antibodies to each of the protein products of the genes listed in Table 4. Kits may comprise an antibody, an antibody derivative, or an antibody fragment, which binds specifically with a marker protein, or a fragment of the protein. Such kits may also comprise a plurality of antibodies, antibody derivatives, or antibody fragments wherein the plurality of such antibody agents binds specifically with a marker protein, or a fragment of the protein.

In some embodiments, kits may comprise antibodies such as a labeled or labelable antibody and a compound or agent for detecting protein in a biological sample; means for determining the amount of protein in the sample; means for comparing the amount of protein in the sample with a standard; and instructions for use. Such kits can be supplied to detect a single protein or epitope or can be configured to detect one of a multitude of epitopes, such as in an antibody detection array. Arrays are described in detail herein for nucleic acid arrays and similar methods have been developed for antibody arrays.

A person skilled in the art will appreciate that a number of detection agents can be used to determine the expression of the biomarkers. For example, to detect RNA products of the biomarkers, probes, primers, complementary nucleotide sequences or nucleotide sequences that hybridize to the RNA products can be used. To detect protein products of the biomarkers, ligands or antibodies that specifically bind to the protein products can be used.

Accordingly, in one embodiment, the detection agents are probes that hybridize to the 15 biomarkers. In a particular embodiment, the probe target sequences are as set out in Table 9. In one embodiment, the probe target sequences are identical to SEQ ID NO: 3, 11-15, 22, 26, 35, 49, 78, 85, 130, 133, and 169. In another embodiment, the detection agents are forward and reverse primers that amplify a region of each of the 15 genes listed in Table 4. In a particular embodiment, the primers are as set out in Table 7. In one embodiment, the primers comprise the polynucleotide sequences of SEQ ID NO: 173-202.

A person skilled in the art will appreciate that the detection agents can be labeled.

The label is preferably capable of producing, either directly or indirectly, a detectable signal. For example, the label may be radio-opaque or a radioisotope, such as $^3H$, $^{14}C$, $^{32}P$, $^{35}S$, $^{123}I$, $^{125}I$, $^{131}I$; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

The kit can also include a control or reference standard and/or instructions for use thereof. In addition, the kit can include ancillary agents such as vessels for storing or transporting the detection agents and/or buffers or stabilizers.

In some aspects, a multi-gene signature is provided for prognosis or classifying patients with lung cancer. In some embodiments, a fifteen-gene signature is provided, comprising reference values for each of the fifteen genes based on relative expression data from a historical data set with a known outcome, such as good or poor survival, and/or known treatment, such as adjuvant chemotherapy. In one embodiment, four reference values are provided for each of the fifteen genes listed in Table 4. In one embodiment, the reference values for each of the fifteen genes are principal component values set forth in Table 10.

In one aspect, relative expression data from a patient are combined with the gene-specific reference values on a gene-by-gene basis for each of the fifteen, and, optionally, additional genes, to generate a test value which allows prognosis or therapy recommendation. In some embodiments, relative expression data are subjected to an algorithm that yields a single test value, or combined score, which is then compared to a control value obtained from the historical expression data for a patient or pool of patients.

In some embodiments, the control value is a numerical threshold for predicting outcomes, for example good and poor outcome, or making therapy recommendations for a subject, for example adjuvant chemotherapy in addition to surgical resection or surgical resection alone. In some embodiments, a test value or combined score greater than the control value is predictive, for example, of a poor outcome or benefit from adjuvant chemotherapy, whereas a combined score falling below the control value is predictive, for example, of a good outcome or lack of benefit from adjuvant chemotherapy for a subject.

In some embodiments, a method for prognosing or classifying a subject with NSCLC comprises:
(a) measuring expression levels of at least 15 biomarkers from Table 4, and optionally, an additional one, two, or three biomarkers from Table 3 in a test sample,
(b) calculating a combined score or test value for the subject from the expression levels of the, and,
(c) comparing the combined score to a control value,
Wherein a combined score greater than the control value is used to classify a subject into a high risk or poor survival group and a combined score lower than the control value is used to classify a subject into a lower risk or good survival group.

In one embodiment, the combined score is calculated from relative expression data multiplied by reference values, determined from historical data, for each gene. Accordingly, the combined score may be calculated using Formula I below:

$$\text{Combined score} = 0.557 \times PC1 + 0.328 \times PC2 + 0.43 \times PC3 + 0.335 \times PC4$$

Where PC1 is the sum of the relative expression level for each gene in a multi-gene signature multiplied by a first principal component for each gene in the multi-gene signature, PC2 is the sum of the relative expression level for each gene multiplied by a second principal component for each gene, PC3 is the sum of the relative expression level for each gene multiplied by a third principal component for each gene, and PC4 is the sum of the relative expression level for each gene multiplied by a fourth principal component for each gene. In some embodiments, the combined score is referred to as a risk score. A risk score for a subject can be calculated by applying Formula I to relative expression data from a test sample obtained from the subject.

In some embodiments, PC1 is the sum of the relative expression level for each gene provided in Table 4 multiplied by a first principal component for each gene, respectively, as set forth in Table 10; PC2 is the sum of the relative expression level for each gene provided in Table 4 multiplied by a second principal component for each gene, respectively, as set forth in Table 10; PC3 is the sum of the relative expression level for each gene provided in Table 4 multiplied by a third principal component for each gene, respectively, as set forth in Table 10; and PC4 is the sum of the relative expression level for each gene provided in Table 4 multiplied by a fourth principal component for each gene, respectively, as set forth in Table 10.

In one embodiment, the control value is equal to −0.1. A subject with a risk score of more than −0.1 is classified as high risk (poor prognosis). A patient with a risk score of less than −0.1 is classified as lower risk (good prognosis). In some embodiments, adjuvant chemotherapy is recommended for a subject with a risk score of more than −0.1 and not recommended for a subject with a risk score of less than −0.1.

In a further aspect, the application provides computer programs and computer implemented products for carrying out the methods described herein. Accordingly, in one embodiment, the application provides a computer program product for use in conjunction with a computer having a processor and a memory connected to the processor, the computer program product comprising a computer readable storage medium having a computer mechanism encoded thereon, wherein the computer program mechanism may be loaded into the memory of the computer and cause the computer to carry out the methods described herein.

In another embodiment, the application provides a computer implemented product for predicting a prognosis or classifying a subject with NSCLC comprising:
(a) a means for receiving values corresponding to a subject expression profile in a subject sample; and
(b) a database comprising a reference expression profile associated with a prognosis, wherein the subject biomarker expression profile and the biomarker reference profile each has fifteen values, each value representing the expression level of a biomarker, wherein each biomarker corresponds to one gene in Table 4;
wherein the computer implemented product selects the biomarker reference expression profile most similar to the subject biomarker expression profile, to thereby predict a prognosis or classify the subject.

In yet another embodiment, the application provides a computer implemented product for determining therapy for a subject with NSCLC comprising:
(a) a means for receiving values corresponding to a subject expression profile in a subject sample; and
(b) a database comprising a reference expression profile associated with a therapy, wherein the subject biomarker expression profile and the biomarker reference profile each has fifteen values, each value representing the expression level of a biomarker, wherein each biomarker corresponds to one gene in Table 4;
wherein the computer implemented product selects the biomarker reference expression profile most similar to the subject biomarker expression profile, to thereby predict the therapy.

Another aspect relates to computer readable mediums such as CD-ROMs. In one embodiment, the application provides computer readable medium having stored thereon a data structure for storing a computer implemented product described herein.

In one embodiment, the data structure is capable of configuring a computer to respond to queries based on records belonging to the data structure, each of the records comprising:
(a) a value that identifies a biomarker reference expression profile of the 15 genes in Table 4;
(b) a value that identifies the probability of a prognosis associated with the biomarker reference expression profile.

In another aspect, the application provides a computer system comprising
(a) a database including records comprising a biomarker reference expression profile of fifteen genes in Table 4 associated with a prognosis or therapy;
(b) a user interface capable of receiving a selection of gene expression levels of the 15 genes in Table 4 for use in comparing to the biomarker reference expression profile in the database; and
(c) an output that displays a prediction of prognosis or therapy according to the biomarker reference expression profile most similar to the expression levels of the fifteen genes.

In some embodiments, the application provides a computer implemented product comprising
(a) a means for receiving values corresponding to relative expression levels in a subject, of at least 15 biomarkers comprising the fifteen genes in Table 4, and optionally, additional one, two, or three genes selected from the genes listed in Table 3;
(b) an algorithm for calculating a combined score based on the relative expression levels of the at least 15 biomarkers;
(c) an output that displays the combined score; and, optionally,
(d) an output that displays a prognosis or therapy recommendation based on the combined score.

The above disclosure generally describes the present invention. A more complete understanding can be obtained by reference to the following specific examples. These examples are described solely for the purpose of illustration and are not intended to limit the scope of the invention. Changes in form and substitution of equivalents are contemplated as circumstances might suggest or render expedient. Although specific terms have been employed herein, such terms are intended in a descriptive sense and not for purposes of limitation.

The following non-limiting example is illustrative of the present invention:

EXAMPLE 1

Results

Figure 2:
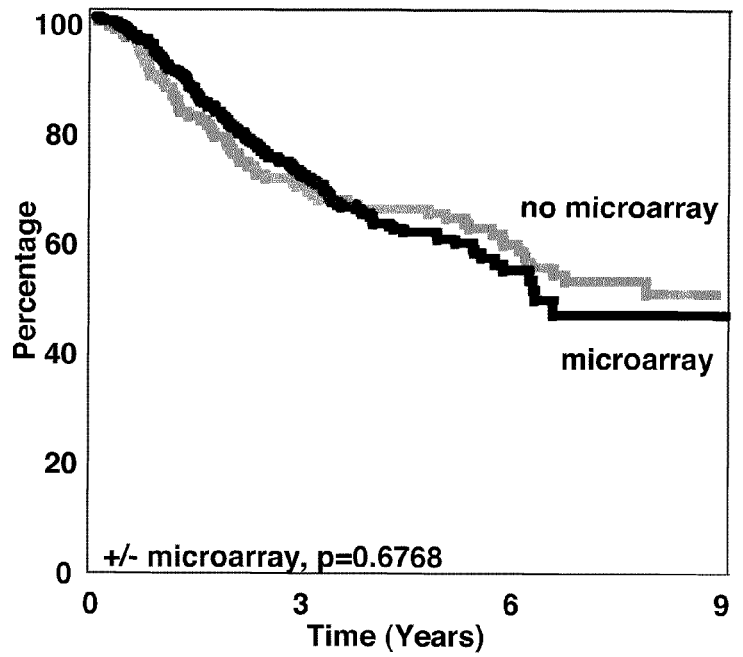
FIG. 2 shows the survival outcome based on the 15-gene signature in training and test sets.
Figure 2:
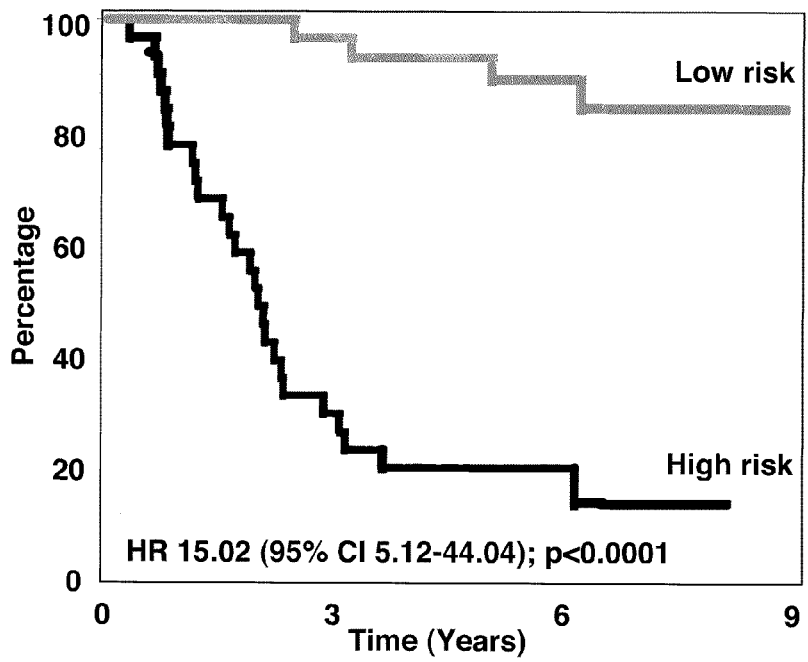
Figure 2:
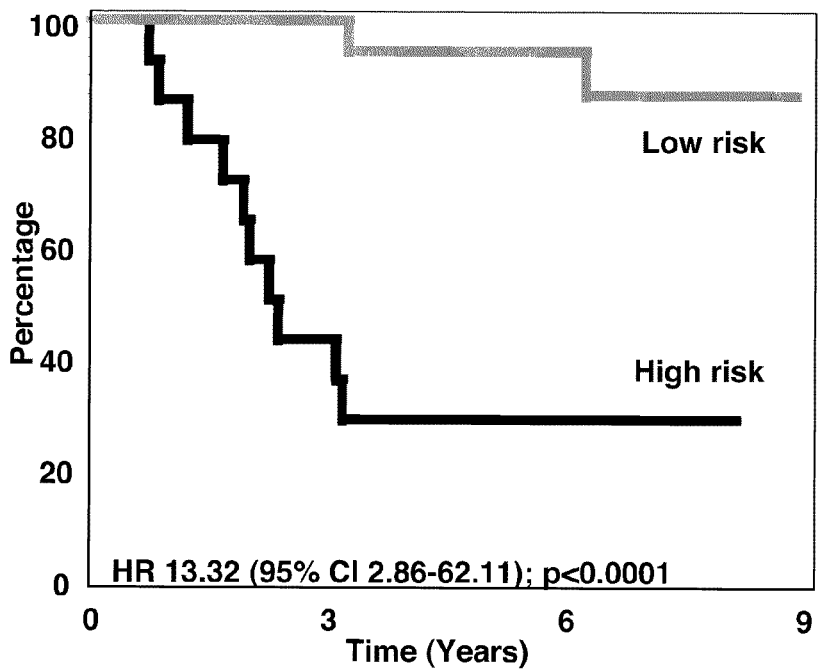
Figure 2:
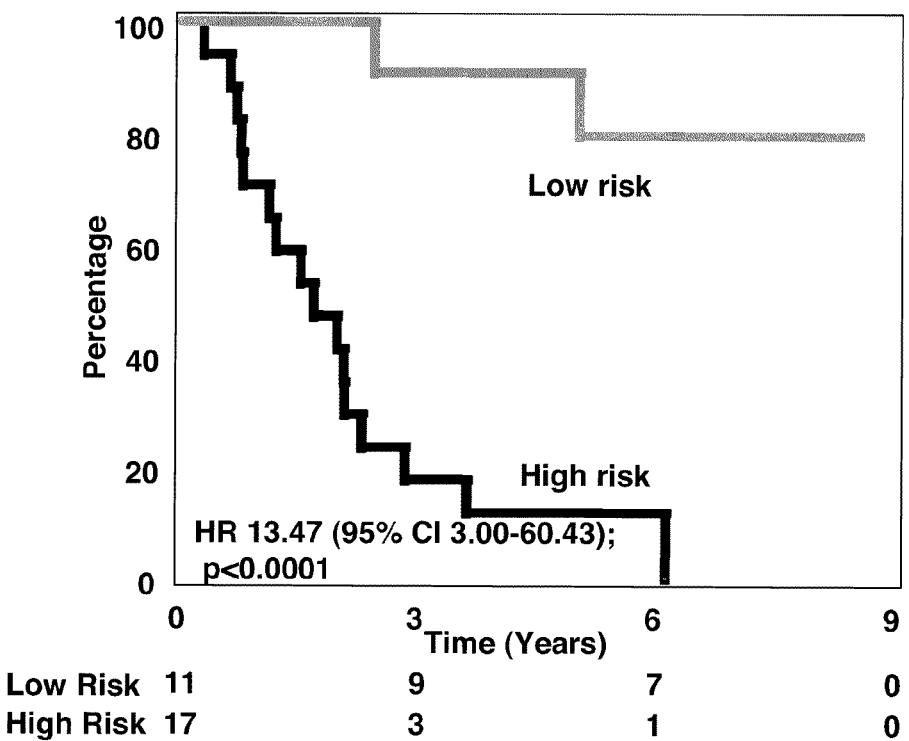
Figure 2:
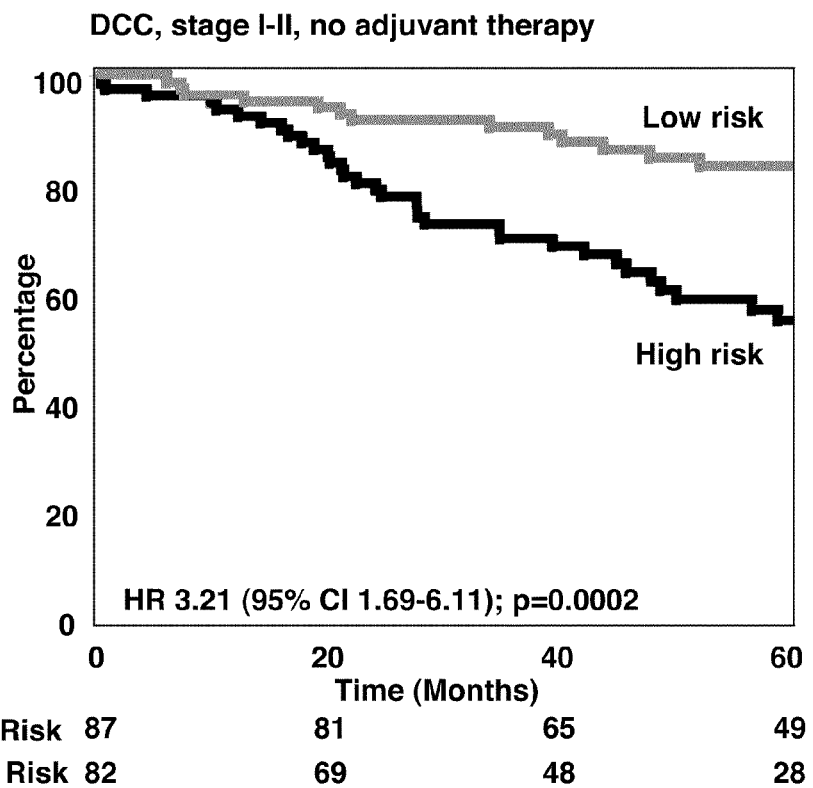
Figure 2:
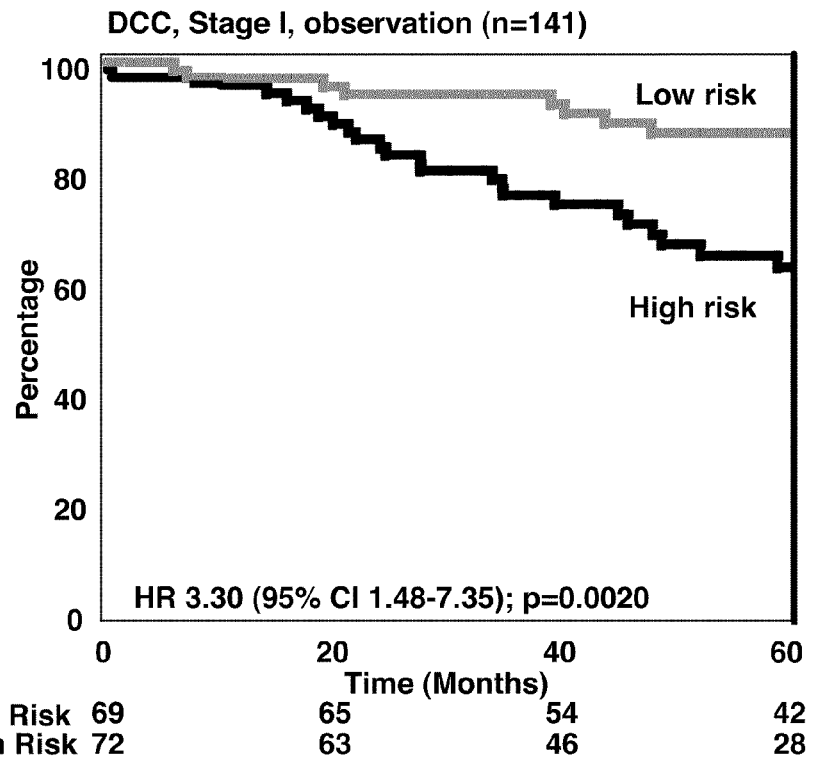
Figure 5:
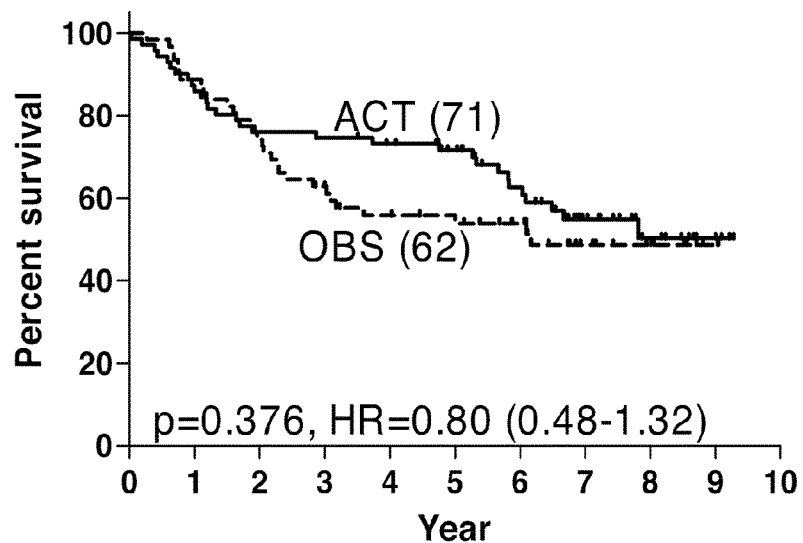
FIG. 5 shows the effect of adjuvant chemotherapy in microarray profiled patients.

Table 1 compared the demographic features of 133 patients with microarray profiling to 349 without the profiling. Stage IB patients had more representation in the observation cohort (55% vs. 42%, p=0.01), but all other factors were similarly distributed. There was no significant difference in the overall survivals of patients with or without gene profiling (FIG. 2A). For these 133 patients, adjuvant chemotherapy reduced the death rate by 20% (HR 0.80, 95% CI 0.48-1.32, p=0.38; FIG. 5).

Prognostic Gene Expression Signature in JBR.10 Patients

Using a p>0.005 as cut-off, 172 of 19,619 probe sets were significantly associated with prognosis in 62 observation patients (FIG. 1A and Table 3). Using a method that was designed to identify the minimum expression gene set that can distinguish most patients with poor and good survival outcomes, a 15-gene prognostic signature was identified (FIG. 1A and Table 4). This signature was able to separate the 62 non-adjuvant treated patients into 31 low-risk and 31 high-risk patients for death (HR 15.020, 95% CI 5.12-44.04, $p<0.0001$; FIG. 2B). Furthermore, stratified analysis showed that the signature was also highly prognostic in 34 stage IB patients (HR 13.32, 95% Cl 2.86-62.11, p<0.0001, FIG. 2C) and 28 stage II patients (HR 13.47, 95% Cl 3.0-60.43, p<0.0001, FIG. 2D). Multivariate analysis adjusting for tumor stage, age, gender and histology showed that the prognostic signature was an independent prognostic marker (HR 18.0, 95% Cl 5.8-56.1; p<0.0001, Table 2). This did not differ following additional adjustment for surgical procedure and tumor size.

Validation of General Applicability of Prognostic Signature (Summary)

Applying the risk score algorithm (equation) established from the 62 BR.10 observation patients, the 15-gene signature was demonstrated to be an independent prognostic marker among all 169 DCC patients (HR 2.9, 95% Cl 1.5-5.6, p=0.002; Table 2). Subgroup analyses also showed significant results among patients from DCC-UM (HR 1.5, 95% Cl 0.54-4.31, p=0.4; Table 2) and HLM (HR 1.2, 95% Cl 0.43-3.6, p=0.7; Table 2). The signature was also prognostic among UM-SQ patients (HR 2.3, 95% Cl 1.1-4.7, p=0.026; Table 2), and in the Duke's patients (HR 1.5, 95% Cl 0.81-2.89, p=0.19; Table 2).

The prognostic value of the signature was tested in stage I patients of the DCC (n=141) patients and was able to identify patients with significantly different survival outcome (Table 8).

Prediction of Chemotherapy Benefit

When tested on the microarray data of 71 JBR.10 patients who received adjuvant chemotherapy, the 15-gene signature was not prognostic (HR 1.5, 95% Cl 0.7-3.3, p=0.28, Table 2). The signature was also not prognostic when applied separately to stage IB and stage II patients (Table 2). Among the Director's Challenge patients, 41 were identified as having received adjuvant chemotherapy with or without radiotherapy. The 15-gene signature was also not prognostic for these 41 patients (HR 1.1, 95% Cl 0.5-2.5, p=0.8) (Table 2).

Figure 3:
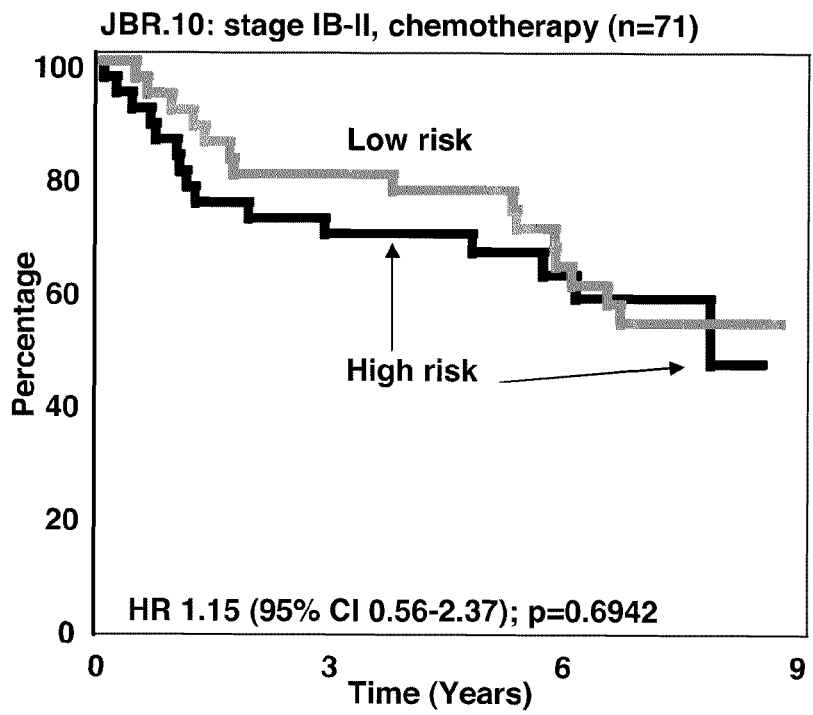
FIG. 3 shows a comparison of chemotherapy vs. observation in low and high risk patients with microarray data.
Figure 3:
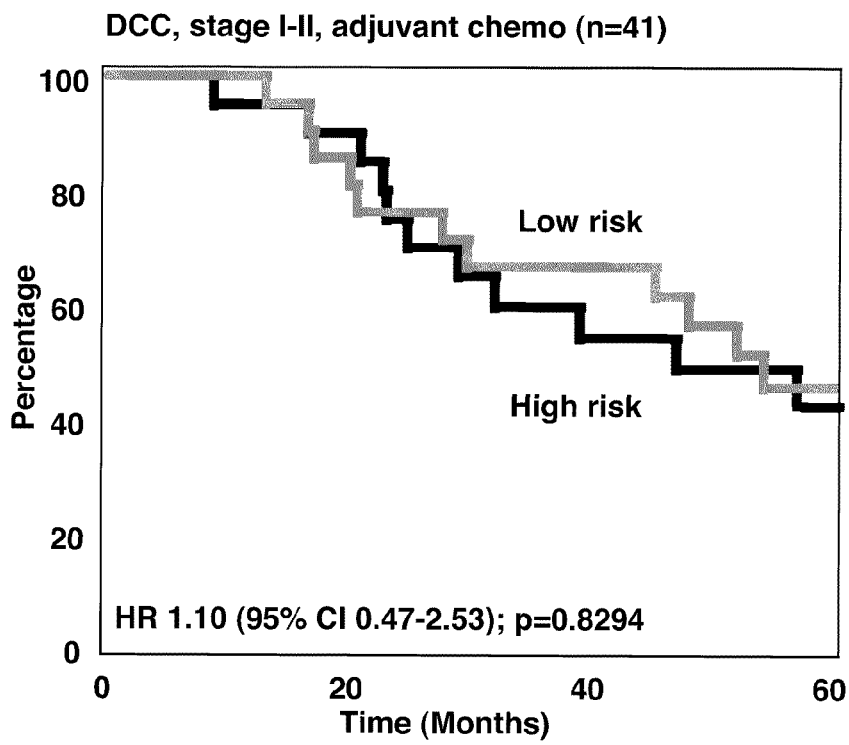
Figure 3:
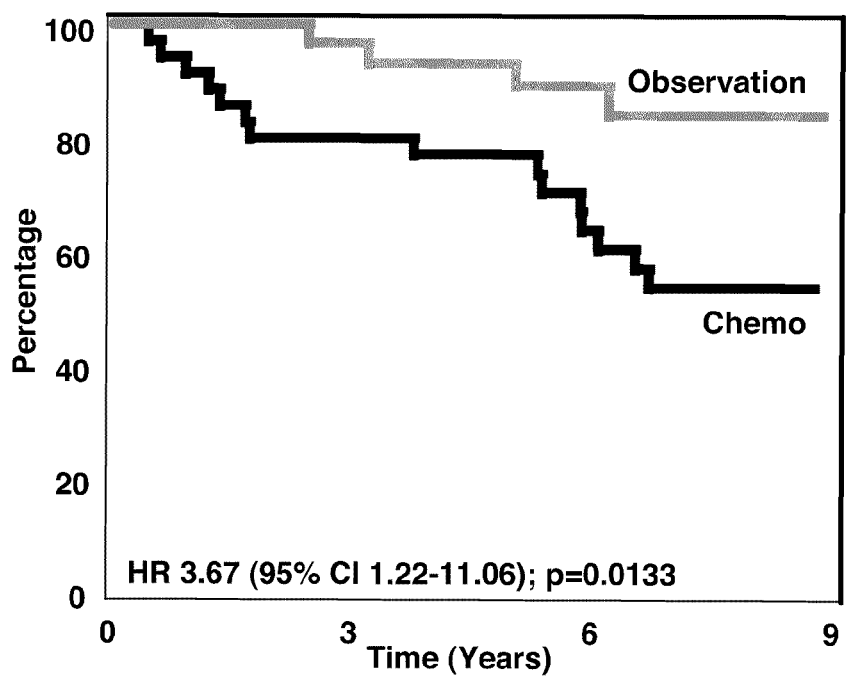
Figure 3:
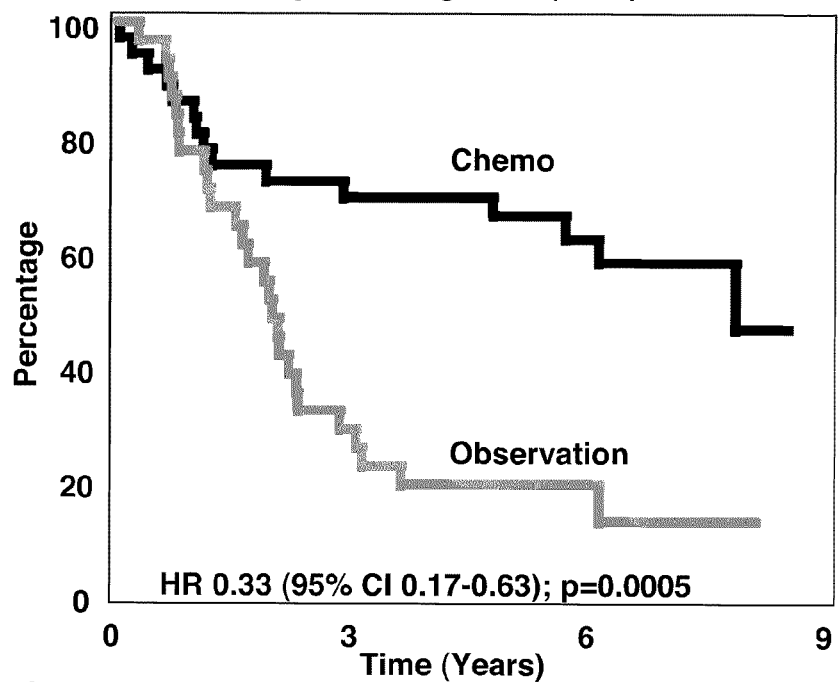
Figure 3:
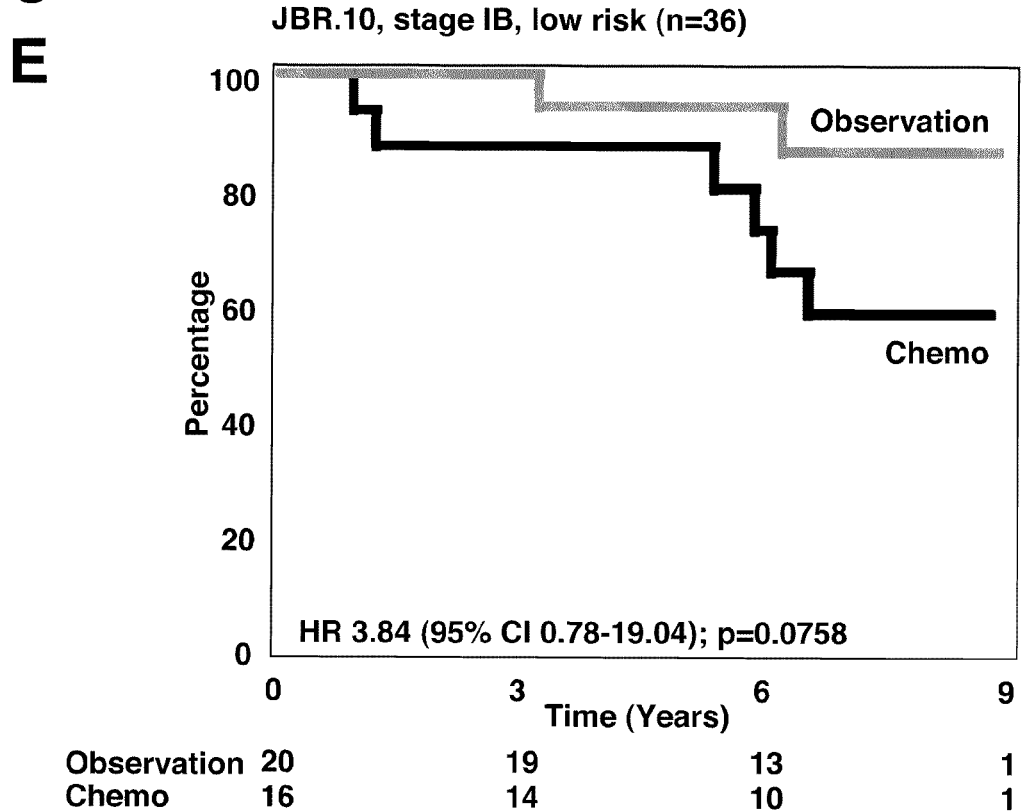
Figure 3:
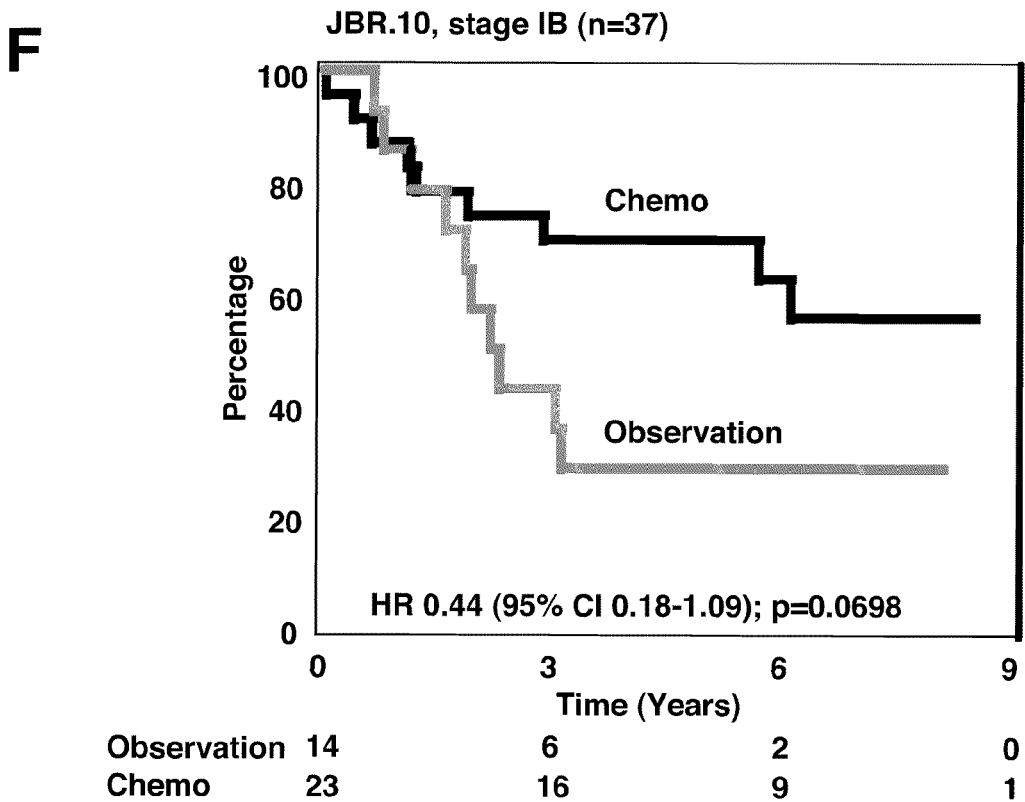
Figure 3:
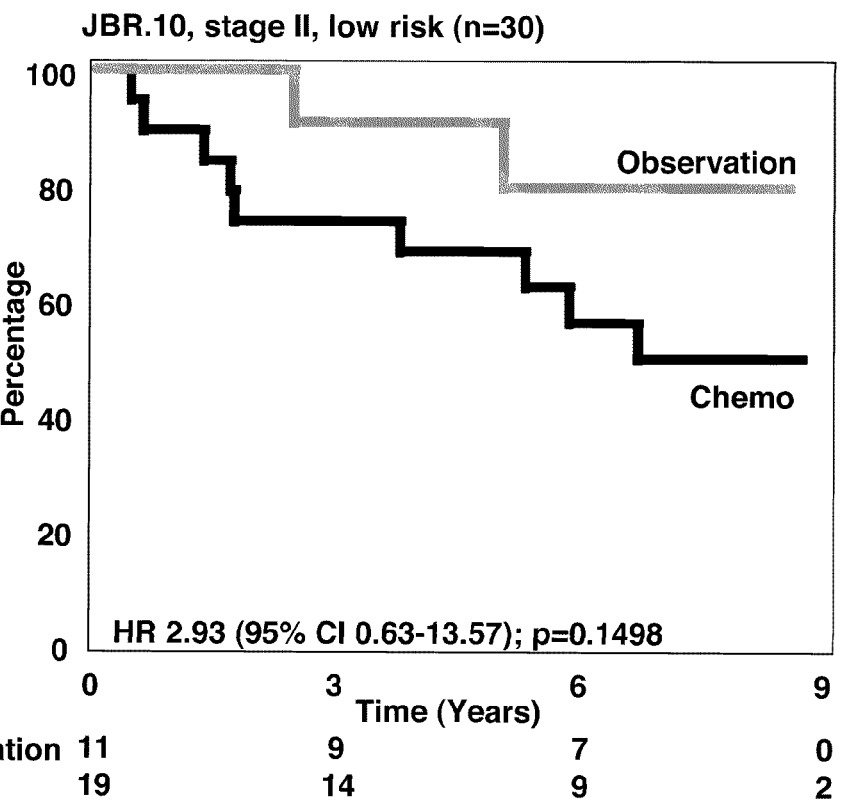
Figure 3:
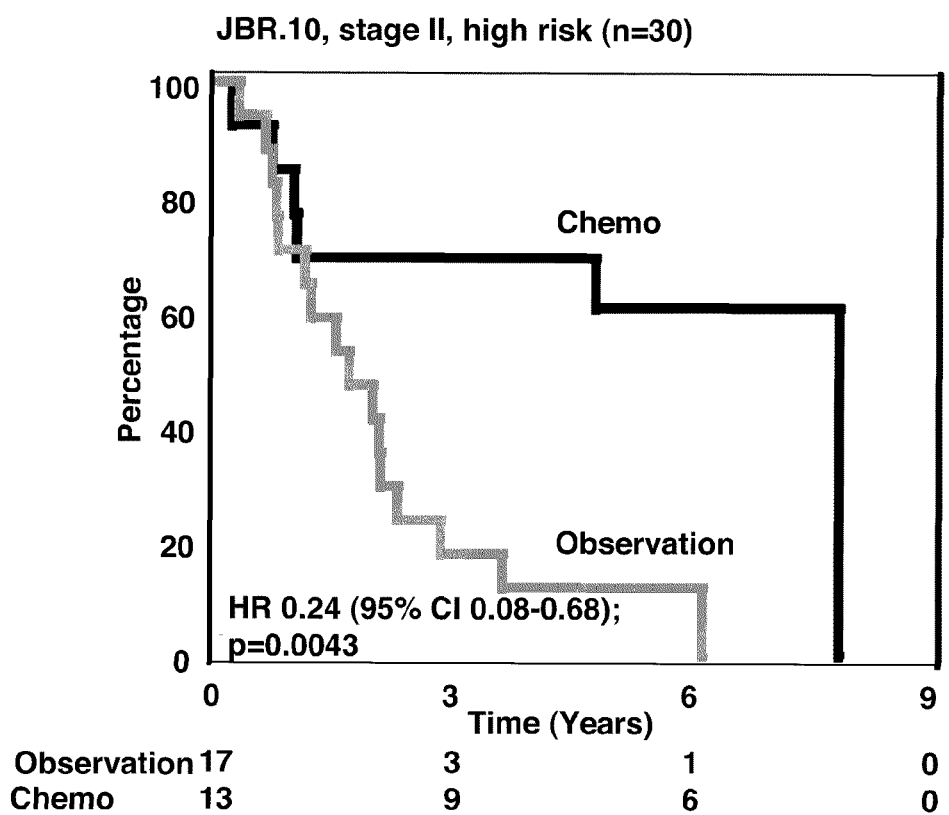

Stratified analysis showed that in JBR.10 patients with microarray data, only patients classified to the high-risk group derived benefit from the adjuvant chemotherapy (FIGS. 3C and 3D). High-risk patients showed 67% improved survival when treated by adjuvant chemotherapy compared to observation (HR=0.33, 95% Cl 0.17-0.63, p=0.0005, FIG. 3D), while those assigned to the low risk group did not benefit (FIG. 3C). These results were reproduced when applied separately to both the stage IB (FIGS. 3E and 3F) and stage II (FIGS. 3G and 3H) patients.

Multivariate analysis showed that the decrease of survival associated with adjuvant chemotherapy was independent of the stage (HR=2.26, 95% Cl 1.03-4.96, p=0.04). A Cox regression model with chemotherapy received and risk group indicator and their interaction term as independent covariates were performed to fit the overall survival data on the 133 patients with microarray data. This analysis revealed that the interaction term is highly significant (p=0.0003) with the high-risk group deriving significantly greater benefit from adjuvant chemotherapy.

The Initial Study Population

Figure 4:
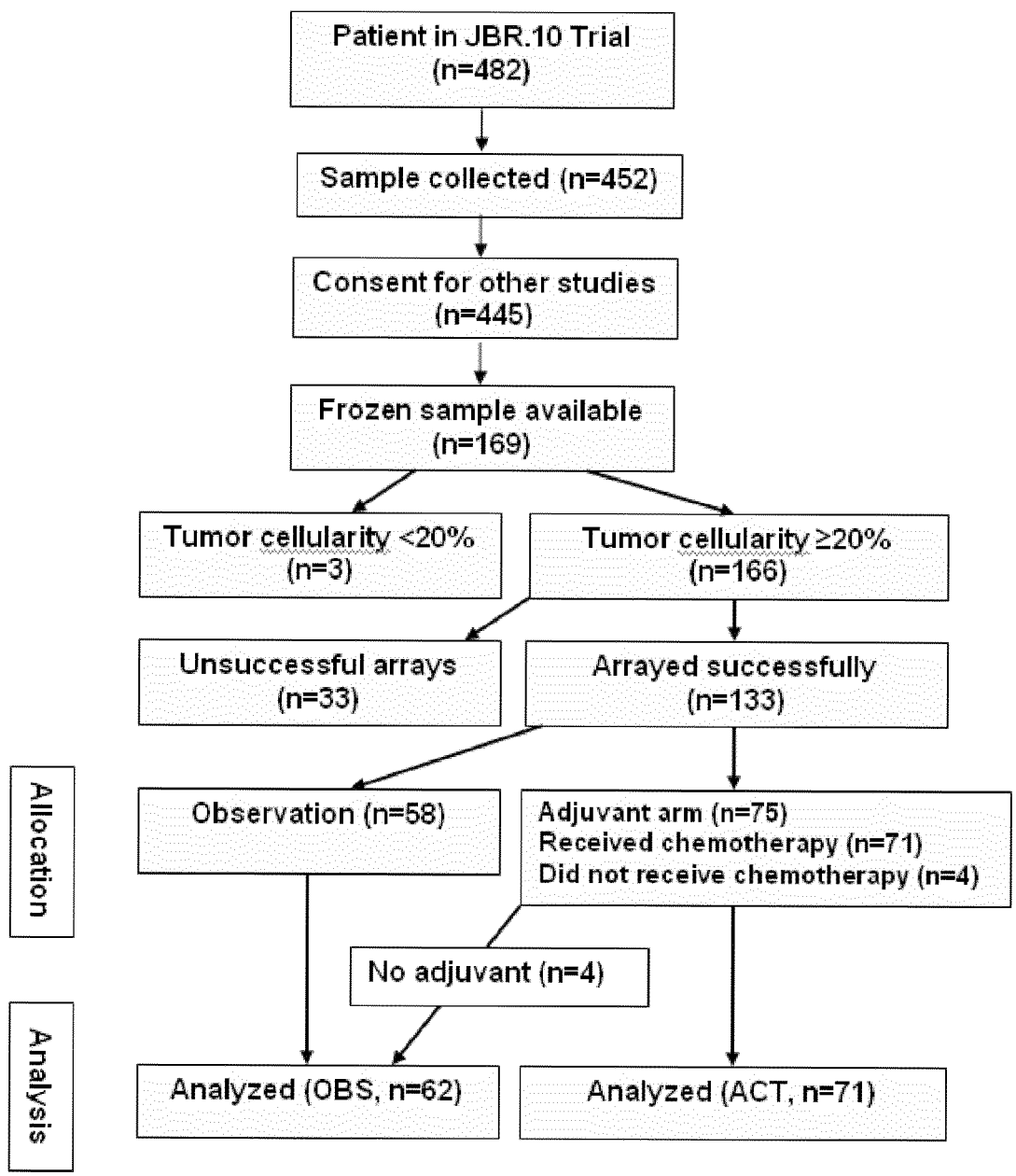
FIG. 4 shows a consort diagram for microarray study of BR. 10 patients.

The initial study population comprised a subset of the patients randomized in the JBR.10 trial. There were 169 frozen tumor samples collected from patients who had their surgery at one of the BR.10 Canadian Centres have consented to the use of their samples for "future" studies in addition to RAS mutation analysis. The samples were harvested using a standardized protocol that was agreed upon during trial protocol development by designated pathologists from each participating centre. All tumors and corresponding normal lung tissue were collected as soon as or within 30 min after resection, and were snap-frozen in liquid nitrogen. For each frozen tissue fragment, a 1 mm cross-section slice was fixed in 10% buffered formalin and submitted for paraffin embedding. Histological evaluation of the HE stained sections revealed 166 samples that contained a ≧20% tumor cellularity. Among the latter, gene expression profiling was completed successfully in samples from 133 patients. These included 58 patients randomized to the observation (OBS) arm and 75 to the adjuvant chemotherapy (ACT) arm. However, 4 ACT patients refused chemotherapy, and for the purpose of this analysis, they were assigned to the OBS arm. Therefore, the final distribution included 62 OBS patients and 71 ACT patients (FIGS. 1 and 4).

Microarray Data Analysis

Figure 6:
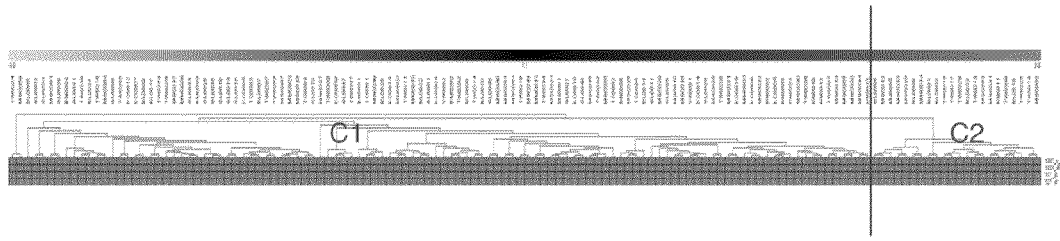
FIG. 6 shows the effect of microarray batch processing at 2 different times. The samples were profiled in 2 batches at 2 times (January 2004 and June 2005). Unsupervised clustering shows that the expression patterns of these two batches differed significantly with samples arrayed on January 2004 aggregated in cluster 1 (93%) and samples arrayed on June 2005 in cluster 2 (73%).

The raw microarray data from Affymetrix U133A (Affymetrix, Santa Clara, Calif.) were pre-processed using RMAexpress v0.32, then were twice log 2 transformed since the distribution of additional log 2 transformed data appeared more normal. Probe sets were annotated using NetAffx™ v4.2 annotation tool and only grade A level probe sets 3 (NA24) were included for further analysis. Affymetrix U133A chip contains 22,215 probe sets (19,619 probe sets with grade A annotation). Since the microarray hybridizations were performed in two batches at two separate occasions (January 2004, and June 2005), and unsupervised clustering showed that a batch difference was significant (FIG. 6), a distance-weighted discrimination (DWD) algorithm (see world wide web at genome.unc.edu/pubsup/dwd/index.html) was applied to homogenize the two batches. The DWD algorithm first finds a hyperplane that separates the two batches and adjusts the data by projecting the different batches on the DWD plane, finds the batch mean, and then subtracts out the DWD plane multiplied by this mean. In addition, the data were Z score transformed which made the validation across different datasets possible.

Univariate Analysis

The association of the expression of the individual probe set with overall survival (date of randomization to date of last follow up or death) was evaluated by Cox proportional hazards regression. The expression data for 62 patients in observation arm revealed 1312 probe sets that were associated with overall survival at p<0.05. Using a more stringent selection criteria of p<0.005, 172 probe sets with grade A annotation were prognostic.

Gene Set Signature Selection

To generate the gene expression signature, an exclusion selection procedure was firstly applied and followed by an inclusion process. The MAximizing R Square Algorithm (MARSA) included 3 sequential steps: a) probe set pre-selection; b) signature optimization; and c) leave-one-out-cross-validation. First, the candidate probe sets were pre-selected by their associations with survival at p<0.005 level. To remove the cross platform variation, expression data was z score transformed and risk score (z score weighted by the coefficient of the univariate Cox regression) was used to synthesize the information of the probe set combination. The candidate probe sets were then subjected to an exclusion followed by an inclusion selection procedure. For the preselected 172 probe sets, the exclusion procedure excluded one probe at a time, summed up the risk score of the remaining 171 probes, the calculated the R square ($R^2$, Goodness-of-fit) of the Cox model[5,6]. Risk score was dichotomized by an outcome-orientated optimization of cutoff macro based on log-rank statistics (http://ndc.mayo.edu/mayo/research/biostat/sasmacros.cfm) before being introduced to the Cox proportional hazards model. A probe set was excluded if its exclusion resulted in obtaining the largest $R^2$. The procedure was repeated until there was only one probe set left. An inclusion procedure was followed using the probe set left by the exclusion procedure as the starting probe set. It included one probe set at a time, summed up the risk score of the included probe sets and risk score was dichotomized and $R^2$ was calculated. The probe set was included if its inclusion resulted in obtaining the largest $R^2$. The exclusion procedure produced a largest R square of 0.67 by a minimal 7 probe combination and the inclusion procedure generated a largest $R^2$ of 0.78 by a minimal 15 probe combination (FIG. 1B), therefore, the 15 gene combination (Table 4) was selected as a candidate signature. Finally, the 15-gene signature (Table 4) was established after passing the internal validation by leave-one-out-cross-validation (LOOCV) and external validation on other datasets (listed below). All statistical analyses were performed using SAS v9.1 (SAS Institute, Calif.). The risk score was calculated as Table 4.

Prognostic Modeling by Principal Component Analysis of Signature Genes

Principal components analysis (PCA) (based on correlation matrix) was carried out to synthesize the information across the chosen gene probe sets and reduce the number of covariates in building the prognostic model. The eigenvalue of greater than or equal to 1 was used as cutoff point in determining how many proponents to include in the model, and those significantly correlated to disease-specific survival (DSS) were included in the final multivariable model. The PCA analysis was done based on all 133 patients with microarray data. When correlated to the DSS based on the 62 observation patients, the first 4 principal components were found to satisfy the criteria and were included in the prognostic model. Table 10 lists the four principal components for each of the 15 genes in the 15-gene signature. The same analysis can be applied to derive principal component coefficients for additional genes selected from the 172 genes listed in Table 3, such as for example, RGS4, UGT2B4, and/or MCF2. Furthermore, one of skill will appreciate from the above description how to obtain the first four principal component coefficients for any of the genes listed in Table 3.

To determine the gene signature prognostic group, multivariate Cox regression model with the first 4 principal components were fitted to the disease specific survival of the 62 observation patients. The linear prognostic scores were calculated by the sum of the multiplication of the estimated coefficient from Cox model and the corresponding principal component value. Using the prognostic score, patients were divided into low and high risk group based on the median of the prognostic score, i.e., those with prognostic score less than the median as low risk group, while those with score no less than the median as high risk group. For the 62 observation patients with microarray data, 31 patients were classified in each group. Applying the same rule to the 73 chemo-treated patients, 36 patients were classified in low risk group and 37 patients in high-risk group.

Validation of General Applicability of Prognostic Signature

Validation of the 15-gene signature was carried out on stage I-II cases from Duke, Raponi, and DC who did not receive adjuvant chemotherapy. When the risk score was dichotomized using the cutoff determined from the BR.10 training set, the 15-gene signature was able to separate 38 cases of low risk from 47 cases of high risk (log rank p=0.226) of NSCLC in the Duke dataset. Multivariate analysis (adjusted for stage, histology and patients' age and gender) showed that the 15-gene signature was an independent prognostic factor (HR=1.5, 95% Cl 0.81-2.89, p=0.19, Table 2). Raponi contains squamous cell carcinoma only and the cases have the worst survival rate. However, the 15-gene signature was still able to separate 50 cases of low risk from 56 cases with high risk (log rank p=0.0447) and this separation was independent of stage and patients' age and gender (HR=2.3, 95% Cl 1.1-4.7 p=0.026, Table 2). The DC dataset contained only adenocarcinoma cases. Applying the 15-gene signature on DC stage I and II, was able to separate 87 low risk cases from the 82 high risk cases (log rank p=0.0002, FIG. 2E). Multivariate analysis (adjusted for stage and patients' age and gender) showed that the prognostic value of the 15-gene signature was independent prognostic factor (HR=2.9, 95% Cl 1.5-5.6, p=0.002, Table 2). There were 67 stage IB-II cases without chemotherapy in MI, the 15-gene signature was able to separate 44 low risk cases from the 23 high risk cases (log rank p=0.013). Multivariate analysis (adjusted for stage and patients' age and gender) showed that the prognostic value of the 15-gene signature was independent prognostic factor (HR=1.5, 95% Cl 0.54-4.31, p=0.4, Table 2). Cases from MSKCC had a significantly better 5-year overall survival compared to other datasets. However, the 15-gene signature was able to separate 32 cases of low risk from 32 cases of high risk in MSKCC (log rank p=0.16). Multivariate analysis (adjusted for stage) revealed that the 15-gene signature was an independent prognostic factor. Validation of the 15-gene signature on HLM revealed that the 15-gene signature was able to separate 26 cases of low risk from 24 cases of high risk (log rank p=0.0084). Multivariate analysis (adjusted for stage) showed that there was a trend to separation by the 15-gene signature (HR=1.2, 95% Cl 0.43-3.6, p=0.7). These validation data confirm that the 15-gene signature is a strong prognostic signature and its power of predicting the outcome of NSCLC is independent of and superior to that of stage.

The Benefit of Chemotherapy was Limited to High Risk Patients

A total of 30 deaths were observed in the ACT. Six of them were due to other malignancies. The 15-gene signature was unable to separate the good/bad outcome patients (p=0.83, data not shown) in the ACT. However, stratified analysis showed that only patients with high risk derived benefit from adjuvant chemotherapy (FIG. 3D). Upon receiving adjuvant chemotherapy, the survival rate of the 36 high-risk patients was significantly improved (HR=0.33, 95% Cl 0.17-0.63, p=0.0005, FIG. 3D). On the other hand, the application of chemotherapy on low risk patients resulted in a decrease in survival rate (HR=3.67, 95% Cl 1.22-11.06, p=0.0133, FIG. 3C). Death was evenly distributed between the low and high risk groups in the ACT arm (15 deaths in low and high risk group, respectively). Each of these two groups contained 3 deaths that were not due to lung cancer. Stratification by risk group and stage showed that the survival rate of high risk patients from both stage IB and stage II was significantly improved by chemotherapy (FIGS. 3F and H). Moreover, for low risk patients of stage II, chemotherapy was associated with significantly decreased survival (FIGS. 3E and G). A Cox regression model with chemotherapy received and risk group indicator and their interaction term as independent covariates was performed to fit the overall survival data on the 133 patients with microarray data. This analysis revealed that the interaction term is highly significant (p=0.0002) with the high-risk group deriving significantly greater benefit from adjuvant chemotherapy.

Discussion:

Gene expression signature is thought to represent the altered key pathways in carcinogenesis and thus is able to predict patients' outcome. However, being able to faithfully represent the altered key pathways, the signature must be generated from genome-wide gene expression data. The present study used all information generated by Affymetrix U133A chip on NSCLC samples from a randomized clinical trial to derive a 15-gene signature. The 15-gene signature was able to identify 50% (31/62) stage IB-II NSCLC patients had relative good outcome. Multivariate analysis indicated that the 15-gene signature was an independent prognostic factor. Moreover, its independent prognostic effect had been in silico validated on 169 adenocarcinomas without adjuvant chemo- or radio-therapy from DC and 85 NSCLC from Duke and 106 squamous cell carcinomas of the lung from the University of Michigan. Importantly, the 15-gene signature was able to predict the response to adjuvant chemotherapy with high-risk patients across the stages being benefited from adjuvant chemotherapy. This finding was also validated on DC dataset.

Adjuvant chemotherapy for completely resected early stage NSCLC was a research question until the results of a series of positive trials[2,4], including BR.10[3], were published. However, whether chemotherapy played a beneficial role in stage IB remained to be clarified[2-6]. The present study showed that the stage IB patients were potentially able to be separated into low (49.3%, 36/73) and high (50.7%, 37/73) risk groups using the 15-gene signature. Upon administering the adjuvant chemotherapy to stage IB patients, the survival rate of patients with high risk was significantly improved (p=0.0698, FIG. 3F) whereas patients with low risk did not experience a benefit in survival (p=0.0758, FIG. 3E). Therefore the effect of chemotherapy on stage IB NSCLC was neutralized and thus gave an incorrect impression that no beneficial effect was existed[3]. Based on the evidence provided here and from the meta-analysis[6], it may be concluded that 50.7% (37/73) stage IB NSCLC patients have the potential to benefit from adjuvant chemotherapy.

Another significance of the present study was that the signature was able to identify a subgroup (50%, 30/60) of patients from stage II who did not benefit from adjuvant chemotherapy (p=0.1498, FIG. 3G). In current practice, adjuvant chemotherapy is recommended for all patients. However, the 15-gene signature suggests that about a half of the stage II patients may not benefit from adjuvant chemotherapy.

The gene ontology analysis showed that in the 15-gene signature, 4 genes (FOSL2, HEXIM1, IKBKAP, MYT1L, and ZNF236) were involved in the regulation of transcription. EDN3 and STMN2 played a role in signal transduction. Transformed 3T3 cell double minute 2 (MDM2), an E3 ubiquitin ligase, which targets p53 protein for degradation, plays a key role in cell cycle and apoptosis. Dworakowska D. et al.[24] reported that overexpression of MDM2 protein was correlated with low apoptotic index, which was associated with poorer survival. Myoglobin (MB) played a role in response to hypoxia and Uridine monophosphate synthetase (UMPS) participated in the 'de novo' pyrimidine base biosynthetic process, however, none of them has not been explored in lung cancer. The L1 cell adhesion molecule (L1CAM) involved in cell adhesion whose overexpression was associated with tumor metastasis and poor prognosis[25-28]. ATPase, Na+/K+ transporting, beta 1 polypeptide (ATP1B1) was involved in ion transport which was reported recently to be able to discriminate the serous low malignant potential and invasive epithelial ovarian tumors[29]. These findings indicated that cellular transcription, cell cycle and apoptosis, cell adhesion and response to hypoxia were important for lung cancer progression.

The range of expression levels of members of the 15-gene signature was broad, from very low expression level such as MDM2 and ZNF236 to fairly high expression such as TRIM14 or very high expression such as ATP1B1 (Table 4). Least variable gene (<5%), such as UMPS (Table 4), was also a member of the signature. These data suggested that it may not be a good practice to exclude low expressed and least variable probe set in the data pre-selection process in an arbitrary way. The signature generated using the present strategy performed better than that of Raponi's method of using the top 50 genes. There are only 3 genes (IKBKAP, L1CAM, and FAM64A) whose significance in association with survival is in the top 50 genes (Table 4).

Materials and Methods:
Patients and Samples

Included in the JBR.10 protocol was the collection of snap-frozen or formalin-fixed paraffin embedded tumor samples for KRAS mutation analysis and tissue banking for future laboratory studies[3]. Altogether 445 of 482 randomized patients consented to banking. Snap-frozen tissues were collected from 169 Canadian patients (FIG. 4). Histological evaluation of the HE section from the snap-frozen tumor samples revealed 166 that contained an estimated >20% tumor cellularity; gene expression profiling was completed in 133 of these patient samples, using the U133A oligonucleotide microarrays (Affymetrix, Santa Clara, Calif.). Profiling was not completed in 33 patient samples. Of 133 patients with microarray profiles, 62 did not received post-operative adjuvant chemotherapy and were group as observation patients, while 71 patients were received chemotherapy. University Health Network Research Ethics Board approved the study protocol.

RNA Isolation and Microarray Profiling

Total RNA was isolated from frozen tumor samples after homogenization in guanidium isothiocyanate solution and acid phenol-chloroform extraction. The quality of isolated RNA was assessed initially by gel electrophoresis, followed by the Agilent Bioanalyzer. Ten micrograms of total RNA was processed, labeled, and hybridized to Affymetrix's HG-U133A GeneChips®. Microarray hybridization was performed at the Center for Cancer Genome Discovery of Dana Farber Cancer Institute.

Microarray Data Analysis and Gene Annotation

The raw microarray data were pre-processed using RMAexpress v0.3[22]. Probe sets were annotated using NetAffx™ v4.2 annotation tool and only grade A level probe sets[23] (NA22) were included for further analysis. Because the microarray profiling was done in two separate batches at different times and unsupervised heuristic K-means clustering identified a systematic difference between the two batches (FIG. 6), the distance-weighted discrimination (DWD) method (see world wide web at genome.unc.edu/pubsup/dwd/index.html) was used to adjust the difference. The DWD method first finds a separating hyperplane between the two batches and adjusts the data by projecting the different batches on the DWD plane, discover the batch mean, and then subtracts out the DWD plane multiplied by this mean. The data were then transformed to Z score by centering to its mean and scaling to its standard deviation. This transformation was necessary for validation on different datasets in which different expression ranges are likely to exist, and for validation on different platforms, such as qPCR where the data scale is different.

Derivation of Signature

The pre-selected probe sets by univariate analysis at p<0.005 were selected by an exclusion procedure. The exclusion selection excluded one probe set at a time based on the resultant R square ($R^2$, Goodness-of-fit[15, 16]) of the Cox model. It kept repeating until there was only one probe set left. The procedure was repeated until there was only one probe set left. An inclusion procedure was followed using the probe set left by the exclusion procedure as the starting probe set. It included one probe set at a time based on the resultant $R^2$ of the Cox model. Finally, the $R^2$ was plotted against the probe set and a set of minimum number of probe sets yet having the largest $R^2$ was chosen as candidate signature. Gene signature was established after passing the internal validation by leave-one-out-cross-validation (LOOCV) and external validation on other datasets (listed below). All statistical analyses were performed using SAS v9.1 (SAS Institute, CA).

Validation in Separate Microarray Datasets

The prognostic value of this 15-gene signature was tested on separate microarray datasets. Three represented subsets of microarray data from the NCI Director's Challenge Consortium (DCC) for the Molecular Classification of Lung Adenocarcinoma (Nature Medicine, in review/in press). In total, the Consortium analyzed the profiles of 442 tumors, including 177 from University of Michigan (UM), 79 from H. L. Moffitt Cancer Centre (HLM), 104 from Memorial Sloan-Kettering Cancer Centre (MSK), and 82 from our group. As 39 of the latter tumors overlap with samples used in this study, only data from the first 3 groups were used for validation. In addition, patients who were noted as either unknown or having received adjuvant chemotherapy and/or radiotherapy were excluded. Therefore, the DCC dataset used in this validation study included only 169 patients: 67 from UM, 46 from HLM, 56 from MSK. Two additional published microarray datasets were also used for validation: the Duke's University dataset of 85 non-small cell lung cancer patients (Potti, et al, NEJM), and the University of Michigan dataset of 106 squamous cell carcinomas patients (UM-SQ) (Rapponi et al). Raw data of these microarray studies were downloaded and RMA pre-processed. The expression levels were Z score transformed after double log 2 transformation. Risk score was the Z score weighted by the coefficient of the Cox model from the OBS. Demographic data of the DC cohort was listed in Table 5.

Statistical Analysis

Risk score was the product of coefficient of Cox proportional model and the standardized expression level. The univariate association of the expression of the individual probe set with overall survival (date of randomization to date of last followup or death) was evaluated by Cox proportional hazards regression. A stringent $p<0.005$ was set as a selection criteria in order to minimize the possibility of false-positive results.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Baseline factors of BR.10 patients with and without microarray profiles

| Factor | All Patients (n = 482) | Microarray profiled (n = 133) | | No microarray profiled (n = 349) | | P value |
|---|---|---|---|---|---|---|
| | | n | % | n | % | |
| Treatment received | | | | | | |
| ACT | 231 | 71 | 53% | 160 | 46% | 0.14 |
| OBS | 251 | 62 | 47% | 189 | 54% | |
| Age | | | | | | |
| <65 | 324 | 87 | 65% | 237 | 68% | 0.6 |

TABLE 1-continued

Baseline factors of BR.10 patients with and without microarray profiles

| Factor | All Patients (n = 482) | Microarray profiled (n = 133) | | No microarray profiled (n = 349) | | P value |
|---|---|---|---|---|---|---|
| | | n | % | n | % | |
| ≧65 | 158 | 46 | 35% | 112 | 32% | |
| Gender | | | | | | |
| Male | 314 | 91 | 68% | 223 | 64% | 0.35 |
| Female | 168 | 42 | 32% | 126 | 36% | |
| Performance Status | | | | | | |
| 0 | 236 | 67 | 50% | 169 | 49% | 0.72 |
| 1 | 245 | 66 | 50% | 179 | 51% | |
| Stage of Disease | | | | | | |
| IB | 219 | 73 | 55% | 146 | 42% | 0.01 |
| II | 263 | 60 | 45% | 203 | 58% | |
| Surgery | | | | | | |
| Pneumonectomy | 113 | 33 | 25% | 80 | 23% | 0.66 |
| Other Resection | 369 | 100 | 75% | 269 | 77% | |
| Pathologic type | | | | | | |
| Adenocarcinoma | 256 | 71 | 53% | 185 | 53% | 0.56 |
| Squamous | 179 | 52 | 39% | 127 | 36% | |
| Other | 47 | 10 | 8% | 37 | 11% | |
| Ras Mutation Status | | | | | | |
| Present | 117 | 28 | 21% | 89 | 26% | 0.12* |
| Absent | 333 | 105 | 79% | 228 | 65% | |
| Unknown | 32 | 0 | 0% | 32 | 9% | |

*P-value: Without include those missing or unknown.

TABLE 2

Comparison of 5-yr Survival (multivariate) of High and Low Risk Groups in Untreated Patients and Patients who Received Adjuvant Chemotherapy.

| | n | HR* | 95% CI | p value |
|---|---|---|---|---|
| Observation/untreated Patients | | | | |
| JBR. 10 (randomized with microarray) | 62 | 18.0 | 5.8-56.1 | <0.0001 |
| Stage IB | 34 | 29.9 | 4.5-197.4 | 0.0004 |
| Stage II | 28 | 16.4 | 3.0-88.1 | 0.001 |
| DCC (no adjuvant therapy) | 169 | 2.9 | 1.5-5.6 | 0.002 |
| UM | 67 | 1.5 | 0.54-4.31 | 0.4 |
| HLM | 46 | 1.2 | 0.43-3.60 | 0.7 |
| MSK | 56 | NA** | NA | |
| Duke | 85 | 1.5 | 0.81-2.89 | 0.19 |
| UM-Squamous | 106 | 2.3 | 1.1-4.7 | 0.026 |
| Patients Treated With Adjuvant Chemotherapy | | | | |
| BR. 10 (randomized with microarray) | 71 | 1.5 | 0.7-3.3 | 0.28 |
| BR. 10 Stage I | 39 | 1.7 | 0.5-5.6 | 0.36 |
| BR. 10 Stage II | 32 | 1.2 | 0.4-3.6 | 0.8 |
| DCC (not randomized) | 41 | 1.1 | 0.5-2.5 | 0.8 | n: number of patients; HR: hazard ratio; CI: confidence interval
*HR compares the survival of the poor prognostic group to that of the good prognostic group as determined by the 15-gene signature with the adjustment of stage and patients' age and gender. For BR. 10, and Duke, the effect of histology was also adjusted
**All events were in high risk group and female patients.

TABLE 3

172 U133A probe sets that were prognostic at p < 0.005 for the 62 BR.10 observation arm patients.

| Probe Set ID | Representative Public ID | UniGene ID | Gene Symbol | Coefficients | HR | HRL | HRH | p value |
|---|---|---|---|---|---|---|---|---|
| 200878_at | AF052094 | Hs.468410 | EPAS1 | −0.58 | 0.56 | 0.37 | 0.84 | 0.0048 |
| 201228_s_at | NM_006321 | Hs.31387 | ARIH2 | 0.47 | 1.60 | 1.17 | 2.18 | 0.0029 |
| 201242_s_at | BC000006 | Hs.291196 | ATP1B1 | −0.69 | 0.50 | 0.35 | 0.71 | 0.0001 |
| 201243_s_at | NM_001677 | Hs.291196 | ATP1B1 | −0.54 | 0.58 | 0.41 | 0.83 | 0.0028 |
| 201301_s_at | NM_001153 | Hs.422986 | ANXA4 | −0.55 | 0.58 | 0.40 | 0.83 | 0.0028 |
| 201502_s_at | NM_020529 | Hs.81328 | NFKBIA | −0.62 | 0.54 | 0.36 | 0.79 | 0.0016 |
| 202023_at | NM_004428 | Hs.516664 | EFNA1 | −0.67 | 0.51 | 0.35 | 0.76 | 0.0009 |
| 202035_s_at | AF017987 | Hs.213424 | SFRP1 | 0.69 | 1.99 | 1.39 | 2.86 | 0.0002 |
| 202036_s_at | AF017987 | Hs.213424 | SFRP1 | 0.84 | 2.31 | 1.56 | 3.44 | 0.0000 |
| 202037_s_at | AF017987 | Hs.213424 | SFRP1 | 0.74 | 2.09 | 1.43 | 3.07 | 0.0002 |
| 202490_at | AF153419 | Hs.494738 | IKBKAP | 0.42 | 1.53 | 1.17 | 1.99 | 0.0018 |
| 202707_at | NM_000373 | Hs.2057 | UMPS | 0.60 | 1.81 | 1.24 | 2.66 | 0.0023 |
| 202814_s_at | NM_006460 | Hs.15299 | HEXIM1 | 0.59 | 1.80 | 1.20 | 2.70 | 0.0045 |
| 203001_s_at | NM_007029 | Hs.521651 | STMN2 | 0.55 | 1.73 | 1.21 | 2.47 | 0.0027 |
| 203147_s_at | NM_014788 | Hs.575631 | TRIM14 | −0.56 | 0.57 | 0.39 | 0.82 | 0.0028 |
| 203438_at | AI435828 | Hs.233160 | STC2 | 0.67 | 1.96 | 1.29 | 2.96 | 0.0015 |
| 203444_s_at | NM_004739 | Hs.173043 | MTA2 | 0.38 | 1.46 | 1.12 | 1.89 | 0.0046 |
| 203475_at | NM_000103 | Hs.511367 | CYP19A1 | 0.56 | 1.76 | 1.23 | 2.52 | 0.0021 |
| 203509_at | NM_003105 | Hs.368592 | SORL1 | −0.58 | 0.56 | 0.39 | 0.81 | 0.0020 |
| 203928_x_at | AI870749 | Hs.101174 | MAPT | 0.44 | 1.55 | 1.15 | 2.10 | 0.0044 |
| 203973_s_at | M83667 | Hs.440829 | CEBPD | −0.61 | 0.54 | 0.38 | 0.77 | 0.0005 |
| 204179_at | NM_005368 | Hs.517586 | MB | 0.47 | 1.60 | 1.16 | 2.22 | 0.0044 |
| 204267_x_at | NM_004203 | Hs.77783 | PKMYT1 | 0.63 | 1.87 | 1.28 | 2.73 | 0.0011 |
| 204338_s_at | AL514445 | Hs.386726 | RGS4 | 0.57 | 1.77 | 1.23 | 2.53 | 0.0021 |
| 204531_s_at | NM_007295 | Hs.194143 | BRCA1 | 0.60 | 1.82 | 1.21 | 2.75 | 0.0043 |
| 204584_at | AI653981 | Hs.522818 | L1CAM | 0.56 | 1.75 | 1.30 | 2.35 | 0.0002 |
| 204684_at | NM_002522 | Hs.645265 | NPTX1 | 0.48 | 1.61 | 1.18 | 2.19 | 0.0024 |
| 204810_s_at | NM_001824 | Hs.334347 | CKM | 0.46 | 1.58 | 1.20 | 2.09 | 0.0012 |
| 204817_at | NM_012291 | — | ESPL1 | 0.53 | 1.70 | 1.24 | 2.34 | 0.0010 |
| 204933_s_at | BF433902 | Hs.81791 | TNFRSF11B | 0.51 | 1.67 | 1.27 | 2.20 | 0.0003 |
| 204953_at | NM_014841 | Hs.368046 | SNAP91 | 0.59 | 1.81 | 1.31 | 2.49 | 0.0003 |
| 205046_at | NM_001813 | Hs.75573 | CENPE | 0.62 | 1.86 | 1.28 | 2.70 | 0.0012 |
| 205189_s_at | NM_000136 | Hs.494529 | FANCC | 0.53 | 1.70 | 1.21 | 2.40 | 0.0023 |
| 205217_at | NM_004085 | Hs.447877 | TIMM8A | 0.64 | 1.90 | 1.26 | 2.85 | 0.0020 |
| 205386_s_at | NM_002392 | Hs.567303 | MDM2 | 0.49 | 1.63 | 1.19 | 2.23 | 0.0025 |
| 205433_at | NM_000055 | Hs.420483 | BCHE | 0.58 | 1.79 | 1.23 | 2.62 | 0.0024 |
| 205481_at | NM_000674 | Hs.77867 | ADORA1 | 0.49 | 1.63 | 1.20 | 2.23 | 0.0020 |
| 205491_s_at | NM_024009 | Hs.522561 | GJB3 | 0.46 | 1.58 | 1.18 | 2.11 | 0.0021 |
| 205501_at | AI143879 | Hs.348762 | — | 0.40 | 1.49 | 1.13 | 1.97 | 0.0043 |
| 205825_at | NM_000439 | Hs.78977 | PCSK1 | 0.59 | 1.81 | 1.24 | 2.65 | 0.0023 |
| 205893_at | NM_014932 | Hs.478289 | NLGN1 | 0.40 | 1.49 | 1.13 | 1.97 | 0.0048 |
| 205938_at | NM_014906 | Hs.245044 | PPM1E | 0.52 | 1.68 | 1.22 | 2.31 | 0.0013 |
| 205946_at | NM_003382 | Hs.490817 | VIPR2 | 0.50 | 1.65 | 1.17 | 2.33 | 0.0043 |
| 206043_s_at | NM_014861 | Hs.6168 | ATP2C2 | −0.55 | 0.57 | 0.39 | 0.84 | 0.0044 |
| 206096_at | AI809774 | Hs.288658 | ZNF35 | 0.55 | 1.73 | 1.20 | 2.49 | 0.0034 |
| 206228_at | AW769732 | Hs.155644 | PAX2 | 0.50 | 1.65 | 1.27 | 2.15 | 0.0002 |
| 206232_s_at | NM_004775 | Hs.591063 | B4GALT6 | 0.44 | 1.56 | 1.17 | 2.07 | 0.0021 |
| 206401_s_at | J03778 | Hs.101174 | MAPT | 0.39 | 1.48 | 1.13 | 1.94 | 0.0049 |
| 206426_at | NM_005511 | Hs.154069 | MLANA | 0.63 | 1.87 | 1.26 | 2.77 | 0.0018 |
| 206496_at | NM_006894 | Hs.445350 | FMO3 | 0.53 | 1.70 | 1.22 | 2.37 | 0.0018 |
| 206505_at | NM_021139 | Hs.285887 | UGT2B4 | 0.61 | 1.84 | 1.26 | 2.69 | 0.0017 |
| 206524_at | NM_003181 | Hs.389457 | T | 0.78 | 2.18 | 1.35 | 3.53 | 0.0015 |
| 206552_s_at | NM_003182 | Hs.2563 | TAC1 | 0.97 | 2.63 | 1.53 | 4.53 | 0.0005 |
| 206619_at | NM_014420 | Hs.159311 | DKK4 | 0.54 | 1.72 | 1.20 | 2.45 | 0.0029 |
| 206622_at | NM_007117 | Hs.182231 | TRH | 0.53 | 1.70 | 1.23 | 2.37 | 0.0015 |
| 206661_at | NM_025104 | Hs.369998 | DBF4B | 0.55 | 1.73 | 1.27 | 2.36 | 0.0005 |
| 206672_at | NM_000486 | Hs.130730 | AQP2 | 0.37 | 1.45 | 1.13 | 1.84 | 0.0030 |
| 206678_at | NM_000806 | Hs.175934 | GABRA1 | 0.39 | 1.48 | 1.16 | 1.89 | 0.0014 |
| 206799_at | NM_006551 | Hs.204096 | SCGB1D2 | 0.41 | 1.51 | 1.15 | 1.99 | 0.0032 |
| 206835_at | NM_003154 | Hs.250959 | STATH | 0.46 | 1.59 | 1.16 | 2.18 | 0.0042 |
| 206940_s_at | NM_006237 | Hs.493062 | POU4F1 | 0.54 | 1.72 | 1.23 | 2.40 | 0.0017 |
| 206984_s_at | NM_002930 | Hs.464985 | RIT2 | 0.47 | 1.59 | 1.16 | 2.20 | 0.0045 |
| 207003_at | NM_002098 | Hs.778 | GUCA2A | 0.62 | 1.85 | 1.23 | 2.79 | 0.0032 |
| 207028_at | NM_006316 | Hs.651453 | MYCNOS | 0.48 | 1.61 | 1.19 | 2.18 | 0.0020 |
| 207208_at | NM_014469 | Hs.121605 | HNRNPG-T | 0.51 | 1.66 | 1.23 | 2.26 | 0.0010 |
| 207219_at | NM_023070 | Hs.133034 | ZNF643 | 0.60 | 1.82 | 1.27 | 2.60 | 0.0011 |
| 207529_at | NM_021010 | — | DEFA5 | 0.65 | 1.91 | 1.38 | 2.64 | 0.0001 |
| 207597_at | NM_014237 | Hs.127930 | ADAM18 | 0.63 | 1.87 | 1.36 | 2.58 | 0.0001 |
| 207814_at | NM_001926 | Hs.711 | DEFA6 | 0.61 | 1.85 | 1.21 | 2.81 | 0.0041 |
| 207843_x_at | NM_001914 | Hs.465413 | CYB5A | −0.55 | 0.58 | 0.39 | 0.84 | 0.0047 |
| 207878_at | NM_015848 | — | KRT76 | 0.41 | 1.51 | 1.17 | 1.95 | 0.0017 |
| 207937_x_at | NM_023110 | Hs.264887 | FGFR1 | 0.43 | 1.54 | 1.14 | 2.08 | 0.0045 |
| 208157_at | NM_009586 | Hs.146186 | SIM2 | 0.45 | 1.56 | 1.19 | 2.05 | 0.0013 |
| 208233_at | NM_013317 | Hs.468675 | PDPN | 0.54 | 1.72 | 1.18 | 2.49 | 0.0043 |
| 208292_at | NM_014482 | Hs.158317 | BMP10 | 0.44 | 1.55 | 1.17 | 2.05 | 0.0025 |

TABLE 3-continued

172 U133A probe sets that were prognostic at p < 0.005 for the 62 BR.10 observation arm patients.

| Probe Set ID | Representative Public ID | UniGene ID | Gene Symbol | Coefficients | HR | HRL | HRH | p value |
|---|---|---|---|---|---|---|---|---|
| 208314_at | NM_006583 | Hs.352262 | RRH | 0.56 | 1.75 | 1.19 | 2.58 | 0.0044 |
| 208368_s_at | NM_000059 | Hs.34012 | BRCA2 | 0.62 | 1.86 | 1.26 | 2.73 | 0.0018 |
| 208399_s_at | NM_000114 | Hs.1408 | EDN3 | 0.48 | 1.61 | 1.18 | 2.20 | 0.0028 |
| 208511_at | NM_021000 | Hs.647156 | PTTG3 | 0.49 | 1.63 | 1.17 | 2.29 | 0.0043 |
| 208684_at | U24105 | Hs.162121 | COPA | −0.52 | 0.59 | 0.41 | 0.85 | 0.0041 |
| 208992_s_at | BC000627 | Hs.463059 | STAT3 | −0.67 | 0.51 | 0.34 | 0.77 | 0.0012 |
| 209434_s_at | U00238 | — | PPAT | 0.43 | 1.54 | 1.15 | 2.06 | 0.0033 |
| 209839_at | AL136712 | Hs.584880 | DNM3 | 0.54 | 1.72 | 1.18 | 2.50 | 0.0049 |
| 209859_at | AF220036 | Hs.368928 | TRIM9 | 0.45 | 1.57 | 1.16 | 2.12 | 0.0032 |
| 210016_at | BF223003 | Hs.434418 | MYT1L | 0.60 | 1.82 | 1.31 | 2.52 | 0.0003 |
| 210247_at | AW139618 | Hs.445503 | SYN2 | 0.64 | 1.89 | 1.30 | 2.75 | 0.0008 |
| 210302_s_at | AF262032 | Hs.584852 | MAB21L2 | 0.59 | 1.81 | 1.34 | 2.44 | 0.0001 |
| 210315_at | AF077737 | Hs.445503 | SYN2 | 0.66 | 1.94 | 1.31 | 2.87 | 0.0009 |
| 210455_at | AF050198 | Hs.419800 | C10orf28 | 0.57 | 1.76 | 1.24 | 2.50 | 0.0015 |
| 210758_at | AF098482 | Hs.493516 | PSIP1 | 0.42 | 1.52 | 1.17 | 1.97 | 0.0015 |
| 210918_at | AF130075 | — | — | 0.46 | 1.59 | 1.24 | 2.04 | 0.0003 |
| 211204_at | L34035 | Hs.21160 | ME1 | 0.54 | 1.72 | 1.26 | 2.33 | 0.0006 |
| 211264_at | M81882 | Hs.231829 | GAD2 | 0.53 | 1.71 | 1.19 | 2.44 | 0.0034 |
| 211341_at | L20433 | Hs.493062 | POU4F1 | 0.57 | 1.77 | 1.21 | 2.58 | 0.0031 |
| 211516_at | M96651 | Hs.68876 | IL5RA | 0.60 | 1.82 | 1.26 | 2.62 | 0.0013 |
| 211772_x_at | BC006114 | Hs.89605 | CHRNA3 | 0.52 | 1.69 | 1.22 | 2.33 | 0.0014 |
| 212359_s_at | W89120 | Hs.65135 | KIAA0913 | −0.53 | 0.59 | 0.42 | 0.82 | 0.0019 |
| 212528_at | AI348009 | Hs.633087 | — | −0.79 | 0.45 | 0.29 | 0.70 | 0.0004 |
| 212531_at | NM_005564 | Hs.204238 | LCN2 | −0.57 | 0.56 | 0.38 | 0.84 | 0.0049 |
| 213197_at | AB006627 | Hs.495897 | ASTN1 | 0.66 | 1.93 | 1.36 | 2.74 | 0.0002 |
| 213260_at | AU145890 | Hs.599993 | — | 0.51 | 1.67 | 1.18 | 2.35 | 0.0036 |
| 213458_at | AB023191 | — | KIAA0974 | 0.43 | 1.54 | 1.19 | 1.99 | 0.0010 |
| 213482_at | BF593175 | Hs.476284 | DOCK3 | 0.53 | 1.70 | 1.19 | 2.42 | 0.0032 |
| 213603_s_at | BE138888 | Hs.517601 | RAC2 | −0.62 | 0.54 | 0.37 | 0.79 | 0.0017 |
| 213917_at | BE465829 | Hs.469728 | PAX8 | 0.52 | 1.69 | 1.21 | 2.36 | 0.0022 |
| 214457_at | NM_006735 | Hs.592177 | HOXA2 | 0.72 | 2.06 | 1.40 | 3.03 | 0.0002 |
| 214608_s_at | AJ000098 | Hs.491997 | EYA1 | 0.55 | 1.73 | 1.24 | 2.42 | 0.0013 |
| 214665_s_at | AK000095 | Hs.406234 | CHP | −0.52 | 0.59 | 0.43 | 0.82 | 0.0014 |
| 214822_at | AF131833 | Hs.495918 | FAM5B | 0.54 | 1.72 | 1.23 | 2.41 | 0.0017 |
| 215102_at | AK026768 | Hs.633705 | DPY19L1P1 | 0.49 | 1.64 | 1.22 | 2.20 | 0.0011 |
| 215180_at | AL109703 | Hs.651358 | — | 0.43 | 1.54 | 1.16 | 2.06 | 0.0029 |
| 215289_at | BE892698 | — | ZNF749 | 0.46 | 1.58 | 1.19 | 2.09 | 0.0017 |
| 215356_at | AK023134 | Hs.646351 | ECAT8 | 0.46 | 1.58 | 1.15 | 2.17 | 0.0048 |
| 215476_at | AF052103 | Hs.159157 | — | 0.49 | 1.63 | 1.21 | 2.21 | 0.0016 |
| 215705_at | BC000750 | — | PPP5C | 0.52 | 1.68 | 1.22 | 2.32 | 0.0016 |
| 215715_at | BC000563 | Hs.78036 | SLC6A2 | 0.75 | 2.12 | 1.37 | 3.29 | 0.0008 |
| 215850_s_at | AK022209 | Hs.651219 | NDUFA5 | 0.48 | 1.62 | 1.18 | 2.23 | 0.0030 |
| 215944_at | U80773 | — | — | 0.49 | 1.64 | 1.20 | 2.24 | 0.0019 |
| 215953_at | AL050020 | Hs.127384 | DKFZP564C196 | 0.47 | 1.59 | 1.16 | 2.19 | 0.0038 |
| 215973_at | AF036973 | — | HCG4P6 | 0.55 | 1.74 | 1.30 | 2.32 | 0.0002 |
| 216050_at | AK024584 | Hs.406847 | — | 0.44 | 1.55 | 1.15 | 2.08 | 0.0035 |
| 216066_at | AK024328 | Hs.429294 | ABCA1 | 0.50 | 1.65 | 1.22 | 2.22 | 0.0010 |
| 216240_at | M34428 | Hs.133107 | PVT1 | 0.46 | 1.58 | 1.15 | 2.18 | 0.0046 |
| 216881_x_at | X07882 | Hs.528651 | PRB4 | 0.41 | 1.51 | 1.14 | 1.99 | 0.0042 |
| 216989_at | L13779 | Hs.121494 | SPAM1 | 0.46 | 1.58 | 1.15 | 2.16 | 0.0044 |
| 217004_s_at | X13230 | Hs.387262 | MCF2 | 0.39 | 1.48 | 1.14 | 1.91 | 0.0032 |
| 217253_at | L37198 | Hs.632861 | — | 0.51 | 1.66 | 1.17 | 2.35 | 0.0041 |
| 217995_at | NM_021199 | Hs.511251 | SQRDL | −0.82 | 0.44 | 0.29 | 0.66 | 0.0001 |
| 218768_at | NM_020401 | Hs.524574 | NUP107 | 0.63 | 1.88 | 1.31 | 2.70 | 0.0006 |
| 218881_s_at | NM_024530 | Hs.220971 | FOSL2 | −0.52 | 0.60 | 0.42 | 0.85 | 0.0044 |
| 218980_at | NM_025135 | Hs.436636 | FHOD3 | 0.63 | 1.88 | 1.29 | 2.74 | 0.0011 |
| 219000_s_at | NM_024094 | Hs.315167 | DCC1 | 1.06 | 2.90 | 1.89 | 4.44 | 0.0000 |
| 219171_s_at | NM_007345 | Hs.189826 | ZNF236 | 0.56 | 1.76 | 1.20 | 2.56 | 0.0035 |
| 219182_at | NM_024533 | Hs.156784 | FLJ22167 | 0.48 | 1.62 | 1.18 | 2.22 | 0.0027 |
| 219425_at | NM_014351 | Hs.189810 | SULT4A1 | 0.74 | 2.11 | 1.41 | 3.14 | 0.0003 |
| 219520_s_at | NM_018458 | Hs.527524 | WWC3 | −0.49 | 0.61 | 0.44 | 0.84 | 0.0029 |
| 219537_x_at | NM_016941 | Hs.127792 | DLL3 | 0.55 | 1.73 | 1.23 | 2.44 | 0.0018 |
| 219617_at | NM_024766 | Hs.468349 | C2orf34 | 0.53 | 1.70 | 1.19 | 2.43 | 0.0035 |
| 219643_at | NM_018557 | Hs.470117 | LRP1B | 0.55 | 1.73 | 1.30 | 2.30 | 0.0001 |
| 219704_at | NM_015982 | Hs.567494 | YBX2 | 0.75 | 2.12 | 1.42 | 3.16 | 0.0002 |
| 219882_at | NM_024686 | Hs.445826 | TTLL7 | 0.51 | 1.66 | 1.18 | 2.35 | 0.0038 |
| 219937_at | NM_013381 | Hs.199814 | TRHDE | 0.54 | 1.71 | 1.23 | 2.38 | 0.0015 |
| 219955_at | NM_019079 | Hs.562195 | L1TD1 | 0.60 | 1.82 | 1.25 | 2.65 | 0.0018 |
| 220029_at | NM_017770 | Hs.408557 | ELOVL2 | 0.52 | 1.68 | 1.18 | 2.40 | 0.0038 |
| 220076_at | NM_019847 | Hs.156727 | ANKH | 0.77 | 2.17 | 1.53 | 3.07 | 0.0000 |
| 220294_at | NM_014379 | Hs.13285 | KCNV1 | 0.45 | 1.56 | 1.16 | 2.11 | 0.0036 |
| 220366_at | NM_022142 | Hs.104894 | ELSPBP1 | 0.53 | 1.69 | 1.19 | 2.41 | 0.0034 |
| 220394_at | NM_019851 | Hs.199905 | FGF20 | 0.61 | 1.84 | 1.30 | 2.60 | 0.0006 |
| 220397_at | NM_020128 | Hs.591036 | MDM1 | 0.41 | 1.51 | 1.17 | 1.95 | 0.0015 |
| 220541_at | NM_021801 | Hs.204732 | MMP26 | 0.50 | 1.64 | 1.24 | 2.18 | 0.0006 |

TABLE 3-continued

172 U133A probe sets that were prognostic at p < 0.005 for the 62 BR.10 observation arm patients.

| Probe Set ID | Representative Public ID | UniGene ID | Gene Symbol | Coefficients | HR | HRL | HRH | p value |
|---|---|---|---|---|---|---|---|---|
| 220653_at | NM_015363 | — | ZIM2 | 0.60 | 1.83 | 1.33 | 2.53 | 0.0002 |
| 220700_at | NM_018543 | Hs.188495 | WDR37 | 0.59 | 1.80 | 1.22 | 2.66 | 0.0029 |
| 220703_at | NM_018470 | Hs.644603 | C10orf110 | 0.59 | 1.80 | 1.26 | 2.58 | 0.0012 |
| 220771_at | NM_016181 | Hs.633593 | LOC51152 | 0.60 | 1.81 | 1.23 | 2.67 | 0.0025 |
| 220817_at | NM_016179 | Hs.262960 | TRPC4 | 0.47 | 1.60 | 1.19 | 2.14 | 0.0019 |
| 220834_at | NM_017716 | Hs.272789 | MS4A12 | 0.52 | 1.68 | 1.27 | 2.22 | 0.0003 |
| 220847_x_at | NM_013359 | Hs.631598 | ZNF221 | 0.50 | 1.65 | 1.19 | 2.28 | 0.0025 |
| 220852_at | NM_014099 | Hs.621386 | PRO1768 | 0.48 | 1.62 | 1.19 | 2.20 | 0.0022 |
| 220970_s_at | NM_030977 | Hs.406714 | KRTAP2-4/LOC644350 | 0.49 | 1.64 | 1.16 | 2.31 | 0.0050 |
| 220981_x_at | NM_022053 | Hs.648337 | NXF2 | 0.45 | 1.56 | 1.19 | 2.05 | 0.0014 |
| 220993_s_at | NM_030784 | Hs.632612 | GPR63 | 0.38 | 1.46 | 1.13 | 1.88 | 0.0041 |
| 221018_s_at | NM_031278 | Hs.333132 | TDRD1 | 0.81 | 2.25 | 1.51 | 3.37 | 0.0001 |
| 221077_at | NM_018076 | Hs.127530 | ARMC4 | 0.56 | 1.76 | 1.25 | 2.47 | 0.0013 |
| 221137_at | AF118071 | — | — | 0.46 | 1.59 | 1.15 | 2.20 | 0.0049 |
| 221168_at | NM_021620 | Hs.287386 | PRDM13 | 0.68 | 1.96 | 1.33 | 2.91 | 0.0007 |
| 221258_s_at | NM_031217 | Hs.301052 | KIF18A | 0.62 | 1.86 | 1.34 | 2.58 | 0.0002 |
| 221319_at | NM_019120 | Hs.287793 | PCDHB8 | 0.40 | 1.49 | 1.14 | 1.96 | 0.0041 |
| 221393_at | NM_014627 | — | TAAR3 | 0.50 | 1.64 | 1.17 | 2.31 | 0.0043 |
| 221591_s_at | BC005004 | Hs.592116 | FAM64A | 0.72 | 2.05 | 1.38 | 3.05 | 0.0004 |
| 221609_s_at | AY009401 | Hs.29764 | WNT6 | 0.40 | 1.50 | 1.15 | 1.95 | 0.0028 |
| 221718_s_at | M90360 | Hs.459211 | AKAP13 | −0.64 | 0.53 | 0.36 | 0.78 | 0.0013 |
| 221950_at | AI478455 | Hs.202095 | EMX2 | 0.67 | 1.96 | 1.41 | 2.72 | 0.0001 |

TABLE 4

Features of 15 probe sets in the gene signature

| Probe Set | Gene Symbol | Gene Title | Entrez Gene ID | Coef.* | Rank of expression [n = 19619 (%)] | Rank of variation [n = 19619 (%)] | Rank of significant [n = 172 (%)] |
|---|---|---|---|---|---|---|---|
| 201243_s_at | ATP1B1 | ATPase, Na+/K+ transporting, beta 1 polypeptide | 481 | −0.54 | 517 (2.6) | 2224 (11.3) | 111 (64.5) |
| 203147_s_at | TRIM14 | Tripartite motif-containing 14 | 8518 | −0.56 | 3532 (18.0) | 9499 (48.4) | 112 (65.1) |
| 221591_s_at | FAM64A | Family with sequence similarity 64, member A | 7372 | 0.72 | 6171 (31.5) | 6108 (31.1) | 29 (16.9) |
| 218881_s_at | FOSL2 | FOS-like antigen 2 | 10614 | −0.52 | 6526 (33.3) | 12445 (63.4) | 155 (90.1) |
| 202814_s_at | HEXIM1 | Hexamethylene bis-acetamide inducible 1 | 11075 | 0.59 | 7415 (37.8) | 9026 (46.0) | 161 (93.6) |
| 204179_at | MB | myoglobin | 9830 | 0.47 | 7703 (39.3) | 7942 (40.5) | 156 (90.7) |
| 204584_at | L1CAM | L1 cell adhesion molecule | 4151 | 0.56 | 9327 (47.5) | 3329 (17.0) | 17 (9.9) |
| 202707_at | UMPS | Uridine monophosphate synthetase | 3897 | 0.60 | 12311 (62.8) | 18737 (95.5) | 101 (58.7) |
| 208399_s_at | EDN3 | Endothelin 3 | 4193 | 0.48 | 16344 (83.3) | 8234 (42.0) | 110 (64.0) |
| 203001_s_at | STMN2 | Stathmin-like 2 | 2315 | 0.55 | 16948 (86.4) | 5690 (29.0) | 109 (63.4) |
| 210016_at | MYT1L | Myelin transcription factor 1-like | 1908 | 0.60 | 17902 (91.2) | 18637 (95.0) | 27 (15.7) |
| 202490_at | IKBKAP | Inhibitor of kappa light polypeptide gene enhancer in B-cells, kinase complex-associated protein | 23040 | 0.42 | 18769 (95.7) | 10412 (53.1) | 84 (48.8) |
| 206426_at | MLANA | Melan-A | 2355 | 0.63 | 19159 (97.7) | 17172 (87.5) | 81 (47.1) |
| 205386_s_at | MDM2 | Mdm2, transformed 3T3 cell double minute 2 | 7776 | 0.49 | 19251 (98.1) | 14275 (72.8) | 104 (60.5) |
| 219171_s_at | ZNF236 | Zinc finger protein 236 | 54478 | 0.56 | 19383 (98.8) | 17046 (86.9) | 132 (76.7) |

*Coefficient of the Cox model

TABLE 5

Demographic distributions of patients in validation sets

| Clinical Factors | DCC, All n = 360 (%) | DCC, UM n = 177 (%) | DCC, HLM n = 79 (%) | DCC, MSK n = 104 (%) | Duke n = 89 (%) | UM-SQ n = 129 (%) |
|---|---|---|---|---|---|---|
| Pathology Type | | | | | | |
| Adeno | 360 (100) | 177 (100) | 79 (100) | 104 (100) | 43 (48) | 0 |
| Non-Adeno | 0 (0) | 0 (0) | 0 (0) | 0 (0) | 46 (52) | 129 (100) |
| Disease stage | | | | | | |
| I | 220 (61) | 116 (66) | 41 (52) | 63 (61) | 67 (75) | 73 (57) |
| II | 69 (19) | 29 (16) | 20 (25) | 20 (19) | 18 (20) | 33 (25) |
| III | 69 (19) | 32 (18) | 16 (20) | 21 (20) | 3 (3) | 23 (18) |

TABLE 5-continued

Demographic distributions of patients in validation sets

| Clinical Factors | DCC, All n = 360 (%) | DCC, UM n = 177 (%) | DCC, HLM n = 79 (%) | DCC, MSK n = 104 (%) | Duke n = 89 (%) | UM-SQ n = 129 (%) |
|---|---|---|---|---|---|---|
| IV | 0 (0) | 0 (0) | 0 (0) | 0 (0) | 1 (2) | 0 (0) |
| Unknown | 2 (1) | 0 (0) | 2 (3) | 0 (0) | 0 (0) | 0 (0) |
| Adjuvant chemotherapy | | | | | | |
| No | 210 (58) | 76 (43) | 61 (77) | 73 (70) | 89 (100) | NS |
| Yes | 64 (18) | 17 (10) | 16 (20) | 31 (30) | 0 (0) | NS |
| Unknown | 86 (24) | 84 (47) | 2 (3) | 0 (0) | 0 (0) | NS |
| Adjuvant radiotherapy | | | | | | |
| No | 209 (58) | 76 (43) | 57 (72) | 76 (73) | 89 (100) | NS |
| Yes | 64 (18) | 17 (10) | 19 (24) | 28 (27) | 0 (0) | NS |
| Unknown | 87 (24) | 84 (47) | 3 (4) | 0 (0) | 0 (0) | NS |
| Age (year) | | | | | | |
| <65 | 163 (45) | 87 (49) | 17 (34) | 49 (47) | 33 (37) | 52 (40) |
| ≧65 | 197 (55) | 90 (51) | 25 (66) | 55 (53) | 56 (63) | 77 (60) |
| Gender | | | | | | |
| Male | 177 (49) | 100 (56) | 40 (51) | 37 (36) | 54 (61) | 82 (64) |
| Female | 183 (51) | 77 (44) | 39 (49) | 67 (64) | 35 (39) | 47 (36) |

DCC: Directors' Challenge Consortium; UM: University of Michigan; HLM: H. Lee Moffitt Cancer Center; MSK: Memorial Sloan-Kettering Cancer Center; NS: Not specified

TABLE 6

Adjuvant therapies in the Director's Challenge Consortium (DCC) Patients

| Adjuvant Chemotherapy | Adjuvant radiotherapy | | | |
|---|---|---|---|---|
| | No | Yes | Unknown | Total |
| All | | | | |
| No | 190 | 20 | 0 | 210 |
| Yes | 19 | 44 | 1 | 64 |
| Unknown | 0 | 0 | 86 | 86 |
| University of Michigan (UM) | | | | |
| No | 76 | 0 | 0 | 76 |
| Yes | 0 | 17 | 0 | 17 |
| Unknown | 0 | 0 | 84 | 84 |
| H. Lee Moffitt (HLM) | | | | |
| No | 51 | 10 | 0 | 61 |
| Yes | 6 | 9 | 1 | 16 |
| Unknown | 0 | 0 | 2 | 2 |
| Memorial Sloan-Kettering (MSK) | | | | |
| No | 63 | 10 | 0 | 73 |
| Yes | 13 | 18 | 0 | 31 |
| Unknown | 0 | 0 | 0 | 0 |

TABLE 7

Primers for qPCR validation

| Gene | SEQ ID NO | Forward | SEQ ID NO | Reverse | Amplicon Length | Tm |
|---|---|---|---|---|---|---|
| FAM64A | 173 | AGTCACTCACCCACTGTGTTTCTG | 188 | GGTAGGGAAAGGAGGGATGAGA | 71 | 83 |
| MB | 174 | CTGTGTTCTGCATGGTTTGGAT | 189 | GGTTGGAAGAAGTTCGGTTGG | 71 | 76 |
| EDN3 | 175 | ATTTGAGTGGGTGTCCAGGG | 190 | GGTCAAGGCCAATGCTCTGT | 71 | 80 |
| ZNF236 | 176 | AAAGGACCGCATCAGTGAGC | 191 | AGCAGTTGGCGTGCTTGG | 71 | 85 |
| FOSL2 | 177 | AAGAAGATTGGGCAGTTGGGT | 192 | TCCTGCTACTCCTGGCTCATTC | 71 | 80 |
| MYT1L | 178 | AAGATAAACAGCCCCAGGAACC | 193 | CCACTGAGGAGCTGTCTGCTTT | 72 | 81 |
| MLANA | 179 | GTAGGAAAAATGCAAGCCATCTCT | 194 | CATGATTAGTACTGCTAGCGGACC | 77 | 74 |
| L1CAM | 180 | AAAGGAAAGATTGGTTCTCCCAG | 195 | AGTAGACCAAGCACAGGCATACAG | 71 | 81 |
| TRIM14 | 181 | TCACAGCTCCCTCCAGAAGC | 196 | GATGAGGACTGGGAGAGGGTT | 71 | 82 |
| STMN2 | 182 | CAGGCTTTTGAGCTGATCTTGAA | 197 | TTTGGAGAAGCTAAAGTTCGTGG | 71 | 79 |

TABLE 7-continued

Primers for qPCR validation

| Gene | SEQ ID NO | Forward | SEQ ID NO | Reverse | Amplicon Length | Tm |
|---|---|---|---|---|---|---|
| UMPS | 183 | GCCAACAGTACAATAGCCCACAA | 198 | CCACGACCTACAATGATGATATCG | 70 | 78 |
| ATP1B1 | 184 | AGTTGGAAATGTGGAGTATTTTGGA | 199 | CATAGTACGGATAATACTGCAGAGGAA | 71 | 78 |
| HEXIM1 | 185 | CTGACCGAGAACGAACTGCA | 200 | AGTCCCCTTTGCCCCCTC | 99 | 83 |
| IKBKAP | 186 | AGCGATTCACGTAGGATCTGC | 201 | ATCACCAGTGTTGGAAGTGGG | 71 | 82 |
| MDM2 | 187 | TGCCCCTTAATGCCATTGAA | 202 | TTTTGCCATGGACAATGCA | 75 | 77 |

TABLE 8

Risk group based on 15-gene signature in stage I patients

| | n | HR | 95% CI | p value |
|---|---|---|---|---|
| BR. 10 Observation arm | 34 | 13.3 | 2.9-62.1 | <0.0001 |
| DCC No adjuvant therapy | 141 | 3.3 | 1.5-7.4 | 0.002 |
| UM | 57 | 1.9 | 0.6-6.1 | 0.28 |
| HLM | 37 | 2.5 | 0.9-6.9 | 0.07 |
| MSK | 47 | NA | NA | 0.05 |
| Duke | 67 | 1.06 | 0.5-2.2 | 0.88 |
| UM-SQ | 73 | 1.4 | 0.6-3.1 | 0.44 | n: number of patients; HR: hazard ratio; CI: confidence interval
* HR and CI cannot be calculated as no death occurred in the good prognosis group, p value the score test.

TABLE 9

Probe set target sequences of the 15-gene signature

| SEQ ID NO: | Probe set ID | Target sequence |
|---|---|---|
| 35 | 205386_S_AT | tttccccctagttgacctgtctataagagaattatatatttctaactatataaccctaggaatttagacaacctgaaatttattcacatatatcaaagtgagaaaatgcctcaattcacatagatttcttctctttagtataattgacctactttggtagtggaatagtgaatacttactataatttgacttgaatatgtagctcatcctttacaccaactcctaattttaaataatttctactctgtcttaaatgagaagtacttggtttttttttcttaaatatgtatatgacatttaaatgtaacttattattttttttgagaccgagtcttgctctgttacccaggctggagtgcagtgggtgatcttggctcactgcaagctctgccctccccgggttcgcaccattctcctgcctcagcctccaattagcttggcctacagtcatctgcc |
| 78 | 208399_S_AT | ccgagccgagcttactgtgagtgtggagatgttatcccaccatgtaaagtcgcctgcgcagggagggctgcccatctccccaacccagtcacagagatagg aaacggcatttgagtgggtgtccagggcccgtagagagacatttaagatggtgtatgacagagcattggccttgaccaaatgttaaatcctctgtgtatttcataagttattacaggtataaaagtgatgacctatcatgaggaaatgaaagtggctgatttgctgtaggattttgtacagtttagagaagcgattatttattgtgaaactgttctccactccaactccttatgtggatctgttcaaagtagtcactgtatatacgtatagagaggtagataggtaggtagatttaaattgcattctgaatacaaactcatactcctttagagcttgaattacattttaaaatgcatatgtgctgtttggcaccgtggcaagatggtatcagagagaaacccatcaattgctcaaatactc |
| 4 | 201243_S_AT | ggtgatgggttgtgttatgcttgtattgaatgctgtcttgacatctcttgccttgtcctccggtatgttctaaagctgtgtctgagatctggatctgcccatcactttggcctagggacagggctaattaatttgctttatacattttctttttact |
| | | ttccttttttcctttctggaggcatcacatgctggtgctgtgtctttatgaatgttttaaccattttcatggtggaagaattttatatttatgcagttgtacaattttattttttctgcaagaaaaagtgtaatgtatgaaataaaccaaagtcacttgtttgaaaataaatctttattttgaacttataaaagcaatgcagtaccccatagactggtgttaaatgttgtctacagtgcaaaatccatgttctaacatatgtaataattgccaggagtacagtgctcttgttgatcttgtattcagtcaggttaaaa |
| 22204179_AT | | tgttccggaaggacatggcctccaactacaaggagctggggcttccagggctaggccctgccgctcccaccccaccc atctgggccccgggttcaagagagagcggggtctgatctcgtgtagccatatagagtttgcttctgagtgtctgctttgtttagtagaggtgggcaggaggagctgaggggctggggctggggtgttgaagttggctttgcatgccagcgatgcgcctccctgtgggatgtcatcacccggggaacccgggagtgcccttggctcactgtgttctgcatggtttggatctgaattaattgtcctttcttctaaatcccaaccgaacttcttccaacctccaaactggctgtaaccccaaatccaagccattaactacacctgacagtagcaattgtctgattaatcactggcccttgaagacagcagaatgtccctttgcaatgaggaggagatctgggctgggcgggccagctggggaagcatttgactatctggaacttgtgtgtgcctcctcaggtatggca |
| 169221591_S_AT | | cacatctggacccatcagtgactgcctgccatagcctgagagtgtcttggggagaccttgcagaggggagaattgttccttctgctttcctaggggactcttgagcttagaaactcatcgtacacttgaccttgagccttctatttgcctcatctataacatgaagtgctagcatcagatatttgagagctcttagctctgtacccgggtgcctggttttgggagtcatccgcagagtcactcacccactgtgttttctggtgccaaggctcttgaggggcccactctcatccctccttttccctaccaggactcggaggaaggcataggagatatttccaggcttacgaccctgggctcacgggtacctattttatatgctcagtgcagagcactgtggatgtgccaggaggggtagccctgttcaagagcaatttctgcccttttgtaaattatttaagaaactgctttgtcatttattagaaagaaaccagcgtgtgactttcctagataacactgcttttc |
| 15203147_S_AT | | accaatcacgcctacagtgctttgaaggtttcctctcctaggctagtttcaaacaggccctaaacaagtctgctgctgccctctcatcagacctccgcacccctcaccccaccatcacttanactacttttaatccagttccttcaaagtgataccccacaggtaagccctcagcatcctgaatacatcatccgcagcctgggaaccttctccctcgtacagcacaggaacctgacacatagtaggcacacagtaaacgtttgtgaatgaatggagtcatccagtcctgactcttctgtctcttgaggtcccttgaatcttccgcttcctcccccaccgatttcagcgtgtccacatcacagctccctccagaagctgcaagagcttcttagcagttcctggtctgaaccctctcccagtcctcatcttccaccctaaaactagagtgatcttcctaaaacttcactta |

TABLE 9-continued

Probe set target sequences of the 15-gene signature

| SEQ ID NO: | Probe set ID | Target sequence |
|---|---|---|
| | | acccctcagctatgaaaaggcttccaggagtttccatgaa |
| 13 | 0218881_S_AT | aggtcacagtatcctcgtttgaaagataattaagatccc ccgtggagaaagcagtgacacattcacacagctgttccc tcgcatgttatttcatgaacatgacctgttttcgtgcac tagacacacagagtggaacagccgtatgcttaaagtaca tgggccagtgggactggaagtgacctgtacaagtgatgc agaaaggagggtttcaaagaaaaaggattttgttttaaaa tactttaaaaatgttattcctgcatccttggctgtga tgcccctctcccgatttcccaggggctctgggagggacc cttctaagaagatttgggcagttgggtttctggcttgaga tgaatccaagcagcagaatgagccaggagtagcaggaga tgggcaaagaaaactggggtgcactcagctctcacaggg gtaatca |
| 8 | 5210016_AT | ataacagcatatgcatttccccaccgcgttgtgtctgca gcttctttgccaatatagtaatgcttttagtagagtact agatagtatcagttttggattcttattgttatcacctat gtacaatggaaagggatttaagcacaaacctgctgctc atctaacgttggtacataatctcaaatcaaaagttatct gtgactattatataggatacaaaagtgtcacatatta gaatgctgaccttcatatggattattgtgagtcatcag agttattataacttattgttcatattcatttctaagtt aatttaagtaatcatttattaagacagaattttgtataa actattattgtgctctctgtggaactgaagtttgattt attttgtactacacggcatgggtttgttgacacttaa ttttgctataaatgtgtggaatcacaagttgctgtgata cttcatttttaaattgtgaacttttgtacaaattttgtca tgctggatgttaacacat |
| 11 | 202490_AT | gaggatggcacaagcgattcacgtaggatctgccctgt gaccaaaacacctcccattgggccccacttccaacactg gtgatcacatttcaacatgagggttagggaaacaaatgc ctaaactacagcactgtacataaactaacaggaaatgct gcttttgatcctcaaagaagtgatatagccaaaattgta atttaagaagcctttgtcagtatagcaagatgttaacta tagaatcaatctaggagtattcactgtaaaattcaactt ttctgtatgtttgaacattttcacaatctcataggagt tttaaaaagaagagaaagaagatatactttgctttggag aaatctacttttttgacttacatgggtttgctgtaattaa gtgcccaatattgaaaggctgcaagtactttgtaatcac tcttttggcatgggtaaataagcatggtaacttatatga aatatagtgctcttgctttggataactgtaaagggaccc atgctgatagactggaaa |
| 12 | 202707_AT | aagttcattcttaagcttgcttttttttgagactggtgtt tgttagacagccacagtcctgtctgggttagggtcttcc acatttgaggatccttcctatctctccatgggactagac tgctttgttattctatttattttttaattttttttcgaga caggatctcactctgttgcccaggatggagtgcagtggt gagatcacggctcattgcagcctcgacctcccaggtgat cctcccacctcagcttccagattagctggtgctataggc atgcaccaccgtccatctaaattctttattatttgt agagatgaggtcttgccatgttacccaggctggtctcaa ctcctgggctcaagcgatcctcctgcctcagtctctcaa agtgctgggattacaggtgtgagccactgtgcccagcct aattgcagtaagacaa |
| 14 | 203001_S_AT | acctcgcaacatcaacatctatacttacgatgatatgga agtgaagcaaatcaacaaacgtgcctctggccaggcttt tgagctgatcttgaagccaccatctcctatctcagaagc cccacgaactttagcttctccaaagaagaaagacctgtc cctggaggagatccagaagaaactggaggctgcaggga aagaagaaagtctcaggaggccaggtgctgaaacaatt ggcagagaagagggaacacgagcgagaagtccttcagaa ggctttggaggagaacaacaacttcagcaagatggcgga ggaaaaactgtcctgaaaatggaacaaattaaggaaaa ccgtgaggctaatctagctgctattattgaacgtctgca ggaaaaggagaggcatgctgcgggaggtgcgcaggaaca ggaactccaggttgaactgtctggctgaagcaagggagg gtctggcacgcc |

TABLE 9-continued

Probe set target sequences of the 15-gene signature

| SEQ ID NO: | Probe set ID | Target sequence |
|---|---|---|
| 13 | 202814_S_AT | tgcctctcgcgcatggaggacgagaacaaccggctgcgg ctggagagcaagcggctgggtggcgacgacgcgcgtgtg cgggagctggagctggagctggaccggctgcgcgccgag aacctccagctgctgaccgagaacgaactgcaccggcag caggagcgagcgccgcttccaagtttggagactagact gaaacttttttggggggagggggcaaaggggacttttttac agtgatggaatgtaacattatatacatggtgtatataaga cagtggacctttttatgacacataatcagaagagaaatc cccctggctttggttggtttcgtaaatttagctatatgt agcttgcgtgcttctcctgttcttttaattatgtgaaa ctgaagagttgcttttcttgttttccttttagaagttt ttttcctaatgtgaaagtaatttgaccaagttataatg cattttgttttaacaaatccctccttaaacggagct ataaggtggccaaatctga |
| 133 | 219171_S_AT | cttttgttcttgctgggttatttatttttgattttagcat taaatgtcatctcaggatatctctaaaaggggttgttta attcctaattgtatagaaagctagtttggtgaattgtat tggttaattgactgtttaaggccttaacaggtgaatcta gagcctacttttatttttggttaaagaaaaagaaaatatc aataattcaattttgtgtcttttctcaatttattagcaa acacaagacattttatgtattttcgatttacttccta attataaaagctgcttttttgcagaacattccttgaaaa tataaggttttgaaaagacataattttacttgaatcttt gtggggtacaggttgatctttatattttactggttgttt taaaaaattctagaaaagagatttctaggcctcatgtata accaggggtttgaggataaagaactgtattttttagaact atctcatcatagcatatctgctttggaataactat |
| 49 | 206426_AT | gtaaagatcctatagctcttttttttttgagatggagttt cgcttttgttgcccaggctggagtgcaatggcgcgatct tggctcaccataacctccgcctcccaggttcaagcaatt ctcctgcctcagcctcctgagtagctgggattacaggcg tgcgccactatgcctgactaattttgtagttttagtaga gacggggtttctccatgttggtcaggctggtctcaaact cctgacctcaggtgatctgcccgcctcagcctcccaaag tgctggaattacaggcgtgagccaccacgcctggctgga tcctatatcttaggtaagacatataacgcagtctaatta cattctcacttcaaggctcaatgctattctaactaatgac aagtatttctactaaaccagaaattggtagaaggattt aaataagtaaaagctactatgtactgccttagtgctgat gcctgtgtactgccttaaatgtaccatggcaatttagc tctcttgggttcccaaatccctctcacaagaatgt |
| 26 | 204584_AT | cctccctatcgtctgaacagttgtcttcctcagcctcct cccgcccccaccttgggaatgtaaatacaccgtgactt gaaagtttgtaccccctgtccttcccttttacgccactagt gtgtaggcagatgtctgagtccctaggtggttttctagga ttgatagcaattagctttgatgaacccatcccaggaaaa ataaaaacagacaaaaaaaaaggaaagattggttctccc agcactgctcagcagccacagcctccctgtatgcctgtg cttggtctactgataagccctctacaaaa |

TABLE 10

Coefficient of individual genes in 15-gene signature: Principal Component values

| Gene | Gene Symbol | Probe set | pc1 | pc2 | pc3 | pc4 |
|---|---|---|---|---|---|---|
| 1 | ATP1B1 | 201243_s_at | −0.189 | −0.423 | 0.229 | 0.059 |
| 2 | IKBKAP | 202490_at | 0.364 | 0.070 | −0.357 | −0.120 |
| 3 | UMPS | 202707_at | 0.353 | −0.009 | 0.136 | 0.011 |
| 4 | HEXIM1 | 202814_s_at | −0.108 | 0.504 | 0.265 | 0.279 |
| 5 | STMN2 | 203001_s_at | 0.326 | 0.044 | −0.100 | −0.122 |
| 6 | TRIM14 | 203147_s_at | −0.148 | 0.212 | 0.132 | −0.368 |
| 7 | MB | 204179_at | 0.197 | 0.028 | 0.548 | −0.161 |
| 8 | L1CAM | 204584_at | 0.042 | 0.510 | 0.077 | 0.276 |
| 9 | MDM2 | 205386_s_at | 0.180 | 0.081 | 0.325 | −0.500 |

TABLE 10-continued

Coefficient of individual genes in 15-gene signature: Principal Component values

| Gene | Gene Symbol | Probe set | pc1 | pc2 | pc3 | pc4 |
|---|---|---|---|---|---|---|
| 10 | MLANA | 206426_at | 0.366 | −0.240 | 0.114 | 0.157 |
| 11 | EDN3 | 208399_s_at | 0.413 | 0.042 | −0.188 | −0.260 |
| 12 | MYT1L | 210016_at | 0.270 | 0.014 | 0.273 | 0.245 |
| 13 | FOSL2 | 218881_s_at | 0.036 | −0.209 | −0.225 | 0.190 |
| 14 | ZNF236 | 219171_s_at | 0.188 | −0.313 | 0.297 | 0.332 |
| 15 | FAM64A | 221591_s_at | 0.283 | 0.216 | −0.174 | 0.320 |
| | Eigenvalues of principal components | | 3.33 | 1.82 | 1.37 | 1.32 |
| | Weight of each PC for risk score | | 0.557 | 0.328 | 0.430 | 0.335 |

Risk score = 0.557*PC1 + 0.328*PC2 + 0.43*PC3 + 0.335*PC4
where
PC1 = Sum [pc1*(expression data)]$_{Gene\ 1-15}$
PC2 = Sum [pc2*(expression data)]$_{Gene\ 1-15}$
PC3 = Sum [pc3*(expression data)]$_{Gene\ 1-15}$
PC4 = Sum [pc4*(expression data)]$_{Gene\ 1-15}$
Patients classified as high risk or lower risk according to risk score ≧−0.1 or <−0.1.

TABLE 11

Probe set target sequences for 172 genes

| SEQ ID NO: | Probe Set ID | Gene Symbol | Target Sequence |
|---|---|---|---|
| 1 | 200878_at | EPAS1 | cactttgcaactccctgggtaagagggacgacactctggttttcaataccaattacatggaactttctgtaatgggtacnaatgaagaagtttctaaaaacacacacaaagcacattgggccaactatttagtaagcccggatagacttattgccaaaaacaaaaatagctttcaaaagaaatttaagttctatgagaaattccttagtcatggtgttgcgtaaatcatatttagctgcacggcattaccccacacagggtggcagaacttgaaggggttactgacgtgtaaatgctggtattttgattcctgtgtgtgttgccctggcattaaggcattttacccttgcagttttactaaaacactgaaaaatattccaagcttcatattaaccctacctgtcaacgtaacgat |
| 2 | 201228_s_at | ARIH2 | cctacccacctcaaaatgtctgtactgcaagagggccctgggcctctgcttttccatattcacgtttggccagagttgtagtcccaaagaagagcatgggtggcagatggtagggaattgaactggcctgtgcaatgggcatggagcacaaggggtcacagcatgcctcctgccttaccgtggcagtacggagacagtccagaacatggtcttcttgccacggggtgttgttgtctctggtggtgctgcatgtctgtggctcacctttattcttgaaactgaggtttacctggatctggctactgagggtagagcccacagcagataggggttgggcctgtggcccccaaactaggggggttgggttcatcacagtgttgccttttgtctcctaaagataggggatctactttttgaagggaattgttcctcccaaata |
| 3 | 201242_s_at | ATP1B1 | agagctgatcacaagcacaaatcttttcccactagccattaataagttaaaaaaaagatacaaaaacaaaaacctactagtcttgaacaaactgtcatacgtatggaacctacacttaatctatatgctttacactagctttctgcatttaataggttagaa |
| 4 | 201243_s_at | ATP1B1 | ggtgatgggttgtgttatgcttgtattgaatgctgtcttgacatctcttgccttgtcctccggtatgttctaaagctgtgtctgagatctggatctgcccatcactttggcctagggacagggctaattaatttgctttatacattttctttttacttttccttttttcctttctggaggcatcacatgctggtgctgtgtctttatgaatgttttaaccattttcatggtggaagaatttatatttatgcagttgtacaattttattttttctgcaagaaaagtgtaatgtatgaaataaaccaaagtcacttgtttgaaaataaatctttattttgaactttataaaagcaatgcagtaccccatagactg |
| | | | gtgttaaatgttgtctacagtgcaaaatccatgttctaacatatgtaataattgccaggagtacagtgctcttgttgatcttgtattcagtcaggttaaaa |
| 5 | 201301_s_at | ANXA4 | ggtgaaatttctaactgttctctgttcccggaaccgaaatcacctgttgcatgtgtttgatgaatacaaaaggatatcacagaaggatattgaacagagtattaaatctgaaacatctggtagctttgaagatgctctgctggctatagtaaagtgcatgaggaacaaatctgcatattttgctgaaaagctctataaatcgatgaagggcttgggcaccgatgataacaccctcatcagagtgatggtttctcgagcagaaattgacatgtggatatccgggcacacttcaagagactctatggaaagtctctgtactcgttcatcaagggtgacacatctgagactacaggaaagtactgcttgttctctgtggaggagatgattaaaataaaaatcccagaaggacaggaggattctcaacactttgaatttttttaacttcatttttctacactgctattatcattatctc |
| 6 | 201502_s_at | NFKBIA | ccaactacaatggccacacgtgtctacacttagcctctatccatggctacctgggcatcgtggagcttttggtgtccttgggtgctgatgtcaatgctcaggagccctgtaatggccggactgccctcacctcgcagtgacctgcaaaatcctgacctggtgtcactctgttgaagtgtggggctgatgtcaacagagttacctaccagggctattctccctaccagctcacctggggcgcccaagcacccggatacagcagcagctgggccagctgacactagaaaaccttcagatgctgcagagagtgaggatgaggagagctatgacacagagtcagagttcacggagttcacagaggacgagctgccctatgatgactgtgtgtttggaggccagcgtctgacgttatgag |
| 7 | 202023_at | EFNA1 | ccaccttcacctcggagggacggagaaagaagtggagacagtccttcccaccattcctgccttaagccaaagaaacaagctgtgcaggcatggtcccttaaggcacagtgggagctgagctggaaggggccacgtggatgggcaaagcttgtcaaagatgccccctccaggagagagccaggatgccagatgaactgactgaaggaaaagcaagaaacagtttcttgcttggaagccaggtacaggagaggcagcatgcttgggctgactgccacagagaagtttgtagccaggtactgcattctctcccatcctggggcagcactccccagagctgtgccagcaggggggctgtgccaacctgttcttagagtgtagctgtaagggcagtgcccatgtgtacattctgcctagagtgtagcctaaagggcagggcccacgtgtatagtatctgta |
| 8 | 202035_s_at | SFRP1 | tcggccagcgagtacgactacgtgagcttccagtcggacatcggcccgtaccagagcgggcgcttacaccaagccacctcagtgcgtggacatccccgcgacctgcggctgtgccacaacgtgggctacaagaagatggtgctgcccaacctgctggagcacgagaccatggcggaggtgaagcagcaggccagcagctgggtgccctgctcaacaagaactgccacgccggcacccaggtcttcctctgctcgctcttcgcgcccgtctgcctggaccggcccatctacccgtgtcgctggctctgcgaggccgtgcgcgactcgtgcgagccggtcatgcagttcttcggcttctactggccggagatgcttaagtgtgacaagttccccgaggggacgtctgcatcgccatgacgccgcccaatgccaccgaagcctccaagccccaaggcacaacggtgtgtcctccctgtgacaacgagttgaaatctgaggccatcattgaacatctctgt |
| 9 | 202036_s_at | SFRP1 | gacaaaccatttccaacagcaacacagccactaaaacacaaaaggggattgggcggaaagtgagagccagcagcaaaatacatttttgcaacttgttggtgtggatctattggctgatctatgcctttcaactagaaaattctaatgattggcaagtcacgttgttttcaggtccagagtagtttctttctgtctgctttaaatggaaacagactcataccacacttacaattaa |

TABLE 11-continued

Probe set target sequences for 172 genes

| SEQ ID NO: | Probe Set ID | Gene Symbol | Target Sequence |
|---|---|---|---|
| | | | ggtcaagcccagaaagtgataagtgcagggagaaaagtgcaagtccattatgtaatagtgacagcaaaggcccaggggagaggcattgccttctctgcccacagtctttccgtgtgattgtctttgaatctgaatcagccagtctcagatgcccaaagtttcggttcctatgagcccggggcatgatctgatccccaagacatg |
| 10 | 202037_s_at | SFRP1 | taacacttggctcttggtacctgtgggttagcatcaagttctccccagggtagaattcaatcagagctccagtttgcatttggatgtgtaaattacagtaatcccatttcccaaacctaaaatctgttttttctcatcagactctgagtaactggttgctgtgtcataactcatagatgcaggaggctcaggtgatctgtttggagagcaccctaggcagccctgcagggaataacatactggccgttctgacctgttgccagcagatacacaggacatggatgaaattcccgtttcctcagttcttcctgtagtactcctcttttagatcc |
| 11 | 202490_at | IKBKAP | gaggatggcacaagcgattcacgtaggatctgcccctgtgaccaaaacacctcccattgggcccactccaacactggtgatcacatttcaacatgaggttagggaaacaaatgcctaaactacagcactgtacataaactaacaggaaatgctgcttttgatcctcaaagaagtgatatagccaaaattgtaatttaagaagcctttgtcagtatagcaagatgttaactatagaatcaatctaggagtattcactgtaaaattcaactttctgtatgtttgacaattttcacaatctcatagggagtttttaaaaagaagagaaagaagatatactttgctttggagaaatctactttttgacttacatgggtttgctgtaattaagtgcccaatattgaaaggctgcaagtacttttgtaatcactctttggcatgggtaaataagcatggtaacttatattgaaatatagtgctcttgcttttggataactgtaaagggacccatgctgatagactggaaa |
| 12 | 202707_at | UMPS | aagttcattcttaagcttgctttttttgagactggtgtttgttagacagccacagtcctgtctgggttagggtcttccacatttgaggatccttcctatctctccatgggactagactgctttgttattctatttatttttttaatttttttcgagacaggatctcactctgttgcccaggatggagtgcagtggtgagatcacggctcattgcagcctcgacctcccaggtgatcctcccacctcagcttccagattagctggtgctataggcatgcaccaccacgtccatctaaatttctttattatttgtagagatgaggtcttgccatgttacccagctggtctcaactcctgggctcaagcgatcctcctgcctcagtctctcaaagtgctgggattacaggtgtgagccactgtgcccagcctaattgcagtaagacaa |
| 13 | 202814_s_at | HEXIM1 | tgcctctcgcgcatggaggacgagaacaaccggctgccggctggagagcaaggcggtgggtgcgacgacgcgcgtgtgcgggagctggagctggagctggaccggctgcgcgccgagaacctccagctgctgaccgagaacgaactgcaccggcagcaggagcgagcgccgctttccaagttttggagactagactgaaacttttttgggggaggggcaaagggggacttttttacagtgatgggaatgtaacattatatacatgtgtatataagacagtggaccttttatgacacataatcagaagagaaatcccctggctttggttggtttcgtaaatttagctatatgtagctcgtgctttctcctgttcttttaattatgtgaaactgaagagttgcttttcttgttttccttttagaagttttttttccttaatgtgaaagtaattgaccaagttataatgcattttttttttaacaaatcccctccttaaacggagctataaggtggccaaatctga |
| 14 | 203001_s_at | STMN2 | acctcgcaacatcaacatctatacttacgatgatatggaagtgaagcaaatcaacaaacgtgcctctggccaggcttttgagctgatcttgaagccaccatctcctatctcagaagccccacgaactttagcttctccaaagaagaaagacctgtccctggaggagataagaagaaactggaggctgcaggggaagaagaaa |
| | | | gtctcaggaggcccaggtgctgaaacaattggcagagaagagggaacacgagcgagaagtccttcagaaggctttggaggagaacaacaacttcagcaagatggcggaggaaaagctgatcctgaaaatggaacaaattaaggaaaaccgtgaggctaatctagctgctattattgaacgtctgcaggaaaggagaggcatgctgccgaggtgcgcaggaacaaggaaactgccaggttgaactgtctggctgaagcaagggagggtctggcacgcc |
| 15 | 203147_s_at | TRIM14 | accaatcacgcctacagtgctttgaaggtttcctctcctaggctagttttcaaacaggccctaaacaagtctgctgctgccctctcatcagacctccgcacccctcaccccaccatcacttaaactactttaatccagttccttcaaagtgataccccacaggtaagccctcagcatcctgaatacatcatccgcagcctgggaaccttctccctcgtacagcacaggaacctgacacatagtaggcacacagtaaacgtttgtgaatgaatggggagtcatccagtcctgactcttcgtgtctcttgaggtcccttgaatcttccgcttcctccccaccgattcagctgtccacatcacagctccctccagaagctgcaagagcttcttagcagttcctggtctgaaccctctcccagtcctcatcttccaccctaaaactagagtgatcttcctaaaaacttcacttaaccccctcagctatgaaaaggcttccaggagtttccatgaa |
| 16 | 203438_at | STC2 | gtccacattcctgcaagcattgattgagacattttgcacaatctaaaatgtaagcaaagtagtcattaaaaatacaccctctacttgggcttatactgcatacaaatttactcatgagccttcctttgaggaaggatgtggatctccaaatcaaagatttagtgtttattttgagctctgcatcttaacaagatgatctgaacacctctccttttgtatcaataaatagccctgttattctgaagtgagaggaccaagtatagtaaaatgctgacatctaaaactaaataaatagaaaaccaccaggccagaactatagtcatactcacacaaagggagaaatttaaactcgaaccaagcaaaaggcttcacggaaatagcatggaaaaacaatgcttccagtggccacttcctaaggagaacaaccccgtctgatctcagaattgcaccacgtgagctgctaagtgataatatctgtttctactacggatttaggcaacaggacctgtacattgtcacattgcat |
| 17 | 203444_s_at | MTA2 | cacaaaggataccagggccctacggaaggctctgacccatctggaaatgcggcgagctgctcgccgacccaacttgcccctgaaggtgaagccaacgctgattgcagtgcggccccctgtccctactctgcacccctcacatcctgccagcaccaatgagcctattgtcctggaggactgagccacctgtgggaagggaggtgggctgagaggtagagggtggatgcccagggcacccaaacctcccttcccttttcgtgtcgaagggagtgaggagtgaattaaggaaagagagcaagtgagtgtgtccctggagggttgggcgccctctggtgttaccacctcgagacttgtctcatgcctccatgcttgccgatggaggacagactgcaggaacttggcccatgtgggaacctagcctgttttgggggtaggacccacagatgtcttggac |
| 18 | 203475_at | CYP19A1 | gaaattcttcccagtctgtcgatttatgcctcagccacttgcctgtgctacaattcattgtgttacctgtagattcaggtaatacaaaccatatataatcatcaagtaatacaaactaatttagtaatagcctgggttaagtatattataggggcctgtgtctgcatgtagaaaaaaaaaattcacatgatgcacttcaaattcaaataaaaaatcctttttggcatgttcccattttttgcttagctcaattagtgtggctaaccaagagataactgtaaatgtagcattgatttgctttactacagtacagtgattgggagggaaaagtccccacccaatgggctcaaactctaagggggtactcctctcatccccttatcctctctccctcgacattttctccctcttttcttcccatgaccccaaagccaagggcaacagatcagta |

TABLE 11-continued

Probe set target sequences for 172 genes

| SEQ ID NO: | Probe Set ID | Gene Symbol | Target Sequence |
|---|---|---|---|
| | | | aagaacgtggtcagagtagaacccctg |
| 19 | 203509_at | SORL1 | gaatatcacagcttaccttgggaatactactg acaatttcttttaaaatttccaacctgaagatg ggtcataattacacgttcaccgtccaagcaag atgcctttttggcaaccagatctgtggggagc ctgccatcctgctgtacgatgagctggggtct ggtgcagatgcatctgcaacgcaggctgccag atctacggatgttgctgctgtggtggtgccca tcttattcctgatactgctgagcctgggggtg gggtttgccatcctgtacacgaagcaccggag gctgcagagcagcttcaccgccttcgccaaca gccactacagctccaggctggggtccgcaatc ttctcctctggggatgacctgggggaagatga tgaagatgccccatgataactggattttcag atgacctcccatggtgatagcctgaaagagc tttcctcactagaaacca |
| 20 | 203928_x_at | MAPT | gagtccagtcgaagattgggtccctggacaat atcacccacgtccctggcggaggaaataaaaa gattgaaaccacaagctgaccttccgcgaga acgccaaagccaagacagaccacggggcggag atcgtgtacaagtcgccagtggtgtctgggaa cacgtctccacggcatctcagcaatgtctcct ccaccggcagcatcgacatggtagactcgccc cagctcgccacgctagctgacgaggtgtctgc ctccctggccaagcagggtttgtgatcaggcc cctggggcggtcaataatgtggagaggagag aatgagagagtgtggaaaaaaaaagaataatg acccggccccgccctctgcccccagctgctc ctcgcagttcggttaattggttaatcacttaa cctgcttttgtcactc |
| 21 | 203973_s_at | CEBPD | aagcggcgcaaccaggagatgcagcagaagtt ggtggagctgtcggctgagaacgagaagctgc accagcgcgtagagcagctcacgcgggacctg gccggcctccggcagttcttcaagcagctgcc cagcccgccttcctgccggccgccgggacag cagactgccggtaacgcgcggccggggcggga gagctcagcaacgacccatctcagacccg acgggcccggagcggagcgcgccctgccctggc gcagccagagccgccgggtgcccgctgcagtt tcttgggacataggagcgcaaagaagctacag cctggacttaccaccactaaactgcgagagaa gctaaacgtgttttattttcccttaaattattt ttgtaatggtagcttttttctacatcttactcc tgttgatgcagctaaggtacatttgtaaaaag aaaaaaaaccagactttttcagacaaacccttt gtattgtagataagaggaaaagactgagcatg ctcactttttttatattaa |
| 22 | 204179_at | MB | tgttccggaaggacatggcctccaactacaag gagctgggcttccagggctaggcccctgccgc tcccacccccacccatctgggccccgggttca agagagagcggggtctgatctcgtgtagccat atagagtttgcttctgagtgtctgctttgttt agtagaggtgggcaggaggagctgagggcctg gggctggggtgttgaagttggctttgcatgcc cagccgatgcgcctccctgtgggatgtcatcac cctgggaaccgggagtgcccttggctcactgt gttctgcatggtttgagatctgaattaattgtc cttcttctaaatcccaaccgaacttcttcca acctccaaactggctgtaaccccaaatccaag ccattaactacacctgacagtagcaattgtct gattaatcactggccccttgaagacagcagaa tgtcccttgcaatgaggaggagatctgggct gggcgggcagctggggaagcatttgactatc tggaacttgtgtgtgcctcctcaggtatggca |
| 23 | 204267_x_at | PKMYT1 | ctgtggtgcatggcagcggaggccctgagccg aggtggggccctgtgcaggccctgcttgccc tgctctgctggctctggcatgggctggctcac cctgccagctggctacagcccctgggcccgcc agccacccgcctggctcaccaccctgcagtt |

TABLE 11-continued

Probe set target sequences for 172 genes

| SEQ ID NO: | Probe Set ID | Gene Symbol | Target Sequence |
|---|---|---|---|
| | | | tgctcctggacagcagcctctccagcaactgg gatgacgacagcctagggccttcactctcccc tgaggctgtcctggcccggactgtggggagca cctccaccccccggagcaggtgcacacccagg gatgccctggacctaagtgacatcaactcaga gcctcctcggggctccttcccctccctttgagc ctcggaacctcctcagccctgctgtttgaggacacc ctagacccaacctgagccccagactctgcctc tgcacttttaaccttttatcctgtgtctctcc cgtcgcccttgaaagctggggcccctcgggaa ctcccatggtcttctctgcctggccgtgtcta ataa |
| 24 | 204338_s_at | RGS4 | gaaacatcggctaggtttcctgctgcaaaaat ctgattcctgtgaacacaattcttcccacaac aaggaaggacaaagtggttatttgccagagagt gagccaagaggaagtcaagaaatgggctgaat cactggaaaacctgattagtcatgaatgtggg ctggcagcttttcaaagctttcttgaagtctga atatagtgaggagaatattgacttctggatca gctgtgaagagtacaagaaaatcaaatcacca tctaaactaagtcccaaggccaaaaagatcta taatgaattcatctcagtccaggcaaccaaag aggtgaacctggattcttgccaccagggaagag acaagccggaacatgctagagcctacaataac ctgctttgatgaggcccagaagaagatttca acctgatggagaaggattcctaccgccgcttc ctcaagtctcgattctatcttgatttggtcaa cccgtcca |
| 25 | 204531_s_at | BRCA1 | ttcaagaaccggtttccaaagacagtcttcta attcctcattagtaataagtaaaatgttatt gttgtagctctggtatataatccattcctctt aaaatataagacctctggcatgaatatttcat atctataaaatgacagatcccaccaggaagga agctgttgctttctttgaggtgattttttttcc tttgctccctgttgctgaaaccatacagcttc ataaataattttgcttgctgaaggaagaaaaa gtgttttcataaacccattatccaggactgt ttatagctgttggaaggactaggtcttcccta gccccccagtgtgcaagggcagtgaagactt gattgtaca |
| 26 | 204584_at | L1CAM | cctcccctatcgtctgaacagttgtcttcctca ggctcctcccgcccccaccttgggaatgtaaa tacaccgtgactttgaaagtttgtacccctgt ccttcccctttacgccactagtgtgtaggcaga tgtctgagtccctcaggtggtttctaggattga tagcaattagctttgatgaacccatcccagga aaaataaaacagacaaaaaaaaaggaaagat tggttctcccagcactgctcagcagccacagc ctcccctgtatgcctgtgcttggtctactgata agcccctctacaaaa |
| 27 | 204684_at | NPTX1 | ttccttttgtagattcccagtttatttctcaa gactgcaaagatcactttgtcaccagccctgg gacctgagaccaaggggtgtcttgtgggcag tgaggggtgaggagaggctggcatgaggttc agtcattccagtgagctccaaagaggggccac ctgttctcaaaagcatgttggggaccaggagg taaaactggccatttatggtgaacctgtgtct tggagctgacttactaagtggaatgagccgag gatttgaatatcagttctaaccttgatagaag aaccttgggttacatgtggttcacattaagag gataagaatccttttgaatcttatggcaaccaa atgtggcttgacgaagtcgtggtttcatctct t |
| 28 | 204810_s_at | CKM | gcaagcacccccaagttcgaggagatcctcacc cgcctgcgtctgcagaagagggtacaggtgc ggtggacacagctgccgtgggctcagtatttg acgtgtccaacgctgatcggctgggctcgtcc gaagtagaacaggtgcagctggtggtggatgg tgtgaagctcatggtggaaatggagaagaagt |

TABLE 11-continued

Probe set target sequences for 172 genes

| SEQ ID NO: | Probe Set ID | Gene Symbol | Target Sequence |
|---|---|---|---|
|  |  |  | tggagaaaggccagtccatcgacgacatgatc cccgcccagaagtaggcgcctgcccacctgcc accgactgctgaaccccagccagtgggaggg cctggccaccagagtcctgctccctcactcc tcgccccgcccctgtcccagagtccacctgg gggctctctccacccttctcagagttccagtt tcaaccagagttccaaccaatgggctccatcc tctggattctggccaatgaaatatctccctgg cagggtcctcttcttttcccagagctcctccc caaccaggagctctagttaatg |
| 29 | 204817_at | ESPL1 | tgtttggctgtagcagtgcggccctggctgtg catggaaacctggaggggggctggcatcgtgct caagtacatcatggctggttgcccccttgtttc tgggtaatctctggatgtgactgaccgcgac attgaccgctacacggaagctctgctgcaagg ctggcttggagcaggcccaggggcccccttc tctactatgtaaaccaggccgccaagctccc cgactcaagtactcttattggggctgcacctat agcctatggcttgcctgtctctctgcggtaac cccatggagctgtcttattgatgctagaagcc tcataactgttctacctc |
| 30 | 204933_s_at | TNFRSF11B | gataaaacggcaacacagctcacaagaacaga cttttccagctgctgaagttatgtgaaacatcaa aacaaagcccaagatatagtcaagaagatcat ccaagatattgacctctgtgaaaacagcgtgc agccgcacattggacatgctaacctcaccttc gagcagcttcgtagcttgatggaaagcttacc gggaaagaaagtgggagcagaagacattgaaa aaacaataaaggcatgcaaacccagtgaccag atcctgaagctgctcagttgttgtgcgaataaa aaatggcgaccaagacacccttgaagggcctaa tgcacgcactaaagcactcaaagacgtaccac tttcccaaaactgtcactcagagtctaaagaa gaccatcaggttccttcacagc |
| 31 | 204953_at | SNAP91 | agagaggtgctattcaagtgattctgaaggca ccccaaggtatatctgtaatttaaagattact gcaaatatctttacttttactgtgggttttag tacatctgttaatttagtgtttcttttgtgtgt tttgtagactagtgttcttccatccttcaact gagctcaaagtaggttttgttgtaacattgtg attaggattaaactaattcagagaattgtat cttttactgtacatactgtattcttttaagttt taatttgttgtcatactgtctgtgctgatggc ttggcttaagattttgatgcataaatgaggtc actgttgatcagtgttgctagtagcttggcag ctcttcataaaagcatattgggttggaaaggt gtttgcctatttttca |
| 32 | 205046_at | CENPE | aatcagcatcttcccaatgaggtcaaaacttg gaaggaaagaaccctttaaaagagaggctcaca aacaagtaacttgtgagaattctccaaagtct cctaaagtgactggaacagcttctaaaaagaa acaaattacaccctctcaatgcaaggaacgga atttacaagatcctgtgcaaaggaatcacca aaatcttgtttttttgatagccgatcaaagtc tttaccatcacctcatccagttcgctattttg ataactcaagtttaggcctttgtccagaggtg caaaatgcaggagcagagagtgtggattctca gccaggtcctcggcacgcctcctcaggcaagg atgtgcctgagtgcaaaactcagtagactcct cctttgtcacttctctggagatccagcattcct tatttgaaatgactttgtttatgtgtctatc cctgtaatgatgttgtagtgcagcttaattt caattcagtctttactttgccactag |
| 33 | 205189_s_at | FANCC | ttcccctccacctccaagacaggtggcggccgg gcaggcactcttaagcccactcctcccctcttg ttgccttcgatttcggcaaagcctgggcaggt gccaccgggaaggaatgcatcgagatgctgg gcggggacgcggcgtggcgaggggcttgacg gcgttggcggggctgggcacaggggcagccgc |
| | | | agggaggcagggatggcaaggcgtgaagccac cctggaaggaactggaccaaggtcttcagagg tgcgacaggtctggaatctgaccttactcta gcaggagttttgtagactctccctgatagtt tagttttgataaagcatgctggtaaaaccac taccctcagagagagccaaaaatacagaagag gcggagagcgccccttccaaccaggctgttatt ccctggactc |
| 34 | 205217_at | TIMM8A | gtacatgggactatgcttttctcaaagcccca ttaactgcttcctataattttgatagtgggac cacatacgtaaaaatctctcatttgtgtggag tcatttctgatttcaggggagatccttgtgtt tatcagaaagggcagaagtaggggaagaataa tttggtatccttatctagtgttgattgtcaa tgctggagaaaaatatctgtaagagtgtttat acagtacacttcagttatcttgatctcccttt cctatatgatgatttgcttaaatatccatatt aagtaagtctcaaggtagggtaggcagcctga gagtctagaggcctttagttataaaggaatct agccagtgaacataattcttattactagactg ccacaaggaagaaattaacttaccctgtatat cagggtacaaaaaattcagtgatgtgcctaaa taagttatataagatttaaggccaatcagaagct aacagcagtttcaggtagaggtgcatgcctaa tgttagttagtgtagattccatttactgcatt ctt |
| 35 | 205386_s_at | MDM2 | tttccctagttgacctgtctataagagaatt atatatttctaactatataaccctaggaattt agacaacctgaaatttattcacatatatcaaa gtgagaaaatgcctcaattcacatagattct tctctttagtataattgacctacttggtagt ggaatagtgaatacttactataatttgacttg aatatgtagctcatcctttacaccaactccta attttaaataatttctactctgtcttaaatga gaagtacttggtttttttttttcttaaatatgt atatgacatttaaatgtaacttattattttt ttgagaccgagtcttgctctgttacccaggct gggagtgcagtggggtgatcttggctcactgcaa gctctgccctccccgggttcgcaccattctcc tgcctcagcctcccaattagcttggcctacag tcatctgcc |
| 36 | 205433_at | BCHE | ggaaagcaggattccatcgctggaacaattac atgatggactggaaaaatcaatttaacgatta cactagcaagaaagaaagttgtgtgggtctct aattaatagatttacccttttatagaacatatt ttcctttagatcaaggcaaaaaatatcaggagc ttttttacacacctactaaaaaagttattatg tagctgaaacaaaaatgccagaaggataatat tgattcctcacatcttttaacttagtattttac ctagcattttcaaaacccaaatggctagaacat gtttaattaaatttcacaatataaagttctac agttaattatgtgcatattaaaacaatggcct ggttcaatttctttcttttccttaataaattta agttttttcccccaaaattatcagtgctctg cttttagtcacgtgtattttcattaccactcg taaaaaggtatcttttttaaatgaattaaata ttgaaacactgtacaccatagtttaca |
| 37 | 205481_at | ADORA1 | gaggagaacactagacatgccaactcgggagc attcgcctgcctgggaacggggtggacgagg gagtgtctgtaaggactcagtgttgactgtag gcgcccctggggtgggtttgcaggctgcag aggcagaggaggagtacccccctgagagcatg tgggggaaggccttgctgtcatgtgaatccct caatacccctagtatctggctgggttttcagg ggctttggaagctctgttgcaggtgctccggg gtctggacttttaggggatctgggatctgaag aggaccaacccatgccctgccaagcctggagc ccctgtgttgggggggcaaggtggggggagcctg gagccctgtgtgggagggcgaggcggggag cctggagccctgtgtgggagggcgaggcggg |

TABLE 11-continued

Probe set target sequences for 172 genes

| SEQ ID NO: | Probe Set ID | Gene Symbol | Target Sequence |
|---|---|---|---|
| | | | ggatcctggagcccctgtgtcgggggggcgagg gaggggaggtggccgtcggttgaccttctgaa catgagtgtcaactccaggacttgcttccaag cccttccctctgttggaaatgggtgtgccct ggctcc |
| 38 | 205491_s_at | GJB3 | tgcttccagccttcgtaattagacttcaccct gagtacacacacaatcactgccactctcacta tagacaaaccacactccctcctctgtcaccca gtcactgccatctcaacacacatccccaccct gtgtacacacaatctctgttattcatactctc actccttatgcgcactctcaacagggcatgta gtctgcactcaagcatgccatcccagcctcac cctgcatttattcggctcatcccattttccc tgaacattttcgctgaactaggggcctggcag gatgctgggactgtgcaaggaggtaggaccta tgcccacggagctaagagacaggaacacaggc tcatctcccgcactaaccaacccctgggatgg ctcacagcctgctcccagtgctgtgtcatgac ctgaa |
| 39 | 205501_at | PDE10A | atgcttgcccaacacactgtgaaatagttacc aaaatttgtacaaatgcagcatcttcattctt tctgagaagacaagatggtttttctttacatga acaaatgaacaaaagagatcctagatccataa cgtagctaaggcatctaagagtttgctgttga taatcttgctgaccaaaaactactggagagta acacaggttatatgccatcacaaatacaatgc tcatgaagaactgatttgtagagtcaatgaac ctgtgtccagaattttaataggctctctattg gaaggagaaagaatttcaagttaacagtatct aactttatcatagttgatgttagtaaattta aaaaatgattttatatgtatgacaaaaatctt tgtaaaatgcgcaagtgcaataattttaaagag gtcttaactttgcatttataaattataaatat tgtacagtgtgtaattttttcatgtattcat ttgcagtctttgtatttaaaa |
| 40 | 205825_at | PCSK1 | tttccattcccaatctagtgctagatgtataa atctttctttgattcttcctaacaaaatatt ttctgggttaaaaccccagccaactcattggg ttgtagccaaaggttcactctcaagaagcttt aatatttaaataaaatcatattgaatgtttcc aacctggagtataaatattcagatataaaacag ttttgtcagtctttcttagtgcctgtgtggat ttttgtgaaaatgtcaaagagaaaacttatat actatttcccttgaaattttaaactatattt ctttacaggtatttataatatacaatgcttt tatcaaacagatttttaaagagcataataaat tatattaaagaaccaaaagttttcctgagaat aagaaagtttcacccaataaaatattttgaa aggcatgttcctctgtcaatgaaaaaaagtac atgtatgtgtgtattatcaatggacatttt gtctaatagcctaatacaacatgtagctgagt ttaacatgtgtggtcttg |
| 41 | 205893_at | NLGN1 | gaacctaggagagtcaacatctggaggatttt agtctttcttacacatatgtgtgattttaaac gaatattctcagaccacaggaaactcttcatc cccctgttgtttaccagtaacagtatatcaca gacctttccaaatgtttgtatatgtaatcaga tgtacatttatattgaaaacaaatgagatgg acttaaagagcacatcctgataaaatactttct ctctcacctgtactatatttctattagactaa agttatgtgattttttttttacattttttcag atgactagcaattttgatagttttaataagataa tgcaaagaacttctctgacaaactaactgca gtaacagaaaccttctttttcagttactcttt ttcaagaatgaaagattattataacaaaaatt gtatactacttgatggaaccaactttgtacat cttggccatgtcactggtcattg |
| 42 | 205938_at | PPM1E | catgctaggctttctcagtggggaaaaaaatg gtggatagaatggggaaaacacagaccccatctt tagggggtctggattttgtaggtccgactacac agcagtgttaactcatttctcatgccattagc tctctacaaaataaagcaaagtagttctagtg tggtcgttataaaaccaatattgtgaaaaatag caactattcatttgttcacaacatgcgtattt atagagtagttaggtaccatttgtaaggtaaa tccttaaaattctataatacatactaaaata gtggttattggtctgatatatgctgctcttgg ttctataaactagataaaagcagtgctttgtg aaatgcagtgttctctcttaacgccactggtg ataggaagtagttcccttcagttcaaatc |
| 43 | 205946_at | VIPR2 | ttcctcccctgtagggtttggacagacccacc cccagccttgcccagctttcaaaggacaaaag ggagcatcccccacctactctcaggtttttga ggaaacaaagtttgtggtaactgaaggtgtt gggtcagtggccaggtgccgacactgagctgt gacccagaggggacgctgaggaagtgggcgtg agtggacntgtcaggtggttaccaggcactgg ttgttgatggtcggtggttgggtgtgggcagt catcagtcatcaggtgtgctcaggggacaatc tcccctcaaccgcacatgtgccactgttcagc gggagctgactggtttcncctggtagagggncc ggctgtttcctgacagatgcctggtggcagg ggaagcaggaccagtggtcancaggtgtcttt aactgtcattgtgtgtggaatgtcgcagact cctccacgtggcgggaatgagct |
| 44 | 206043_s_at | ATP2C2 | gcaccacgacgatgacgttcacttgttttgtg ttttttcgatctcttcaacgccttgacctgcc ctctcagaccaagctgatatttgagatcggct ttctcaggaaccacatgttcctctactccgtc ctggggtccatcctggggcagctggcggtcat ttacatccccccgctgcagagggtcttccaga cggagaacctgggagcgcttgatttgctgttt ttaactggattggcctcatccgtcttcattt gtcagagctcctcaaactatgtgaaaatact gttgcagcccaagagagtccagatgcaccct gaagatgtgtagtggaccgcactccgcggcac cttccctaatcatctcgatctggttgtgactg tggccctgccgtgtctcctcgtcagggagga cttttaggaggccgcagccttccatcaccgga tcagttttctcctcttaggaaagctgcaggaac ctcgtgggc |
| 45 | 206096_at | ZNF35 | gtggctttcctaggaatgggtcgtacaaagct aagtggtaatgatgctatttggggaaaggtct tttttgcttaantttgtttttaaaactctga tgattncttgagcacaggcaggtttatctgcc tggttgaattctggttgaaccgtgtattctaa tatttctggttaagtggtgactgggtaaggaa accacttggggtagcagttcaacaattcactt acgaatgtttataagctttccatttcctaggt aatttttaaaagccagtcaaaacaaaaactt tactgaaaatggacagaaataggaaatggact ttttccttactgtctataccctcctgaaccttg gtattgtaaagatctggggacctctgggtctg ttctgaccattccctagtctccatggccaagc actcaaggattgatggacaccacacaccagct atattcatttgccaagatcaacagctccttct ccaaacaactcaagcccccaattccnatcgca ttcnnttngggtgagatgcaactaacagcccc tt |
| 46 | 206228_at | PAX2 | gcaggctagatccgaggtggcagctccagccc ccggggctcgcccctngcgggcgtgccccgcg cgccccgggcggccgaaggccgggccgcccg tcccgcccgtagttgctcttcggtagtggc gatgcgcctgcatgtctcctcaccgtgcat cgtgacgactcgaaataacagaaacaaagtca ataaagtgaaataaataaaaatccttgaaca aatccgaaaggcttggagtcctcgcccagat ctctctcccctgcgagccctttttatttgaga aggaaaagagaaaagaatcgtttaaggga |

TABLE 11-continued

Probe set target sequences for 172 genes

SEQ ID NO: | Probe Set ID | Gene Symbol | Target Sequence
---|---|---|---

| | | acccggcgcccagccaggctccagtggcccga
acgggcggcgagggcggcgagggcgccgagg
tccggcccatcccagtcctgtggggctggccg
ggcagagaccccggacccaggcccaggcctaa
cctgctaaatgtccccggacggttctggtctc
ctcggccactttcagtgcgtcggttcgttttg
attcttt |
| 47 | 20623 2_s_at | B4GALT 6 | tgcagttttgcatgtaatcggttataccttta
ttggacttttatagacattttttatttgcatg
aaaaaaactcactaaatttacatcactaaaca
aaggttaaccttgtgtgaaatgaaggaactg
tcaataattgacagccaactaatacagtaaac
tgttatactagttttgagctttagacctcagc
cttttgtgtggaagaagtcacagctttcttag
gctttaaaggaaaagaaggaaggacttaaata
gcttttcttcctaccgggattacctatgtttt
tccttgcttgcaatctcatctgattttgctag
aaatcacaaccatattgtttatgcatattgca
tgagtattaccaagaaaaaaatctttaaaagt
tgtgatgtgacatgatataaaggatctcttta
tgttaaatgtctttccatgtacctctggtgtg
tcagggattttgtgcctcaaaaaaatgtttca
aggttgtgtgtttatactgtgtatttttttta
aattcacggtgaacagcacttttattattcc
a |
| 48 | 20640 1_s_at | MAPT | aggtggcagtggtccgtactccacccaagtcg
ccgtcttccgccaagagccgcctgcagacagc
ccccgtgcccatgccagacctgaagaatgtca
agtccaagatcggctccactgagaacctgaag
caccagccgggaggcgggaaggtgcaaatagt
ctacaaaccagttgacctgagcaaggtgacct
ccaagtgtggctcattaggcaacatccatcat
aaaccaggaggtggccaggtggaagtaaaatc
tgagaagcttgacttcaaggacagagtccagt
cgaagattgggtccctggacaatatcacccac
gtccctggcggaggaaataaaaagattgaaac
ccacaagctgacctccgcgagaacgccaaag
ccaagacagaccacggagacgatcgtgtac
aagtcgccagtggtgtctggggacacgtctcc
acggcatctcagcaatgtctcctccaccggca
gcatcgacatggtagactcgccccagctcgcc
acgctagctgacgaggtgtctgcctcc |
| 49 | 20642 6_at | MLANA | gtaaagatcctatagctcttttttttttgagat
ggagtttcgcttttgttgcccaggctggagtg
caatggcgcgatcttggctcaccataacctcc
gcctcccaggttcaagcaattctcctgcctta
gcctcctgagtagctgggattacaggcgtgcg
ccactatgcctgactaattttgtagttttagt
agagacgggtttctccatgttggtcaggctg
gtctcaaactcctgacctcaggtgatctgccc
gcctcagcctcccaaagtgctggaattacagg
cgtgagccaccacgcctggctggatcctatat
cttaggtaagacatataacgcagtctaattac
atttcacttcaaggctcaaatgctattctaact
aatgacaagtattttctactaaaccagaaatt
ggtagaaggattttaaataagtaaaagctacta
tgtactgccttagtgctgatgcctgtgtactg
ccttaaatgctacctatggcaatttagctctct
tgggttcccaaatccctctcacaagaatgt |
| 50 | 20649 6_at | FMO3 | aaagcccaacatcccatggctgttttctcacag
atcccaaattggccatggaagttttattttggc
cctttgtagtccctaccagtttaggctggtggg
cccagggcagtggccaggagccagaaatgcca
tgctgacccagtgggaccggtcgttgaaaccc
atgcaacacgagtggacagcttcagaa
gccttgctcttttttccattggctgaagctct
ttgcaattcctattctgttaatcgctgttttc
cttgtgttgacctaatcatcattttctctagg
atttctgaaagttactgacaatacccagacag
gggctttgc |
| 51 | 20650 5_at | UGT2B4 | taattacgtctgaggctggaagctgggaaacc
caataaatgaactccttttagtttattacaaca
agaagacgttgtgatcaagagattccttttct
tcttgtgacaaaacatctttcaaaacttacct
tgtcaagtcaaaatttgtttagtacctgttt
aaccattagaaatatttcatgtcaaggaggaa
aacattagggaaaacaaaaatgatataaagcc
atatgaggttatattgaaatgtattgagcttta
tattgaaatttattgttccaattcacaggtta
catgaaaaaaatttactaagcttaactacat
gtcacacattgtacatggaaacaagaacatta
agaagtccgactgacagtatcagtactgtttt
gcaaatactcagcatactttggatccatttca
tgcaggattgtgttgttttaac |
| 52 | 20652 4_at | T | agcagtggaggagcacacggacctttcccag
agcccccagcatcccttgctcacacctgcagt
agcggtgctgtccaggtggcttacagatgaac
ccaactgtgggagatgatgcagttggcccaacc
tcactgacggtgaaaaaatgtttgccagggtc
cagaaacttttttttggtttatttctcatacag
tgtattggcaactttggcacaccagaatttgt
aaactccaccagtctactttagtgagataaa
aagcacactcttaatcttcttccttgttgctt
tcaagtagttagagttgagctgttaaggacag
aataaaaatcatagttgaggacagcaggttta
gttgaattgaaaatttgactgctctgccccct
agaatgtgtgtattttaagcatatgtagctaa
tctcttgtgtt |
| 53 | 20655 2_s_at | TAC1 | ttcagcttcatttgtgtcaatgggcaatgaca
ggtaaattaagacatgcactatgaggaataat
tatttatttaataacaattgttggggttgaa
aattcaaaaagtgttttattttcatattgtgc
caatatgtattgtaaacatgtgttttaattcc
aatatgatgactcccttaaaatagaaataagt
ggttatttctcaacaaagcacagtgttaaatg
aaattgtaaaacctgtcaatgatacagtccct
aaagaaaaaaatcattgctttgaagcagttg
tgtcagctactgcggaaaaggaaggaaactcc
tgacagtcttgtgctttttcctatttgttttca
tggtgaaaatgtactgagattttggtattaca
ctgtatttgtatctctgaagcatgtttcatgt
tttgtgactatatagagatgtttttaaaagtt
tcaatgtgattctaatgtcttcatttcattgt
atgatg |
| 54 | 20661 9_at | DKK4 | ctgtctgacacggactgcaataccagaaagtt
ctgcctccagccccgcgatgagaagccgttct
gtgctacatgtcgtgggttgcggaggaggtgc
cagcgagatgccatgtgctgccctgggacact
ctgtgtgaacgatgtttgtactacgatggaag
atgcaacccaatattagaaaggcagcttgat
gagcaagatggcacacatgcagaaggaacaac
tgggcacccagtccaggaaaaccaacccaaaa
ggaagccaagtattaagaaatcacaaggcagg
aagggacaagagggagaaagttgtctgagaag
ttttgactgtggccctggactttgctgtgctc
gtcattttttggacgaaaattttgtaagccagtc
cttttggagggacaggtctgctccagaaggag
gcataaagacactgctcaagctccagaaatct
tccagccgttgcgactgtggcccctggactactg
tgtcgaagccaattgaccagcaatcggcagca
tgctcgat |
| 55 | 20662 2_at | TRH | gccctcttcctttaggcatgtgagaaaatcag
cctagcagtttaaacccccacttccctcccactt
agcaccataggcaaggggcagatccccagagc
ccctctcacccccccccaccacaggcctgctcc
ttccttagccttggctaagatggtccttctgt
gtcttgcaaagactcccaagtggacagggag
ccctgggagggcagccagtgagggtggggtg
ggactgaagcgttgtgtgcaaatccagcttcc |

TABLE 11-continued

Probe set target sequences for 172 genes

| SEQ ID NO: | Probe Set ID | Gene Symbol | Target Sequence |
|---|---|---|---|
| | | | atcccctcccaacctggcaggattctccatg tgtaaacttcaccccaggacccaggatcttc tcctttctgggcatcccttgtgggtgggcag agccctgacccacagctgtgttactgcttgga gaagcatatgtaggggcatacccctgtggtgtt gtgctgtgtctggctgtgggataaatgtgtgt gggaatattgaaacatcgcctaggaattgtgg tttgtatataaccctctaagcccctatcccctt gtcgatgacagtca |
| 56 | 206661_at | DBF4B | accaggagtgtcagcttttagaaggatcatgg tcatgtgagcttctggtcaccggaagccagaa atactcagctgccatgttgatccacaaaggtg ggaggatgtggggaaggggaaagcggtgagg acgcagagtgcaggctgtgggcctcggcatcc gcaggaggtccctagaacatgccgtttcatgt cacctgctacagctctccccagctagtatga tgatccgttttacaaatgcagaaatgatctta atattcatgaccactggccaggcgaggtggct cacacctgtaatcccagcactttgggaggcca aggcgggtggatcacaaggtcaagagttcgag accagcctgaccaacgtggtgaaaccccgtct ctactaaaaatagaagcattagccgagcctgg tgg |
| 57 | 206672_at | AQP2 | gcgcagagtagctgcttcctggacgtgcgcgc ccaggccagtgctgtgagcaggcgggaggag gctgccggagggagcctgagcctggcaggttcc cctgccctgaggctgtgagcagctagtggtgg cttctcctgcctttcagggaactgggaaac ttaggggactgagctggggagggaggcaggtg ggtggtaaggaggaaactctggagagcctgca cccaggtactgagtgggagtgtacagaccct gccttgggggttctgggaatgatgcaactggt tttactagtgtgcaagtgtgttcatccccaag ttctcttttgtcctcacatgcagagttgtgca tgcccctgagtgtgaacaggtttgcctacgtt ggtgca |
| 58 | 206678_at | GABRA1 | tggttttattgccgtgtgctatgcctttgtgtt ctcagctctgattgagtttgccacagtaaact atttcactaagagaggttatgcatgggatggc aaaagtgtggttccagaaaagccaaagaaagt aaaggatcctcttattaagaaaaacaacactt acgctccaacagcaaccagctacacccctaat ttggccagggcgacccgggcttagccaccat tgctaaaagtgcaaccatagaacctaaagagg tcaagcccgaaacaaaaccaccagaacccaag aaaccttttaacagtgtcagcaaaattgaccg actgtcaagaatagccttcccgctgctatttg gaatctttaacttagtctactgggctacgtat ttaaacagagagcctcagctaaaagccccac accacatcaataactcttttactcacattctg ttgttcagttcctctgcactgggaatttattt atgttctcaacgcagtaattccca |
| 59 | 206799_at | SCGB1D2 | tagaagtccaaatcactcattgtttgtgaaag ctgagctcacagcaaaacaagccaccatgaag ctgtcggtgtgtctcctgctggtcacgctggc cctctgctgctaccaggccaatgccgagttct gcccagctcttgtttctgagctgttagacttc ttcttcattagtgaacctctgttcaagttaag tcttgccaaatttgatgcccctccggaagctg ttgcagccaagttaggagtgaagagatgcacg gatcagatgtccctcagaaacgaagcctcat tgcggaagtcctggtgaaaatattgaagaaat gtagtgtgtgacatgtaaaaactttcatcctg gtttccactgtctttcaatgacaccctgatct t |
| 60 | 206835_at | STATH | aagcttcacttcaacttcactacttctgtagt ctcatcttgagtaaagagaacccagccaact atgaagttccttgtctttgccttcatcttggc tctgatggttttccatgattggagctgattcat |

TABLE 11-continued

Probe set target sequences for 172 genes

| SEQ ID NO: | Probe Set ID | Gene Symbol | Target Sequence |
|---|---|---|---|
| | | | ctgaagagaaattttgcgtagaattggaaga ttcggttatgggtatggcccttatcagccagt tccagaacaccactatacccacaaccatacc aaccacaataccaacaatatacctttaatat catcagtaactgcaggacatgattattgaggc ttgattggcaaatacgacttctacatccatat tctcatctttcataccatatcacactactacc actttttgaagaatcatcaaagagcaatgcaa atgaaaaacactataatttactgtatactctt tgtttcaggatacttgccttttcaattgtcac ttgatgatataattgcaatttaaactgttaag ctgtgttcagtactgtttc |
| 61 | 206940_s_at | LOC100131317 /// POU4F1 | ggtttgttaccatcctttaatcataactaaaa cattgaaaacagaacaaatgagaaaagaaaaa aaacctgccgattaacaatgacgaaaatcatg catgatctgaaaggtgtggaaagaaacacaat taggtctcactctggttaggcattatttattt aattatgttgtatatcattgtttgcagggcaa cattctatgcattgaactgagcactaactggg ctagcttctggtagacgtttgtggctagtgcg attcacagtctactgcctgttccactgaaaca ttttgtcatattcttgtattcaaagaaaaaag gaaaaaaagattattgtaaatattttatttaa tgcacacattcacacagtggtaacagactgcc agtgttcatcctgaaatgtctcacggattgat ctacctgtccatgtatgtctgctgagctttct ccttggttatgttttt |
| 62 | 206984_s_at | RIT2 | taaagagctcattttcaggtccgccacacct atgaaattccccctggtgctggtgggtaacaaa attgatctggaacagttccgccaggtttctac agaagaaggcttgagtcttgcccaagaatata attgtggttttttttgagacctctgcagccctc agattctgtattgatgatgcttttcatggctt agtgagggaaattcgcaagaaggagtccatgc catccttgatgaaaagaaactgaagagaaaa gacagcctgtggaagaagctcaaaggttcttt gaagaagaagagagaaaatatgacatgatatc tttgctttgagttcctcacgctctctgaatt ttattagttggacaattccatatgtagcattc tgcttcaatattatctctctatgtgtctctct ctctttaaatatctgcctgtaggtaaaagcaa gctctgcatatctgtacctcttgagatagttt tgttttgcctttaacagttggatgga |
| 63 | 207003_at | GUCA2A | gaggggtcaccgtgcaggatggaaatttctcc ttttctctggagtcagtgaagaagctcaaaga cctccaggagcccaggagccagggttggga aactcaggaactttgcacccatccctggtgaa cctgtggttcccatcctctgtagcaacccgaa cttttccagaagaactcaagcctctctgcaagg agcccaatgcccaggagatacttcagaggctg gaggaaatcgctcaggaggacccgggcacatgtga aatctgtgcctacgctgcctgtaccggatgct aggggggcttgcccactgcctgcctcccctcc gcagcaggggagtcttttctcctgcagaaag ggccacccatgatactccactcccagcagctc aacctaccctggtccagtcgggaggagcagcc cggggaggaactgggtgact |
| 64 | 207028_at | LOC100129296 /// MYCNOS | ctcccccccgagagaaggctgcaaagctgggaa gccaggtgtgctcctccgcgccctttgggac ccccgggcttgcaccggctgcactctgagaac cagctgcgcgcgcggagcggtgcaatgcagcacc caccctgcgagcctggcaattgcttgtcatta aaagaaaaaaaaatttacggagggctccgggg tgtgtgttgggaggggagccgatgcttctca acccagccccgctttgactgcgtgttgtgca gctgagcgcgaggccaacgttgagcaaggct tgcagggaggttgctcctgtgtaattacgaaa gaaggctagtccgaaggtgcaaaatagcaggg agaggacgcgcccccttaggaacaagacctct |

TABLE 11-continued

Probe set target sequences for 172 genes

| SEQ ID NO: | Probe Set ID | Gene Symbol | Target Sequence |
|---|---|---|---|
| | | | ggatgtttccagtttcaaattgaaagaagagg ggcgcccccttg |
| 65 | 207208_at | RBMXL2 | acagcagcagttatggccggagcgaccgctac tcgaggggccgacaccgggtgggcagaccaga tcgtgggctctctctgtccatggaaaggggct gccctccccagcgtgattcttacagccggtca ggctgcagggtgcccaggggcggaggccgtct aggaggccgcttggagagaggaggaggccgga gcagatactaagcaggaacagacttgggacca aaaatcccttctcaacgaaactaacaaaaaga agaacctgttgtatggtaactacccaaggact agtacaaggaagagttgttttttacctttaag aatttcctgttaagatcgtctccatttttatg cttttgggagaaaaaacttaaaattcgtttag tttagttttggaattgttaacgtttctttcaa caagctcctgttaaaagtatatgaacctgagt actagtcttcttacatttacaagtagaaattc gattaatggcttcttccttgtaaattttctt g |
| 66 | 207219_at | ZNF643 | cagccagagcattggactgatccagcatttga gaactcatgttagagagaaaccttttacatgc aaagactgtggaaaagcgttttttccagattag acaccttaggcaacatgagattattcatactg gtgtgaaaccctatatttgtaatgtatgtagt aaaaccttcagccatagtacatacctaactca acaccagagaactcatactggagaaagaccat ataaatgtaaggaatgtgggaaagcctttagc cagagaatacatctttctatccatcagagagt ccatactggagtaaaaccttatgaatgcagtc attgtgggaaagcctttaggcatgatcatcc tttgctaaacatcagagaattcatactggaga aaaaccttatgattgtaatgagtgtggaaaag ccttcagctgtagttcatcccttattagacac tgcaaaacatttaagaaataccttcagcaa tgttgtgtgaaatatactaaacatcaaagaat ctatgttggagcacaagattctaaatcagtgg ttccctg |
| 67 | 207529_at | DEFA5 | gagtcactccaggaaagagctgatgaggctac aacccagaagcagtctggggaagacaaccagg accttgctatctcctttgcaggaaatggactc tctgctcttagaacctcaggttctcaggcaag agccacctgctattgccgaaccggccgttgtg ctaccgtgagtccctctcgggtgtgtgaa atcagtggccgcctctacagactctgctgtcg ctgagcttcctagatagaaaccaaagcagtgc aagattcagttcaaggtcctgaaaaaagaaaa acatttttactctgtgtaccttgtgtctt |
| 68 | 207597_at | ADAM18 | gtgacgctcaatctacagtttattcatatatt caagaccatgtatgtgtatctatagccactgg ttcctccatgagatcagatggaacagacaatg cctatgtggctgatggcaccatgtgtggtcca gaaatgtactgtgtaaataaacctgcagaaa agttcatttaatgggtataactgtaatgcca ccacaaaatgcaaaggggaaagggatatgtaat aattttggtaattgtcaatgcttccctggaca tagacctccagattgtaaattccagtttggtt ccccagggggtagtattgatgatggaaatttt cagaaatctggtgacttttatactgaaaaagg ctacaatacacactggaacaactggtttattc tgagtttctgcatttttctgccgttttcata gttttcaccactgtgatctttaaaagaaatga aataagtaaatcatgtaacagagagaatgcag agtataatcgtaattcatccgttgtatcag |
| 69 | 207814_at | DEFA6 | gagccactccaagctgaggatgatccactgca ggcaaagcttatgaggctgatgccaggagc agcgtggggcaaatgaccaggactttgccgtc tcctttgcagaggatgcaagctcaagtcttag agctttgggctcaacaagggcttcacttgcc attgcagaaggtcctgttattcaacagaatat |
| | | | tcctatgggacctgcactgtcatgggtattaa ccacagattctgctgcctctgagggatgagaa cagagagaaatatattcataatttacttttatg acctagaaggaaactgtcgtgtgtcccataca ttgccatcaactttgttctcat |
| 70 | 207843_x_at | CYB5A | gctggaggtgacgctactgagaactttgagga tgtcgggcactctacagatgccagggaaatgt ccaaaacattcatcattggggagctccatcca gatgacagaccaaagttaaacaagcctccaga accttaaaggcggtgttcaaggaaactctta tcactactattgattctagttccagttggtgg accaactgggtgatccctgccatctctgcagt ggccgtcgccttgatgtatcgcctatacatgg cagaggactgaacacctcctcagaagtcagcg caggaagagcctgctttggacacgggagaaaa gaagccattgctaactacttcaactgacagaa accttcacttgaaaacaatgattttaatatat ctcttctttttcttccgacattagaaacaa acaaaaagaactgtcctttctgcgctcaaatt tttcgagtgtgccttttattcatctacttt |
| 71 | 207878_at | KRT76 | gagctcaagccagcatagctccaccaagtgat ctactgttccaaatctctataaccacctgctt cccactcagcctgcaatagtgtttcccactct ctgcttggcatcaatagatgcataagggtcaa ccacattttcctcaagttccctggagaagaa gctgaacctctggtttctccatccccatgacc ttcccagggcatggaggtcctgctgctggtc tgggatgatgatgccccctgaaaccttcctgc aatggccccttactttggacagcaaccctga gcccaagccagttttggccttcacagcctggc cggttccactctggccatctcccattctta ctgggagttggagattgaagccagtcatctc agcactgtctgaggagggcagagccatgggtt ctgtgctggagggtgcacggccagatctcca gactgctggttcccaggaaccctccctacat ctgggcttcagatcctgactcccttctgtccc ctaattccctgagctgtagatcctctggt |
| 72 | 207937_x_at | FGFR1 | cgcaccccgcatcacaggggaggaggtggaggt gcaggactccgtgcccgcagactccggcctct atgcttgcgtaaccagcagcccctcgggcagt gacaccacctacttctccgtcaatgtttcagc ttgcccagatctccaggaggctaagtggtgct cggccagcttccactccatcactcccttgcca tttggacttggtactcggcttagtgattagag gccctgaacaggtggtggtatccctgctctgc tggagaggaacccagatgctctcccctcctcg gaggatgatgatgatgatgatgactcctcttc agaggagaaagaaacagataacaccaaaaccaa accccgtagctccatattggacatcccccagaa aagatgaaaagaaattgcatgcagtgccggc tgccaagacagtgaagttcaaatgcccttcca gtgggaccccaaaccccacactgcgctggttg aaaaatggcaaagaattcaaacctgaccacag aattggaggctacaaggtccgttatgccacct gga |
| 73 | 208157_at | SIM2 | ctgccctgtacatgctagttcaacagaaagga atggcctttcaccttctcctggtggcaggcaa gcagatgtcctctgcggagataccgccagctc cccaggacgcagactgactcctgtttgctcgc tggaccaaccccaggcagaaggtggaaggtgg gaacagaggtttagctgcaggacatgtattcc cattgcaccgagacctaactgccgctcagagt gtagaccggatgcagatgcctgcagtgc cattaaaatgtgggtgaaggtgacatcaggat tatgtgcccccaggccgggctcagtggctcaca cctgtaatcccagcactttgggaggccaaggt gggcggatcacctgaggtcaggagtttgcgac aagtgctgccaacaagctgaaaccc |

TABLE 11-continued

Probe set target sequences for 172 genes

| SEQ ID NO: | Probe Set ID | Gene Symbol | Target Sequence |
|---|---|---|---|
| 74 | 208233_at | PDPN | gaaatctctgatataagctgggtgtggtggct cgtgcctgtagtctcagctgctgggcaactgc agaccagcctgggcaacatagtaagaccctgt ctcaaaaaaataatctctggtacaatggtcat gttccaaagttccttacttgggcctcttgagt gcagtggctcacacctggaatcccagtgcttt gagagggctgaggaggcaggaggttcacttgtg cccaggaatttgaggctgcagtgagctatgat tgtgccactgcactccagcctgggtgacagag caagactgtgctcttaaaaaataagaaagag cctcttcatcttcaaaaggactacatctgaag tttccccagaaggacaaatgtctacttagacc ttataaatttccaaaataagagagtcagagcc agaggtggcttgtaagttgacttctgttgaga tctgaccacatttgatctcttgttttaatttt ccaactaactgaacttggaagaaaacccaaac caagttttaatctgatgccta |
| 75 | 208292_at | BMP10 | ccatgagcaacttccagagctggacaacttgg gcctggatagctttttccagtggacctgggaa gagggctttgttgcagatgagatcaaacatcat ctatgactccactgcccgaatcagaaggaacg ccaaaggaaactactgtaagagggaccccgctc tacatcgacttcaaggagattgggtgggactc ctggatcatcgctccgcctggatacgaagcct atgaatgccgtggtgtttgtaactaccccctg gcagagcatctcacacccacaaagcatgcaat tatccaggccttggtccacctcaagaattccc agaaagcttccaaagcctgctgtgtgcccaca aagctagagcccatctccatcctctatttaga caaaggcgtcgtcacctacaagtttaaatacg aaggcatggccgtctccgaatgtggctgtaga tagaagaagagtcctatggcttatttaataac tgtaaatgtgtatatttggtgttcctatttaa tgagatatttaataagggtgtacagtaataga ggcttgctgccttcaggaa |
| 76 | 208314_at | RRH | atgatctgcatgtttctggtggcatggtcccc ttattccatcgtgtgcttatgggcttcttttg gtgaccaaagaagattcctcccccccatggcc atcatagctccactgtttgcaaaatcttctac attctataaaccctgcatttatgtggttgcta ataaaaagtttcggagggcaatgcttgccatg ttcaaatgtcagactcaccaaacaatgcctgt gacaagtattttaccccatggatgtatctcaaa acccattggcttctggaagaatctgaaataag agaaaaggacacgctatcaaaacactttagtt ttttgacaatgcttttcttttaaatatgagcc catttagatcaagtgcagacatggatcattgt cctatgagagtgtaagctcctcaagcacagct cgtgcttccgtttgtgcactctggctgctgta gtgtatgcttctctgtgtcctgatatatcaac ttattgctcatctcctttgatgaattaggcat cagaggttaaggtcccctttc |
| 77 | 208368_s_at | BRCA2 | gaacaggagagttccaggccagtacggaaga atgtgagaaaaataagcaggacacaattacaa ctaaaaaatatatctaagcatttgcaaaggcg acaataaattattgacgcttaacctttccagt ttataagactggaatataattttcaaaccacac attagtacttatgttgcacaatgagaaaagaa attagtttcaaatttacctcagcgtttgtgta tcgggcaaaaatcgttttgcccgattccgtat tggtatacttttgcttcagttgcatatcttaa aactaaatgtaattattaactaatcaagaaa aacatcttttggctgagctgggtggctcatgcc tgtaatcccaacactttgagaagctgaggtgg gaggagtgcttgaggccaggagttcaagacca gcctgggcaacatagggagaccccccatctta cgaagaaaaaaaaagggggaaaagaaaatct tttaaatcttttggatttgatcactcaacagt |
| 78 | 208399_s_at | EDN3 | ccgagccgagcttactgtgagtgtggagatgt tatcccaccatgtaaagtcgcctcgcgcagggg agggctgcccatctccccaacccagtcacaga gagatagggaaacggcatttgagtgggtgtcca gggcccccgtagagagacatttaagatggtgta tgacagagcattggccttgaccaaatgttaaa tcctctgtgtgtatttcataagttattacagg tataaaagtgatgacctatcatgaggaaatga aagtggctgatttgctggtaggattttgtaca gtttagagaaggcgattatttattgtgaaactg ttctccactccaactccttatgtggatctgt tcaaagtagtcactgtatatacgtatagagag gtagataggtaggtagattttaaattgcattc tgaatacaaactcatactccttagagcttgaa ttacattttttaaatgcatatgtgctgtttgg caccgtggcaagatggtatcagagagaaaccc atcaattgctcaaatactc |
| 79 | 208511_at | PTTG3 | ttgtggctacaaaggatgggctgaagctgggg tctgaccttcaatcaaagccttagatgggag atctcaagtttcaatatcatgttttggcaaaa cattcgatgctcccacatccttacctaaagct accagaaaggcttgggaactgtcaacagagc tacagaaaagtcagtaaagaccaatgaccccc tcaaacaaaaacagccaagcttttctgccaaa aagatgactgagaagactgttaaagcaaaaa ctctgttcctgcctcagatgatggctatccag aaatagaaaaattatttcccttcaatcctcta ggcttcgagagttttgacctgcctgaagagca ccagattgcacatctcccccttgagtgaagtgc ctctcatgatactttgatgaggagagagcttt gaaaagctgttttcagctgggcccccttcacc tttgaagatgccctctccaccatggaaatcca atctgttgcagtctcctttaagcattctgttg accctggatg |
| 80 | 208684_at | COPA | ggtttaaggatcagtcctctgcagtttcgcta aggccccctttgtgtgcatgggtcagtcacca tatgttccccccagagaatgtgtctatatcct ccttctaacagcaccttccccctgcagctact cttcagatctggctctctgtaccctaaaacct agtatcttttttctcttctatggaaaatccgaa ggtctaaacttgacttttttgaggtcttctca acttgactacagttgtgctcataattgtcctt gccttttccagcttaatttatttaaggaacaaa tgaaaactctgggctgggtggagtggctcata cctgtaatcccagcactttgggaggctacggt gggcagatcatctgagccgggagttcgagac ctgcctggccaacatggcaacaccccgtctct aataaaaatataaaaattagccgggcatggta gcatgcgcctatagtcccagctgctcaggagg ctgaggcatgagaatcgcttgaacctaggagg tggaggttgcattcaactgagatcatacc |
| 81 | 208992_s_at | STAT3 | actggtctatctctatcctgacattcccaagg aggaggcattcggaaagtattgtcggccagag agccaggagcatcctgaagctgacccaggcgc tgcccccatacctgaagaccaagtttatctgtg tgacaccaacgacctgcagcaataccattgac ctgccgatgtcccccgcacttttagattcatt gatgcagtttggaaataatggtgaaggtgctg aaccctcagcaggagggcagtttgagtccctc acctttgacatggagttgacctcggagtgcgc tacctcccccatgtgaggagctgagaacggaa gctgcagaaagatacgactgaggcgcctacct gcattctgccacccctcacacagccaaacccc agatcatctgaaactactaactttgtggttcc agatttttttttaatctcctacttctgctatct ttgagc |
| 82 | 209434_s_at | PPAT | ttgacagctctttaagcccacatgcagcagtg ggtcagataaccctgtggcagtgacacgggca aattggcatttgaataaagcccctgggaccacc |

TABLE 11-continued

Probe set target sequences for 172 genes

| SEQ ID NO: | Probe Set ID | Gene Symbol | Target Sequence |
|---|---|---|---|
| | | | tcaacatgcgtagcctcttgtcttaaatgtac tccccatggcagcatggaggaggcaagacctg tgggtcaattttgaactggccttactttgatt tttaaaacaagagactcagggaaagtactaaa ccaaaatctctgattttactttgcgttttctg tagtttttgtttactgagatgcttttgtaaa ggaaaataatactgtgacagtttagtaattct acagattcttaatatttctccatcatggcctt ttacttcacaattttctgaagtctgaattcaa ttacaattttttttttttaccaatttaatctc aaatgttgttaactgctttaaattcatatac gtagagtattataaactgcagagatgaaaaat gtgttttcacgggatttatattgtgaactaaa ctaagcctacttttgtgact |
| 83 | 209839_at | DNM3 | gagacttctcacttctggttggaggtttcaca tatggctcaactcaagtcattaatctcttttt aatttttactcttgaattccttaaacttcgct cattatgaaatgttttaaaattactgacaaaaa ttactctgtctaaccacttgccttgtctgcta ccagtttgttaaaaattattcccccaaccag taattccaccagtactacttgatttgtgttat atttcctatgtacatgtacagcctttgttttg cttgcttgtctatttttacttttccctttttg ggtcaaattttctttgctttgtttgaagaa ggaatatacagaagtaaaatcttgtcttctct gctgattctttaattaatatgagccggatact ttccactgtcttcttggcacttcaggatttc ttaatgctgatatatggactcttagaatggaa ttttttgaagaaaaatctcaaagcctgtatcgt tct |
| 84 | 209859_at | TRIM9 | ataggttaccttgaaattcattagtttgtca taaggttttaggaaaggtaggacccggaaaga agttctaattagttgtctaaatatttttcagt gagccaagaaattcaccatgaaaaaacaagaa taacaaatagaagggaagagataggatgggaa agctaacaaattaaagttttggcaaaaaggaa tatatgtaaatagctaatttatttacttttgtg cttacttttatttagattatttctatcagttac aatctttttctagttaagtgtacctaatttat ggaatgggtgctatcctgtttatgtgtgtcttt ggttttttcttggctacagaaaaactgttgcag ggcaacactagtttgatatttgatttactctc caatgagactcaatggctgggccgtggtagac tcatagttcctcttgttcttattaaattcat cctgctaattagatttctagtgacttgtaaca tgtagtttacactgaattgcaattacagatgc atacaactactatacta |
| 85 | 210016_at | LOC100 134306 /// MYT1L | ataacagcatatgcatttccccaccgcgttgt gctgtcagcttctttgccaatatagtaatgct tttagtagagtactagatagtacagttttgg ttcttattgttatcacctatgtacaatggaa agggattttaagcacaaacctgctgctcatct aacgttggtacataatctcaaatcaaaagtta tctgtgactattatagggatcacaaaagtg tcacatattagaatgctgacctttcatatgga ttattgtgagtcatcagagtttattataactt attgttcatattcatttctaagttaatttaag taatcatttattaagacagaattttgtataaa ctatttattgtgctctctgtggaactgaagtt tgatttattttttgtactacacggcatgggttt gttgacacttaatttgctataaatgtgtgg aatacaagttgctgtgatacttcatttttaa attgtgaacttttgtacaaattttgtcatgctg gatgttaacacat |
| 86 | 210247_at | SYN2 | tcatgtcttattcttccctgtgaaaccaggat taatcgtggactcctggcagcttaacctagct cagttgcagtgctaagcatgccccgcccccat tcagtgatacctgtttgggaagtatatacttc cccaaaagtactcttggccctaagttttagga actttcccgacctggatcccttgtcataacct gtgttactgtttaaagcacacccacccaactt acaagatcttaggctgctgtggtggtgaagca ccttgagtctgctgatattcgggagaacaagg atctgcagtttcccctttctccctctgaag agtggttcttatgtgcaatctgcagtaacctt gaactccagagctgcactatagaggagaatgc atgccactatgacagcagtatgccaagctttg tgttcatctcctaata |
| 87 | 210302_s_at | MAB21L 2 | atttcgttttgcttttggttgcctgaatgttg tcaccaagtgaaaaattatttaactatatgt aaaatttctcttttaaaaaaaagtttttactga tgttaaacgttctcagtgccaatgtcagactg tgctcctccctctcctgaacctctaccctcac cctgagctgtcttgttgaaaacagt |
| 88 | 210315_at | SYN2 | tattctcgactgtaatggcattgcagtagggc caaaacaagtccaagcttcttaaaatgattgg tggttaattttcaaagcagaaattttaagcc aaaaacaaacgaaagtgaaagcggggagggaa aacagaccctcccactggtgccgttgctgcgt tctttcaatgctgactggactgtgttttcct atgcagtgtcagctcctcctctgtctggttgttta cctgttcctgttcgtgcttgtaatgctcactt atgttttctctgtataacttgtgattccaggg ctgtttgtcaacagtatacaaaagaattgtgc ctctcccaagtccagtgtgactttatcttctg ggtggtttg |
| 89 | 210455_at | C10orf 28 | gaaatcagcgaggctcaagttccaagcaaacc attccaaaatgtggaattctgtgacttcagta ggcatgaacctgatggggaagcattgaagac aaagatttggaaggcagaattgaaactgatac caaggttttggagatactatatgagtttccta gagttttagttctgtcatgaaacctgagaat atgattgtaccaacaaagcatgcaaacatcag atggaatattgaatcccagcagcggaggcatc accactacttctgttcctggaagtccagatgg tgtctttgatcaaacttgcgtagattttgaag ttgagagtgtaggtggtatagccaatagtaca ggtttcatcttagatcaaaagatacagattcc attcctgcaactatgggtcacatctctctgtc agagagcacaaatgacactgttagtccagtaa tgattagaaatgtgagaagaatgacagcact gctgatgagttacatgtaaagcacgaacctcc tgatacag |
| 90 | 210758_at | PSIP1 | gggctcaaagcattaatccagttactgaaaag agaatacaagtggagcaaacaagagatgaaga tcttgatacagactcattggactgaatttccc ccttccccccatgatggaagaatgttcagatt ctaaattgaggacttcattattaatggcatta ctgtgttatgattaacaaatttcttgtaaggt acacactacatactaaggtcggccatcattcc gttttttttttttttttttttttaaccaagc ttaaatgaagcttaaaatgaagctttgtgtt tgaaagtaataacaagctcagacgaagatggt ggttgtacattattcatctagaaaatataaaa attcattttgttttgaagctagttattaaact ggaatagcagttatatccctgagaatgggcc ctt |
| 91 | 210918_at | — | gctgctgtttttcttctaactgcagggaaaatg ctgtctaaaagaaaataataaatttgtatctg ctgagttctcttagcataaggcaccaacaaaa caaccttcaggaagggagaagaaaccatcctc ccactcatccttcagaggatttagataaagtg aaggagaagatcgttctccagctcctcctgga tttacgccggcatcagggcaggcttgttactg ctggatccattgtctgctcaaggttacttatt ccactaagacgtacatcctaccacggaccacg gctttgtagctagccaggctctgagtgtgtgt gtagatgaaccatttctctctccagtaaatga |

TABLE 11-continued

Probe set target sequences for 172 genes

| SEQ ID NO: | Probe Set ID | Gene Symbol | Target Sequence |
|---|---|---|---|
| | | | atgacagtctttctagggctcttgtcttctgctgggaggcag |
| 92 | 211204_at | ME1 | agtcactctcccagatggacggactctgtttcctggccaaggcaacaattcctacgtgttccctggagttgctcttggggtggtggcctgcggactgagacacatcgatgataaggtcttcctcaccactgctgaggtcatatctcagcaagtgtcagataaaacacctgcaagaaggccggctctatcctcctttgaataccattcgagacgtttcgttgaaaattgcagtaaagatttgtgcaagatgcatacaaagaaaagatggccactgtttatcctgaaccccaaaacaaagaagaatttgtctcctcccagatgtacagcactaattatgaccagatcctacctgattgttatccgtggcctgcagaagtccagaaaatacagaccaaagtcaaccagtaacgcaacagcta |
| 93 | 211264_at | GAD2 | gttccacttctctaggtagacaattaagttgtcacaaactgtgtgaatgtatttgtagtttgttccaaagtaaatctatttctatattgtggtgtcaaagtagagtttaaaaattaaacaaaaaagacattgctcctttttaaagtcctttcttaagtttagaataccctctaagaattcgtgacaaaaggctatgttctaatcaataaggaaaagcttaaaattgttataaatacttcccttacttttaatatagtgtgcaaagcaaactttattttcacttcagactagtaggactgaatagtgccaaattgcccctgaatcataaaaggttctttggggtgcagtaaaaaggacaaagtaaatataaaatatgttgacaataaaaaactcttgcctttttcatagtattagaaaaaatttctaatttacctatagcaacatttcaaat |
| 94 | 211341_at | LOC1001313177 /// POU4F1 | gcatttgaaactgagcactaaactgggctagctttttcggtagaccgttttgtgagtcagtgcgattttcacagtctactgcctgtttccactgaaaacattttgtcatattcttgtattcaaagaaaacaggaaaaaagttattgtaaatattttatttaatgcacacattcacacagtggtaacagactgccagtgttcatcctgaaatgtctcacggattgatctacctgtctatgtatgtctgctgagctttctccttggttatgttttttctcttttacctttctcctcccttacttctatcagaaccaattctatgcgccaaatacaacagggggatgtgtcccagtacacttacaaaataaaacataactgaaagaagagcagttttatgatttgggtgcgttttttgtgtttatactgggcaggtcctg |
| 95 | 211516_at | IL5RA | ggcagccttccttgtgatcaaaaaaggtaatccagaaacgtaccgttcactcgtgggtcttaaaatggtttcatatctctattgtgactaatttctctcggtctactgcctttcaatcaggaatagatttgccatgaagccagtgaagtttttaagtgtctaggcttctcattagtgccaactctcctagacctggtgcctgttttttttccaagttttgttttctacttctatcattttttaaattaaacttttattttgaaataattatcacactcacaagctgtgggaagaaataatagagatcctgtgtctcttttcatccagttttcctcaagggtaacatct |
| 96 | 211772_x_at | CHRNA3 | tgctcaacgtgcactacagaaccccgacgacacacacaatgccctcatgggtgaagactgtattcttgaacctgctccccagggtcatgttcatgaccaggccaacaagcaacgagggcaacgctcagaagctgcgagggccctctacggtgccgagctctcaaatctgaattgcttcagccgcgcagagtccaaaggctgcaaggagggctaccctgccaggacgggatgtggttactgccaccaccgcaggataaaattccaatttcagtgctaacctcacgagaagctctagttctgaatctgttgatgctgtgctgtccctctctgctttgtcaccagaaatcaaagaagccatccaaagtgtcaagtatattgctgaaaatatgaaagcacaaaatgaagcaaagag |

TABLE 11-continued

Probe set target sequences for 172 genes

| SEQ ID NO: | Probe Set ID | Gene Symbol | Target Sequence |
|---|---|---|---|
| | | | gaacaaaaagcccaagagatccaacaattgaaacgaaaagaaaagtccacagaaacatccgatcaagaacctgggctgtgaatttccaatcttcaacaacctgtt |
| 97 | 212359_s_at | KIAA0913 | cagcgctgccagcaggcatacatgcagtacatccaccaccgcttgattcacctgactcctgcggactacgacgactttgtgaatgcgatccggagtgcccgcagcgccttctgcctgacgcccatgggcatgatgcagttcaacgacatcctacagaacctcaagcgcagcaaacagacaaggagctgtggcagcgggtctcactcgagatggccaccttctcccctgagtctttcacccttagggtcctatacagggacccaggcctgtggctatggggcccctcacacaggggggagtgaaacttggctggacagatcatcctcactcagttccctggtagcacagactgacagctgctcttgggctatagcttggggccaagatgtctcacaccctagaagcctagggctggggagacagccctgtctgggaggggcgttggtggcctctggtatttattt |
| 98 | 212528_at | — | gtcactcatttccttgaacagcaccccctttatactagcagccattttgtgccattgcctgtgcctaggggtttgtggggagagcgagggatcactgagcagttttcccagagctccatgggaaggcaagctctccctcccaatgggagcccactgtcactaactgtaaactcaggctcaggcttcaactgcctaccccccatcctcatatttctctgtctgtcccagcacccctcaggagcattcattgtggccgctaactccgcctggatgtgaacaggcaagcacagtgggaaatgagtcacgtacttgtattgcacagtggacacctctagaggtccattggtttaaagggatagggaaggaggagggatgagaccatcacccccctcccagaagtaaatctagtatctgagttttcttat |
| 99 | 212531_at | LCN2 | caagagctacaatgtcacctccgtcctgtttaggaaaaagaagtgtgactactggattcaggactttgttccaggttgccagcccggcgagttcacgctgggcaacattaagagttaccctggattaacgagttacctcgtccgagtggtgagcaccaactacaaccagcatgctatggtgttcttcaagaaagtttctcaaaacagggagtacttcaagatcacctctacgggagaaccaaggagctgacttcggaactaaaggagaacttcatccgcttctccaaatctctgggcctccctgaaaaaccacatcgtctcccttgtcccaatcgaccagtgtatcgacggctgagtgcacaggtgccgccagntgccgcaccagcccgaacaccattgaggga |
| 100 | 213197_at | ASTN1 | tttcccctttggaagacactattgatctcaacctgctgacttttcctaatgcttacctgaaggaacccatcctggctagaaagggtgatggtactggaccggtattcaaccttgagttttcaagctgccaaacaggtcttaagggaggtgcttatatcccaccaacactctcccagctcccatgtccccaagacctctggagtttcctcttgaatgtacatgacacactggtaatagcattagacttttaattgagtgtgcaatcgttttccatggagtttggtccgttcattattttttagttaactacacttcttgatatctcaaatgttctattaaaaaaactgagtatgaagaaaaacactttactactgcagaa |
| 101 | 213260_at | FOXC1 | tcccccatttacaatccttcatgtattacatagaaggattgcttttttaaaaatatactgcgggttgaaagggatatttaatctttgngaaactattttagaaaatatgtttgtagaacaattttttgaaaaagatttaaagcaataacaagaaggaaggcgagaggcagaacattttggctactgagggtggtttcttttttaaaccatttttttcttgttaatttacagttaaacctaggggacaatccggattggccctccccttttgtaaataacccaggaaatgtaataaattcattatcttagggtgatctgccctgccaatcagactttggggagatggcgatt |

TABLE 11-continued

Probe set target sequences for 172 genes

| SEQ ID NO: | Probe Set ID | Gene Symbol | Target Sequence |
|---|---|---|---|
| | | | tgattacagacgttcggggggggtgggggggctt gcagtttgttttggagataatacagtttcctg ctatctgccgctcctatctagaggcaacactt aagcagtaattgctgttgcttgttgtca |
| 102 | 213458_at | FAM149 B1 | agcctgaaacaggaactcacatgagactcagg gccaccaggaaatgcttaaaatacatactctt tcccaaaagcaaatctataattctgtttcaat tttatgaatatatgaatagacaaaatgaatcg aattacataactatgtcattcattaaatggca acaatgctgacagcaagcagtagatcctctga ttccaattacctttgttttttaccccaattct atttgctagaggtagtaagtactctggcactc ataaatcacatgatgataaaaaggaacatgag gccgggtatggtggctcacaactgtaatcccc ataccttggg |
| 103 | 213482_at | DOCK3 | tatgggtcagttacagcagccctcacctcaaa gggctggcctgcttctcagcctacattcattt gcaagctcaatctctggaccatctggtgttc acaggtgttagagggtaggggttaggggcta gttttggatttgattcataggtaggagggctt agattttaaggcacttctgaaagtcaatccct ggacaaggcagtcatcacataagaacagctac cttctccacttggtggcacaagaggtagggag gggagtatgggttcatttgncttcgcattatg caaggtgaaaccgtttgttttccctctccatt ttccctaactaaatgaaaaggacacattctga aatcccttttgttggagaataagtcagtctga gggaaatgggaggccagagatgagaaccctt tgaaaagattgtaaaatactgattttcattct ttcaagcttatttgtaaatacctatttgaatg ctgtgtatttgtacaggaattgagcaaaaaaa tgtatagagtgtgatgtccaattggtattcag cactat |
| 104 | 213603_s_at | RAC2 | gagcttcgttgatggtctttctgtactggag gcctcctgaggcnnnnnnagccccaggaccca ttaagccaccccgtgttcctgccgtcagtgc caactnnnnnatgctgaagcatctaccccgttc actccagtcccacccacgcctgactccccctc tggaaactgcaggccagatggttgctgccaca acttgtgtaccttcagggatgggctcttact ccctcctgaggccagctgtctaatatcgatg gtcctgcttgccagagagttcctctaccagc aaaaatgagtgtctcagaagtgtgctcctctg gcctcagttctcctcttttggaacaacataaa acaaatttaatttttctacgcctctggggatat ctgctcagcaatggaaaatctgggttcaacc agccctgccattcttaagactttctgctcc actcacaggatcctgagctgcacttacctgtg agagtcttcaaacttttaaaccttgccagtca ggacttttgctattgcaaatagaaaacccaac tcaacctgctt |
| 105 | 213917_at | PAX8 | ctgcctggttaccgtggcgatgtgcttaatgc agcgttgaaaatacagaatactgactcctctg tccctcctggccccggactccctccctccctc ccttcctcttctggagcgtgaaatgagattgg tcaagataaaaaggaaaagattcggttattt ttttaagagtgtggataatgggcctctcaat caaaatcccagtctccagtcggttcccccat tcccttccaaccctccaccttcccctgccg cctgcttagaggaggaggaagaaacataaagc acaaggcttttctcttaattatgaatcattcc ctgagggcaggcccagggcaagggttcctgg gggccagagtctgacctgtgaggtagctagaa ggcttgagcctctcatcaaagtcc |
| 106 | 214457_at | HOXA2 | cttttgcaggactttagcgtttctccacagat tcctgcctgcagctttcagatgcagtttcacc cagttgccaggttccctcgacagtcccgtag atatttcagctgacagcttagactttttaca gacacactcaccacaatcgacttgcagcatct |

TABLE 11-continued

Probe set target sequences for 172 genes

| SEQ ID NO: | Probe Set ID | Gene Symbol | Target Sequence |
|---|---|---|---|
| | | | gaattactaaaaacattaaagcaaaacaaagc atcaccaaacaaaaactcctttgaccaggtgg ttttgccttctttattgggagtttatttt tattttcttcttgacctaccccttccctcctt taagtgttgaggattttctgtttagtgattcc ctgacccagtttcaaacagagccatcttttac agattattttggagttttagttgttttaaacc taactcaacaacccttatgtgattcctgaga gc |
| 107 | 214608_s_at | EYA1 | gtcaccctgaggaaggttcattgccattgtca tcaccatggaaacaacgttcctctccacctgc attatgtactacatgacaggcatcaatctggg gaaataataaaattatcacctttgtcagacca taagagtttctccaaaagtggtcagtttggct gggcaatatttctctcatctaacaaaacacaa tccattgtcatgaaattacccttaggatgagt cttctttaatcaatcatatattgggcggaaaa aacaccagcttgacccgaagtagttgaagag ctacttcattcttttctgaagttgtgtgttgc tgctagaaatagtcatttgtgaattatccaaa ttgtttaaattcacaattgaattagttttttc ttccttttgcttgaagcaaacagttgacaat ttttaacttttcattttatgttttttgtactc tgcagactgaaaagacaaagtttatcttggcc ttactgtataaaggtgtgctgtgtccaccgtt gtgtacaga |
| 108 | 214665_s_at | CHP | gaggtctggcactagtagcacaacctaaggtg gcattacagatctttgagcgagccacagcaac ttttctgccaagtcagcttagttagacttc agtgaatcaggntattgctatcctaatgtatg tctctatgagtgtataatagccacanantctgc ccttggttganttctgactcattgcttgctt gcttgtttccttgctttggaaaactatnnaag attgctaaaaaataccactgcaaagtgatgga aaagggtggagaacaggggagtagccaggctg gatggctcaaatataaatgaatgaggaattct ttatgaagtatcagtcagattttatgattaag tgatgtaataataggaattatgtaaaagggaag aatgtctgatactgatctattagagaggtact ttagaggcttcttgattggcataaagttccta aggttatagattttcccccctttttggctgtat agcaaagtgttttaatccacggttgtgcctta ttgttccattaaaa |
| 109 | 214822_at | FAM5B | caatgggagggtcggagctcttccttcccct ctgtggagtcacttttgtattctttttaacca gatttcttaaaatgttgttgttttgtgaatcc tgacattggttcttacttttgtatgctgcctc ctctgtgccctcccagacgctgactgggaaac acaagaagtacaaccaacaggaaccagcgcca agggcaggcagcggggcctccttgctccctcc ttactccccctctgctgcctcctccccccac caagtttcagggccctggattgttcccagttc ccattgtggtcccttcagagctcctttccaac agcatctctctgtcgaagaaagaagctctgtc aagttagagagagacaatgtgtaggaaatgtt ctttttttaaaaaaaaataacaaaaacaaaaca aaactatnnannntgtgattgttttccttgtt aatctgctccaaccacctgaacatctaagta |
| 110 | 215102_at | DPY19L 1P1 | gagacgggagtttacccccgatcacagaaacca taccaactgaaagacaaatcagcatcttgctg gacgaccccctcacagagctcctagatccttga agtgtgaacttcagcagctgagagagatgggg tctcactatgttgccaggctggtcttgaact cctggactcaagcaatcctctcacctcagcct cccaaagtgctgggattacagatttttataat attgttgatcttttgaaaaaccaactgttggg cttcatttttttttattgtgtaatactaccttta gaggacagcagttcctaatacctactttatt atgagtctctgccattttataaagaactgtgga cagcacagggaatggggaagaaaactctggt |

TABLE 11-continued

Probe set target sequences for 172 genes

| SEQ ID NO: | Probe Set ID | Gene Symbol | Target Sequence |
|---|---|---|---|
| | | | gcagcttgaatcttggtagcaaaacagtgact tcatcagaaaattttgtcactctctattagat ataatgagtttgaccatttggaatttggaat ttttcaaatgaatatgacaaaaatttaaaaaa ctcttgtattactatgtgataacacagatctt tacaacttta |
| 111 | 215180_at | — | aagccttcaccagatggtcaagcagatgctgg tgccatgcccttgancntcncnccaccatccc ccacctagccactatatgggttgttagatatt ttgaccacctcctcttcnctcactccactatt caactcactgcatcatcaatgtacttattaca aacctgtcacaagccaggtcttatgctaggtg ctcctctcaacaggttcttgagctggcagggg agagagagacattcaaacaccaaggattaata taccattacaggtttaaagacagaggcctata agggtccctggcagtgccatgaggtagggc atggtcggctgtacctgtagaggtgtctaaag ggaggcttgcaagctgcccttgaaggacgag cagaaaattgtacatgaggacaagtaggaaag gaattccaggaggagggatcagcatgtgca |
| 112 | 215289_at | HLA-DRB1 /// HLA-DRB2 /// HLA-DRB3 /// HLA-DRB5 /// LOC100 133484 /// LOC100 133661 /// LOC100 133811 /// LOC730 415 /// RNASE2 /// ZNF749 | ggactaaatcgagccttattatacatcagcag tctcacactggagaaagtccttttaagttaag gganngnnnnnnannntnnancaaatgtaata ctggtcagcgccaaaaaactcacactggagaa aggtcttatgagtgtggtgaatccagcaaagt gtttaaatacaactccagcctcattaaacatc agataattcatactggaaaaaggccttagtgg agtgaatgcaggaaagtcaccaaaactgtcac ctcattcagcaccaaaaggttcacatcggacc aagaacctattaatatatgtaaatctaatgtt gaaagagttcagatgtgaaatctgcgaggattt cctgctgggaactacatta |
| 113 | 215356_at | TDRD12 | aattgggcaggctcttgggaagtagaaagttc tggtgttttgctggtgaaggttttgactgtg gagctcttctaacacccatatcagtgtgctgtt tctctgcatgtggctgctgccctgttggtgga gctctgggggcagagaccaggccgccgtccag tggcgcnccgtgcgcaccagctgcctgctgtt tacaccaggtgcgcgcctcttttcataca gcacagcaaatgataatagctagtgacaatgt gtttcctgtgcactcgtgaaaatgcagggagg acaactgcatgcttagatctgttctttttc agacattcaaatgttctaatatctgaagctaa cattttgtaggatataggatgctgattatgtg aacaattagtcattggttttctgtactgctat gaatatgtctgatttcaagttttggtcaaata tctaaaatgcaaggtgaaagtgcctttgtctc tatgcttctaaaatcgctcatgcttagttgtg gtatggatgtcttccgcagtg |
| 114 | 215476_at | — | cttggtaagccttgcctgtagcggctccgctg ccgagtgctttgacaccaggcgctcccagagc tctgcccccactgccaagcggcagctgctccg gagggcacgggggctggattggctgtggct tctccagctctgcacaagagccccccttccct ggccctgctgcagcatgactgcctcctggctc gtgtcacccactctgtctctgtctctcttcat acgtttccagctgagctgggatccatagtctg tttccctctccacgaccaatctctatttatcttc tctggaacttcttgtaatgccgggagtgcaga gcttacaagttggggcaggaagctttagaagc ccaggnagccctgagaggctctttccttgtaa gtgggtctctccccaggagcctcttggaatat ttagcagggacttttacccatgctgggtctag agaccctcccgcccctctgtttcctgccctcc tacttagactgggatctggtttccctcagctg gttcccttgctagcgtgtgactctgtgtgtct |
| 115 | 215705_at | PPP5C | gttcacagcagtgggtaggcccagcagtggtt cttgacatcacacgatgaggcgngcatctccc gtcatccaggggagaccagaggaccccttgtctc actcccagttggctntttagtcacagccccgct ttgtctttgacatggacgtttgtgatgatcac gttcctcccgctcccgtgtntgaagagtgct ccctgactggtgccgtctcctccctgtcgggg tctggctgggttctccanagggagtgctgcgg aggggacacagcanaggccccatgctcgtgat gtatgttgcagatcattttccccccattctgtc cttttttgttaaattgtggtaaaaagcacata acataaaactgtaccncccttaaccatttgaaag tatatatcccagactgtctttttatctttgac ttcacttgtggtttgttgcc |
| 116 | 215715_at | SLC6A2 | tcccctggaagttgtcctttctgatcctctct tcttttttcccattacaaatgatttcgtgactg tagttttgttcaccttctgtgcatctggcct gggggctgttagctcagaggagaggagcaaac aggaaaatgacttctgttctgtccccgctgtt ttgggggaagtctctccacttttgggatcctg ctgaagctaggttcatgaggtcggaaatccc accacatttgcctagacttttgggcacaggagt tcttagtccaccaaatcaga |
| 117 | 215850_s_at | NDUFA5 | cattttctctaactttatctcctatgcatttc cttatgtgtcctgtacagcagtatattccaaa atccccagtggatgtctgaaaaccacatatag taccaaactgtatatatgctatgttttgttc atacatacctataataaagtttaattatgaa ttaggcacaataagagataagcaggctggacg tgctggctcacgcctgtaatcccagcactttg ggaggctgaggcgggtggattgctttagccca ggagtttaagaccagcctggccaacatggcaa aaccccgtctctataaaaaatgtggaaattaa tcaggtgtggt |
| 118 | 215944_at | — | gagatgaccgaaaacttcaaccctgcagtca gcaatggcaacagaaagggcccaattctcca cgacaatgcatgatcgcacattacacaactaa agcttcaaaagttgaactaacgagctacgaa gttttgcctcatccaccatattcacctgacct cccgccaaccgactaccacttcttcaatcatc tcgacaacttttttgcaaggaaaacacttccac aaccagtagaatgcaaaaagtgctttccaaga gttcactgaatcctgaagcacggattttttatg ctacaggaataaacaaacttattttttcattgg taaaaatgtgttgattgtaatggatcctattt tgattaatgaagatgtgtttgagcctagttat aatgatttaaaattcacgatccaaaaccgcaa ttacttttgcatcagcctaatatgaggaagta atagttgaacagaataattcttttcctggaagt ct |
| 119 | 215953_at | DKFZP5 64C196 | ttggtttggtctggtttggctacctgattcct gctgtcttttttctacgccaggtgaagaggcac tttcaagatcctttctctgagacctgcacaat aagctataccaatgttcagttgaaacatcag gtataagtttagcggaaacgaaagtacaacct gctttgaaataaattccaaggacagattgtca ttaacgaaatagaaagtggactatgcccctca tgctgccagcgcctggtatgatgcggcgtgac |

TABLE 11-continued

Probe set target sequences for 172 genes

| SEQ ID NO: | Probe Set ID | Gene Symbol | Target Sequence |
|---|---|---|---|
| | | | acgcagcgcttgcggcagtacaatgccccaa<br>tcacccgccccgccccgacgcgccgcccactc<br>acggcaaagagagcgcacctagtgagggattat<br>tctcatttccgcggtggggttctgcttttctt<br>tctaccatgagcgcccaaggatagacactcct<br>actacctattacctcaaatagcctacatttct<br>ttccgaa |
| 120 | 215973_at | HCG4P6 | agaacactgagcgaggctctgtagatggatgt<br>aataaaaatctataaaacaatgtgtttaaacc<br>taagaattctactgcttttccaattccttccct<br>ctgctcctttttcctaacctcctgcttctcag<br>cccttccctctgtcccttttcancccctcaggcc<br>ctcctctcccttagtccccaccaccctgtca<br>cttctaaatttgtggctctagcattgtcccatt<br>acctgctangtgactgttctctccacagtggt<br>cctgctcctgtgagtcagagtgtgtcatttcc<br>tcacctaaaaacactccagtggctccacctcgg<br>tcttgtgaagcttctagaatgtcaggcacgtg<br>agcatatgagggcatacctggttcatcttagg<br>cactaaattnnnnttgttgactgaatgaatg<br>aaatatgaatgtattaaattgcatcacagaaa<br>gttataaaatgtaaaacactgaaaaattaaga<br>aatattttatnttatgtaactagtgtgcatat<br>caattcattccgagtctgttgagcctgtgtat |
| 121 | 216050_at | — | aatgattcaactcatgtgatccagtgttacat<br>tcagtgtggtaatgaagaacagtcaaaacagg<br>cttttgaagaattgggagataatttggttgaa<br>ttaagtaaagccaaatactccagaaatatttt<br>aaagaaatgtctcacgttgtgaacatgtaccc<br>tagaacttaaagtataataaaaaaaaaaaaa<br>nnggaaagtatcttgcacaagctcacgtagct<br>ggtaagttacatagttgggatctgaattcagt<br>tgtgggcttcatgcctgagcttttaactactac<br>tactaaactgagaaggcacttgcttgagtaaa<br>ttatgtcatcctcttaat |
| 122 | 216066_at | ABCA1 | gatgtggcatgtgatgacattgcacatggnca<br>gttaantgngccaagaagngcagcagtagcag<br>caacnggagatgcaaagcccaacatgatgggg<br>agagaaantnttctttcaatatgtgcttctgt<br>accaaaagtggaatttcacgagagacatattt<br>tggaacattttttcctttttgtgtgtgcgtgagt<br>gtttccctgtttccagccaaggtgtattgtgag<br>tttctcctgggcctccttcagaatctgggtgc<br>tctggaaagcagtgttttggcaacatggggaa<br>agtaggcagtgtgggagggtcagctgggtct<br>gggtttgaatattgcatttgaatatttttacca<br>gcattgatgtcggataaattatttagtccctg<br>taagcctcagtttttntcttnttctacatacac<br>ataatatatttgactctttgttgtgat |
| 123 | 216240_at | PVT1 | tttcctaactttctgatcccttggaggtgata<br>atcaaatattctagtctgaggcattgggatac<br>atggtgctaggttctgagactctgcgtcaggc<br>ctgaaccctgcagtttggaggtgggtggga<br>gaatgtnccctggggaacatgcctagacacg<br>ggggacaacagttgccctcatggggaggtacc<br>tgtttactcgctgttatgggaccgctttcaca<br>aaaccactgcagttgggttcctgctgaa<br>tatcaggcctggtgtctctagactcattattn<br>cccccaccaccccctatgttagttcatctcg<br>agccacatttttattgccataatccaggcctg<br>gacaggccaagatcttttaacaatttttaatta<br>ctgaaaataataactgcattttttttnaaagc<br>ccaacttttnggtanagtcagcccaaaataca<br>gtctttgtgttgccatctgggaactggatttg<br>gaatgttcttccatgagactgcagagcag |
| 124 | 216881_X_at | PRB1 /// PRB4 /// PRH1 /// PRH2 /// PRR4 | ccacctcctccaggaaagccagaaagaccacc<br>cccacaaggaggtaaccagtcccaaggtcccc<br>cacctcatccaggaaagccacaaggaccaccc<br>ccacaggaaggaaacaagtcccgaagtgcccg<br>atctcctccaggaaagccacaaggaccaccccc<br>aacaagaaggcaacaagcctcaaggtccccca<br>cctcctggaaagccacaaggcccacccccagc<br>aggaggcaatcccagcagcctcaggcacctc<br>ctgctggaaagcccaggggccacctccacctc<br>cctcaagggggcaggccacccagacctgccca<br>gggacaacagcctccccagtaatctaggattc<br>aatgacaggaagtgaataagaagatatcagtg<br>aattcaaataattcaattgctacaaatgccgt<br>gacattggaacaaggtcatcatagctctaac |
| 125 | 216989_at | SPAM1 | gtttgatgtctattatctcacttcatcctcac<br>caggaccccatccgagcctaatttcagttga<br>cagtaactattggatccccaggaatatgtttg<br>catatttggggagaaaatactattggagggga<br>acagaaatgctactaagggtctcactgtgtca<br>cccaggctggagtccatcaaagctcactgcag<br>ccttaaccttctgtgctcaagggatcctccca<br>cttaagcctcctgagtagctggctaactacaggc<br>atatgccaccgagcctggctaatctttgattt<br>ttttgtacagattgtgtctccttatgttgctc<br>aggctggactcaaacttctggtctcaagcgat<br>ctttccatcttagcttcccaaattgttggaat<br>tatgacatgagccagtgtgcttggcctgatt<br>tttttttttttttttaatgagaaaaacgttcct<br>taagaaaagtttcattgtaagacgaggacttg<br>ctatgttgccagtttggtcttgaactcggtct<br>caagtgattctcctgcctttgggttcccaaagc<br>gtttgggccggcagatgt |
| 126 | 217004_s_at | MCF2 | ctgaattggaacacaccagcactgtggtggag<br>gtctgtgaggcaatttgcgtcagttcaggcaga<br>agcaaatacagtttggactgaggcatcacaat<br>ctgcagaaatctctgaagaacctgcggaatgg<br>tcaagcaactatttctaccctacttatgatga<br>aaatgaagaagaaaataggcccctcatgagac<br>ctgtgtcggagatggctctcctatattgatga<br>agctactatgtcaaatggcaagtagctctttc<br>ctgcctgcttctcagctcatttggaaaaatac<br>tgcgcaaaagacattgagctcaaatgatgcag<br>atgtgtttttcaggttaatgacacgcaaaga<br>aaccacagcacatacttcttttctttcattta<br>ataaagcttttaattatggtacgctgtcttt<br>taaaatcatgtatttaatgtgtcagatattgt<br>gcttgaaagattctcatctcagaatactttg<br>gact |
| 127 | 217253_at | SH3BP2 | gagtgtcttgactattctggctctttgtattt<br>tcatgtaaggtttttctcccatataagttta<br>aaatcagcttgtcaattccaacaacaatgatg<br>cacttgatagtttgggaatttattatagctat<br>caatcagtttgggaaaattgacgtctttaca<br>atattgagttttctgattcatgaacatgattt<br>acctctcttcccatgggggtctcctttaaggt<br>ttaccaataggatttatatttgggccattg<br>nggtcttgcttatcttaagtnnnnnnnnnnnn<br>nnnaaatctcttgaccncatgatctgcccgc<br>ttgtcctcccaaagtgctgggattacaggcgt<br>gagccaccgcacctggcctgcaatacagtatt<br>gttaaccgtcttcaccatgttgtacgttagag<br>ctccagaaattatttancatgcataactgaaa<br>ctttatactctttgaacaccacctccccattt<br>ccctctcccggcagccatttgtgcctctcggt<br>tctctttattagcttccattttgtgggtcagt |
| 128 | 217995_at | SQRDL | tacgtcaaagaccgctgctgcagtagctgccc<br>agtcaggaatacttgataggacaatttctgta<br>attatgaagaatcaaacaccaacaaagaagta<br>tgtctacacatcatgtccactggtgacaagg<br>gctacaaccgtgtgattcttgctgagtttgac<br>tacaaagcagagcgctagaaaccttcccctt<br>tgatcaaagcaaagagcgcctttccatgtatc<br>tcatgaaagctgacctgatgcctttcctgtat<br>tggaatatgatgctaaggggttactggggagg |

TABLE 11-continued

Probe set target sequences for 172 genes

| SEQ ID NO: | Probe Set ID | Gene Symbol | Target Sequence |
|---|---|---|---|
| | | | accagcgtttctgcgcaagttgtttcatctag gtatgagttaaggatggctcagcacttgctca tcttggatggcttctgggccaaaactgcagtc actgaatgaccaagagcagcacgaaggacttg gaacctatccttgtaaagagttccttgatggg taatggtgaccaaatgcctccctttcagtac ctttgaacagcaaccatgtgggctactcatga tgggcttgat |
| 129 | 218768_at | NUP107 | ttggatgccctaactgctgatgtgaaggagaa aatgtataacgtcttgttgtttgttgatggag ggtggatggtggatgttagagaggatgccaaa gaagaccatgaaagaacacatcaaatggtctt actgagaaagctttgtctgccaatgttgtgtt ttctgcttcatacgatattgctgagtactggt cagtatcaggaatgcctacagttagcagatat ggtatcctctgagcgccacaaactgtacctgg tattttctaaggaagagctaaggaagttgctg cagaagctcagagagtcctctctctaatgctcct agaccagggacttgacccattagggtatgaaa ttcagttatagtttaatctttgtaatctcact aattttcatgataaatgaagttttaataaaa tatacttgttattagtaattttttcttttgca ttaccatgtaaaattttagacatttgaattttg tacttttcagaatattatcgtgacactttcaa catgtagggatatcagctgtttctctgtgtgct |
| 130 | 218881_s_at | FOSL2 | aggtcacagtatcctcgtttgaaagataatta agatcccccgtgtgagaaagcagtgacacattc acacagctgttccctcgcatgttatttcatga acatgacctgttttcgtgcactagacacacag agtggaacgacgtatgcttaaagtacatggg ccagtgggactggaagtgacctgtacaagtga tgcagaaaggagggtttcaaagaaaaaggatt ttgtttaaaatactttaaaaatgttatttcct gcatcccttggctgtgatgccctctcccgat ttcccaggggctctgggagggacccttctaag aagattgggcagttgggtttctggcttgagat gaatccaagcagcagaatgagccaggagtagc aggagatgggcaaagaaaactggggtgcactc agctctcacaggggtaatca |
| 131 | 218980_at | FHOD3 | gcacctcggagttgcagctgtgacactcatag gttactcccaggagtgtgtgacagaaggca agctcttgctggatgaaaccccctccaaggtggg gttggggagacttgatattcacatccaacagt ttgaaaagggagagctcaattcccagcgtcac cccatgcttgtgttgcctgctacgcattgac ttggatctccaggagtccctgcacataccctt ctccatcgtgtcagctgtgttttctcttgattc cgtgacacccggtttattagttcaaaagtgtg acaccttttctgggcaaggaacagccccttta aggagcaaatcacttcttgtcacagttattatg gtaatatgaggcaatctgattagcttcacaga ctgagtctccacaacacc |
| 132 | 219000_s_at | DSCC1 | tcaagtgagtgagttcccctctacttttagcc ttccacccaaactggaagcctctaggtgctat caattatttatatccatcgtttacatccatga aattggctgaataattactcctctgcctggcg tagacatgtcttgggaaaaaacgagttta taatcctataatgaagaatactggcacaggca atgctcactcgaaaacttcaagtaatttctag ttggttttggaatgcttgataaagttccttta cagctttattttcctgatttgttttggttag atcaaagttcaaattaattttaacttagctaa tgaactcatcaccaggacagttggagggggta ggccgaggttaaatggtccacgtttcaaaaat gttaat |
| 133 | 219171_s_at | ZNF236 | cttttgttcttgctgggttatttattttgatt ttagcattaaatgtcatctcaggatatctcta aaaggggttgtttaattcctaattgtatagaa agctagtttggtgaattgtattggttaattga ctgtttaaggccttaacaggtgaatctagagc ctacttttattttggttaaagaaaaagaaaat atcaataattcaattttgtgtctttctcaat ttattagcaaacacaagacattttatgtatta tttcgatttacttcctaattataaaagctgct ttttttgcagaacattccttgaaaatataaggt tttgaaaagacataattttacttgaatctttg tggggtacaggttgatctttatattttactgg ttgttttaaaaattctagaaaagagatttcta ggcctcatgtataaccagggttttgaggataa agaactgtattttttagaactatctcatcatag catatctgctttggaataactat |
| 134 | 219182_at | FLJ22167 | ttaccctcgtggctaagcaagtgtctgcagga gcagagatggctggaagggccctctgcacacg gaagatggcttgttcagcccattcacctcctg aggatgtgggcagtctcctccaagaacacatg gagctgcttcctgatcccaagcaggtcattgc cactggaaggacatggccccggtgatccatgc ttcatgccccacccagaaacacaccccctcagtg tgtgcctcagttactttggagatcagttgtc gttttagtgctcctttaggcttactaaaaca gttttggaaacaaagctattttgaagtattca agcagaggaattcccctaacactgacc |
| 135 | 219425_s_at | SULT4A1 | gaccatttttgcgagtgtagcccctgtttcactc ggatcaggttggcacggccgcctgcgtgtctg tccacctcatccctccgtgtatctgagggagt aaaggtgaggtctttattgcttcactgcctaa ttttctcacccacattcgctgaagcgatggag agtcgggggccagtagccagccaacccgtgg ggaccggggttgtctgtcatttatgtggctgg aaagcacccaaagtggtggtcaggagggtcgc tgctgtggaaggggtctccgttcttggtgctg tatttgaaacgggtgtagagagaagcttgtgt ttttgtttgtaatggggagaagcgttgacagg cagtggcacgtggcatcgcatggtgggctcgg cagcaccttgcctgtgtttctgtgagggaggc tgctttctgtgaatttctttatattttttcta tttttagtactgtatggatgttactgagcact acacatgatccttctgtgcttgcttg |
| 136 | 219520_s_at | WWC3 | aaggaaggccagagagccgcgcagttctctgc aggtgcagatgcaggcagtgggaggtggcctga gcaggcagaaggacaccaagcgccctatgttg cttgtcattcatgacgtggtcttggagcttct gactagttcagactgccacgccaaccccagaa aataccccacatgccagaaaagtgaagtccta ggtgtttccatctatgttttcaatctgtccatc taccaggcctcgcgataaaaacaaaacaaaaa aacgctgccaggttttagaagcagttctggtc tcaaaaccatcaggatcctgccaccagggttc ttttgaaatagtaccacatgtaaaagggaatt tggctttcacttcatctaatcactga |
| 137 | 219537_x_at | DLL3 | tcccggctacatgggagcgcggtgtgagttcc cagtgcaccccgcacggcgcaagcgccttcgcc gcggccccgccgggcctcaggcccggggaccc tcagcgctaccttttgcctccggctctgggac tgctcgtggccgcgggcgtggccggcgctgcg ctcttgctgttccacgtgccgcgccgtggcca ctcccaggatgctgggctctgcttgctggctg gaccccggagccgtcagtccacgcactcccg gatgcactcaacaacctaaggacgcaggaggg ttccgggatggtccgagctcgtcctgtagatt ggaatcgccctgaagatgtagaccctcaagggg attttatgtcatatctgctccttccatctacgc tcgggaggtagcgacgcccctttttccccccgc tacacaggcgcgtgggcagaggcagcac ctgcttttccctaccttcctcgattctgtc cgtgaaatgaattgggtagagtctctggaagg tttttaagcccattttcagttctaacttactt catcctattttgcatccc |

TABLE 11-continued

Probe set target sequences for 172 genes

| SEQ ID NO: | Probe Set ID | Gene Symbol | Target Sequence |
|---|---|---|---|
| 138 | 219617_at | C2orf34 | tgaagaaaaccttcattacccgcttctgcttatttttgaccaaacatggatagaagattaagcttctcaaagacgaagaaacgtatcaagtgcataggaatattttacaaaaacggaaatctgtaagggtataatcgcctgcctgcgccctttgcagcatttcacgtgtgggctatggactccacctgtcctcacccacgttattccccagctgccctctccagctccctccccgcctctttttacactctgcttgttgctcgtcctgccctaaacctttgtttgtcttttaaatgtgtataagctgcctgtctgtgacttgaatttgactggtgaacaaactaaatatttttccctgtaattgagacagaatttctttttgatgatacccatccctccttcattttttttttttttttggtctttgttctgttttggtggtgtagtttttaatcagtaaaccagcaaatatcatgattcttttcctggttagaaaatatataaagtgtatcttttttatctccctc |
| 139 | 219643_at | LRP1B | tattcacaagttttggagggcttttttgttcctctgatagacatgactgacttttagctgtcataatgtattaacctaacagatgaaatatgttaaatatgtggttgctctttatccctttgtacaagcattaaaaaaaactgctgttttataagaagacttttgttgtactatgtgcatgcatactacctatttctaaactttgccatattgaggcctttataaactattgatttatgtaatactagtgcaattttgcttgaacaatgttatgcatatcataaactttttcaggttcttgtttaagtacattttttaaatgaacagtattttcattttggttataatatagtcatttgcctatgtttc |
| 140 | 219704_at | YBX2 | ctcagcccctgtcaacagtggggaccccaccaccaccatcctggagtgattccaactcaactcaaaggacacccagagctgccatctggtatctgccagttttttccaaatgacctgtaccctacccagtaccctgctccccctttcccataatcatgacatcaaaacaccagcttttcacctttttccttgagactcaggaggaccaaagcagcagcctttgctttttcttttttcttccctccccttatcaaggttgaaggaagggagccatccttactgttcagagacagcaactcccctcccgtaactcaggctgaagaag |
| 141 | 219882_at | TTLL7 | gtttctgtgattcaggatcctcttgggagagtatattcaataaaagcccggaggtggtgactcctttgcagctccagtgttgccagcgcctagtggagctttgtaaacagtgcctgctagtggtttacaaatatgcaactgacaaaagaggatcactttcaggcattggtcctgactggggtaattccaggtatttactaccagggagcacccaattcttcttgagaacaccaacctacaacttgaagtacaattcacctggaatgactcgctccaatgtttttgtttacatccagatatgccatctgtgaaacagaagggaagatcgccattggttat |
| 142 | 219937_at | TRHDE | ggaggtcccaaatatgtggtctatcaccactgaattcatgtaatagataagaaaaaaattagaggtggatgtcttgtttttgtgtcatgaattactaaaatctcttagtagttgtggtatattttttgagtaaaattaccatttccagatttgagtttgaagggcttttatagttgtattttcctcctcactgttaataatcataatcctttttcagtatttttagtggccttgaacaactggtttatctacaatctcaaatcctaagtgtaattatgtgcaatgttcaatacctcatataataacttgctcaacagtatagtggtaccaatggcattaagatggtgttttgttctacatattttttcaataattttattcttctaatgttgaaattatatcaggctttaccggtt |
| 143 | 219955_at | L1TD1 | gaagttgcaacattcgtttgataggaattccagaaaaggagagttatgagaatagggcaggagacataattaaagaaataattgatgaaaactttgcagaactaaagaaaggttcaagtcttgagattgtcagtgcttgtcgagtacctagtaaaattgatgaaagagactgactcctagacacatcttggtgaaattttggaattctagtgataaagagaaataataagggctttctagagagagaagagaaattacctaccaaggaacaagaatcaggttgacagcagacttatcactggacacactggatgctagaagtaaatggagcaatgtcttcaaagttctgctggaaaaaggctttaatcctagaatcctatatccagccaaaatggcatttgattttaggggcaaaacaaaggtatttcttagtattgaagaatttagagattatgttttgcatatgcccaccttgagagaattactggggaataatataccttagcacgccagggtgactaca |
| 144 | 220029_at | ELOVL2 | gttatacagatgccatgctccacaccacgagcagtgtacaaatctggctgcccgtttacttttctgagcaagcactggagtccactccgacccttttctttgaacatgcatgctgctggaatatgtataaatcagaactagcagaagtagcagagtgatgggagcaaaataggcactgaattcgtcaactcttttttgtgagcctacttgtgaatattaccctcagatacctgttgtcactcttcacaggttatttaagttcttgaagctgggaggaaaaagatggagtagcttggaaagattccagcactgagccgtgagccggtcatgagccacgataaaaaatgccagtttggcaaactcagcactcctgttccctgctcaggtatatgcgatctctactgagaagcaagcacaaaagtagaccaaagtattaatgagtatttccttctccataagtgcaggactgttactcactactaaactct |
| 145 | 220076_at | ANKH | gaacgtcgtatgagatcctacaatggaagaataaaatcacctcattcttcatttcagatctgaacattagcagtgatctagatttttttttttttttaaacaaaattaagtgtgcttagagtcatccctctacatgggctgtggctgtcagcccataggtttgtcagtttcacatcaaaactgtgggtataaactgttgaaaccaatcacattaaaatatttagctgggcacagtggtgtgcatctgtagtcccagctacttgggaggctgaggcaggaggatcgcttaagcacaggagttggaatccagcctgagcaacagagcaaaaccccgtctctaaaatacaaataaaatatttgtgtagttttttgattaaaattgactacagcggtcagtataaaatacatgtcgcttttaaggaagtgctcttttatgtatctaacagatggaagttttgcattggtaagagcatttatatatgctttgtttcagggtttatggatttgtattcatatattgtcaaataggtttcatactctaattttactt |
| 146 | 220294_at | KCNV1 | agattatatccctatcttcttttttcatgtaaaccactggtcacaaatgaactgatctctgtatcccattattactataagaggtgggaatcccaaactgcttagattgcagtacatgagtttacacaaagacttcaacaattgcacatcttcattctccaactgagtgtagtatgtggagcataaaacagcatattcttagtatttcatgaatatcagatggtcttttaaatgtctcttttatggatgtattgttcacattatggctttaaaataatgaatatgtaaaagtgaggtagtgaacatcctaaatttctacactggaattactaaataatcttatttcataaaatgggaaatatagtttaaatgacatcactggatgaacttgaagatcttttacttgttaacaaaaaaatactatggacagctttctgattgttgggtaaatagcaaatgttcaaactttgcaggcattttgacattcatcataacaacacaattcctagacatt |
| 147 | 220366_at | ELSPBP1 | ttaggcagtctgtggtgctcagtcacctctgtcttcgatgagaaacagcaggtggaaattctgtgaaaacgaatgagtatggggaaattctctcaggaagccctgcatcttccctcctcatctacagaaataatgtggtctctgattgcatggaggatgaaagcaacaagctctggtgcccaaccacagagaacatggataaggatggaaagtggagttctgtgc |

TABLE 11-continued

Probe set target sequences for 172 genes

| SEQ ID NO: | Probe Set ID | Gene Symbol | Target Sequence |
|---|---|---|---|
| | | | cgacaccagaatttccgcgttggtccctggct ttccttgtcactttccgttcaactataaaaac aagaattattttaactgcactaacaaaggatc aaaggagaaccttgtgtggtgtgcaacttctt acaactacgaccaagaccacacctgggtgtat tgctgatgctgaggaaaggagaaatatcttca gaggaagactgccgccatactgaggctgagca cagatttgtcttttcattgcatctgtcaa |
| 148 | 220394_at | FGF20 | gtgtggcagtgggactggtcagtattagaggt gtggacagtggtctctatcttggaatga caaaggagaactctatggatcagagaaactta cttccgaatgcatctttagggagcagtttgaa gagaactggtataacacctattcatctaacat atataaacatggagacacttggccgcaggtat ttgtggcacttaacaaagacggaactccaaga gatggcgccaggtccaagaggcatcagaaatt tacacattcttacctagaccagtggatccag aaagagttccagaattgtacaaggacctactg atgtacacttgaagtgcgatagtgacattatg gaagagtcaaaccacaaccattcttcttgtc atagttcccatcataaaataatgacccaagca gacgttcaaa |
| 149 | 220397_at | MDM1 | tatgcatttttaccacaatttttaaaaagtt tgaatagaaattttaatgtctttgagtggat tttgtttttgaacagttggatagactct gtaagaaagctggattgactgttgttcctca tataatgccttgagaaattctgaatatcaaag gcagtttgttggaagacttctaaagaaactg ctccagctttgcagccaatcaggtagcttaa tggatgtaatactctgagtaccattatct tatctagtaatgtagatttacatagaattaag agttgaaagaaattaagtacttaagtagcctg gaggtaggttctagaaaaccaaaatgagagtt ttgctaaaatcatccctattacttatgatttat ggtagtaatattatactgtcctaggcttctga tgatcattgttgccagatgcagcacatatact aaatatgagacagggtaatgaaaacttgggga actggtaagttttttgcatgctac |
| 150 | 220541_at | MMP26 | tgaccccttttgatattccagcaagtgcagaat ggagatgcagacatcaaggtttcttctggca gtgggcccatgaagatggttggcccctttgatg ggccaggtggtatcttaggccatgccttttta ccaaattctggaaatcctggagttgtccattt tgacaagaatgaacactggtcagcttcagaca ctgacatataatctgttcctggttgcaactcat gagattgggcattctttgggcctgcagcactc tgggaatcagagctccataatgtaccccactt actggtatcacgaccctagaaccttccagctc agtgccgatgatatccaaaggatccagcattt gtatggagaaaaatgttcatctgacatacctt aatgttagcacagaggacttattcaaacctgtc cttcagggagtttattggaggatcaaagaac tgaaagcactagagcagccttggggactgcta ggatgaagccctaaagaatgcaacctagtcag gttagctgaaccgacactcaaaacgctac |
| 151 | 220653_at | PEG3 /// ZIM2 | aaggtagaaagccttccgtccagtgtgcgaat ctctgtgaacgtgtaagaattcacagtcagga ggactactttgaatgtttcagtgcggcaaag cttttctccagaatgtgcatcttcttcaacat ctcaaagcccatgaggcagcaagagtccttcc tcctggggttgtcccacagcaagacatacttaa ttcgttatcagcggaaacatgactacgttgga gagagagcctgccagtgttgtgactgtggcag agtcttcagtcgaagtcatatctcattcagc attataagaactcacactcaagagaggccttac cagtgtcagctatgtgggaaatgtttcggccg accctcatacctcactcaacattatcaactcc attctcaagagaaaactgttgagtgcgatcac tgttgagaaacctttagtcacagcacacactt |
| 152 | 220700_at | — | ttctcaacattattggcttcctcctagagtgt tgtgagtgtgagaaggcctttcactagcccc atgttactacaaacttgattaaacttctggtg gaaattccatcacatttatgcaattttcaat ttatttctccaatttattttaatgccacatg gacattatattccttaaccattcttttgcatg tgattaacatttgtgaaattaaccacttaagc aagtgttttgctttgatgaaagaaaatgtt taaaatcctactggatatgaaactgaaagtaa tgttttgtgtttttgtttcaaatgaaagtgt aaattaagaatttgttggcagggcgtggtggc tcatgcctgtaatcccagcactttgggaggc gaggtgggcagatcacctgaggtcagcagtcc aagaccacctggccaacatggtgaagtcccg tctctactaaaaatacaaaaatcagctgggca tggtggcgggcacttgtagtcccagctactca ggaggctgaagcaggagaatcacttgaactca ggaggcagaagttgcggttagccga |
| 153 | 220703_at | C10orf 110 | cctctctccactctctagaaatattaaggcta ggctgctgctgtatgtcagggctagtcccctc ttctatgaatccagaataactctgaagaagcc gagtaacaggcatgaagtgaagagaaatcgct gtaacaggaagacagcaaagcagatgctaatg accacactatttaacgaactggaaccaacgag aaaatacggtattactgaagactgcacttcct tgaacagagtgctcttctcagcaaatcggaaa tgcctacacaaatcgctttacaagaaagactg tttcaaagcagcacccttctcaatgttctcgt tcaggtgacaattcttcttggtctcagctcca attttattgtcattttcatcaataaggatca catctctgccaggagttgaacctgttgcttgt cgaggtggttagtgtttatttcaggcatcatt acaaaatgtctgatctgttctagaaccct |
| 154 | 220771_at | LOC511 52 | aagtatctccatacaaaatacggttgaattac aaaagaaaattgtaacattagcatggacaaa cctggcaggtactccttaactctcctaagtaa taaaaactgtaaaatgcaaataagccttcgat gacatttactaacctttactaaagtatcaatg atgacttggttgtttaaacagctgacatttgg gcaatttgagtatgtcaaactcaataatactg gttttcatttgcaagatccacttaaaacttaa ggaggccaaaaaacatcatttaaaaatacccta taaattataatcatacatatgatacgaaaaat atcctacttcag |
| 155 | 220817_at | TRPC4 | catacacatacgtatttccgtagtgctctgg gtgggggaaaatgtttaaattgtattagcaaa tgctaacttacactttatagcatttatcagct gtggcatattacctgtaacatgttaaattaa ggcaaaggcaatcaaaaaccttttttgttttgt agcctgcttttgctttcacaatttgtcttaca att |
| 156 | 220834_at | MS4A12 | gctggccaagactactgggccgtgctttctgg aaaaggcatttcagccacgctgatgatcttct ccctcttggagttctttcgtagcttgtgccaca gcccattttgccaaccaagcaaacaccacaac caatatgtctgtcctggttattccaaatgt atgaaagcaacctgtgacaccagcgtcttct tcagctcctcccagatgcaacaactactcagc taatgccctaaatagtaaagaaaaaggggt atcagtctaatctcatggagaaaaactacttg caaaaactctttaagaagatgtcttttattgt ctacaatgatttgtcttttaaaaactgtgt ttgagatttgttttaggttggtcgctaatga tggctgtatctccccttcactgtctcttcctac attaccactactacatgctggcaaaggtgaag gatcagaggactgaaaaatgattctgcaactc tcttaaa |

TABLE 11-continued

Probe set target sequences for 172 genes

| SEQ ID NO: | Probe Set ID | Gene Symbol | Target Sequence |
|---|---|---|---|
| 157 | 2208477_x_at | ZNF221 | tgacatgcaccagagggtccacaggggagagc gaccctataattgtaaggaatgtggaaagagc tttggctgggcttcatgtcttttgaaacatca gagactccacagtggagaaaagccattgaaat ctggagtgtgggaagagatctactcagaattc acagcttcatttacatcagtaagtctatgtgt gagaaaagccatataaatgtgagaagtgtggg aagggctttggctgggcctcaactcatctgac ccatcaattctccacagcagagaaaaaccatt caaatatgagaactgtgggaagagcttttgtac atagatcatatctttttttttttttttgagac agagtctcactcttcacccaagcctgactcg agtggcg |
| 158 | 2208522_at | PRO1768 | gaaaagcgccctgtgctgagtaaagcagccag tcttctccttgtcacagtaaaaggctgggagta aaatttcccataaacacaggggaaacctacat ttactcacatgccaaggaaaatggcacggaag acccacgtgtagccacacagagtctatgcag agggcctgcaaatgcctggggtgcgagtgaat gcctggaggggcggagtttccaagataacagc tattgtgttttcttttttcacacttcagaagag aatcctaaggactagactccgctcagtgcatt cctttttcatacactgatctcaagtacaatca cataattttgaaaatccatgtagtcctccctta aataaaattataaggataggtttctattcctt tccgattacctagatacctccgtcttctggaa aaccccaaaaagaccagtagacgaatcaggaa ggtcctaggagtgattcctccaat |
| 159 | 2209700_s_at | KAP2.1B /// KRTAP2-4 /// LOC644350 /// LOC728285 /// LOC728934 /// LOC730755 | tgccccccacagagcaatacactgaagcctaaa catctatctggtgtttttaaaaagttaaaaga aaaatagattttttttcacaaggtgacaatag tgattttaccatctggatacagcctggtgta agcagacgtccattaccaccctcacccacatt ttcaggtgtctacatcagccttagtcattatg gatagtaaatcgacctttaagaattcctgggg tggactttgcaaacacattctacaacctgatg gttttttactgctcaaactgtcaccatcatctt ttgcaatgtgttgctcactgttgtcaata |
| 160 | 2209811_x_at | LOC650686 /// NXF2 /// NXF2B | ggacagtctcagggttctgttctcgccttcac ccggaccttcattgctacccctggcagcagtt ccagtctgtgcatcgtgaatgacgagctgttt gtgagggatgccagccccccaagagactcagag tgccttctccatcccagtgttgcacactctcct ccagctctgagccctccctctcccaggagcag caggaaatggtgcaggctttctctgcccagtc tgggatgaaactggagtggtctcagaagtgcc ttcaggacaatggtggaactacactagagct ggccaggccttcactatgctccagaccgaggg caagatccccgcagaggcctcaagcaaatct cctaaaaggagccctccgatgtcttctttgtc ttcgttcacatcctctttgtttcctcttttca ccagcctaaggcctggctgaccaggaagccaa cgttaacttgcaggccacgtgacataac |
| 161 | 2209933_s_at | GPR63 | aagtctgcattgaatccgctgatctactactg gaggattaagaaattccatgatgcttgcctgg acatgatgcctaagtccttcaagttttttgccg cagctccctggtcacacaaagcgacggatacg tcctcagtctgtctagtggtggtgggggaacata ggacggggtgtgaatattggaactggctgac atttggggtgatgcttgttcttttattgacatt gaattctcttttctcatagcctctccactttat ttttttttataggggtttgtgtatgtatgtgtg tgagcagtgtaaagaaagaatggaattatag |
| 162 | 2210108_s_at | TDRD1 | gggactgtcgatgtagctgataagctagtgac atttggtctggcaaaaaacatcacacctcaaa ggcagagtgctttaaatacagaaaaagatgtat aggacgaattgctgctgcacagagttacagaa acaagttgaaaaacatgaacatattcttctct tcctcttaaacaattcaaccaatcaaaataaa tttattgaaatgaaaaaactggtaaaaagtta agtaagttaaatcgtatgttttcgcctcttct gtgatcaccaataggacatcttcaggcatatt ggcaggatagagctaatggagtgaaacctatt gtaaggctgtactttcgtgatttaatgacctg aggtttggtcataatgcttctgctgtttttgt aggtttatctgatcgttttcctttgctactgc taatggaactgaaccccccaggggtattccagt tgtaataagcttttcttactgttgtttgg |
| 163 | 2210777_at | ARMC4 | gttgagttgaaaattctgccgcttactcaatgg ccttgggtgatgatgctgtaccctaattctaa aggaagcaatgaaccccttttcagctaccctt actgataagcacttatgttctgcctctgcta tcctgatggttcggggttgtctgtcttactatc tacttcttgagtagagagaccacattaaatt attgctgtatctcacagggcatcttgctagtg tgcacagtccgcctccctacctctgcccga tgtgtgaaggggagagggcgaggttccttag tggcagggctttgctgttcttcactctcagcc ccctgaaagcagttcttcctgcctctgagcct gtctttccttctgctgttaacttcttttcctac ttttcttgcatccctctccttcctttccttg ccgtctcttcttgtagacat |
| 164 | 2211377_at | — | aaaaggactaactcacatggctgcagtaagtg ctggctgttagctggaagcacaaccaaggctg ttaacaggtgtgccttggttctcttccatatg gcttctctttttgtttcagtactctgcagttt aattatgatgcatgcaggtgtgaatttctgtt tattctgctgggatgtgttttcctccttctgggga tctgtgaatcggttttctcattattttttgtaaa acctgaagccagttatctcttaaaataccagc tctcctttg |
| 165 | 2211688_at | PRDM13 | ctggacttcttggatgagctcaccctgaaccg cccaggcggtctgctcttggtgttcagaatca catcaatgcgaacgtcacagcgccttcgaggg cgcagatttaactgccacgtattttaagtt gtactttctgtggaggaaattgtgccttttg aaacgacgttttgtgtgtgtatttcacgttag cattcattgcataggcaaaacactagtcaca attgggtagatgtgacatccatatacttgtt acattttatctgttctcatgtcaaagactact ccttgcccattgaatatatagtggtagcagg tgtacaaattggtcaagttgcaattatttatg agagaataattaaatgtaaaatatctaaag catgaatctaagagcacgcaatatataatttt aaagaaaatattctatttggtagaatacaaat gttggtgtgtgttgttttataatgactgctgta cagtgggtatagtatttttggttttggttccag attgtgcaatc |
| 166 | 2212588_s_at | KIF18A | gtgaagacatcaagagctcgaagtgtaaatta cccgaacaagaatcactaccaaatgataacaa agacatttacaacgtgttgatccttcttcat tctcaactaagcattctatgcctgtaccaagc atggtgccatcctacatggcaatgactactgc tgccaaaaggaaacggaaattaacaagttcta catcaaacagttcgttaactgcagacgtaaat |

TABLE 11-continued

Probe set target sequences for 172 genes

| SEQ ID NO: | Probe Set ID | Gene Symbol | Target Sequence |
|---|---|---|---|
| | | | tctggatttgccaaacgtgttcgacaagataa ttcaagtgagaagcacttacaagaaaacaaac caacaatggaacataaaagaaacatctgtaaa ataaatccaagcatggttagaaaatttggaag aaatatttcaaaaggaaatctaagataaatca cttcaaaaccaagcaaaatgaagttgatcaaa tctgcttttcaaagtttatcaatacccttca aaaatatatttaaaatctttgaaagaagaccc atcttaaagctaagtttacccaagtactttca gcaagc |
| 167 | 221319_at | PCDHB8 | cgggagcctgtctcagaactatcagtacgagg tgtgcctggcaggaggctcagggacgaatgag ttccagttcctgaaaccagtattacctaatat tcagggccattcttttggggccagaaatggaac aaaactctaactttaggaatggctttggtttc agccttcagttaaagta |
| 168 | 221393_at | TAAR3 | gaactccaccataaagcaactgctggcatttt gctggtcagttcctgctcttttttcttttggt ttagttctatctgaggccgatgtttccggtat gcagagctataagatacttgttgcttgcttca atttctgtgcccttactttcaacaaattctgg gggacaatattgttcactacatgtttctttac ccctggctccatcatggttggtatttatggca aaatctttatcgtttccaaacagcatgctcga gtcatcagccatgtgcctgaaaacacaaaggg ggcagtgaaaaaacacctatccaagaaaaagg acaggaaagcagcgaagacactgggtatagta atgggggtgtttctggcttgctggttgccttg ttttcttgctgttctgattgacccatacctag actactccactccatactaatattggatctt ttagtgtggctccggtacttcaactctacttg caaccctcttattcatggctttttttaatccat ggtttcagaaagcattcaagtacatagtgtca ggaaaaatatttagctcccattcagaaactgc |
| 169 | 221591_s_at | FAM64A | cacatctggacccatcagtgactgcctgccat agcctgagagtgtcttggggagaccttgcaga ggggagaattgttccttctgcttctcctaggg gactcttgagcttagaaactcatcgtacactt gaccttgagccttctatttgcctcatctataa catgaagtgctagcatcagatatttgagagct cttagctctgtacccgggtgcctggttttgg ggagtcatccgcagagtcactcaccoactgtg ttctggtgccaaggctcttgagggcccact ctcatccctcctttccctaccagggactcgga ggaaggcataggagatattccaggcttacga ccctgggctcacgggtacctatttatatgctc agtgcagagcactgtggatgtgccaggagggg tagccctgttcaagagcaatttctgcccttg taaattatttaagaaacctgctttgtcatttt attagaaagaaaccagcgtgtgactttcctag ataacactgctttc |
| 170 | 221609_s_at | WNT6 | ccgccaggagagcgtgcagctcgaagagaact gcctgtgccgcttccactggtgctgcgtagta cagtgccaccgttgccgtgtgcgcaaggagct cagcctctgcctgtgacccgccgccccggccgc tagactgacttcgcgcagcggtggctcgcacc tgtgggacctcagggcaccggcaccgggcgcc tctcgccgctcgagcccagcctctccctgcca aagcccaactcccaggggctctgaaatggtga ggcgaggggcttgagaggaacgcccacccacg aaggcccagggcgccagacggccccgaaaagg cgctcggggagcgtttaaaggacactgtacag gccctcctcccttggcctctaggaggaaac agttttttagactggaaaaaagccagtctaaa ggcctctggatactgggctcccagaactgc |
| 171 | 221718_s_at | AKAP13 | gcgatgcagaaatgaaccaccggagttcaatg cgagttcttggggatgttgtcaggagacctcc cattcataggagaagtttcagtctagaaggct tgacaggaggagctggtgtcggaaacaagcca tcctcatctctagaagtaagctctgcaaatgc cgaagagctcagacacccattcagtggtgagg aacgggttgactctttggtgtcactttcagaa gaggatctggagtcagaccagagagaacatag gatgtttgatcagcagatatgtcacagatcta agcagcagggatttaattactgtacatcagcc atttcctctccattgacaaaatccatctcatt aatgacaatcagccatcctggattggacaatt cacggcccctt |
| 172 | 221950_at | EMX2 | gtaggctcagcgatagtggtcctcttacagag aaacggggagcaggacgacgggggngctgggg ntggcggggagggtgcccacaaaaagaatca ggacttgtactgggaaaaaaaccccctaaatta attatatttcttggacattcccttttcctaaca tcctgaggcttaaaaccctgatgcaaacttct cctttcagtggttggagaaattggccgagttc aaccattcactgcaatgcctattccaaacttt aaatctatctattgcaaaacctgaaggactgt agttagcggggatgatgttaagtgtggccaag cgcacggcggcaagttttcaagcactgagttt ctattccaagatcatagacttactaaagagag tgacaaatgcttccttaatgtcttctataccaa gaatgtaaatatttttgtgttttgtgttaatt tgttagaattctaacacactatatacttccaa |

REFERENCES

1. Jemal A, Siegel R, Ward E, Murray T, Xu J, Thun M J. Cancer Statistics, 2007. CA Cancer J Clin 2007; 57:43-66.
2. Arriagada R, Bergman B, Dunant A, Le Chevalier T, Pignon J P, Vansteenkiste J. Cisplatin-based adjuvant chemotherapy in patients with completely resected non-small-cell lung cancer. N Engl J Med 2004; 350:351-60.
3. Winton T, Livingston R, Johnson D, et al. Vinorelbine plus cisplatin vs. observation in resected non-small-cell lung cancer. N Engl J Med 2005; 352:2589-97.
4. Douillard J Y, Rosell R, De Lena M, et al. Adjuvant vinorelbine plus cisplatin versus observation in patients with completely resected stage IB-IIIA non-small-cell lung cancer (Adjuvant Navelbine International Trialist Association [ANITA]): a randomised controlled trial. Lancet Oncol 2006; 7:719-27.
5. Strauss G M, Herndon J E, II, Maddaus M A, et al. Adjuvant chemotherapy in stage IB non-small cell lung cancer (NSCLC): Update of Cancer and Leukemia Group B (CALGB) protocol 9633. ASCO Meeting Abstracts 2006; 24:7007-.
6. Pignon J P, Tribodet H, Scagliotti G V, et al. Lung Adjuvant Cisplatin Evaluation (LACE): A pooled analysis of five randomized clinical trials including 4,584 patients. ASCO Meeting Abstracts 2006; 24:7008-.
7. Scagliotti G V, Fossati R, Torri V, et al. Randomized study of adjuvant chemotherapy for completely resected stage I, II, or IIIA non-small-cell Lung cancer. J Natl Cancer Inst 2003; 95:1453-61.
8. Waller D, Peake M D, Stephens R J, et al. Chemotherapy for patients with non-small cell lung cancer: the surgical setting of the Big Lung Trial. Eur Cardiothorac Surg 2004; 26:173-82.
9. Douillard J Y, Rosell R, Delena M, Legroumellec A, Torres A, Carpagnano F. ANITA: Phase III adjuvant vinorelbine (N) and cisplatin (P) versus observation (OBS) in completely resected (stage I-III) non-small-cell lung cancer (NSCLC) patients (pts): Final results after 70-month median follow-up. On behalf of the Adjuvant Navelbine International Trialist Association. ASCO Meeting Abstracts 2005; 23:7013-.
10. Hoffman P C, Mauer A M, Vokes E E. Lung cancer. Lancet 2000; 355:479-85.
11. Nesbitt J C, Putnam J B, Jr., Walsh G L, Roth J A, Mountain C F. Survival in early-stage non-small cell lung cancer. Ann Thorac Surg 1995; 60:466-72.
12. Beer D G, Kardia S L, Huang C C, et al. Gene-expression profiles predict survival of patients with lung adenocarcinoma. Nat Med 2002; 8:816-24.
13. Chen H Y, Yu S L, Chen C H, et al. A five-gene signature and clinical outcome in non-small-cell lung cancer. N Engl J Med 2007; 356:11-20.
14. Lu Y, Lemon W, Liu P Y, et al. A gene expression signature predicts survival of patients with stage I non-small cell lung cancer. PLOS Med 2006; 3:e467.
15. Potti A, Mukherjee S, Petersen R, et al. A genomic strategy to refine prognosis in early-stage non-small-cell lung cancer. N Engl J Med 2006; 355:570-80.
16. Raponi M, Zhang Y, Yu J, et al. Gene expression signatures for predicting prognosis of squamous cell and adenocarcinomas of the lung. Cancer Res 2006; 66:7466-72.
17. Wigle D A, Jurisica I, Radulovich N, et al. Molecular profiling of non-small cell lung cancer and correlation with disease-free survival. Cancer Res 2002; 62:3005-8.
18. Bianchi F, Nuciforo P, Vecchi M, et al. Survival prediction of stage I lung adenocarcinomas by expression of 10 genes. J Clin Invest 2007; 117:3436-44.
19. Sun Z, Wigle D A, Yang P. Non-overlapping and non-cell-type-specific gene expression signatures predict lung cancer survival. J Clin Oncol 2008; 26:877-83.
20. Lau S K, Boutros P C, Pintilie M, et al. Three-gene prognostic classifier for early-stage non small-cell lung cancer. J Clin Oncol 2007; 25:5562-9.
21. Oshita F, Ikehara M, Sekiyama A, et al. Genomic-wide cDNA microarray screening to correlate gene expression profile with chemoresistance in patients with advanced lung cancer. J Exp Ther Oncol 2004; 4:155-60.
22. Bolstad B M, Irizarry R A, Astrand M, Speed T P. A comparison of normalization methods for high density oligonucleotide array data based on variance and bias. Bioinformatics 2003; 19:185-93.
23. Affymetrix, ed. Transcript assignment for NetAfx™ annotation; 2006.
24. Dworakowska D, Jassem E, Jassem J, et al. Clinical significance of apoptotic index in non-small cell lung cancer: correlation with p53, mdm2, pRb and p21WAF1/CIP1 protein expression. J Cancer Res Clin Oncol 2005; 131:617-23.
25. Allory Y, Matsuoka Y, Bazille C, Christensen E I, Ronco P, Debiec H. The L1 cell adhesion molecule is induced in renal cancer cells and correlates with metastasis in clear cell carcinomas. Clin Cancer Res 2005; 11:1190-7.
26. Boo Y J, Park J M, Kim J, et al. L1 expression as a marker for poor prognosis, tumor progression, and short survival in patients with colorectal cancer. Ann Surg Oncol 2007; 14:1703-11.
27. Gast D, Riedle S, Schabath H, et al. L1 augments cell migration and tumor growth but not beta3 integrin expression in ovarian carcinomas. Int J Cancer 2005; 15:658-65.
28. Thies A, Schachner M, Moll I, et al. Overexpression of the cell adhesion molecule L1 is associated with metastasis in cutaneous malignant melanoma. Eur J Cancer 2002; 38:1708-16.
29. Ouellet V, Provencher D M, Maugard C M, et al. Discrimination between serous low malignant potential and invasive epithelial ovarian tumors using molecular profiling. Oncogene 2005; 24:4672-87.

What is claimed is:

1. A method for prognosing or classifying a subject with non-small cell lung cancer (NSCLC) comprising:
   a. calculating a combined score from relative expression levels of 15 different biomarkers in a test sample from the subject, wherein the 15 biomarkers are FAM64A, MB, EDN3, ZNF236, FOSL2, MYT1L, MLANA, L1CAM, TRIM14, STMN2, UMPS, ATP1B1, HEXIM1, IKBKAP, and MDM2,
   b. classifying the subject into a high or low risk group based on the combined score, and
   c. selecting adjuvant chemotherapy if the subject is in the high risk group, wherein steps a, b, and c are performed on a computer.

2. The method according to claim 1, wherein the combined score is calculated according to Formula I:

$$\text{Combined score} = 0.557 \times PC1 + 0.328 \times PC2 + 0.43 \times PC3 + 0.335 \times PC4 \quad \text{(Formula I)},$$

wherein PC1 is the sum of the relative expression level for each biomarker multiplied by a first principal component for each biomarker, PC2 is the sum of the relative expression level for each biomarker multiplied by a second principal component for each biomarker, PC3 is the sum of the relative expression level for each biomarker multiplied by a third principal component for each biomarker, and PC4 is the sum of the relative expression level of each biomarker multiplied by a fourth principal component for each biomarker.

3. A method for selecting therapy comprising the steps of claim 1, and wherein the subject has stage I or stage II NSCLC.

4. The method of claim 1, wherein the test sample from the subject is a tumor tissue sample.

5. A method for prognosing or classifying a subject with non-small cell lung cancer (NSCLC) comprising:
   a. determining relative expression levels of 15 different biomarkers in a test sample from the subject, wherein the biomarkers are FAM64A, MB, EDN3, ZNF236, FOSL2, MYT1L, MLANA, L1CAM, TRIM14, STMN2, UMPS, ATP1B1, HEXIM1, IKBKAP, and MDM2,
   b. calculating a combined score from the relative expression levels of the 15 different biomarkers in the test sample from the subject,
   c. classifying the subject into a high or low risk group based on the combined score, and
   d. selecting adjuvant chemotherapy if the subject is in the high risk group, wherein steps b, c, and d are performed on a computer.

6. The method according to claim 5, wherein the combined score is calculated according to Formula I:

$$\text{Combined score} = 0.557 \times PC1 + 0.328 \times PC2 + 0.43 \times PC3 + 0.335 \times PC4 \quad \text{(Formula I)},$$

PC1 is the sum of the relative expression level for each biomarker multiplied by a first principal component for each biomarker, PC2 is the sum of the relative expression level for each biomarker multiplied by a second principal component for each biomarker, PC3 is the sum of the relative expression level for each biomarker multiplied by a third principal component for each biomarker, and PC4 is the sum of the relative expression level of each biomarker multiplied by a fourth principal component for each biomarker.

7. A method for selecting therapy comprising the steps of claim 5, wherein the subject has stage I or stage II NSCLC.

8. The method of claim 5, wherein the test sample from the subject is a tumor tissue sample.

9. A kit to prognose or classify a subject with non-small cell lung cancer (NSCLC) comprising a set of detection agents consisting of detection agents capable of detecting the expression products of 15 different biomarkers in a test sample wherein the 15 different biomarkers are FAM64A, MB, EDN3, ZNF236, FOSL2, MYT1L, MLANA, L1CAM, TRIM14, STMN2, UMPS, ATP1B1, HEXIM1, IKBKAP, and MDM2.

10. The kit of claim 9, the kit comprising an addressable array comprising the set of detection agents in the form of probes for the expression products of the 15 biomarkers.

11. The kit of claim 9, wherein the set of detection agents comprise primers capable of hybridizing to the expression products of the 15 biomarkers.

12. A kit according to claim 9, further comprising a computer product for calculating a combined score for a subject.

13. A method for preparing a gene expression profile that is prognostic for non-small cell lung cancer (NSCLC), the method comprising the steps of determining the expression level of 15 genes that are prognostic for NSCLC in a tumor tissue sample from a stage I or stage II NSCLC subject, the 15 genes being FAM64A, MB, EDN3, ZNF236, FOSL2, MYT1L, MLANA, L1CAM, TRIM14, STMN2, UMPS, ATP1B1, HEXIM1, IKBKAP, and MDM2.

* * * * *

```
                              SEQUENCE LISTING

<160> NUMBER OF SEQ ID NOS: 202

<210> SEQ ID NO 1
<211> LENGTH: 420
<212> TYPE: DNA
<213> ORGANISM: Homo sapiens
<220> FEATURE:
<221> NAME/KEY: misc_feature
<222> LOCATION: (83)..(83)
<223> OTHER INFORMATION: n is a, c, g, or t

<400> SEQUENCE: 1
cactttgcaa ctccctgggt aagagggacg acacctctgg tttttcaata ccaattacat      60 ggaactttc tgtaatgggt acnaatgaag aagtttctaa aaacacacac aaagcacatt    120
gggccaacta tttagtaagc ccggatagac ttattgccaa aaacaaaaaa tagctttcaa    180
aagaaattta agttctatga gaaattcctt agtcatggtg ttgcgtaaat catattttag    240
ctgcacggca ttacccaca cagggtggca gaacttgaag ggttactgac gtgtaaatgc     300
tggtatttga tttcctgtgt gtgttgccct ggcattaagg gcattttacc cttgcagttt    360
tactaaaaca ctgaaaaata ttccaagctt catattaacc ctacctgtca acgtaacgat    420

<210> SEQ ID NO 2
<211> LENGTH: 437
<212> TYPE: DNA
<213> ORGANISM: Homo sapiens
```

<400> SEQUENCE: 2

```
cctacccacc tcaaaatgtc tgtactgcaa gagggccctg ggcctctgct ttccatattc      60
acgtttggcc agagttgtag tcccaaagaa gagcatgggt ggcagatggt agggaattga     120
actggcctgt gcaatgggca tggagcacaa ggggtcacag catgcctcct gccttaccgt     180
ggcagtacgg agacagtcca gaacatggtc ttcttgccac ggggtgttgt tgtctctggt     240
ggtgctgcat gtctgtggct cacctttatt cttgaaactg aggtttacct ggatctggct     300
actgaggcta gagcccacag cagaatgggg ttgggcctgt ggccccccaa actaggtggt     360
gtgggttcat cacagtgttg ccttttgtct cctaaagata gggatctact tttgaaggga     420
attgttcctc ccaaata                                                    437
```

<210> SEQ ID NO 3  
<211> LENGTH: 161  
<212> TYPE: DNA  
<213> ORGANISM: Homo sapiens

<400> SEQUENCE: 3

```
agagctgatc acaagcacaa atctttccca ctagccattt aataagttaa aaaaagatac      60
aaaaacaaaa acctactagt cttgaacaaa ctgtcatacg tatgggacct acacttaatc     120
tatatgcttt acactagctt tctgcattta ataggttaga a                         161
```

<210> SEQ ID NO 4  
<211> LENGTH: 475  
<212> TYPE: DNA  
<213> ORGANISM: Homo sapiens

<400> SEQUENCE: 4

```
ggtgatgggt tgtgttatgc ttgtattgaa tgctgtcttg acatctcttg ccttgtcctc      60
cggtatgttc taaagctgtg tctgagatct ggatctgccc atcactttgg cctaggaca     120
gggctaatta atttgcttta tacattttct tttacttttcc tttttttcctt tctggaggca   180
tcacatgctg gtgctgtgtc tttatgaatg ttttaaccat tttcatggtg aagaatttt     240
atatttatgc agttgtacaa ttttatttt ttctgcaaga aaaagtgtaa tgtatgaaat     300
aaaccaaagt cacttgtttg aaaataaatc tttattttga actttataaa agcaatgcag   360
taccccatag actggtgtta aatgttgtct acagtgcaaa atccatgttc taacatatgt   420
aataattgcc aggagtacag tgctcttgtt gatcttgtat tcagtcaggt taaaa         475
```

<210> SEQ ID NO 5  
<211> LENGTH: 477  
<212> TYPE: DNA  
<213> ORGANISM: Homo sapiens

<400> SEQUENCE: 5

```
ggtgaaattt ctaactgttc tctgttcccg gaaccgaaat cacctgttgc atgtgtttga      60
tgaatacaaa aggatatcac agaaggatat tgaacagagt attaaatctg aaacatctgg     120
tagctttgaa gatgctctgc tggctatagt aaagtgcatg aggaacaaat ctgcatattt     180
tgctgaaaag ctctataaat cgatgaaggg cttgggcacc gatgataaca ccctcatcag     240
agtgatggtt tctcgagcag aaattgacat gttggatatc cggcacacact tcaagagact     300
ctatggaaag tctctgtact cgttcatcaa gggtgacaca tctggagact acaggaaagt     360
actgcttgtt ctctgtggag gagatgatta aaataaaaat cccagaagga caggaggatt     420
ctcaacactt tgaatttttt taacttcatt tttctacact gctattatca ttatctc        477
```

<210> SEQ ID NO 6
<211> LENGTH: 420
<212> TYPE: DNA
<213> ORGANISM: Homo sapiens

<400> SEQUENCE: 6

```
ccaactacaa tggccacacg tgtctacact tagcctctat ccatggctac ctgggcatcg      60
tggagctttt ggtgtccttg ggtgctgatg tcaatgctca ggagccctgt aatggccgga     120
ctgcccttca cctcgcagtg gacctgcaaa atcctgacct ggtgtcactc ctgttgaagt     180
gtggggctga tgtcaacaga gttacctacc agggctattc tccctaccag ctcacctggg     240
gccgcccaag cacccggata cagcagcagc tgggccagct gacactagaa aaccttcaga     300
tgctgccaga gagtgaggat gaggagagct atgacacaga gtcagagttc acggagttca     360
cagaggacga gctgccctat gatgactgtg tgtttggagg ccagcgtctg acgttatgag     420
```

<210> SEQ ID NO 7
<211> LENGTH: 493
<212> TYPE: DNA
<213> ORGANISM: Homo sapiens

<400> SEQUENCE: 7

```
ccaccttcac ctcggaggga cggagaaaga agtggagaca gtcctttccc accattcctg      60
cctttaagcc aaagaaacaa gctgtgcagg catggtccct taaggcacag tgggagctga     120
gctggaaggg gccacgtgga tgggcaaagc ttgtcaaaga tgcccccctcc aggagagagc     180 caggatgccc agatgaactg actgaaggaa aagcaagaaa cagtttcttg cttggaagcc     240
aggtacagga gaggcagcat gcttgggctg acccagcatc tcccagcaag acctcatctg     300
tggagctgcc acagagaagt ttgtagccag gtactgcatt ctctcccatc ctggggcagc     360
actccccaga gctgtgccag caggggggct gtgccaacct gttcttagag tgtagctgta     420
agggcagtgc ccatgtgtac attctgccta gagtgtagcc taaagggcag ggcccacgtg     480
tatagtatct gta                                                         493
```

<210> SEQ ID NO 8
<211> LENGTH: 522
<212> TYPE: DNA
<213> ORGANISM: Homo sapiens

<400> SEQUENCE: 8

```
tcggccagcg agtacgacta cgtgagcttc cagtcggaca tcggcccgta ccagagcggg      60
cgcttctaca ccaagccacc tcagtgcgtg gacatccccg cggacctgcg gctgtgccac     120
aacgtgggct acaagaagat ggtgctgccc aacctgctgg agcacgagac catggcggag     180
gtgaagcagc aggccagcag ctgggtgccc ctgctcaaca gaactgcca cgccggcacc     240 caggtcttcc tctgctcgct cttcgcgccc gtctgcctgg accggcccat ctaccccgtgt     300 cgctggctct gcgaggccgt gcgcgactcg tgcgagccgg tcatgcagtt cttcggcttc     360
tactggcccg agatgcttaa gtgtgacaag ttccccgagg gggacgtctg catcgccatg     420
acgccgccca tgccaccgga agcctccaag ccccaaggca acggtgtg tcctccctgt     480 gacaacgagt tgaaatctga ggccatcatt gaacatctct gt                         522
```

<210> SEQ ID NO 9
<211> LENGTH: 444
<212> TYPE: DNA
<213> ORGANISM: Homo sapiens

<400> SEQUENCE: 9

| | | |
|---|---|---|
| gacaaaccat ttccaacagc aacacagcca ctaaaacaca aaaaggggga ttgggcggaa | 60 | |
| agtgagagcc agcagcaaaa actacatttt gcaacttgtt ggtgtggatc tattggctga | 120 | |
| tctatgcctt tcaactagaa aattctaatg attggcaagt cacgttgttt tcaggtccag | 180 | |
| agtagtttct ttctgtctgc tttaaatgga aacagactca taccacactt acaattaagg | 240 | |
| tcaagcccag aaagtgataa gtgcagggag gaaaagtgca agtccattat gtaatagtga | 300 | |
| cagcaaaggc ccaggggaga ggcattgcct tctctgccca cagtcttttcc gtgtgattgt | 360 | |
| cttttgaatct gaatcagcca gtctcagatg ccccaaagtt tcggttccta tgagcccggg | 420 | |
| gcatgatctg atccccaaga catg | 444 | |

<210> SEQ ID NO 10
<211> LENGTH: 335
<212> TYPE: DNA
<213> ORGANISM: Homo sapiens

<400> SEQUENCE: 10

| | | |
|---|---|---|
| taacacttgg ctcttggtac ctgtgggtta gcatcaagtt ctccccaggg tagaattcaa | 60 | |
| tcagagctcc agtttgcatt tggatgtgta aattacagta atcccatttc ccaaacctaa | 120 | |
| aatctgtttt tctcatcaga ctctgagtaa ctggttgctg tgtcataact tcatagatgc | 180 | |
| aggaggctca ggtgatctgt ttgaggagag caccctaggc agcctgcagg gaataacata | 240 | |
| ctggccgttc tgacctgttg ccagcagata cacaggacat ggatgaaatt cccgtttcct | 300 | |
| ctagtttctt cctgtagtac tcctcttttta gatcc | 335 | |

<210> SEQ ID NO 11
<211> LENGTH: 525
<212> TYPE: DNA
<213> ORGANISM: Homo sapiens

<400> SEQUENCE: 11

| | | |
|---|---|---|
| gaggatggca caagcgattc acgtaggatc tgcccctgtg accaaaacac ctcccattgg | 60 | |
| gccccacttc caacactggt gatcacattt caacatgagg tttagggaaa caaatgccta | 120 | |
| aactacagca ctgtacataa actaacagga aatgctgctt ttgatcctca aagaagtgat | 180 | |
| atagccaaaa ttgtaatttta agaagccttt gtcagtatag caagatgtta actatagaat | 240 | |
| caatctagga gtattcactg taaaattcaa ctttttctgta tgtttgaaca ttttcacaat | 300 | |
| ctcataggag ttttttaaaaa gaagagaaag aagatatact ttgctttgga gaaatctact | 360 | |
| ttttgactta catgggtttg ctgtaattaa gtgcccaata ttgaaaggct gcaagtactt | 420 | |
| tgtaatcact ctttggcatg ggtaaataag catggtaact tatattgaaa tatagtgctc | 480 | |
| ttgctttgga taactgtaaa gggacccatg ctgatagact ggaaa | 525 | |

<210> SEQ ID NO 12
<211> LENGTH: 445
<212> TYPE: DNA
<213> ORGANISM: Homo sapiens

<400> SEQUENCE: 12

| | | |
|---|---|---|
| aagttcattc ttaagcttgc tttttttgag actggtgttt gttagacagc cacagtcctg | 60 | |
| tctgggttag ggtcttccac atttgaggat ccttcctatc tctccatggg actagactgc | 120 | |
| tttgttattc tatttatttt ttaattttt tcgagacagg atctcactct gttgcccagg | 180 | |
| atggagtgca gtggtgagat cacggctcat tgcagcctcg acctcccagg tgatcctccc | 240 | |

```
acctcagctt ccagattagc tggtgctata ggcatgcacc accacgtcca tctaaatttc    300
tttattattt gtagagatga ggtcttgcca tgttacccag gctggtctca actcctgggc    360
tcaagcgatc ctcctgcctc agtctctcaa agtgctggga ttacaggtgt gagccactgt    420
gcccagccta attgcagtaa gacaa                                          445

<210> SEQ ID NO 13
<211> LENGTH: 526
<212> TYPE: DNA
<213> ORGANISM: Homo sapiens

<400> SEQUENCE: 13
tgcctctcgc gcatggagga cgagaacaac cggctgcggc tggagagcaa gcggctgggt     60
ggcgacgacg cgcgtgtgcg ggagctggag ctggagctgg accggctgcg cgccgagaac    120
ctccagctgc tgaccgagaa cgaactgcac cggcagcagg agcgagcgcc gctttccaag    180
tttggagact agactgaaac ttttttgggg gaggggcaa aggggacttt ttacagtgat     240
ggaatgtaac attatataca tgtgtatata agacagtgga cctttttatg acacataatc    300
agaagagaaa tcccctggc tttggttggt ttcgtaaatt tagctatatg tagcttgcgt    360
gctttctcct gttcttttaa ttatgtgaaa ctgaagagtt gcttttcttg ttttcctttt    420
tagaagtttt tttccttaat gtgaaagtaa tttgaccaag ttataatgca tttttgtttt    480
taacaaatcc cctccttaaa cggagctata aggtggccaa atctga                    526

<210> SEQ ID NO 14
<211> LENGTH: 480
<212> TYPE: DNA
<213> ORGANISM: Homo sapiens

<400> SEQUENCE: 14
acctcgcaac atcaacatct atacttacga tgatatggaa gtgaagcaaa tcaacaaacg     60
tgcctctggc caggcttttg agctgatctt gaagccacca tctcctatct cagaagcccc    120
acgaacttta gcttctccaa agaagaaaga cctgtccctg gaggagatcc agaagaaact    180
ggaggctgca ggggaaagaa gaaagtctca ggaggcccag gtgctgaaac aattggcaga    240
gaagagggaa cacgagcgag aagtccttca gaaggctttg gaggagaaca caacttcag    300 caagatggcg gaggaaaagc tgatcctgaa aatggaacaa attaaggaaa accgtgaggc    360
taatctagct gctattattg aacgtctgca ggaaaaggag aggcatgctg cggaggtgcg    420
caggaacaag gaactccagg ttgaactgtc tggctgaagc aagggagggt ctggcacgcc    480

<210> SEQ ID NO 15
<211> LENGTH: 508
<212> TYPE: DNA
<213> ORGANISM: Homo sapiens
<220> FEATURE:
<221> NAME/KEY: misc_feature
<222> LOCATION: (121)..(121)
<223> OTHER INFORMATION: n is a, c, g, or t

<400> SEQUENCE: 15
accaatcacg cctacagtgc tttgaaggtt tcctctccta ggctagtttc aaacaggccc     60
taaacaagtc tgctgctgcc ctctcatcag acctccgcac cctcacccca ccatcactta    120
nactacttta atccagttcc ttcaaagtga tacccccaca ggtaagccct cagcatcctg    180
aatacatcat ccgcagcctg ggaaccttct ccctcgtaca gcacaggaac ctgacacata    240
gtaggcacac agtaaacgtt tgtgaatgaa tgggagtcat ccagtcctga ctcttctgtc    300
```

```
tcttgaggtc ccttgaatct tccgcttcct ccccaccgat ttcagcgtgt ccacatcaca    360
gctccctcca gaagctgcaa gagcttctta gcagttcctg gtctgaaccc tctcccagtc    420
ctcatcttcc accctaaaac tagagtgatc ttcctaaaac ttcacttaac ccctcagcta    480
tgaaaaggct tccaggagtt tccatgaa                                       508

<210> SEQ ID NO 16
<211> LENGTH: 526
<212> TYPE: DNA
<213> ORGANISM: Homo sapiens

<400> SEQUENCE: 16
gtccacattc ctgcaagcat tgattgagac atttgcacaa tctaaaatgt aagcaaagta     60
gtcattaaaa atacaccctc tacttgggct ttatactgca tacaaattta ctcatgagcc    120
ttcctttgag gaaggatgtg gatctccaaa taaagattta gtgtttattt tgagctctgc    180
atcttaacaa gatgatctga acacctctcc tttgtatcaa taaatagccc tgttattctg    240
aagtgagagg accaagtata gtaaaatgct gacatctaaa actaaataaa tagaaaacac    300
caggccagaa ctatagtcat actcacacaa agggagaaat ttaaactcga accaagcaaa    360
aggcttcacg gaaatagcat ggaaaaacaa tgcttccagt ggccacttcc taaggaggaa    420
caaccccgtc tgatctcaga attggcacca cgtgagcttg ctaagtgata atatctgttt    480
ctactacgga tttaggcaac aggacctgta cattgtcaca ttgcat                   526

<210> SEQ ID NO 17
<211> LENGTH: 456
<212> TYPE: DNA
<213> ORGANISM: Homo sapiens

<400> SEQUENCE: 17
cacaaaggat accagggccc tacggaaggc tctgacccat ctggaaatgc ggcgagctgc     60
tcgccgaccc aacttgcccc tgaaggtgaa gccaacgctg attgcagtgc ggcccctgt    120 ccctctacct gcaccctcac atcctgccag caccaatgag cctattgtcc tggaggactg    180
agcacctgtg gggaagggag gtgggctgag aggtagaggg tggatgccca gggcacccaa    240
acctcccttc cctttcgtgt cgaagggagt gaggagtgaa ttaaggaaga gagcaagtga    300
gtgtgtgtcc ctggaggggt tgggcgccct ctggtgttac cacctcgaga cttgtctcat    360
gcctccatgc ttgccgatgg aggacagact gcaggaactt ggcccatgtg ggaacctagc    420
ctgttttggg gggtaggacc cacagatgtc ttggac                              456

<210> SEQ ID NO 18
<211> LENGTH: 475
<212> TYPE: DNA
<213> ORGANISM: Homo sapiens

<400> SEQUENCE: 18
gaaattcttt cccagtctgt cgatttatgc ctcagccact tgcctgtgct acaattcatt     60
gtgttacctg tagattcagg taatacaaac catatataat catcaagtaa tacaaactaa    120
tttagtaata gcctgggtta agtattatta gggccctgtg tctgcatgta gaaaaaaaaa    180
ttcacatgat gcacttcaaa ttcaaataaa atccttttg gcatgttccc attttgtgctt    240 agctcaatta gtgtggctaa ccaagagata actgtaaatg tgacattgat ttgctcttac    300
tacagctaca gtgattgggg gaggaaaagt cccaacccaa tgggctcaaa cttctaaggg    360
gtactcctct catccccttat ccttctccc tcgacatttt ctccctcttt cttcccatga    420
```

```
cccaaagcc aagggcaaca gatcagtaaa gaacgtggtc agagtagaac ccctg        475
```

<210> SEQ ID NO 19
<211> LENGTH: 466
<212> TYPE: DNA
<213> ORGANISM: Homo sapiens

<400> SEQUENCE: 19

```
gaatatcaca gcttaccttg ggaatactac tgacaatttc tttaaaattt ccaacctgaa    60
gatgggtcat aattacacgt tcaccgtcca agcaagatgc cttttttggca accagatctg  120
tggggagcct gccatcctgc tgtacgatga gctggggtct ggtgcagatg catctgcaac  180
gcaggctgcc agatctacgg atgttgctgc tgtggtggtg cccatcttat tcctgatact  240
gctgagcctg ggggtggggt ttgccatcct gtacacgaag caccggaggc tgcagagcag  300
cttcaccgcc ttcgccaaca gccactacag ctccaggctg ggtccgcaa tcttctcctc  360
tggggatgac ctgggggaag atgatgaaga tgccccctatg ataactggat tttcagatga  420
cgtccccatg gtgatagcct gaaagagctt tcctcactag aaacca               466
```

<210> SEQ ID NO 20
<211> LENGTH: 432
<212> TYPE: DNA
<213> ORGANISM: Homo sapiens
<220> FEATURE:
<221> NAME/KEY: misc_feature
<222> LOCATION: (307)..(307)
<223> OTHER INFORMATION: n is a, c, g, or t

<400> SEQUENCE: 20

```
gagtccagtc gaagattggg tccctggaca atatcaccca cgtccctggc ggaggaaata    60
aaaagattga aacccacaag ctgaccttcc gcgagaacgc caaagccaag acagaccacg  120
gggcggagat cgtgtacaag tcgccagtgg tgtctgggga cacgtctcca cggcatctca  180
gcaatgtctc ctccaccggc agcatcgaca tggtagactc gccccagctc gccacgctag  240
ctgacgaggt gtctgcctcc ctggccaagc agggtttgtg atcaggcccc tggggcggtc  300
aataatngtg gagaggagag aatgagagag tgtggaaaaa aaaagaataa tgacccggcc  360
cccgccctct gccccccagct gctcctcgca gttcggttaa ttggttaatc acttaacctg  420
cttttgtcac tc                                                     432
```

<210> SEQ ID NO 21
<211> LENGTH: 530
<212> TYPE: DNA
<213> ORGANISM: Homo sapiens

<400> SEQUENCE: 21

```
aagcggcgca accaggagat gcagcagaag ttggtggagc tgtcggctga gaacgagaag    60
ctgcaccagc gcgtggagca gctcacgcgg gacctggccg gcctccggca gttcttcaag  120
cagctgccca gcccgccctt cctgccggcc gccgggacag cagactgccg gtaacgcgcg  180
gccggggcgg gagagactca gcaacgaccc atacctcaga cccgacggcc cggagcggag  240
cgcgccctgc cctggcgcag ccagagccgc cgggtgcccg ctgcagttc ttgggacata  300
ggagcgcaaa gaagctacag cctggactta ccaccactaa actgcgagag aagctaaacg  360
tgtttatttt cccttaaatt attttttgtaa tggtagcttt ttctacatct tactcctgtt  420
gatgcagcta aggtacattt gtaaaaagaa aaaaaccag acttttcaga caaacccttt  480
gtattgtaga taagaggaaa agactgagca tgctcacttt tttatattaa               530
```

<210> SEQ ID NO 22
<211> LENGTH: 544
<212> TYPE: DNA
<213> ORGANISM: Homo sapiens

<400> SEQUENCE: 22

```
tgttccggaa ggacatggcc tccaactaca aggagctggg cttccagggc taggcccctg      60
ccgctcccac ccccacccat ctgggccccg ggttcaagag agagcggggt ctgatctcgt     120
gtagccatat agagtttgct tctgagtgtc tgctttgttt agtagaggtg ggcaggagga     180
gctgaggggc tggggctggg gtgttgaagt tggctttgca tgcccagcga tgcgcctccc     240
tgtgggatgt catcaccctg ggaaccggga gtgcccttgg ctcactgtgt tctgcatggt     300
ttggatctga attaattgtc ctttcttcta aatcccaacc gaacttcttc caacctccaa     360
actggctgta accccaaatc caagccatta actacacctg acagtagcaa ttgtctgatt     420
aatcactggc cccttgaaga cagcagaatg tcccttttgca atgaggagga gatctgggct     480
gggcgggcca gctggggaag catttgacta tctggaactt gtgtgtgcct cctcaggtat     540
ggca                                                                  544
```

<210> SEQ ID NO 23
<211> LENGTH: 516
<212> TYPE: DNA
<213> ORGANISM: Homo sapiens

<400> SEQUENCE: 23

```
ctgtggtgca tggcagcgga ggccctgagc cgagggtggg ccctgtggca ggccctgctt      60
gccctgctct gctggctctg gcatgggctg gctcaccctg ccagctggct acagcccctg     120
ggcccgccag ccaccccgcc tggctcacca ccctgcagtt tgctcctgga cagcagcctc     180
tccagcaact gggatgacga cagcctaggg ccttcactct cccctgaggc tgtcctggcc     240
cggactgtgg ggagcacctc cacccccgg agcaggtgca cacccaggga tgccctggac     300
ctaagtgaca tcaactcaga gcctcctcgg ggctccttcc cctcctttga gcctcggaac     360
ctcctcagcc tgtttgagga cacctagac ccaacctgag cccagactc tgcctctgca     420
cttttaacct tttatcctgt gtctctcccg tcgcccttga aagctggggc ccctcgggaa     480
ctcccatggt cttctctgcc tggccgtgtc taataa                               516
```

<210> SEQ ID NO 24
<211> LENGTH: 488
<212> TYPE: DNA
<213> ORGANISM: Homo sapiens

<400> SEQUENCE: 24

```
gaaacatcgg ctaggtttcc tgctgcaaaa atctgattcc tgtgaacaca attcttccca      60
caacaagaag gacaaagtgg ttatttgcca gagagtgagc caagaggaag tcaagaaatg     120
ggctgaatca ctggaaaacc tgattagtca tgaatgtggg ctgcagctt tcaaagcttt     180
cttgaagtct gaatatagtg aggagaatat tgacttctgg atcagctgtg aagagtacaa     240
gaaaatcaaa tcaccatcta aactaagtcc caaggccaaa aagatctata atgaattcat     300
ctcagtccag gcaaccaaag aggtgaacct ggattcttgc accagggaag agacaagccg     360
gaacatgcta gagcctacaa taacctgctt tgatgaggcc cagaagaaga ttttcaacct     420
gatggagaag gattcctacc gccgcttcct caagtctcga ttctatcttg atttggtcaa     480
cccgtcca                                                              488
```

<210> SEQ ID NO 25
<211> LENGTH: 361
<212> TYPE: DNA
<213> ORGANISM: Homo sapiens

<400> SEQUENCE: 25

| | |
|---|---|
| ttcaagaacc ggtttccaaa gacagtcttc taattcctca ttagtaataa gtaaaatgtt | 60 |
| tattgttgta gctctggtat ataatccatt cctcttaaaa tataagacct ctggcatgaa | 120 |
| tatttcatat ctataaaatg acagatccca ccaggaagga agctgttgct ttctttgagg | 180 |
| tgatttttt cctttgctcc ctgttgctga aaccatacag cttcataaat aattttgctt | 240 |
| gctgaaggaa gaaaaagtgt ttttcataaa cccattatcc aggactgttt atagctgttg | 300 |
| gaaggactag gtcttcccta gcccccccag tgtgcaaggg cagtgaagac ttgattgtac | 360 |
| a | 361 |

<210> SEQ ID NO 26
<211> LENGTH: 302
<212> TYPE: DNA
<213> ORGANISM: Homo sapiens

<400> SEQUENCE: 26

| | |
|---|---|
| cctccctatc gtctgaacag ttgtcttcct cagcctcctc ccgcccccac cttgggaatg | 60 |
| taaatacacc gtgactttga agtttgtac ccctgtcctt cccttacgc cactagtgtg | 120 |
| taggcagatg tctgagtccc taggtggttt ctaggattga tagcaattag ctttgatgaa | 180 |
| cccatcccag gaaaaataaa aacagacaaa aaaaaggaa agattggttc tcccagcact | 240 |
| gctcagcagc cacagcctcc ctgtatgcct gtgcttggtc tactgataag ccctctacaa | 300 |
| aa | 302 |

<210> SEQ ID NO 27
<211> LENGTH: 385
<212> TYPE: DNA
<213> ORGANISM: Homo sapiens

<400> SEQUENCE: 27

| | |
|---|---|
| ttccttttgt agattcccag tttatttct aagactgcaa agatcacttt gtcaccagcc | 60 |
| ctgggacctg agaccaaggg ggtgtcttgt gggcagtgag ggggtgagga gaggctggca | 120 |
| tgaggttcag tcattccagt gagctccaaa gaggggccac ctgttctcaa aagcatgttg | 180 |
| gggaccagga ggtaaaactg gccatttatg gtgaacctgt gtcttggagc tgacttacta | 240 |
| agtggaatga gccgaggatt tgaatatcag ttctaacctt gatagaagaa ccttgggtta | 300 |
| catgtggttc acattaagag gatagaatcc tttggaatct tatggcaacc aaatgtggct | 360 |
| tgacgaagtc gtggtttcat ctctt | 385 |

<210> SEQ ID NO 28
<211> LENGTH: 502
<212> TYPE: DNA
<213> ORGANISM: Homo sapiens

<400> SEQUENCE: 28

| | |
|---|---|
| gcaagcaccc caagttcgag gagatcctca cccgcctgcg tctgcagaag agggggtacag | 60 |
| gtgcggtgga cacagctgcc gtgggctcag tatttgacgt gtccaacgct gatcggctgg | 120 |
| gctcgtccga agtagaacag gtgcagctgg tggtggatgg tgtgaagctc atggtggaaa | 180 |
| tggagaagaa gttggagaaa ggccagtcca tcgacgacat gatccccgcc cagaagtagg | 240 |

```
cgcctgccca cctgccaccg actgctggaa ccccagccag tgggagggcc tggcccacca    300
gagtcctgct ccctcactcc tcgccccgcc cctgtccca gagtccacct gggggctctc    360
tccacccttc tcagagttcc agtttcaacc agagttccaa ccaatgggct ccatcctctg    420
gattctggcc aatgaaatat ctccctggca gggtcctctt cttttcccag agctcctccc    480
caaccaggag ctctagttaa tg                                             502
```

<210> SEQ ID NO 29
<211> LENGTH: 338
<212> TYPE: DNA
<213> ORGANISM: Homo sapiens

<400> SEQUENCE: 29

```
tgtttggctg tagcagtgcg gccctggctg tgcatggaaa cctggagggg gctggcatcg     60
tgctcaagta catcatggct ggttgcccct tgtttctggg taatctctgg gatgtgactg    120
accgcgacat tgaccgctac acggaagctc tgctgcaagg ctggcttgga gcaggcccag    180 gggccccct tctctactat gtaaaccagg cccgccaagc tccccgactc aagtatctta    240
ttggggctgc acctatagcc tatggcttgc ctgtctctct gcggtaaccc catggagctg    300
tcttattgat gctagaagcc tcataactgt tctacctc                            338
```

<210> SEQ ID NO 30
<211> LENGTH: 406
<212> TYPE: DNA
<213> ORGANISM: Homo sapiens

<400> SEQUENCE: 30

```
gataaaacgg caacacagct cacaagaaca gactttccag ctgctgaagt tatggaaaca     60
tcaaaacaaa gcccaagata tagtcaagaa gatcatccaa gatattgacc tctgtgaaaa    120
cagcgtgcag cggcacattg acatgctaa cctcaccttc gagcagcttc gtagcttgat    180
ggaaagctta ccgggaaaga agtgggagc agaagacatt gaaaaaacaa taaaggcatg    240
caaacccagt gaccagatcc tgaagctgct cagtttgtgg cgaataaaaa atggcgacca    300
agacaccttg aagggcctaa tgcacgcact aaagcactca aagacgtacc actttcccaa    360
aactgtcact cagagtctaa agaagaccat caggttcctt cacagc                   406
```

<210> SEQ ID NO 31
<211> LENGTH: 400
<212> TYPE: DNA
<213> ORGANISM: Homo sapiens

<400> SEQUENCE: 31

```
agagaggtgc tattcaagtg attctgaagg cacccccaagg tatatctgta atttaaagat     60
tactgcaaat atctttactt tactgtgggt ttttagtaca tctgttaatt tagtgtttct    120
ttgtgtgttt tgtagactag tgttcttcca tccttcaact gagctcaaag taggttttgt    180
tgtaacattg tgattaggat ttaaactaat tcagagaatt gtatctttta ctgtacatac    240
tgtattcttt aagttttaat ttgttgtcat actgtctgtg ctgatggctt ggcttaagat    300
tttgatgcat aaatgaggtc actgttgatc agtgttgcta gtagcttggc agctcttcat    360
aaaagcatat tgggttggaa aggtgtttgc ctattttttca                         400
```

<210> SEQ ID NO 32
<211> LENGTH: 506
<212> TYPE: DNA
<213> ORGANISM: Homo sapiens

```
<400> SEQUENCE: 32
aatcagcatc tttccaatga ggtcaaaact tggaaggaaa gaacccttaa aagagaggct      60
cacaaacaag taacttgtga gaattctcca aagtctccta aagtgactgg aacagcttct     120
aaaaagaaac aaattacacc ctctcaatgc aaggaacgga atttacaaga tcctgtgcca     180
aaggaatcac caaaatcttg tttttttgat agccgatcaa agtctttacc atcacctcat     240
ccagttcgct atttttgataa ctcaagttta ggcctttgtc cagaggtgca aaatgcagga     300
gcagagagtg tggattctca gccaggtcct tggcacgcct cctcaggcaa ggatgtgcct     360
gagtgcaaaa ctcagtagac tcctctttgt cacttctctg gagatccagc attccttatt     420
tggaaatgac tttgtttatg tgtctatccc tggtaatgat gttgtagtgc agcttaatt      480 caattcagtc tttactttgc cactag                                          506

<210> SEQ ID NO 33
<211> LENGTH: 427
<212> TYPE: DNA
<213> ORGANISM: Homo sapiens

<400> SEQUENCE: 33
ttccctccac ctccaagaca ggtggcggcc gggcaggcac tcttaagccc acctccccct      60
cttgttgcct tcgatttcgg caaagcctgg gcaggtgcca ccgggaagga atggcatcga     120
gatgctgggc ggggacgcgg cgtggcgagg gggcttgacg gcgttggcgg ggctgggcac     180
aggggcagcc gcaggaggc agggatggca aggcgtgaag ccaccctgga aggaactgga     240
ccaaggtctt cagaggtgcg acagggtctg gaatctgacc ttactctagc aggagttttt     300
gtagactctc cctgatagtt tagttttttga taaagcatgc tggtaaaacc actaccctca     360
gagagagcca aaaatacaga agaggcggag agcgcccctc caaccaggct gttattcccc     420
tggactc                                                               427

<210> SEQ ID NO 34
<211> LENGTH: 547
<212> TYPE: DNA
<213> ORGANISM: Homo sapiens

<400> SEQUENCE: 34
gtacatggga ctatgctttt ctcaaagccc cattaactgc ttcctataat tttgatagtg      60
ggaccacata cgtaaaaatc tctcatttgt gtgggagtcat ttctgatttc aggggagatc     120
cttgtgttta tcagaaaggg cagaagtagg ggaagaataa tttggtatcc ttatctagtg     180
tttgattgtc aatgctggag aaaaaatatct gtaagagtgt ttatacagta cacttcagtt     240
atcttgatct ccctttccta tatgatgatt tgcttaaata tccatattaa gtaagtctca     300
aggtagggta ggcagcctga gagtctagag gcctttagtt ataaaggaat ctagccagtg     360
aacataattc ttattactag actgccacaa ggaagaaatt aacttaccct gtatatcagg     420
gtacaaaaaa ttcagtgatg tgcctaaata agttataaag atttaggcca atcagaagct     480
aacagcagtt tcaggtagag gtgcatgcct aatgttagtt agtgtagatt ccatttactg     540
cattctt                                                               547

<210> SEQ ID NO 35
<211> LENGTH: 457
<212> TYPE: DNA
<213> ORGANISM: Homo sapiens

<400> SEQUENCE: 35
```

```
tttcccctag ttgacctgtc tataagagaa ttatatattt ctaactatat aaccctagga    60
atttagacaa cctgaaattt attcacatat atcaaagtga gaaaatgcct caattcacat   120
agatttcttc tctttagtat aattgaccta ctttggtagt ggaatagtga atacttacta   180
taatttgact tgaatatgta gctcatcctt tacaccaact cctaatttta aataatttct   240
actctgtctt aaatgagaag tacttggttt ttttttctt aaatatgtat atgcacattta   300 aatgtaactt attattttt ttgagaccga gtcttgctct gttacccagg ctggagtgca   360
gtgggtgatc ttggctcact gcaagctctg ccctccccgg ttcgcacca ttctcctgcc    420 tcagcctccc aattagcttg gcctacagtc atctgcc                            457

<210> SEQ ID NO 36
<211> LENGTH: 507
<212> TYPE: DNA
<213> ORGANISM: Homo sapiens

<400> SEQUENCE: 36
ggaaagcagg attccatcgc tggaacaatt acatgatgga ctggaaaaat caatttaacg    60
attacactag caagaaagaa agttgtgtgg gtctctaatt aatagattta ccctttatag   120
aacatatttt cctttagatc aaggcaaaaa tatcaggagc ttttttacac acctactaaa   180
aaagttatta tgtagctgaa acaaaaatgc cagaaggata atattgattc ctcacatctt   240
taacttagta ttttacctag catttcaaaa cccaaatggc tagaacatgt ttaattaaat   300
ttcacaatat aaagttctac agttaattat gtgcatatta aaacaatggc ctggttcaat   360
ttctttcttt ccttaataaa tttaagtttt ttccccccaa aattatcagt gctctgcttt    420
tagtcacgtg tattttcatt accactcgta aaaaggtatc ttttttaaat gaattaaata   480
ttgaaacact gtacaccata gtttaca                                       507

<210> SEQ ID NO 37
<211> LENGTH: 550
<212> TYPE: DNA
<213> ORGANISM: Homo sapiens

<400> SEQUENCE: 37
gaggagaaca ctagacatgc caactcggga gcattctgcc tgcctgggaa cggggtggac    60
gagggagtgt ctgtaaggac tcagtgttga ctgtaggcgc ccctggggtg ggtttagcag   120
gctgcagcag gcagaggagg agtaccccc tgagagcatg tggggaagg ccttgctgtc    180 atgtgaatcc ctcaataccc ctagtatctg gctgggtttt caggggcttt ggaagctctg   240
ttgcaggtgt ccggggggtct aggactttag ggatctggga tctggggaag gaccaaccca   300
tgccctgcca agcctggagc ccctgtgttg ggggcaagg tggggagcc tggagcccct   360 gtgtgggagg gcgaggcggg ggagcctgga gccctgtgt gggagggcga ggcggggat    420 cctggagccc ctgtgtcggg gggcgaggga ggggaggtgg ccgtcggttg accttctgaa   480
catgagtgtc aactccagga cttgcttcca agcccttccc tctgttggaa attgggtgtg   540
ccctggctcc                                                         550

<210> SEQ ID NO 38
<211> LENGTH: 421
<212> TYPE: DNA
<213> ORGANISM: Homo sapiens

<400> SEQUENCE: 38
tgcttccagc cttcgtaatt agacttcacc ctgagtacac acacaatcac tgccactctc    60
```

```
actatagaca aaccacactc cctcctctgt cacccagtca ctgccatctc aacacacatc    120
cccaccctgt gtacacacaa tctctgttat tcatactctc actccttatg cgcactctca    180
acagggcatg tagtctgcac tcaagcatgc catcccagcc tcaccctgca ttttattcgg    240
ctcatcccat tttccctgaa cattttcgct gaactagggc cctggcagga tgctgggact    300
gtgcaaggag gtaggaccta tgcccacgga gctaagagac aggaacacag gctcatctcc    360
cgcactaacc aaccctggg atggctcaca gcctgctccc agtgctgtgt catgacctga     420
a                                                                    421

<210> SEQ ID NO 39
<211> LENGTH: 501
<212> TYPE: DNA
<213> ORGANISM: Homo sapiens

<400> SEQUENCE: 39
atgcttgccc aacacactgt gaaatagtta ccaaaatttg tacaaatgca gcatcttcat    60
tctttctgag aagacaagat ggttttcttt acatgaacaa atgaacaaaa gagatcctag   120
atccataacg tagctaaggc atctaagagt ttgctgttga taatcttgct gaccaaaaac   180
tactggagag taacacaggt tatatgccat cacaaataca atgctcatga gaactgatt    240 tgtagagtca atgaacctgt gtccagaatt ttaataggct ctctattgga aggagaaaga   300
atttcaagtt aacagtatct aactttatca tagttgatgt tagtaaattt taaaaaatga   360
ttttatatgt atgacaaaaa tctttgtaaa atgcgcaagt gcaataattt aaagaggtct   420
taactttgca tttataaatt ataaatattg tacatgtgtg taatttttc atgtattcat    480 ttgcagtctt tgtatttaaa a                                             501

<210> SEQ ID NO 40
<211> LENGTH: 530
<212> TYPE: DNA
<213> ORGANISM: Homo sapiens

<400> SEQUENCE: 40
tttccattcc caatctagtg ctagatgtat aaatcttttct tttgattctt cctaacaaaa   60
tattttctgg gttaaaaccc cagccaactc attgggttgt agccaaaggt tcactctcaa   120
gaagctttaa tatttaaata aaatcatatt gaatgtttcc aacctggagt ataatattca   180
gatataaaac agttttgtca gtctttctta gtgcctgtgt ggattttgt gaaaatgtca    240 aagagaaaac ttatatacta tttcccttga aatttttaaac tatattttct ttacaggtat   300
ttataatata ccaatgcttt tatcaaacag aattttaaag agcataataa attatattaa   360
agaaccaaaa gttttcctga gaataagaaa gtttcaccca ataaaatatt tttgaaaggc   420
atgttcctct gtcaatgaaa aaagtacat gtatgtgttg tgatattaaa agtgacattt    480
gtctaatagc ctaatacaac atgtagctga gtttaacatg tgtggtcttg                530

<210> SEQ ID NO 41
<211> LENGTH: 471
<212> TYPE: DNA
<213> ORGANISM: Homo sapiens

<400> SEQUENCE: 41
gaacctagga gagtcaacat ctggaggatt ttagtctttc ttacacatat gtgtgatttt    60
aaacgaatat tctcagacca caggaaactc ttcatccccc tgttgtttac cagtaacagt   120
atatcacaga cctttccaaa tgtttgtata tgtaatcaga tgtacattta tattgaaaaa   180
```

-continued

```
caaatgagat ggacttaaag agcacatcct gataaatact ttctctctca cctgtactat      240
atttctatta gactaaagtt atgtgatttt ttttttacat tttttcagat gactagcaat      300
tttgatagtt tataagataa tgcaaagaac tttctctgac aaactaactg cagtaacaga      360
aacctttctt ttcagttact cttttttcaag aatgaaagat tattatacaa aaaattgtat    420
actacttgat ggaaccaact tgtacatct tggccatgtc actggtcatt g                471
```

<210> SEQ ID NO 42
<211> LENGTH: 416
<212> TYPE: DNA
<213> ORGANISM: Homo sapiens

<400> SEQUENCE: 42

```
catgctaggc tttctcagtg gggaaaaaaa tggctggata gaactgggac aaacacagac       60
ccatctttag gggtctggat tttgtaggtc cgactacaca gcagtgttaa ctcatttctc      120
atgccattag ctctctacaa aataaagcaa agtagttcta gtgtggtcgt tataaaccaa     180
tattgtgaaa aatagcaact attcatttgt tcacaacatg cgtatttata gagtagttag    240
gtaccatttg taaggtaaat cctttaaaat tctataatac atactaaaat agtggttatt    300
ggtctgatat atgctgctct tggttctata aactagataa aagcagtgct ttgtgaaatg    360
cagtgttctc tcttaacgcc actggtgata ggaagtagtt cccttcagtt caaatc         416
```

<210> SEQ ID NO 43
<211> LENGTH: 471
<212> TYPE: DNA
<213> ORGANISM: Homo sapiens
<220> FEATURE:
<221> NAME/KEY: misc_feature
<222> LOCATION: (200)..(200)
<223> OTHER INFORMATION: n is a, c, g, or t
<220> FEATURE:
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (406)..(406)
<223> OTHER INFORMATION: n is a, c, g, or t

<400> SEQUENCE: 43

```
ttcctcccct gtagggtttg gacagaccca cccccagcct tgcccagctt tcaaaggaca       60
aaagggagca tccccacct actctcaggt ttttgaggaa acaaagattt gtggtaactg      120
aaggtgttgg gtcagtggcc aggtgccgac actgagctgt gacccagagg ggacgctgag    180
gaagtgggcg tgagtggacn tgtcaggtgg ttaccaggca ctggttgttg atggtcggtg    240
gttgggtgtg ggcagtcatc agtcatcagg tgtgctcagg gacaatctc ccctcaaccg     300 cacatgtgcc actgttcagc ggagctgact ggtttcncct ggtagagggn ccggctgttt    360
cctgacagat gcctggtgag caggggaagc aggacccagt ggtcancagg tgtctttaac    420
tgtcattgtg tgtggaatgt cgcagactcc tccacgtggc gggaatgagc t              471
```

<210> SEQ ID NO 44
<211> LENGTH: 489
<212> TYPE: DNA
<213> ORGANISM: Homo sapiens

<400> SEQUENCE: 44

```
gcaccacgac gatgacgttc acttgttttg tgttttttcga tctcttcaac gccttgacct    60
gccgctctca gaccaagctg atatttgaga tcggctttct caggaaccac atgttcctct   120
actccgtcct ggggtccatc ctggggcagc tggcggtcat ttacatcccc ccgctgcaga   180
gggtcttcca gacggagaac ctgggagcgc ttgatttgct gttttttaact ggattggcct   240 catccgtctt cattttgtca gagctcctca aactatgtga aaaatactgt tgcagcccca   300
agagagtcca gatgcaccct gaagatgtgt agtggaccgc actccgcggc accttcccta   360
atcatctcga tctggttgtg actgtggccc ctgccgtgtc tcctcgtcag gggagacttt   420
taggaggccg cagccttcca tcaccggatc agttttttcct cttaggaaag ctgcaggaac   480
ctcgtgggc                                                           489
```

```
<210> SEQ ID NO 45
<211> LENGTH: 546
<212> TYPE: DNA
<213> ORGANISM: Homo sapiens
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (506)..(506)
<223> OTHER INFORMATION: n is a, c, g, or t
<220> FEATURE:
<221> NAME/KEY: misc_feature
<222> LOCATION: (516)..(517)
<223> OTHER INFORMATION: n is a, c, g, or t
<220> FEATURE:
<221> NAME/KEY: misc_feature
<222> LOCATION: (520)..(520)
<223> OTHER INFORMATION: n is a, c, g, or t

<400> SEQUENCE: 45
gtggctttcc taggaatggg tcgtacaaag ctaagtggta atgatgctat ttggggaaag    60
gtcttttttg cttaantttg tttttttaaaa ctctgatgat tncttgagca acaggcaggt   120
tatctgcctg gttgaattct ggttgaaccg tgtattctaa tatttctggt taagtggtga   180
ctgggtaagg aaaccacttg gggtagcagt tcaacaattc acttacgaat gtttataagc   240
tttccatttc ctaggtaatt ttttaaaagc cagtcaaaac aaaaacttta ctgaaaatgg   300
acagaaatag gaaatggact ttttccttac tgtctatacc tcctgaacct tggtattgta   360
aagatctggg gacctctggg tctgttctga ccattcccta gtctccatgg ccaagcactc   420
aaggattgat ggacaccaca caccagctat attcatttgc caagatcaac agctccttct   480
ccaaacaact caagcccccca attccnatcg cattcnnttn gggtgagatg caactaacag   540
ccccctt                                                             546
```

```
<210> SEQ ID NO 46
<211> LENGTH: 520
<212> TYPE: DNA
<213> ORGANISM: Homo sapiens
<220> FEATURE:
<221> NAME/KEY: misc_feature
<222> LOCATION: (48)..(48)
<223> OTHER INFORMATION: n is a, c, g, or t

<400> SEQUENCE: 46
gcaggctaga tccgaggtgg cagctccagc ccccgggctc gccccctngc gggcgtgccc    60
```

```
cgcgcgcccc gggcggccga aggccgggcc gccccgtccc gccccgtagt tgctctttcg    120
gtagtggcga tgcgccctgc atgtctcctc acccgtggat cgtgacgact cgaaataaca    180
gaaacaaagt caataaagtg aaaataaata aaaatccttg aacaaatccg aaaaggcttg    240
gagtcctcgc ccagatctct ctcccctgcg agccttttt atttgagaag gaaaaagaga     300
aaagagaatc gtttaaggga acccggcgcc cagccaggct ccagtggccc gaacggggcg    360
gcgagggcgg cgagggcgcc gaggtccggc ccatcccagt cctgtggggc tggccgggca    420
gagaccccgg acccaggccc aggcctaacc tgctaaatgt ccccggacgg ttctggtctc    480
ctcggccact ttcagtgcgt cggttcgttt tgattctttt                          520

<210> SEQ ID NO 47
<211> LENGTH: 545
<212> TYPE: DNA
<213> ORGANISM: Homo sapiens

<400> SEQUENCE: 47
tgcagttttg catgtaatcg gttatacctt tattggactt ttatagacat tttttatttg    60
catgaaaaaa actcactaaa tttacatcac taaacaaagg ttaaccttg tgtgaaatga     120 aggaactgtc aataattgac agccaactaa tacagtaaac tgttatacta gttttgagct    180
ttagacctca gccttttgtg tggaagaagt cacagctttc ttaggcttta aaggaaaaga   240
aggaaggact taaatagctt tcttcctac cgggattacc tatgttttc cttgcttgca     300 atctcatctg attttgctag aaatcacaac catattgttt atgcatattg catgagtatt    360
accaagaaaa aaatctttaa aagttgtgat gtgacatgat ataaaggatc tctttatgtt    420
aaatgtcttt ccatgtacct ctggtgtgtc agggattttg tgcctcaaaa aatgtttcca   480
aggttgtgtg tttatactgt gtattttttt taaattcacg gtgaacagca ctttattat    540 ttcca                                                               545

<210> SEQ ID NO 48
<211> LENGTH: 539
<212> TYPE: DNA
<213> ORGANISM: Homo sapiens

<400> SEQUENCE: 48
aggtggcagt ggtccgtact ccacccaagt cgccgtcttc cgccaagagc cgcctgcaga    60
cagcccccgt gccatgcca gacctgaaga atgtcaagtc caagatcggc tccactgaga     120
acctgaagca ccagccggga ggcgggaagg tgcaaatagt ctacaaacca gttgacctga    180
gcaaggtgac ctccaagtgt ggctcattag gcaacatcca tcataaacca ggaggtggcc    240
aggtggaagt aaaatctgag aagcttgact tcaaggacag agtccagtcg aagattgggt    300
ccctggacaa tatcacccac gtccctggcg gaggaaataa aaagattgaa acccacaagc    360
tgaccttccg cgagaacgcc aaagccaaga cagaccacgg ggcggagatc gtgtacaagt    420
cgccagtggt gtctggggac acgtctccac ggcatctcag caatgtctcc tccaccggca    480
gcatcgacat ggtagactcg ccccagctcg ccacgctagc tgacgaggtg tctgcctcc    539

<210> SEQ ID NO 49
<211> LENGTH: 542
<212> TYPE: DNA
<213> ORGANISM: Homo sapiens

<400> SEQUENCE: 49
gtaaagatcc tatagctctt ttttttgag atggagtttc gcttttgttg cccaggctgg     60
```

```
agtgcaatgg cgcgatcttg gctcaccata acctccgcct cccaggttca agcaattctc    120
ctgccttagc ctcctgagta gctgggatta caggcgtgcg ccactatgcc tgactaattt    180
tgtagtttta gtagacggg gtttctcca tgttggtcag gctggtctca aactcctgac      240
ctcaggtgat ctgcccgcct cagcctccca aagtgctgga attacaggcg tgagccacca    300
cgcctggctg gatcctatat cttaggtaag acatataacg cagtctaatt acatttcact    360
tcaaggctca atgctattct aactaatgac aagtattttc tactaaacca gaaattggta    420
gaaggattta ataagtaaa agctactatg tactgcctta gtgctgatgc ctgtgtactg     480
ccttaaatgt acctatggca atttagctct cttgggttcc caaatccctc tcacaagaat   540
gt                                                                   542

<210> SEQ ID NO 50
<211> LENGTH: 329
<212> TYPE: DNA
<213> ORGANISM: Homo sapiens

<400> SEQUENCE: 50
aaagcccaac atcccatggc tgtttctcac agatcccaaa ttggccatgg aagtttattt     60
tggcccttgt agtccctacc agtttaggct ggtgggccca gggcagtggc caggagccag    120
aaatgccatg ctgacccagt gggaccggtc gttgaaaccc atgcagacac gagtggtcgg    180
gagacttcag aagccttgct tctttttcca ttggctgaag ctctttgcaa ttcctattct    240
gttaatcgct gttttccttg tgttgaccta atcatcattt tctctaggat ttctgaaagt    300
tactgacaat acccagacag gggctttgc                                      329

<210> SEQ ID NO 51
<211> LENGTH: 438
<212> TYPE: DNA
<213> ORGANISM: Homo sapiens

<400> SEQUENCE: 51
taattacgtc tgaggctgga agctgggaaa cccaataaat gaactccttt agtttattac     60
aacaagaaga cgttgtgata caagagattc cttcttctt gtgacaaaac atctttcaaa    120
acttaccttg tcaagtcaaa atttgtttta gtacctgttt aaccattaga aatatttcat    180
gtcaaggagg aaaacattag ggaaaacaaa aatgatataa agccatatga ggttatattg    240
aaatgtattg agcttatatt gaaatttatt gttccaattc acaggttaca tgaaaaaaaa    300
tttactaagc ttaactacat gtcacacatt gtacatgaa acaagaacat taagaagtcc     360
gactgacagt atcagtactg ttttgcaaat actcagcata ctttggatcc atttcatgca    420
ggattgtgtt gttttaac                                                  438

<210> SEQ ID NO 52
<211> LENGTH: 427
<212> TYPE: DNA
<213> ORGANISM: Homo sapiens

<400> SEQUENCE: 52
agcagtggag gagcacacgg acctttcccc agagccccca gcatcccttg ctcacacctg     60
cagtagcggt gctgtccagg tggcttacag atgaacccaa ctgtggagat gatgcagttg   120
gcccaacctc actgacggtg aaaaaatgtt tgccagggtc cagaaacttt ttttggttta   180
tttctcatac agtgtattgg caactttggc acaccagaat tgtaaactc caccagtcct    240 actttagtga gataaaaagc acactcttaa tcttcttcct tgttgctttc aagtagttag   300
```

| | |
|---|---:|
| agttgagctg ttaaggacag aataaaatca tagttgagga cagcaggttt tagttgaatt | 360 |
| gaaaatttga ctgctctgcc ccctagaatg tgtgtatttt aagcatatgt agctaatctc | 420 |
| ttgtgtt | 427 |

<210> SEQ ID NO 53
<211> LENGTH: 486
<212> TYPE: DNA
<213> ORGANISM: Homo sapiens

<400> SEQUENCE: 53

| | |
|---|---:|
| ttcagcttca tttgtgtcaa tgggcaatga caggtaaatt aagacatgca ctatgaggaa | 60 |
| taattattta tttaataaca attgtttggg gttgaaaatt caaaaagtgt ttatttttca | 120 |
| tattgtgcca atatgtattg taaacatgtg ttttaattcc aatatgatga ctcccttaaa | 180 |
| atagaaataa gtggttattt ctcaacaaag cacagtgtta aatgaaattg taaaacctgt | 240 |
| caatgataca gtccctaaag aaaaaaaatc attgctttga agcagttgtg tcagctactg | 300 |
| cggaaaagga aggaaactcc tgacagtctt gtgcttttcc tatttgtttt catggtgaaa | 360 |
| atgtactgag attttggtat tacactgtat ttgtatctct gaagcatgtt tcatgttttg | 420 |
| tgactatata gagatgtttt taaaagtttc aatgtgattc taatgtcttc atttcattgt | 480 |
| atgatg | 486 |

<210> SEQ ID NO 54
<211> LENGTH: 520
<212> TYPE: DNA
<213> ORGANISM: Homo sapiens

<400> SEQUENCE: 54

| | |
|---|---:|
| ctgtctgaca cggactgcaa taccagaaag ttctgcctcc agccccgcga tgagaagccg | 60 |
| ttctgtgcta catgtcgtgg gttgcggagg aggtgccagc gagatgccat gtgctgccct | 120 |
| gggacactct gtgtgaacga tgtttgtact acgatggaag atgcaacccc aatattagaa | 180 |
| aggcagcttg atgagcaaga tgcacacat gcagaaggaa caactgggca cccagtccag | 240 |
| gaaaaccaac ccaaaaggaa gccaagtatt aagaaatcac aaggcaggaa gggacaagag | 300 |
| ggagaaagtt gtctgagaac ttttgactgt ggccctggac tttgctgtgc tcgtcatttt | 360 |
| tggacgaaaa tttgtaagcc agtccttttg gagggacagg tctgctccag aagagggcat | 420 |
| aaagacactg ctcaagctcc agaaatcttc cagcgttgcg actgtggccc tggactactg | 480 |
| tgtcgaagcc aattgaccag caatcggcag catgctcgat | 520 |

<210> SEQ ID NO 55
<211> LENGTH: 526
<212> TYPE: DNA
<213> ORGANISM: Homo sapiens

<400> SEQUENCE: 55

| | |
|---|---:|
| gccctcttcc tttaggcatg tgagaaaatc agcctagcag tttaaacccc actttcctcc | 60 |
| acttagcacc ataggcaagg gggcagatcc cagagcccct ctcaccccc ccaccacagg | 120 |
| cctgctcctt ccttagcctt ggctaagatg gtccttctgt gtcttgcaaa gactccccaa | 180 |
| gtggacaggg agccctggg agggcagcca gtgagggtgg ggtgggactg aagcgttgtg | 240 |
| tgcaaatcca gcttccatcc cctccccaac ctggcaggat tctccatgtg taaacttcac | 300 |
| ccccaggacc caggatcttc tcctttctgg gcatccctt gtgggtgggc agagccctga | 360 |
| cccacagctg tgttactgct tggagaagca tatgtagggg catacctgt ggtgttgtgc | 420 |

```
tgtgtctggc tgtgggataa atgtgtgtgg gaatattgaa acatcgccta ggaattgtgg    480
tttgtatata accctctaag cccctatccc ttgtcgatga cagtca                   526

<210> SEQ ID NO 56
<211> LENGTH: 419
<212> TYPE: DNA
<213> ORGANISM: Homo sapiens

<400> SEQUENCE: 56
accaggagtg tcagcttttä gaaggatcat ggtcatgtga gcttctggtc accggaagcc     60
agaaatactc agctgccatg ttgatccaca aaggtgggag gatgtgggga aggggggaaag  120 cggtgaggac gcagagtgca ggctgtggcc tcggcatccc gcaggaggtc cctagaacat   180
gccgtttcat gtcacctgct acagctctcc cccagctagt atgatgatcc gttttacaaa   240
tgcagaaatg atcttaatat tcatgaccac tggccaggcg aggtggctca cacctgtaat   300
cccagcactt tgggaggcca aggcgggtgg atcacaaggt caagagttcg agaccagcct   360
gaccaacgtg gtgaaacccc gtctctacta aaaatagaag cattagccga gcctggtgg    419

<210> SEQ ID NO 57
<211> LENGTH: 390
<212> TYPE: DNA
<213> ORGANISM: Homo sapiens

<400> SEQUENCE: 57
gcgcagagta gctgcttcct ggacgtgcgc gcccaggcca gtgctgtgag caggcgggga    60
ggaggctgcc ggaggagcct gagcctggca ggttcccctg ccctgaggct gtgagcagct   120
agtggtggct tctcctgcct ttttcaggga actgggaaac ttaggggact gagctgggga   180
gggaggcagg tgggtggtaa gagggaaact ctggagagcc tgcacccagg tactgagtgg   240
ggagtgtaca gaccctgcct tggggttct gggaatgatg caactggttt tactagtgtg    300
caagtgtgtt catccccaag ttctcttttg tcctcacatg cagagttgtg catgcccctg   360
agtgtgaaca ggttttgccta cgttggtgca                                    390

<210> SEQ ID NO 58
<211> LENGTH: 504
<212> TYPE: DNA
<213> ORGANISM: Homo sapiens

<400> SEQUENCE: 58
tggtttattg ccgtgtgcta tgcctttgtg ttctcagctc tgattgagtt tgccacagta    60
aactatttca ctaagagagg ttatgcatgg gatggcaaaa gtgtggttcc agaaaagcca  120
aagaaagtaa aggatcctct tattaagaaa acaacacttt acgctccaac agcaaccagc   180 tacacccta atttggccag gggcgacccg ggcttagcca ccattgctaa aagtgcaacc   240
atagaaccta aagaggtcaa gcccgaaaca aaaccaccag aacccaagaa aacctttaac   300
agtgtcagca aaattgaccg actgtcaaga atagccttcc cgctgctatt tggaatcttt   360
aacttagtct actgggctac gtatttaaac agagagcctc agctaaaagc ccccacacca   420
catcaataga tcttttactc acattctgtt gttcagttcc tctgcactgg gaatttattt   480
atgttctcaa cgcagtaatt ccca                                           504

<210> SEQ ID NO 59
<211> LENGTH: 385
<212> TYPE: DNA
<213> ORGANISM: Homo sapiens
```

<400> SEQUENCE: 59

```
tagaagtcca aatcactcat tgtttgtgaa agctgagctc acagcaaaac aagccaccat        60
gaagctgtcg gtgtgtctcc tgctggtcac gctggccctc tgctgctacc aggccaatgc       120
cgagttctgc ccagctcttg tttctgagct gttagacttc ttcttcatta gtgaacctct       180
gttcaagtta agtcttgcca aatttgatgc ccctccggaa gctgttgcag ccaagttagg       240
agtgaagaga tgcacggatc agatgtccct tcagaaacga agcctcattg cggaagtcct       300
ggtgaaaata ttgaagaaat gtagtgtgtg acatgtaaaa actttcatcc tggtttccac       360 tgtcttttcaa tgacaccctg atctt                                            385
```

<210> SEQ ID NO 60
<211> LENGTH: 499
<212> TYPE: DNA
<213> ORGANISM: Homo sapiens

<400> SEQUENCE: 60

```
aagcttcact tcaacttcac tacttctgta gtctcatctt gagtaaaaga gaacccagcc        60
aactatgaag ttccttgtct tgccttcat cttggctctc atggttttcca tgattggagc       120 tgattcatct gaagagaaat ttttgcgtag aattggaaga ttcggttatg ggtatggccc       180
ttatcagcca gttccagaac aaccactata cccacaacca taccaaccac aataccaaca       240 atatacctt taatatcatc agtaactgca ggacatgatt attgaggctt gattggcaaa       300
tacgacttct acatccatat tctcatcttt cataccatat cacactacta ccactttttg       360
aagaatcatc aaagagcaat gcaaatgaaa aacactataa tttactgtat actctttgtt       420
tcaggatact tgccttttca attgtcactt gatgatataa ttgcaattta aactgttaag       480
ctgtgttcag tactgtttc                                                   499
```

<210> SEQ ID NO 61
<211> LENGTH: 464
<212> TYPE: DNA
<213> ORGANISM: Homo sapiens

<400> SEQUENCE: 61

```
ggtttgttac catcctttaa tcataactaa aacattgaaa acagaacaaa tgagaaaaga        60
aaaaaaacct gccgattaac aatgacgaaa atcatgcatg atctgaaagg tgtggaaaga       120
aacacaatta ggtctcactc tggttaggca ttatttattt aattatgttg tatatcattg       180
tttgcagggc aacattctat gcattgaact gagcactaac tgggctagct tctggtagac       240
gtttgtggct agtgcgattc acagtctact gcctgttcca ctgaaacatt ttgtcatatt       300
cttgtattca agaaaaaag gaaaaaaga ttattgtaaa tatttttattt aatgcacaca       360 ttcacacagt ggtaacagac tgccagtgtt catcctgaaa tgtctcacgg attgatctac       420
ctgtccatgt atgtctgctg agctttctcc ttggttatgt tttt                        464
```

<210> SEQ ID NO 62
<211> LENGTH: 506
<212> TYPE: DNA
<213> ORGANISM: Homo sapiens

<400> SEQUENCE: 62

```
taaagagctc atttttcagg tccgccacac ctatgaaatt cccctggtgc tggtgggtaa        60
caaaattgat ctggaacagt tccgccaggt ttctacagaa gaaggcttga gtcttgccca       120
agaatataat tgtggttttt ttgagacctc tgcagccctc agattctgta ttgatgatgc       180
```

-continued

```
ttttcatggc ttagtgaggg aaattcgcaa gaaggagtcc atgccatcct tgatggaaaa    240
gaaactgaag agaaaagaca gcctgtggaa gaagctcaaa ggttctttga agaagaagag    300
agaaaatatg acatgatatc tttgcttttg agttcctcac gctctctgaa ttttattagt    360
tggacaattc catatgtagc attctgcttc aatattatct ctctatgtgt ctctctctct    420
ttaaatatct gcctgtaggt aaaagcaagc tctgcatatc tgtacctctt gagatagttt    480
tgttttgcct ttaacagttg gatgga                                         506

<210> SEQ ID NO 63
<211> LENGTH: 436
<212> TYPE: DNA
<213> ORGANISM: Homo sapiens

<400> SEQUENCE: 63 gagggggtcac cgtgcaggat ggaaatttct ccttttctct ggagtcagtg aagaagctca     60
aagacctcca ggagcccag gagcccaggg ttgggaaact caggaacttt gcacccatcc    120
ctggtgaacc tgtggttccc atcctctgta gcaacccgaa cttccagaa gaactcaagc    180 ctctctgcaa ggagcccaat gcccaggaga tacttcagag gctggaggaa atcgctgagg    240
acccgggcac atgtgaaatc tgtgcctacg ctgcctgtac cggatgctag gggggcttgc    300
ccactgcctg cctcccctcc gcagcaggga agctctttc cctgcagaa agggccaccc    360 atgatactcc actcccagca gctcaaccta ccctggtcca gtcgggagga gcagcccggg    420
gaggaactgg gtgact                                                    436

<210> SEQ ID NO 64
<211> LENGTH: 429
<212> TYPE: DNA
<213> ORGANISM: Homo sapiens

<400> SEQUENCE: 64 ctcccccga gagaaggctg caaagctggg aagcccaggg tgtgctcctc ccgccctttt     60
ggacccccgg gcttgcaccg gctgcactct gagaaccagc tgcgcgcgga gcggtgcaat    120
gcagcaccca ccctgcgagc ctggcaattg cttgtcatta aagaaaaaa aaattacgga    180 gggctccggg ggtgtgtgtt ggggagggga gaccgatgct tctaacccag cccccgcttt    240
gactgcgtgt tgtgcagctg agcgcgaggc caacgttgag caaggccttg cagggaggtt    300
gctcctgtgt aattacgaaa gaaggctagt ccgaaggtgc aaaatagcag ggagaggacg    360 cgcccccctta ggaacaagac ctctggatgt ttccagtttc aaattgaaag aagaggggcg    420
ccccccttg                                                            429

<210> SEQ ID NO 65
<211> LENGTH: 513
<212> TYPE: DNA
<213> ORGANISM: Homo sapiens

<400> SEQUENCE: 65
acagcagcag ttatggccgg agcgaccgct actcgagggg ccgacaccgg gtgggcagac     60
cagatcgtgg gctctctctg tccatggaaa ggggctgccc tccccagcgt gattcttaca    120
gccggtcagg ctgcagggtg cccaggggcg gaggccgtct aggaggccgc ttggagagag    180
gaggaggccg gagcagatac taagcaggaa cagacttggg accaaaaatc ccttttcaac    240
gaaactaaca aaaagaagaa cctgttgtat ggtaactacc caaggactag tacaaggaag    300
agttgttttt acctttttaag aatttcctgt taagatcgtc tccatttttta tgcttttggg    360
```

| | | |
|---|---|---|
| agaaaaaact taaaattcgt ttagtttagt tttggaattg ttaacgtttc tttcaacaag | 420 | |
| ctcctgttaa aagtatatga acctgagtac tagtcttctt acatttacaa gtagaaattc | 480 | |
| gattaatggc ttcttccctt gtaaattttc ttg | 513 | |

<210> SEQ ID NO 66
<211> LENGTH: 551
<212> TYPE: DNA
<213> ORGANISM: Homo sapiens

<400> SEQUENCE: 66

| | |
|---|---|
| cagccagagc attggactga tccagcattt gagaactcat gttagagaga aaccttttac | 60 |
| atgcaaagac tgtggaaaag cgttttttcca gattagacac cttaggcaac atgagattat | 120 |
| tcatactggt gtgaaaccct atatttgtaa tgtatgtagt aaaaccttca gccatagtac | 180 |
| atacctaact caacaccaga gaactctatac tggagaaaga ccatataaat gtaaggaatg | 240 |
| tgggaaagcc tttagccaga gaatacatct ttctatccat cagagagtcc atactggagt | 300 |
| aaaaccttat gaatgcagtc attgtgggaa agcctttagg catgattcat cctttgctaa | 360 |
| acatcagaga attcatactg gagaaaaacc ttatgattgt aatgagtgtg aaaagccttt | 420 |
| cagctgtagt tcatccctta ttagacactg caaaacacat ttaagaaata ccttcagcaa | 480 |
| tgttgtgtga aatatactaa acatcaaaga atctatgttg gagcacaaga ttctaaatca | 540 |
| gtggttccct g | 551 |

<210> SEQ ID NO 67
<211> LENGTH: 316
<212> TYPE: DNA
<213> ORGANISM: Homo sapiens

<400> SEQUENCE: 67

| | |
|---|---|
| gagtcactcc aggaaagagc tgatgaggct acaacccaga agcagtctgg ggaagacaac | 60 |
| caggaccttg ctatctcctt tgcaggaaat ggactctctg ctcttagaac ctcaggttct | 120 |
| caggcaagag ccacctgcta ttgccgaacc ggccgttgtg ctaccgtga gtccctctcc | 180 |
| ggggtgtgtg aaatcagtgg ccgcctctac agactctgct gtcgctgagc ttcctagata | 240 |
| gaaaccaaag cagtgcaaga ttcagttcaa ggtcctgaaa aagaaaaac attttactct | 300 |
| gtgtaccttg tgtctt | 316 |

<210> SEQ ID NO 68
<211> LENGTH: 510
<212> TYPE: DNA
<213> ORGANISM: Homo sapiens

<400> SEQUENCE: 68

| | |
|---|---|
| gtgacgctca atctacagtt tattcatata ttcaagacca tgtatgtgta tctatagcca | 60 |
| ctggttcctc catgagatca gatggaacag acaatgccta tgtggctgat ggcaccatgt | 120 |
| gtggtccaga aatgtactgt gtaaataaaa cctgcagaaa agttcattta atgggatata | 180 |
| actgtaatgc caccacaaaa tgcaaaggga aagggatatg taataatttt ggtaattgtc | 240 |
| aatgcttccc tggacataga cctccagatt gtaaattcca gtttggttcc caggggggta | 300 |
| gtattgatga tggaaatttt cagaaatctg gtgacttttta tactgaaaaa ggctacaata | 360 |
| cacactggaa caactggttt attctgagtt tctgcatttt tctgccgttt ttcatagttt | 420 |
| tcaccactgt gatctttaaa agaaatgaaa taagtaaatc atgtaacaga gagaatgcag | 480 |
| agtataatcg taattcatcc gttgtatcag | 510 |

<210> SEQ ID NO 69
<211> LENGTH: 344
<212> TYPE: DNA
<213> ORGANISM: Homo sapiens

<400> SEQUENCE: 69

```
gagccactcc aagctgagga tgatccactg caggcaaaag cttatgaggc tgatgcccag      60
gagcagcgtg gggcaaatga ccaggacttt gccgtctcct ttgcagagga tgcaagctca     120
agtcttagag ctttgggctc aacaagggct ttcacttgcc attgcagaag gtcctgttat     180
tcaacagaat attcctatgg gacctgcact gtcatgggta ttaaccacag attctgctgc     240
ctctgaggga tgagaacaga gagaaatata ttcataattt actttatgac ctagaaggaa     300
actgtcgtgt gtcccataca ttgccatcaa ctttgtttcc tcat                      344
```

<210> SEQ ID NO 70
<211> LENGTH: 479
<212> TYPE: DNA
<213> ORGANISM: Homo sapiens

<400> SEQUENCE: 70

```
gctggaggtg acgctactga aactttgag gatgtcgggc actctacaga tgccagggaa       60
atgtccaaaa cattcatcat tgggagctc catccagatg acagaccaaa gttaaacaag      120
cctccagaac cttaaaggcg gtgtttcaag gaaactctta tcactactat tgattctagt     180
tccagttggt ggaccaactg ggtgatccct gccatctctg cagtggccgt cgccttgatg     240
tatcgcctat acatggcaga ggactgaaca cctcctcaga agtcagcgca ggaagagcct     300
gctttggaca cgggagaaaa gaagccattg ctaactactt caactgacag aaaccttcac     360
ttgaaaacaa tgattttaat atatctcttt cttttcttc cgacattaga aacaaaacaa     420
aaagaactgt cctttctgcg ctcaaatttt tcgagtgtgc ctttttattc atctactttt    479
```

<210> SEQ ID NO 71
<211> LENGTH: 541
<212> TYPE: DNA
<213> ORGANISM: Homo sapiens

<400> SEQUENCE: 71

```
gagctcaagc cagcatagct ccaccaagtg atctactgtt ccaaatctct ataaccacct      60
gcttcccact cagcctgcaa tagtgtttcc cactctctgc ttggcatcaa tagatgcata    120
agggtcaacc acattttcc tcaagttccc tggagaagaa gctgaactcc tggtttctcc    180
atccccatga ccttcccagg gccatggagg tcctgctgct ggtctgggat gatgatgccc    240
ctggaaacct tcctgcaatg gccccttact ttggacagca cccctgagc ccaagccagt    300
tttggccttc acagcctggc cggttccac tctggcccat ctcccattct tactgggagt    360
tggagatttg aagccagtca tctcagcact gtctgaggag ggcagagcca tgggttctgt    420
gctggagggt gcacggccaa gatctccaga ctgctggttc ccaggaacc ctccctacat    480
ctgggcttca gatcctgact cccttctgtc ccctaattcc ctgagctgta gatcctctgg    540
t                                                                    541
```

<210> SEQ ID NO 72
<211> LENGTH: 547
<212> TYPE: DNA
<213> ORGANISM: Homo sapiens

<400> SEQUENCE: 72

```
cgcacccgca tcacagggga ggaggtggag gtgcaggact ccgtgcccgc agactccggc      60
ctctatgctt gcgtaaccag cagcccctcg ggcagtgaca ccacctactt ctccgtcaat     120
gtttcagctt gcccagatct ccaggaggct aagtggtgct cggccagctt ccactccatc     180
actcccttgc catttggact tggtactcgg cttagtgatt agaggccctg aacaggtggt     240
ggtatccctg ctctgctgga gaggaaccca gatgctctcc cctcctcgga ggatgatgat     300
gatgatgatg actcctcttc agaggagaaa gaaacagata caccaaacc aaaccccgta      360 gctccatatt ggacatcccc agaaaagatg gaaagaaat tgcatgcagt gccggctgcc      420
aagacagtga agttcaaatg cccttccagt gggaccccaa ccccacact gcgctggttg      480 aaaaatggca agaattcaa acctgaccac agaattggag gctacaaggt ccgttatgcc      540
acctgga                                                               547

<210> SEQ ID NO 73
<211> LENGTH: 407
<212> TYPE: DNA
<213> ORGANISM: Homo sapiens

<400> SEQUENCE: 73
ctgccctgta catgctagtt caacagaaag gaatggcctt tcaccttctc ctggtggcag      60
gcaagcagat gtcctctgcg gagataccgc cagctcccca ggacgcagac tgactcctgt     120
ttgctcgctg gaccaacccc aggcagaagg tggaaggtgg aacagaggt ttagctgcag      180 gacatgtatt cccattgcac cgagacctaa ctgccgctca gagtgtagac cgagatggtg     240
cagatgcctg cagtgccatt aaaatgtggg tgaaggtgac atcaggatta tgtgccccag     300
gccgggctca gtggctcaca cctgtaatcc cagcactttg ggaggccaag gtgggcggat     360
cacctgaggt caggagtttg cgacaagcct gccaacaagc tgaaacc                   407

<210> SEQ ID NO 74
<211> LENGTH: 533
<212> TYPE: DNA
<213> ORGANISM: Homo sapiens

<400> SEQUENCE: 74
gaaatctctg atataagctg ggtgtggtgg ctcgtgcctg tagtctcagc tgctgggcaa      60
ctgcagacca gcctgggcaa catagtaaga ccctgtctca aaaaaataat ctctggtaca     120
atggtcatgt tccaaagttc cttacttggg cctcttgagt gcagtggctc acacctggaa     180
tcccagtgct ttgagaggct gaggaggcag gaggttcact tgtgcccagg aatttgaggc     240
tgcagtgagc tatgattgtg ccactgcact ccagcctggg tgacagagca agactgtgct     300
ctcttaaaaa taagaaagag cctcttcatc ttcaaaagga ctacatctga gtttccccca     360
gaaggacaaa tgtctactta gaccttataa atttccaaaa taagagagtc agagccagag     420
gtggcttgta agttgacttc tgttgagatc tgaccacatt tgatctcttg ttttaatttt     480
ccaactaact gaacttggaa gaaaacccaa accaagtttt aatctgatgc cta            533

<210> SEQ ID NO 75
<211> LENGTH: 564
<212> TYPE: DNA
<213> ORGANISM: Homo sapiens

<400> SEQUENCE: 75
ccatgagcaa cttccagagc tggacaactt gggcctggat agcttttcca gtggacctgg      60
ggaagaggct ttgttgcaga tgagatcaaa catcatctat gactccactg cccgaatcag     120
```

```
aaggaacgcc aaaggaaact actgtaagag gaccccgctc tacatcgact tcaaggagat    180
tgggtgggac tcctggatca tcgctccgcc tggatacgaa gcctatgaat gccgtggtgt    240
ttgtaactac cccctggcag agcatctcac acccacaaag catgcaatta tccaggcctt    300
ggtccacctc aagaattccc agaaagcttc caaagcctgc tgtgtgccca caaagctaga    360
gcccatctcc atcctctatt tagacaaagg cgtcgtcacc tacaagttta aatacgaagg    420
catggccgtc tccgaatgtg gctgtagata gaagaagagt cctatggctt atttaataac    480
tgtaaatgtg tatatttggt gttcctattt aatgagatta tttaataagg gtgtacagta    540
atagaggctt gctgccttca ggaa                                          564

<210> SEQ ID NO 76
<211> LENGTH: 533
<212> TYPE: DNA
<213> ORGANISM: Homo sapiens

<400> SEQUENCE: 76
atgatctgca tgtttctggt ggcatggtcc ccttattcca tcgtgtgctt atgggcttct     60
tttggtgacc caagaagat tcctcccccc atggccatca tagctccact gtttgcaaaa    120
tcttctacat tctataaccc ctgcattat gtggttgcta ataaaaagtt tcggagggca    180
atgcttgcca tgttcaaatg tcagactcac caaacaatgc ctgtgacaag tattttaccc    240
atggatgtat ctcaaaaccc attggcttct ggaagaatct gaaataagag aaaaggacac    300
gctatcaaaa cactttagtt ttttgacaat gcttttcttt taaatatgag cccatttaga    360
tcaagtgcag acatggatca ttgtcctatg agagtgtaag ctcctcaagc acagctcgtg    420
cttccgtttg tgcactctgg ctgctgtagt gtatgcttct ctgtgtcctg atatatcaac    480
ttattgctca tctcctttga tgaattaggc atcagaggtt aaggtcccct ttc            533

<210> SEQ ID NO 77
<211> LENGTH: 510
<212> TYPE: DNA
<213> ORGANISM: Homo sapiens

<400> SEQUENCE: 77
gaacaggaga gttcccaggc cagtacggaa gaatgtgaga aaaataagca ggacacaatt     60
acaactaaaa aatatatcta agcatttgca aaggcgacaa taaattattg acgcttaacc    120
tttccagttt ataagactgg aatataattt caaaccacac attagtactt atgttgcaca    180
atgagaaaag aaattagttt caaatttacc tcagcgtttg tgtatcgggc aaaaatcgtt    240
ttgcccgatt ccgtattggt atactttttgc ttcagttgca tatcttaaaa ctaaatgtaa    300
tttattaact aatcaagaaa aacatctttg gctgagctcg gtggctcatg cctgtaatcc    360
caacactttg agaagctgag gtgggaggag tgcttgaggc caggagttca agaccagcct    420
gggcaacata gggagacccc catctttacg aagaaaaaaa aaaggggaa aagaaaatct    480 tttaaatctt tggatttgat cactacaagt                                    510

<210> SEQ ID NO 78
<211> LENGTH: 531
<212> TYPE: DNA
<213> ORGANISM: Homo sapiens

<400> SEQUENCE: 78
ccgagccgag cttactgtga gtgtggagat gttatcccac catgtaaagt cgcctgcgca     60
ggggagggct gcccatctcc ccaacccagt cacagagaga taggaaacgg catttgagtg    120
```

| | |
|---|---|
| ggtgtccagg gccccgtaga gagacattta agatggtgta tgacagagca ttggccttga | 180 |
| ccaaatgtta aatcctctgt gtgtatttca taagttatta caggtataaa agtgatgacc | 240 |
| tatcatgagg aaatgaaagt ggctgatttg ctggtaggat tttgtacagt ttagagaagc | 300 |
| gattatttat tgtgaaactg ttctccactc caactccttt atgtggatct gttcaaagta | 360 |
| gtcactgtat atacgtatag agaggtagat aggtaggtag attttaaatt gcattctgaa | 420 |
| tacaaactca tactccttag agcttgaatt acatttttaa aatgcatatg tgctgtttgg | 480 |
| caccgtggca agatggtatc agagagaaac ccatcaattg ctcaaatact c | 531 |

<210> SEQ ID NO 79
<211> LENGTH: 522
<212> TYPE: DNA
<213> ORGANISM: Homo sapiens

<400> SEQUENCE: 79

| | |
|---|---|
| ttgtggctac aaaggatggg ctgaagctgg ggtctggacc ttcaatcaaa gccttagatg | 60 |
| ggagatctca agtttcaata tcatgttttg gcaaaacatt cgatgctccc acatccttac | 120 |
| ctaaagctac cagaaaggct ttgggaactg tcaacagagc tacagaaaag tcagtaaaga | 180 |
| ccaatggacc cctcaaacaa aaacagccaa gcttttctgc caaaagatg actgagaaga | 240 |
| ctgttaaagc aaaaaactct gttcctgcct cagatgatgg ctatccagaa atagaaaaat | 300 |
| tatttccctt caatcctcta ggcttcgaga gttttgacct gcctgaagag caccagattg | 360 |
| cacatctccc cttgagtgaa gtgcctctca tgatacttga tgaggagaga gagcttgaaa | 420 |
| agctgtttca gctgggcccc ccttcacctt tgaagatgcc ctctccacca tggaaatcca | 480 |
| atctgttgca gtctccttta agcattctgt tgaccctgga tg | 522 |

<210> SEQ ID NO 80
<211> LENGTH: 541
<212> TYPE: DNA
<213> ORGANISM: Homo sapiens

<400> SEQUENCE: 80

| | |
|---|---|
| ggtttaagga tcagtcctct gcagtttcgc taaggccccc tttgtgtgca tgggtcagtc | 60 |
| accatatgtt cccccagag aatgtgtcta tatcctcctt ctaacagcac cttcccctg | 120 |
| cagctactct tcagatctgg ctctctgtac cctaaaacct agtatctttt tctcttctat | 180 |
| ggaaaatccg aaggtctaaa cttgactttt ttgaggtctt ctcaacttga ctacagttgt | 240 |
| gctcataatt gtccttgcct ttccagctta attattttaa ggaacaaatg aaaactctgg | 300 |
| gctgggtgga gtggctcata cctgtaatcc cagcactttg ggaggctacg gtgggcagat | 360 |
| catctgaggc caggagttcg agacctgcct ggccaacatg gcaacacccc gtctctaata | 420 |
| aaaatataaa aattagcctg gcatggtagc atgcgcctat agtcccagct gctcaggagg | 480 |
| ctgaggcatg agaatcgctt gaacctagga ggtggaggtt gcattcaact gagatcatac | 540 |
| c | 541 |

<210> SEQ ID NO 81
<211> LENGTH: 454
<212> TYPE: DNA
<213> ORGANISM: Homo sapiens

<400> SEQUENCE: 81

| | |
|---|---|
| actggtctat ctctatcctg acattcccaa ggaggaggca ttcggaaagt attgtcggcc | 60 |
| agagagccag gagcatcctg aagctgaccc aggcgctgcc ccatacctga agaccaagtt | 120 |

```
tatctgtgtg acaccaacga cctgcagcaa taccattgac ctgccgatgt ccccccgcac    180
tttagattca ttgatgcagt ttggaaataa tggtgaaggt gctgaaccct cagcaggagg    240
gcagtttgag tccctcacct ttgacatgga gttgacctcg gagtgcgcta cctcccccat    300
gtgaggagct gagaacggaa gctgcagaaa gatacgactg aggcgcctac ctgcattctg    360 ccaccctca cacagccaaa ccccagatca tctgaaacta ctaactttgt ggttccagat     420 ttttttaat ctcctacttc tgctatcttt gagc                                 454

<210> SEQ ID NO 82
<211> LENGTH: 533
<212> TYPE: DNA
<213> ORGANISM: Homo sapiens

<400> SEQUENCE: 82
ttgacagctc tttaagccca catgcagcag tgggtcagat aaccctgtgg cagtgacacg     60
ggcaaattgg catttgaata agccctggg accacctcaa catgcgtagc ctcttgtctt    120
aaatgtactc cccatggcag catggaggag gcaagacctg tgggtcaatt ttgaactggc    180
cttactttga ttttaaaac aagagactca gggaaagtac taaaccaaaa tctctgattt     240
tactttgcgt tttctgtagt ttttgtttta ctgagatgct tttgtaaagg aaaataatac    300
tgtgacagtt tagtaattct acagattctt aatatttctc catcatggcc ttttacttca    360 caatttctg aagtctgaat tcaattacaa ttttttttt ttaccaattt aatctcaaat      420
gttgtttaac tgctttaaat tcatatacgt agagtattat aaactgcaga gatgaaaaat    480
gtgttttcac gggatttata ttgtgaacta aactaagcct acttttgtg act            533

<210> SEQ ID NO 83
<211> LENGTH: 483
<212> TYPE: DNA
<213> ORGANISM: Homo sapiens

<400> SEQUENCE: 83
gagacttctc acttctggtt ggaggtttca catatggctc aactcaagtc attaatctct     60
ttttaatttt tactcttgaa ttccttaaac ttcgctcatt atgaaatgtt ttaaaattat    120
gacaaaaatt actctgtcta accacttgcc ttgtctgcta ccagtttgtt aaaaattatt    180 cccccaacc agtaattcca ccagtactac ttgatttgtg ttatatttcc tatgtacatg     240
tacagccttt gttttgcttg cttgtctatt tttactttcc cttttttggg tcaaattttt    300
cttttgcttt gtttgaagaa ggaatataca gaagtaaaat cttgtcttct ctgctgattc    360
tttaattaat atgagccgga tactttccac tgtcttcttg gcactttcag gatttcttaa    420
tgctgatata tggactctta gaatggaatt tttgaagaaa aatctcaaag cctgtatcgt    480
tct                                                                  483

<210> SEQ ID NO 84
<211> LENGTH: 529
<212> TYPE: DNA
<213> ORGANISM: Homo sapiens

<400> SEQUENCE: 84
ataggttacc cttgaaattc attagtttgt cataaagttt taggaaaggt aggacccgga     60
aagaagttct aattagttgt ctaaatattt ttcagtgagc caagaaattc accatgaaaa    120
aacaagaata acaaatagaa gggaagagat aggatgggaa agctaacaaa ttaaagtttt    180
ggcaaaaagg aatatatgta aatagctaat tatttacttt tgtgcttact ttatttagat    240
```

-continued

```
tatttctatc agttacaatc tttttctagt taagtgtacc taattatgg aatgggtgct      300 atcctgttta tgtgtgtctt ggttttcctt ggctacagaa aaactgttgc agggcaacac    360
tagtttgata tttgatttac tctccaatga gactcaatgg ctgggccgtg gtagactcat    420
agttcctctt gttctttatt aaattcatcc tgctaattag atttctagtg acttgtaaca    480
tgtagtttac actgaattgc aattacagat gcatacaact actatacta               529
```

<210> SEQ ID NO 85
<211> LENGTH: 525
<212> TYPE: DNA
<213> ORGANISM: Homo sapiens

<400> SEQUENCE: 85

```
ataacagcat atgcatttcc ccaccgcgtt gtgtctgcag cttctttgcc aatatagtaa     60
tgcttttagt agagtactag atagtatcag ttttggattc ttattgttat cacctatgta    120
caatggaaag ggattttaag cacaaacctg ctgctcatct aacgttggta cataatctca    180
aatcaaaagt tatctgtgac tattatatag ggatcacaaa agtgtcacat attagaatgc    240 tgaccttca tatggattat tgtgagtcat cagagtttat tataacttat tgttcatatt     300
catttctaag ttaatttaag taatcattta ttaagacaga attttgtata aactatttat    360
tgtgctctct gtggaactga agtttgattt attttttgtac tacacggcat gggtttgttg    420
acactttaat tttgctataa atgtgtggaa tcacaagttg ctgtgatact tcattttaa    480 attgtgaact ttgtacaaat tttgtcatgc tggatgttaa cacat                    525
```

<210> SEQ ID NO 86
<211> LENGTH: 432
<212> TYPE: DNA
<213> ORGANISM: Homo sapiens

<400> SEQUENCE: 86

```
tcatgtctta ttcttccctg tgaaaccagg attaatcgtg gactcctggc agcttaaccct    60 agctcagttg cagtgctaag catgccccgc ccccattcag tgatacctgt ttgggaagta    120
tatacttccc caaaagtact cttggcccta agttttagga actttccccg acctggatcc    180
cttgtcatac ctgtgttact gtttaaagca cacccaccca acttacaaga tcttaggctg    240
ctgtggtggt gaagcacctt gagtctgctg atattcggga gaacaaggat ctgcagtttc    300 ccctttctc ccctctgaag agtggttctt atgtgcaatc tgcagtaacc ttgaactcca     360
gagctgcact atagaggaga atgcatgcca ctatgacagc agtatgccaa gctttgtgtt    420
catctcctaa ta                                                        432
```

<210> SEQ ID NO 87
<211> LENGTH: 185
<212> TYPE: DNA
<213> ORGANISM: Homo sapiens

<400> SEQUENCE: 87

```
atttcgtttt gcttttggtt gcctgaatgt tgtcaccaag tgaaaaaatt atttaactat     60
atgtaaaatt tctcttttaa aaaaagttt tactgatgtt aaacgttctc agtgccaatg    120
tcagactgtg ctcctccctc tcctgaacct ctaccctcac cctgagctgt cttgttgaaa    180
acagt                                                                185
```

<210> SEQ ID NO 88
<211> LENGTH: 361

```
<212> TYPE: DNA
<213> ORGANISM: Homo sapiens

<400> SEQUENCE: 88
tattctcgac tgtaatggca ttgcagtagg gccaaaacaa gtccaagctt cttaaaatga      60
ttggtggtta attttttcaaa gcagaaattt taagccaaaa acaaacgaaa ggaaagcggg    120
gaggggaaaa cagaccctcc cactggtgcc gttgctgcgt tctttcaatg ctgactggac    180 tgtgttttc ctatgcagtg tcagctcctc tgtctggttg tttacctgtt cctgttcgtg     240
cttgtaatgc tcacttatgt tttctctgta taacttgtga ttccagggct gtttgtcaac    300
agtatacaaa agaattgtgc ctctcccaag tccagtgtga ctttatcttc tgggtggttt    360
g                                                                    361

<210> SEQ ID NO 89
<211> LENGTH: 552
<212> TYPE: DNA
<213> ORGANISM: Homo sapiens

<400> SEQUENCE: 89
gaaatcagcg aggctcaagt tccaagcaaa ccattccaaa atgtggaatt ctgtgacttc      60
agtaggcatg aacctgatgg ggaagcattt gaagacaaag atttggaagg cagaattgaa    120
actgatacca aggttttgga gatactatat gagtttccta gagttttag ttctgtcatg     180 aaacctgaga atatgattgt accaataaaa ctaagctctg attctgaaat tgtacaacaa    240
agcatgcaaa catcagatgg aatattgaat cccagcagcg gaggcatcac cactacttct    300
gttcctggaa gtccagatgg tgtctttgat caaacttgcg tagattttga agttgagagt    360
gtaggtggta tagccaatag tacaggtttc atcttagatc aaaagataca gattccattc    420
ctgcaactat gggtcacatc tctctgtcag agagcacaaa tgacactgtt agtccagtaa    480
tgattagaga atgtgagaag aatgacagca ctgctgatga gttacatgta aagcacgaac    540
ctcctgatac ag                                                        552

<210> SEQ ID NO 90
<211> LENGTH: 419
<212> TYPE: DNA
<213> ORGANISM: Homo sapiens

<400> SEQUENCE: 90
gggctcaaag cattaatcca gttactgaaa agagaataca agtggagcaa acaagagatg      60
aagatcttga tacagactca ttggactgaa tttccccctt ccccccatga tggaagaatg    120
ttcagattct aaattgagga cttcattatt aatggcatta ctgtgttatg attaacaaat    180
ttcttgtaag gtacacacta catactaagg tcggccatca ttccgttttt ttttttttt    240 ttttttttaa ccaagcttaa aatgaagctt aaaatgaagc tttgtgtttg aaagtaataa    300
caagctcaga cgaagatggt ggttgtacat tattcatcta gaaaatataa aaattcattt    360
tgttttgaag ctagttatta aactggaata gcagttatat ccctgagaat ggggcccctt    419

<210> SEQ ID NO 91
<211> LENGTH: 394
<212> TYPE: DNA
<213> ORGANISM: Homo sapiens

<400> SEQUENCE: 91
gctgctgttt tcttctaact gcagggaaaa tgctgtctaa aagaaaataa taaatttgta      60
tctgctgagt tctcttagca taaggcacca acaaaacaac cttcaggaag ggagaagaaa    120
```

```
ccatcctccc actcatcctt cagaggattt agataaagtg aagggaagaa tcgttctcca    180
gctccttcgg aatttacgcc ggcatcaggg caggcttgtt actgctggat ccattgtctg    240
ctcaaggtta cttattccac taagacgtac atcctaccac ggaccacggc tttgtagcta    300
gccaggctct gagtgtgtgt gtagatgaac catttctctc tccagtaaat gaatgacagt    360
ctttctaggg ctcttgtctt ctgctgggag gcag                                394
```

<210> SEQ ID NO 92
<211> LENGTH: 417
<212> TYPE: DNA
<213> ORGANISM: Homo sapiens

<400> SEQUENCE: 92

```
agtcactctc ccagatggac ggactctgtt tcctggccaa ggcaacaatt cctacgtgtt     60
ccctggagtt gctcttgggg tggtggcctg cggactgaga cacatcgatg ataaggtctt    120
cctcaccact gctgaggtca tatctcagca agtgtcagat aaacacctgc aagaaggccg    180
gctctatcct cctttgaata ccattcgaga cgtttcgttg aaaattgcag taaagattgt    240
gcaagatgca tacaaagaaa agatggccac tgtttatcct gaaccccaaa acaaagaaga    300
atttgtctcc tcccagatgt acagcactaa ttatgaccag atcctacctg attgttatcc    360
gtggcctgca gaagtccaga aaatacagac caaagtcaac cagtaacgca acagcta       417
```

<210> SEQ ID NO 93
<211> LENGTH: 454
<212> TYPE: DNA
<213> ORGANISM: Homo sapiens

<400> SEQUENCE: 93

```
gttccacttc tctaggtaga caattaagtt gtcacaaact gtgtgaatgt atttgtagtt     60
tgttccaaag taaatctatt tctatattgt ggtgtcaaag tagagtttaa aaattaaaca    120
aaaaagacat tgctcctttt aaaagtcctt tcttaagttt agaatacctc tctaagaatt    180
cgtgacaaaa ggctatgttc taatcaataa ggaaaagctt aaaattgtta taaatacttc    240 ccttacttt aatatagtgt gcaaagcaaa ctttatttc acttcagact agtaggactg    300
aatagtgcca aattgcccct gaatcataaa aggttctttg gggtgcagta aaaaggacaa    360
agtaaatata aatatatgt tgacaataaa aactcttgcc ttttcatag tattagaaaa    420 aaatttctaa tttacctata gcaacattc aaat                                 454
```

<210> SEQ ID NO 94
<211> LENGTH: 435
<212> TYPE: DNA
<213> ORGANISM: Homo sapiens

<400> SEQUENCE: 94

```
gcatttgaaa ctgagcacta aactgggcta gctttctggt agaccgtttt gtggctagtg     60
cgatttcaca gtctactgcc tgtttccact gaaaacattt ttgtcatatt cttgtattca    120
aagaaaacag gaaaaaagtt attgtaaata ttttatttaa tgcacacatt cacacagtgg    180
taacagactg ccagtgttca tcctgaaatg tctcacggat tgatctacct gtctatgtat    240
gtctgctgag ctttctcctt ggttatgttt tttctctttt acctttctcc tcccttactt    300
ctatcagaac caattctatg cgccaaatac aacaggggga tgtgtcccag tacacttaca    360
aaataaaaca taactgaaag aagagcagtt ttatgatttg ggtgcgtttt tgtgtttata    420
ctgggccagg tcctg                                                    435
```

<210> SEQ ID NO 95
<211> LENGTH: 352
<212> TYPE: DNA
<213> ORGANISM: Homo sapiens

<400> SEQUENCE: 95

```
ggcagccttc cttgtgatca aaaaaggtaa tcccagaaac gtacccgttc actcgtgggt    60
cttaaaatgg tttcatatct ctattgtgac taattttctc tcggtctact gccttttcaa   120
tcaggaatag atttgccatg aagccagtga agttttaag  tgtctaggct tctcattagt   180
gccaactctc ctagacctgg tgcctgtttt ttttccaagt tttgtttcta cttctatcca   240
tttttaaat  taaactttt  attttgaaat aattatcaca ctcacaagct gtgggaagaa   300
ataatagaga tcctgtgtct ctttcatcca gttttcctca agggtaacat ct           352
```

<210> SEQ ID NO 96
<211> LENGTH: 521
<212> TYPE: DNA
<213> ORGANISM: Homo sapiens

<400> SEQUENCE: 96

```
tgctcaacgt gcactacaga accccgacga cacacacaat gccctcatgg gtgaagactg    60
tattcttgaa cctgctcccc agggtcatgt tcatgaccag ccaacaagc  aacgagggca   120
acgctcagaa gccgaggccc ctctacggtg ccgagctctc aaatctgaat tgcttcagcc   180
gcgcagagtc caaaggctgc aaggagggct acccctgcca ggacgggatg tgtggttact   240
gccaccaccg caggataaaa atctccaatt tcagtgctaa cctcacgaga agctctagtt   300
ctgaatctgt tgatgctgtg ctgtccctct ctgctttgtc accagaaatc aaagaagcca   360
tccaaagtgt caagtatatt gctgaaaata tgaaagcaca aaatgaagcc aagaggaac   420
aaaaagccca agagatccaa caattgaaac gaaagaaaa  gtccacagaa acatccgatc   480
aagaacctgg gctatgaatt tccaatcttc aacaacctgt t                       521
```

<210> SEQ ID NO 97
<211> LENGTH: 469
<212> TYPE: DNA
<213> ORGANISM: Homo sapiens

<400> SEQUENCE: 97

```
cagcgctgcc agcaggcata catgcagtac atccaccacc gcttgattca cctgactcct    60
gcggactacg acgactttgt gaatgcgatc cggagtgccc gcagcgcctt ctgcctgacg   120
cccatgggca tgatgcagtt caacgacatc ctacagaacc tcaagcgcag caaacagacc   180
aaggagctgt ggcagcgggt ctcactcgag atggccacct tctcccctg  agtctttcac   240
ccttagggtc ctatacaggg acccaggcct gtggctatgg gggccctca  cacagggga   300
gtgaaacttg gctggacaga tcatcctcac tcagttccct ggtagcacag actgacagct   360
gctcttgggc tatagcttgg ggccaagatg tctcacaccc tagaagccta gggctggggg   420
agacagccct gtctgggagg gggcgttggg tggcctctgg tatttattt                469
```

<210> SEQ ID NO 98
<211> LENGTH: 426
<212> TYPE: DNA
<213> ORGANISM: Homo sapiens

<400> SEQUENCE: 98

```
gtcactcatt tccttgaaca gcaccccct  ttatactagc agccatttgt gccattgcct    60
```

| | |
|---|---|
| gtgccctagg gtttgtgggg agagagcgag ggatcactga gcagttttcc cagagctcca | 120 |
| tgggaaggca agctctccct cccaatggga gccccactgt cactaactgt aaactcaggc | 180 |
| tcaggcttca actgcctacc cccatcctca tatttctgtc tgtcccagca cctcaggagc | 240 |
| attctcattg tggccggcta actccgcctg gatgtgaaca ggcaagcaca gtgggaaatg | 300 |
| agtcacgtac ttgtattgca cagtggacac ctctagaggt ccattggttt aaagggatag | 360 |
| ggaaggagga gggatgagac catcaccccc tcccagaagt aaatctagta tctgagtttt | 420 |
| ctttat | 426 |

<210> SEQ ID NO 99
<211> LENGTH: 404
<212> TYPE: DNA
<213> ORGANISM: Homo sapiens
<220> FEATURE:
<221> NAME/KEY: misc_feature
<222> LOCATION: (374)..(374)
<223> OTHER INFORMATION: n is a, c, g, or t

<400> SEQUENCE: 99

| | |
|---|---|
| caagagctac aatgtcacct ccgtcctgtt taggaaaaag aagtgtgact actggatcag | 60 |
| gacttttgtt ccaggttgcc agcccggcga gttcacgctg ggcaacatta agagttaccc | 120 |
| tggattaacg agttacctcg tccgagtggt gagcaccaac tacaaccagc atgctatggt | 180 |
| gttcttcaag aaagtttctc aaaacaggga gtacttcaag atcaccctct acggagaac | 240 |
| caaggagctg acttcggaac taaaggagaa cttcatccgc ttctccaaat ctctgggcct | 300 |
| ccctgaaaac cacatcgtct tccctgtccc aatcgaccag tgtatcgacg gctgagtgca | 360 |
| caggtgccgc cagntgccgc accagcccga acaccattga ggga | 404 |

<210> SEQ ID NO 100
<211> LENGTH: 376
<212> TYPE: DNA
<213> ORGANISM: Homo sapiens

<400> SEQUENCE: 100

| | |
|---|---|
| tttccccttg gaagacacta ttgatctcaa cctgctgact tttcctaatg cttacctgaa | 60 |
| ggaacccatc ctggctagaa agggtgatgg tactggaccg gtattcaacc ttgagttttc | 120 |
| aagctgccaa acaggtctta agggaggtgc ttatatccca ccaacactct cccagctccc | 180 |
| atgtccccaa gacctctgga gtttcctctt gaatgtacat gaaccactgt aatagcatta | 240 |
| gacttttaat tgagtgtgca atcgttttcc atggagtttg gtccgttcat tattttttag | 300 |
| ttaactacac ttcttgatat tcaaatgttc tattaaaaaa actgagtatg aagaaaaaca | 360 |
| ctttactact gcagaa | 376 |

<210> SEQ ID NO 101
<211> LENGTH: 476
<212> TYPE: DNA
<213> ORGANISM: Homo sapiens
<220> FEATURE:
<221> NAME/KEY: misc_feature
<222> LOCATION: (89)..(89)
<223> OTHER INFORMATION: n is a, c, g, or t

<400> SEQUENCE: 101

| | |
|---|---|
| tcccccattt acaatccttc atgtattaca tagaaggatt gctttttttaa aaatatactg | 60 |
| cgggttggaa agggatattt aatctttgng aaactattt agaaaatatg tttgtagaac | 120 |
| aattattttt gaaaaagatt taaagcaata acaagaagga aggcgagagg agcagaacat | 180 |

-continued

| tttggtctag ggtggtttct tttaaaacca ttttttcttg ttaatttaca gttaaaccta | 240 |
| ggggacaatc cggattggcc ctcccccttt tgtaaataac ccaggaaatg taataaattc | 300 |
| attatcttag ggtgatctgc cctgccaatc agactttggg gagatggcga tttgattaca | 360 |
| gacgttcggg ggggtggggg gcttgcagtt tgttttggag ataatacagt ttcctgctat | 420 |
| ctgccgctcc tatctagagg caacacttaa gcagtaattg ctgttgcttg ttgtca | 476 |

<210> SEQ ID NO 102
<211> LENGTH: 330
<212> TYPE: DNA
<213> ORGANISM: Homo sapiens

<400> SEQUENCE: 102

| agcctgaaac aggaactcac atgagactca gggccaccag gaaatgctta aaatacatac | 60 |
| tctttcccaa aagcaaatct ataattctgt ttcaatttta tgaatatatg aatagacaaa | 120 |
| atgaatcgaa ttcataact atgtcattca ttaaatggca acaatgctga cagcaagcag | 180 |
| tagatcctct gattccaatt accatttgtt ttttacccaa ttctatttgc tagaggtagt | 240 |
| aagtactctg gcactcataa atcacatgat gataaaaagg aacatgaggc cgggtatggt | 300 |
| ggctcacaac tgtaatcccc ataccttggg | 330 |

<210> SEQ ID NO 103
<211> LENGTH: 550
<212> TYPE: DNA
<213> ORGANISM: Homo sapiens
<220> FEATURE:
<221> NAME/KEY: misc_feature
<222> LOCATION: (276)..(276)
<223> OTHER INFORMATION: n is a, c, g, or t

<400> SEQUENCE: 103

| tatgggtcag ttacagcagc cctcacctca aagggctggc ctgcttctca gcctacattc | 60 |
| atttgcaagc ttcaatctct ggaccatctg gtgttcacag gtgttagagg gttaggggtt | 120 |
| aggggctagt tttggatttg attcataggt aggagggctt agattttaag gcacttctga | 180 |
| aagtcaatcc ctggacaagg cagtcatcac ataagaacag ctaccttctc cacttggtgg | 240 |
| cacaagaggt agggagggga gtatgggttc atttgncttc gcattatgca aggtgaaacc | 300 |
| gtttgttttc cctctccatt ttccctaact aaatgaaaag gacacattct gaaatccctt | 360 |
| ttgttggaga ataagtcagt ctgagggaa atggaggcc agagatgaga accctttgaa | 420 |
| aagattgtaa aatactgatt ttcattcttt caagcttatt tgtaaatacc tatttgaatg | 480 |
| ctgtgtattt gtacaggaat ttgagcaaaa aatgtataga gtgtgatgtc caattggtat | 540 |
| tcagcactat | 550 |

<210> SEQ ID NO 104
<211> LENGTH: 555
<212> TYPE: DNA
<213> ORGANISM: Homo sapiens
<220> FEATURE:
<221> NAME/KEY: misc_feature
<222> LOCATION: (45)..(50)
<223> OTHER INFORMATION: n is a, c, g, or t
<220> FEATURE:
<221> NAME/KEY: misc_feature
<222> LOCATION: (102)..(106)
<223> OTHER INFORMATION: n is a, c, g, or t

<400> SEQUENCE: 104

| gagcttcgtt gatggtcttt tctgtactgg aggcctcctg aggcnnnnnn agccccagga | 60 |

| | |
|---|---|
| cccattaagc cacccccgtg ttcctgccgt cagtgccaac tnnnnnatgt ggaagcatct | 120 |
| acccgttcac tccagtccca ccccacgcct gactcccctc tggaaactgc aggccagatg | 180 |
| gttgctgcca caacttgtgt accttcaggg atggggctct tactccctcc tgaggccagc | 240 |
| tgctctaata tcgatggtcc tgcttgccag agagttcctc tacccagcaa aaatgagtgt | 300 |
| ctcagaagtg tgctcctctg gcctcagttc tcctcttttg gaacaacata aaacaaattt | 360 |
| aattttctac gcctctgggg atatctgctc agccaatgga aaatctgggt tcaaccagcc | 420 |
| cctgccattt cttaagactt tctgctccac tcacaggatc ctgagctgca cttacctgtg | 480 |
| agagtcttca aacttttaaa ccttgccagt caggacttttt gctattgcaa atagaaaacc | 540 |
| caactcaacc tgctt | 555 |

<210> SEQ ID NO 105
<211> LENGTH: 408
<212> TYPE: DNA
<213> ORGANISM: Homo sapiens

<400> SEQUENCE: 105

| | |
|---|---|
| ctgcctggtt accgtggcga tgtgcttaat gcagcgttga aaatacagaa tactgactcc | 60 |
| tctgtccctc ctggccccgg actccctccc tccctccctt cctcttctgg agcgtgaaat | 120 |
| gagattggtc aagataaaaa aggaaaagat tcggttattt ttttaagagt gtggataatg | 180 |
| gggcctctca atcaaaatcc cagtctccag tcggttcccc ccattcccct tccaacccct | 240 |
| ccaccttccc ctgccgcctg cttagaggag gaggaagaaa cataaagcac aaggcttttc | 300 |
| tcttaattat gaatcattcc ctgagggcag gcccagggca aggggttcct ggggcccaga | 360 |
| gtctgacctg tgaggtagct agaaggcttg agcctctcat caaagtcc | 408 |

<210> SEQ ID NO 106
<211> LENGTH: 418
<212> TYPE: DNA
<213> ORGANISM: Homo sapiens

<400> SEQUENCE: 106

| | |
|---|---|
| ctttgcagga ctttagcgtt ttctccacag attcctgcct gcagctttca gatgcagttt | 60 |
| cacccagttt gccaggttcc ctcgacagtc ccgtagatat ttcagctgac agcttagact | 120 |
| tttttacaga cacactcacc acaatcgact tgcagcatct gaattactaa aaacattaaa | 180 |
| gcaaaacaaa gcatcaccaa acaaaaactc ctttgaccag gtggttttgc cttcttttat | 240 |
| ttgggagttt attttttatt ttcttcttga cctaccccctt ccctcctttta agtgttgagg | 300 |
| attttctgtt tagtgattcc ctgacccagt ttcaaacaga gccatctttt acagattatt | 360 |
| ttggagtttt agttgtttta aacctaactc aacaacccct tatgtgattc ctgagagc | 418 |

<210> SEQ ID NO 107
<211> LENGTH: 521
<212> TYPE: DNA
<213> ORGANISM: Homo sapiens
<220> FEATURE:
<221> NAME/KEY: misc_feature
<222> LOCATION: (172)..(172)
<223> OTHER INFORMATION: n is a, c, g, or t

<400> SEQUENCE: 107

| | |
|---|---|
| gtcaccctga ggaaggttca ttgccattgt catcaccatg gaaacaacgt tcctctccac | 60 |
| ctgcattatg tactacatga caggcatcaa tctggggaaa taataaaatt atcacctttg | 120 |
| tcagaccata agagtttctc caaaagtggt cagtttggct gggcaatatt tnctctcatc | 180 |

```
taacaaacac aatccattgt catgaaatta cccttaggat gagtcttcct taatcaatca    240
tatattgggc ggaaaaaaca ccagctttga cccgaagtag ttgaagagct acttcattct    300
tttctgaagt tgtgtgttgc tgctagaaat agtcatttgt gaattatcca aattgtttaa    360
attcacaatt gaattagttt tttcttcctt tttgcttgaa gcaaacagtt gacaattttt    420
aaccttttca ttttatgttt ttgtactctg cagactgaaa agacaaagtt tatcttggcc    480
ttactgtata aaggtgtgct gtgtccaccg ttgtgtacag a                        521
```

<210> SEQ ID NO 108
<211> LENGTH: 526
<212> TYPE: DNA
<213> ORGANISM: Homo sapiens
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (220)..(221)
<223> OTHER INFORMATION: n is a, c, g, or t

<400> SEQUENCE: 108

```
gaggtctggc actagtagca caacctaagg tggcattaca gatctttgag cgagccacag     60
caacttttct gccaagtcag cttnagttna gacttcagtg aatcaggnta ttgctatcct    120
aatgtatgtc tctatgagtg tatntagcca canantctgc ccttggttga ntttctgact    180
cattgcttgc ttgcttgttt ccttgctttg gaaaactatn naagattgct aaaaaatacc    240
actgcaaagt gatggaaaag ggtggagaac aggggagtag ccaggctgga tggctcaaat    300
ataaatgaat gaggaattct ttatgaagta tcagtcagat tttatgatta agtgatgtaa    360
tataggaatt atgtaaaagg gaagaatgtc tgatactgat ctattagaga ggtactttag    420
aggcttcttg attggcataa agttcctaag gttatagatt ttccccccctt ttggctgtat    480 agcaaagtgt tttaatccac ggttgtgcct tattgttcca ttaaaa                   526
```

<210> SEQ ID NO 109
<211> LENGTH: 479
<212> TYPE: DNA
<213> ORGANISM: Homo sapiens
<220> FEATURE:
<221> NAME/KEY: misc_feature
<222> LOCATION: (424)..(425)
<223> OTHER INFORMATION: n is a, c, g, or t
<220> FEATURE:
<221> NAME/KEY: misc_feature
<222> LOCATION: (427)..(429)
<223> OTHER INFORMATION: n is a, c, g, or t

<400> SEQUENCE: 109
caatgggagg ggtcggagct cttccttccc ctctgtggag tcacttttgt attctttta    60
accagatttc ttaaaatgtt gttgttttgt gaatcctgac attggttctt acttttgtat   120
gctgcctcct ctgtgccctc ccagacgctg actgggaaac acaagaagta caaccaacag   180
gaaccagcgc caagggcagg cagcggcctc cttgctcccc tcccttactc ctccctctgc   240
tgcctcctcc ccccaccaag tttcagggcc ctggattgtt cccagttccc attgtggtcc   300
cttcagagct cctttccaac agcatctctc tgtcgaagaa agaagctctg tcaagttaga   360
gagagacaat gtgtaggaaa tgttcttttt taaaaaaaaa taacaaaaac aaaacaaaac   420
tatnnannnt gtgattgttt ccttgttaa tctgctccaa ccacctgaac atctaagta    479

<210> SEQ ID NO 110
<211> LENGTH: 554
<212> TYPE: DNA
<213> ORGANISM: Homo sapiens
<220> FEATURE:
<221> NAME/KEY: misc_feature
<222> LOCATION: (266)..(266)
<223> OTHER INFORMATION: n is a, c, g, or t

<400> SEQUENCE: 110
gagacgggag tttaccccga tcacagaaac cataccaact gaaagacaaa tcagcatctt    60
gctggacgac ccctcacaga gctcctagat ccttgaagtg tgaacttcag cagctgagag   120
agatggggtc tcactatgtt gcccaggctg gtcttgaact cctggactca agcaatcctc   180
tcacctcagc ctcccaaagt gctgggatta cagatttat aaatattgtt gatcttttg   240
aaaaaccaac tgttggcttc attttnttta ttgtgtaata ctaccttaga ggacagcagt   300
tcctaatacc tacttttatt atgagtctct gccatttata aagaactgtg gacagcacag   360
ggaatggggg aagaaaactc tggtgcagct tgaatcttgg tagcaaaaca gtgacttcat   420
cagaaaattt tgtcactctc tattagatat aatggagttt gaccatttgg aatttggaat   480
ttttcaaatg aatatgacaa aaatttaaaa aactcttgta ttactatgtg ataacacaga   540
tctttacaac ttta                                                    554

<210> SEQ ID NO 111
<211> LENGTH: 446
<212> TYPE: DNA
<213> ORGANISM: Homo sapiens
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t

<400> SEQUENCE: 111

```
aagccttcac cagatggtca agcagatgct ggtgccatgc ccttgancnt cncnccacca      60
tcccccacct agccactata tgggttgtta gatattttga ccacctcctc ttcnctcact     120
ccactattca actcactgca tcatcaatgt acttattaca aacctgtcac aagccaggtc     180
ttatgctagg tgctcctctc aacaggttct tgagctggca ggggagagag agacattcaa     240
acaccaagga ttaatatacc attacaggtt taaagacaga ggcctataag ggtcccctgg     300
cagtgccatg gaggtagggc atggtcggct gtacctgtag aggtgtctaa agggaggctt     360
gcaagctgcc ccttgaagga cgagcagaaa attgtacatg aggacaagta ggaaaggaat     420
tccaggagga gggatcagca tgtgca                                          446
```

<210> SEQ ID NO 112
<211> LENGTH: 371
<212> TYPE: DNA
<213> ORGANISM: Homo sapiens
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(76)
<223> OTHER INFORMATION: n is a, c, g, or t
<220> FEATURE:
<221> NAME/KEY: misc_feature
<222> LOCATION: (78)..(80)
<223> OTHER INFORMATION: n is a, c, g, or t
<220> FEATURE:
<221> NAME/KEY: misc_feature
<222> LOCATION: (82)..(83)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t

<400> SEQUENCE: 112

```
ggactaaatc gagccttatt atacatcagc agtctcacac tggagaaagt ccttttaagt      60
taagggannng nnnnnnannn tnnancaaat gtaatactgg tcagcgccaa aaaactcaca    120
ctggagaaag gtcttatgag tgtggtgaat ccagcaaagt gtttaaatac aactccagcc     180
tcattaaaca tcagataatt catactggaa aaaggcctta gtggagtgaa tgcaggaaag     240
tcaccaaaac tgtcacctca ttcagcacca aaaggttcac atcggaccaa gaacctatta     300
atatatgtaa atctaatgtt gaaagagttc agatggaaat ctgcgaggat ttcctgctgg     360
gaactacatt a                                                           371
```

<210> SEQ ID NO 113
<211> LENGTH: 533
<212> TYPE: DNA
<213> ORGANISM: Homo sapiens
<220> FEATURE:
<221> NAME/KEY: misc_feature
<222> LOCATION: (167)..(167)
<223> OTHER INFORMATION: n is a, c, g, or t

<400> SEQUENCE: 113

```
aattgggcag gctcttggga agtagaaagt tctggtgttt ttgctggtga aggttttgac      60
tgtggagctc ttctaacacc catatcagtg tctgtttctc tgcatgtggc tgctgccctg     120
ttggtggagc tctgggggca gagaccaggc cgccgtccag tggcgcnccg tgcgcaccag     180
ctgcctgctg tttacaccca ggtgcgccga gtctctttca tacagcacag caaatgataa     240
```

```
tagctagtga caatgtgttt cctgtgcact cgtgaaaatg cagggaggac aactgcatgc    300
ttagatctgt ttcttttttc agacattcaa atgttctaat atctgaagct aacatttgt    360 aggatatagg atgctgatta tgtgaacaat tagtcattgg ttttctgtac tgctatgaat    420
atgtctgatt tcaagttttg gtcaaatatc taaaatgcaa ggtgaaagtg cctttgtctc    480
tatgcttcta aaatcgctca tgcttagttg tggtatggat gtcttccgca gtg           533
```

<210> SEQ ID NO 114
<211> LENGTH: 544
<212> TYPE: DNA
<213> ORGANISM: Homo sapiens
<220> FEATURE:
<221> NAME/KEY: misc_feature
<222> LOCATION: (358)..(358)
<223> OTHER INFORMATION: n is a, c, g, or t

<400> SEQUENCE: 114

```
cttggtaagc cttgcctgta gcggctccgc tgccgagtgc tttgacacca ggcgctccca    60
gagctctgcc cccactgcca agcggcagct gctccggagg gcacgggggg ctggatttgg   120
ctgtggcttc tccagctctg cacaagagcc ccccttccct ggccctgctg cagcatgact   180
gcctcctggc tcgtgtcacc cactctgtct ctgtctctct tcatacgttt ccagctgagc   240
tgggatccat agtctgtttc cctctccacg accaatctat ttatcttctc tggaacttct   300
tgtaatgccg ggagtgcaga gcttacaagt tggggcagga agctttagaa gcccaggnag   360
ccctgagagg ctctttcctt gtaagtgggt ctctccccag gagcctcttg gaatatttag   420
cagggacttt tacccatgct gggtctagag accctcccgc ccctctgttt cctgccctcc   480
tacttagact gggatctggt ttccctcagc tggttccctt gctagcgtgt gactctgtgt    540
gtct                                                                544
```

<210> SEQ ID NO 115
<211> LENGTH: 436
<212> TYPE: DNA
<213> ORGANISM: Homo sapiens
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t

<400> SEQUENCE: 115

```
gttcacagca gtgggtaggc ccagcagtgg ttcttgacat cacacgatga ggcgngcatc    60
tcccgtcatc cagggagacc agaggaccct tgtctcactc ccagttggct nttagtcaca   120
gccccgcttt gtctttgaca tggacgtttg tgatgatcac gttcctcccg ctccccgtgt   180
```

```
ntgaagagtg ctccctgact ggctgccgtc tcctccctgt cgggtctggc tgggttctcc      240
anagggagtg ctgcggaggg gacacagcan aggccccatg ctcgtgatgt atgttgcaga      300
tcattttccc ccattctgtc cttttttgtt aaattgtggt aaaaagcaca taacataaac      360
tgtaccncct taaccatttg aaagtatata tcccagactg tcttttatct ttagacttca      420
cttgtggttt gttgcc                                                     436

<210> SEQ ID NO 116
<211> LENGTH: 276
<212> TYPE: DNA
<213> ORGANISM: Homo sapiens

<400> SEQUENCE: 116 tccccctggaa gttgtccttt ctgatcctct cttcttttcc catttacaaa tgatttcgtg     60
actgtagttt ttgttcacct tctgtgcatc tggcctgggg gctgttagct cagaggagag    120
gagcaaacag gaaaatgact tctgttctgt ccccgctgtt ttgggggaag tctctcccac    180
tttgggatcc tgctgaagct aggttcatga ggtcggaaat ccccaccaca tttgcctaga    240
ctttgggcac aggagttctt agtccaccaa atcaga                              276

<210> SEQ ID NO 117
<211> LENGTH: 331
<212> TYPE: DNA
<213> ORGANISM: Homo sapiens

<400> SEQUENCE: 117
cattttctct aactttatct cctatgcatt tccttatgtg tcctgtacag cagtatattc     60
caaaatcccc agtggatgtc tgaaaaccac atatagtacc aaactgtata tatgctatgt    120
tttgtttcat acatacctat aataaagttt aatttatgaa ttaggcacaa taagagataa    180
gcaggctgga cgtgctggct cacgcctgta atcccagcac tttgggaggc tgaggcgggt    240
ggattgcttt agcccaggag tttaagacca gcctggccaa catggcaaaa ccccgtctct    300
ataaaaaatg tggaaattaa tcaggtgtgg t                                   331

<210> SEQ ID NO 118
<211> LENGTH: 482
<212> TYPE: DNA
<213> ORGANISM: Homo sapiens

<400> SEQUENCE: 118
gagatgaccg aaaacttcaa cccctgcagt cagcaatggt caacagaaag ggcccaattc     60
tccacgacaa tgcatgatcg cacattacac aactaaagct tcaaaagttg aactaactgg    120
gctacgaagt tttgcctcat ccaccatatt cacctgacct cccgccaacc gactaccact    180
tcttcaatca tctcgacaac ttttttgcaag gaaaacactt ccacaaccag tagaatgcaa    240
aaagtgcttt ccaagagttc actgaatcct gaagcacgga tttttatgct acaggaataa    300
acaaacttat ttttcattgg taaaaatgtg ttgattgtaa tggatcctat tttgattaat    360
gaagatgtgt ttgagcctag ttataatgat ttaaaattca cgatccaaaa ccgcaattac    420
ttttgcatca gcctaatatg aggaagtaat agttgaacag ataattcttc cctggaagt    480 ct                                                                  482

<210> SEQ ID NO 119
<211> LENGTH: 455
<212> TYPE: DNA
<213> ORGANISM: Homo sapiens
```

```
<400> SEQUENCE: 119
ttggtttggt ctggtttggc tacctgattc ctgctgtctt tttctacgcc aggtgaagag      60
gcactttcaa gatccttctc tgagacctgc accaataaga ctataccaat gttcagttga     120
aacatcaggt ataagtttag cggaaacgaa agtacaacct gctttgaaat aaattccaag     180
gacagattgt cattaacgaa atagaaagtg gactatgccc ctcatgctgc cagcgcctgg     240
tatgatgcgg cgtgacacgc agcgcttgcg gcagtacaat gccccaatc acccgccccg      300 ccccgacgcg ccgcccactc acggcaaaga gagccaccta gtgagggatt attctcattt     360
ccgcggtggg gttctgcttt tctttctacc atgagcgccc aaggatagac actcctacta     420
cctattacct caaatagcct acatttcttt ccgaa                                455

<210> SEQ ID NO 120
<211> LENGTH: 544
<212> TYPE: DNA
<213> ORGANISM: Homo sapiens
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (233)..(233)
<223> OTHER INFORMATION: n is a, c, g, or t
<220> FEATURE:
<221> NAME/KEY: misc_feature
<222> LOCATION: (394)..(397)
<223> OTHER INFORMATION: n is a, c, g, or t
<220> FEATURE:
<221> NAME/KEY: misc_feature
<222> LOCATION: (491)..(491)
<223> OTHER INFORMATION: n is a, c, g, or t

<400> SEQUENCE: 120
agaacactga gcgaggctct gtagatggat gtaataaaaa tctataaaac aatgtgttta      60
aacctaagaa ttctactgct ttccaattcc ttccctctgc tccttttcct aacctcctgc     120
ttctccagcc cttccctctg tccctttcan ccctcaggcc ctcctctccc cttagtcccc     180 accacctgt cacttctaaa ttgtggctct agcattgtcc cattacctgc tangtgactg      240
ttctctccac agtggtcctg ctcctgtgag tcagagtgtg tcatttcctc acctaaaaca     300
ctccagtggc tccacctcgg tcttgtgaag cttctagaat gtcaggcacg tgagcatatg     360
agggcatacc tggttcatct taggcactaa attnnnnttt gttgactgaa tgaatgaaat     420
atgaatgtat taaattgcat cacagaaagt tataaaatgt aaaacactga aaaattaaga     480
aatattttat nttatgtaac tagtgtgcat atcaattcat tccgagtctg ttgagcctgt     540
gtat                                                                  544

<210> SEQ ID NO 121
<211> LENGTH: 338
<212> TYPE: DNA
<213> ORGANISM: Homo sapiens
<220> FEATURE:
<221> NAME/KEY: misc_feature
<222> LOCATION: (193)..(194)
<223> OTHER INFORMATION: n is a, c, g, or t

<400> SEQUENCE: 121
aatgattcaa ctcatgtgat ccagtgttac attcagtgtg gtaatgaaga acagtcaaaa      60
caggcttttg aagaatgggg agataaattg gttgaattaa gtaaagccaa atactccaga     120 aatatttaa agaaatgtct cacgttgtga acatgtaccc tagaacttaa agtataataa     180
```

```
aaaaaaaaaa aannggaaag tatcttgcac aagctcacgt agctggtaag ttacatagtt      240
gggatctgaa ttcagttgtg gcttcatgcc tgagctttta actactacta ctaaactgag      300
aaggcacttg cttgagtaaa ttatgtcatc ctcttaat                              338
```

```
<210> SEQ ID NO 122
<211> LENGTH: 443
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (404)..(404)
<223> OTHER INFORMATION: n is a, c, g, or t

<400> SEQUENCE: 122
gatgtggcat gtgatgacat tgcacatggn cagttaantg ngccaagaag ngcagcagta       60
gcagcaacng gagatgcaaa gcccaacatg atggggagag aaantnttct ttcaatatgt      120
gcttctgtac caaaagtgga atttcacgag agacatattt tggaacattt ttccttttgt      180
gtgtgcgtga gtgtttccct gtttccagcc aagggtattg tgagtttctc ctgggcctcc      240
ttcagaatct gggtgctctg gaaagcagtg ttttggcaac atggggaaag tatggcagtg      300
tgggagggtc agctgggtct gggtttgaat attgcatttg aatattttac cagcattgat      360
gtcggataaa ttatttagtc cctgtaagcc tcagttttnt cttnttctac atacacataa      420
tatatttgac tctttgttgt gat                                              443
```

```
<210> SEQ ID NO 123
<211> LENGTH: 510
<212> TYPE: DNA
<213> ORGANISM: Homo sapiens
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (288)..(288)
<223> OTHER INFORMATION: n is a, c, g, or t
```

```
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (431)..(431)
<223> OTHER INFORMATION: n is a, c, g, or t

<400> SEQUENCE: 123
tttcctaact ttctgatccc ttggaggtga taatcaaata ttctagtctg aggcattggg      60
atacatggtg ctaggttctg agactctgcg tcaggcctga accctgcatt ttgtggaggt     120
gggtgggaga atgtncccct ggggaacatg cctagacacg ggggacaaca gttgccctca     180
tggggaggta cctgtttact cgctgttatg ggaccgcttt cacaaaacca ctgcaggtga     240
gtgagttcct gctgaatatc aggcctggtg tctctagact cattattncc cccacccaac     300
ccctatgtta gttcatctcg agccacattt ttattgccat aatccaggcc tggacaggcc     360
aagatctttt aacaatttta attactgaaa ataataactg catttttttt naaagcccaa     420 cttttngta nagtcagccc aaaatacagt cttttgtgttg ccatctggga actggatttg     480
gaattgttct tccatgagac tgcagagcag                                      510

<210> SEQ ID NO 124
<211> LENGTH: 447
<212> TYPE: DNA
<213> ORGANISM: Homo sapiens

<400> SEQUENCE: 124
ccacctcctc caggaaagcc agaaagacca ccccacaag gaggtaacca gtcccaaggt      60 ccccacctc atccaggaaa gccagaagga ccacccccac aggaaggaaa caagtcccga     120
agtgcccgat ctcctccagg aaagccacaa ggaccacccc aacaagaagg caacaagcct     180
caaggtcccc cacctcctgg aaagccacaa ggcccacccc cagcaggagg caatccccag     240
cagcctcagg cacctcctgc tggaaagccc caggggccac ctccacctcc tcaaggggc     300 aggccaccca gacctgccca gggacaacag cctcccagt aatctaggat tcaatgacag     360
gaagtgaata agaagatatc agtgaattca ataattcaa ttgctacaaa tgccgtgaca     420
ttggaacaag gtcatcatag ctctaac                                        447

<210> SEQ ID NO 125
<211> LENGTH: 562
<212> TYPE: DNA
<213> ORGANISM: Homo sapiens

<400> SEQUENCE: 125
gtttgatgtc tattatctca cttcatcctc accaggaccc catccgagcc ttaatttcag      60
ttgacagtaa ctattggatc cccaggaata tgtttgcata tttggggaga aaatactatt     120
ggaggggaac agaaatgcta ctaagggtct cactgtgtca cccaggctgg agtccatcaa     180
agctcactgc agccttaacc ttctgtgctc aagggatcct cccacttaag cctcctgagt     240
agctggaact acaggcatat gccaccgagc ctggctaatc tttgattttt ttgtacagat     300
tgtgtctcct tatgttgctc aggctggact caaacttctg gtctcaagcg atctttccat     360
cttagcttcc caaattgttg gaattatgga catgagccag tgtgcttggc ctgatttttt     420
tttttttttt aatgagaaaa acgttcctta agaaaagttt cattgtaaga cgaggacttg     480
```

```
ctatgttgcc agtttggtct tgaactcggt ctcaagtgat tctcctgcct tgggttccca    540
aagcgtttgg gccggcagat gt                                              562

<210> SEQ ID NO 126
<211> LENGTH: 484
<212> TYPE: DNA
<213> ORGANISM: Homo sapiens

<400> SEQUENCE: 126
ctgaattgga acacaccagc actgtggtgg aggtctgtga ggcaattgcg tcagttcagg     60
cagaagcaaa tacagtttgg actgaggcat cacaatctgc agaaatctct gaagaacctg    120
cggaatggtc aagcaactat ttctacccta cttatgatga aaatgaagaa gaaaataggc    180
ccctcatgag acctgtgtcg gagatggctc tcctatattg atgaagctac tatgtcaaat    240
ggcaagtagc tctttcctgc ctgcttctca gctcatttgg aaaaatactg cgcaaaagac    300
attgagctca aatgatgcag atgttgtttt caggttaatg gacacgcaaa gaaccacag     360 cacatacttc ttttctttca tttaataaag cttttaatta tggtacgctg tcttttaaa    420 atcatgtatt taatgtgtca gatattgtgc ttgaaagatt ctcatctcag aatacttttg    480
gact                                                                 484

<210> SEQ ID NO 127
<211> LENGTH: 544
<212> TYPE: DNA
<213> ORGANISM: Homo sapiens
<220> FEATURE:
<221> NAME/KEY: misc_feature
<222> LOCATION: (257)..(257)
<223> OTHER INFORMATION: n is a, c, g, or t
<220> FEATURE:
<221> NAME/KEY: misc_feature
<222> LOCATION: (277)..(291)
<223> OTHER INFORMATION: n is a, c, g, or t
<220> FEATURE:
<221> NAME/KEY: misc_feature
<222> LOCATION: (305)..(305)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t

<400> SEQUENCE: 127
gagtgtcttg actattctgg ctctttgtat tttcatgtaa ggttttctc ccatataagt      60 tttaaaatca gcttgtcaat tccaacaaca atgatgcact tgatagtttg ggaatttatt    120
atagctatca atcagttttg ggaaaattga cgtctttaca atattgagtt ttctgattca    180
tgaacatggt ttacctctct tcccatgggg gtctccttta aggtttacca ataggatttt    240
atatttgggg ccattgnggt cttgcttatc ttaagtnnnn nnnnnnnnnn naaatctctt    300
gaccncatga tctgcccgcc ttgtcctccc aaagtgctgg gattacaggc gtgagccacc    360
gcacctggcc tgcaatacag tattgttaac cgtcttcacc atgttgtacg ttagagctcc    420
agaaattatt tancatgcat aactgaaact ttatactctt tgaacaccac ctccccattt    480
ccctctcccg gcagccattt gtgcctctcg gttctcttta ttagcttcca ttttgtgggt    540
cagt                                                                 544

<210> SEQ ID NO 128
<211> LENGTH: 522
<212> TYPE: DNA
<213> ORGANISM: Homo sapiens
```

<400> SEQUENCE: 128

| | | |
|---|---|---|
| tacgtcaaag accgctgctg cagtagctgc ccagtcagga atacttgata ggacaatttc | 60 | |
| tgtaattatg aagaatcaaa caccaacaaa gaagtatgat ggctacacat catgtccact | 120 | |
| ggtgaccggc tacaaccgtg tgattcttgc tgagtttgac tacaaagcag agccgctaga | 180 | |
| aaccttcccc tttgatcaaa gcaaagagcg cctttccatg tatctcatga agctgacct | 240 | |
| gatgcctttc ctgtattgga atatgatgct aaggggttac tggggaggac cagcgtttct | 300 | |
| gcgcaagttg tttcatctag gtatgagtta aggatggctc agcacttgct catcttggat | 360 | |
| ggcttctggg ccaaaactgc agtcactgaa tgaccaagag cagcacgaag gacttggaac | 420 | |
| ctatccttgt aaagagttcc ttgatgggta atggtgacca aatgcctccc ttttcagtac | 480 | |
| cttttgaacag caaccatgtg ggctactcat gatgggcttg at | 522 | |

<210> SEQ ID NO 129
<211> LENGTH: 544
<212> TYPE: DNA
<213> ORGANISM: Homo sapiens

<400> SEQUENCE: 129

| | | |
|---|---|---|
| ttggatgccc taactgctga tgtgaaggag aaaatgtata acgtcttgtt gtttgttgat | 60 | |
| ggagggtgga tggtggatgt tagagaggat gccaaagaag accatgaaag aacacatcaa | 120 | |
| atggtcttac tgagaaagct ttgtctgcca atgttgtgtt ttctgcttca tacgatattg | 180 | |
| cacagtactg gtcagtatca ggaatgccta cagttagcag atatggtatc ctctgagcgc | 240 | |
| cacaaactgt acctggtatt ttctaaggaa gagctaagga agttgctgca gaagctcaga | 300 | |
| gagtcctctc taatgctcct agaccaggga cttgacccat tagggtatga aattcagtta | 360 | |
| tagtttaatc tttgtaatct cactaatttt catgataaat gaagttttta ataaaatata | 420 | |
| cttgttatta gtaattttt cttttgcatt accatgtaaa atttagacat ttgaattttg | 480 | |
| tacttttcag aatattatcg tgacactttc aacatgtagg gatatcagcg tttctctgtg | 540 | |
| tgct | 544 | |

<210> SEQ ID NO 130
<211> LENGTH: 436
<212> TYPE: DNA
<213> ORGANISM: Homo sapiens

<400> SEQUENCE: 130

| | | |
|---|---|---|
| aggtcacagt atcctcgttt gaaagataat taagatcccc cgtggagaaa gcagtgacac | 60 | |
| attcacacag ctgttccctc gcatgttatt tcatgaacat gacctgtttt cgtgcactag | 120 | |
| acacacagag tggaacagcc gtatgcttaa agtacatggg ccagtgggac tggaagtgac | 180 | |
| ctgtacaagt gatgcagaaa ggagggtttc aagaaaaag gattttgttt aaaatacttt | 240 | |
| aaaaatgtta tttcctgcat cccttggctg tgatgcccct ctcccgattt cccaggggct | 300 | |
| ctgggaggga cccttctaag aagattgggc agttgggttt ctggcttgag atgaatccaa | 360 | |
| gcagcagaat gagccaggag tagcaggaga tgggcaaaga aaactggggt gcactcagct | 420 | |
| ctcacagggg taatca | 436 | |

<210> SEQ ID NO 131
<211> LENGTH: 402
<212> TYPE: DNA
<213> ORGANISM: Homo sapiens

<400> SEQUENCE: 131

```
gcacctcgga gttgcagctg tgacactcat aggttactcc caggagtgtg ctgagcagaa      60
ggcaagctct tgctggatga aacccctcca ggtggggttg gggagacttg atattcacat     120
ccaacagttt gaaagggag agctcaattc ccagcgtcac cccatggctt gtgttgcctg     180
ctacgcattg acttggatct ccaggagtcc cctgcacata ccttctccat cgtgtcagct     240
gtgtttctct tgattccgtg cacccggtt tattagttca aaagtgtgac acctttctg     300 ggcaaggaac agccccttta aggagcaaat cacttctgtc acagttatta tggtaatatg     360
aggcaatctg attagcttca cagactgagt ctccacaaca cc                        402

<210> SEQ ID NO 132
<211> LENGTH: 390
<212> TYPE: DNA
<213> ORGANISM: Homo sapiens

<400> SEQUENCE: 132
tcaagtgagt gagttcccct ctactttag ccttccaccc aaactggaag cctctaggtg      60
ctatcaatta tttatatcca tcgtttacat ccatgaaatt ggctgaataa ttactcctct    120
gcctggcgta gacatgtgct ttgggaaaaa aacgagttta taatcctata atgaagaata    180
ctggcacagg caatgctcac tcgaaaactt caagtaattt ctagttggtt ttggaatgct    240
tgataaagtt cctttacagc tttattttcc tgatttgttt tggtttagat caaagttcaa    300
attaatttta acttagctaa tgaactcatc accaggacag ttggagggg taggccgagg     360 ttaaatggtc cacgtttcaa aaatgttaat                                      390

<210> SEQ ID NO 133
<211> LENGTH: 503
<212> TYPE: DNA
<213> ORGANISM: Homo sapiens

<400> SEQUENCE: 133
cttttgttct tgctgggtta tttattttga ttttagcatt aaatgtcatc tcaggatatc      60
tctaaagggg gttgtttaat tcctaattgt atagaaagct agtttggtga attgtattgg    120
ttaattgact gtttaaggcc ttaacaggtg aatctagagc ctacttttat tttggttaaa    180
gaaaaagaaa atatcaataa ttcaattttg tgtcttttct caatttatta gcaaacacaa    240 gacatttat gtattatttc gatttacttc ctaattataa aagctgcttt tttgcagaac      300
attccttgaa aatataaggt tttgaaaaga cataattta cttgaatctt tgtggggtac     360
aggttgatct ttatatttta ctggttgttt taaaaattct agaaagaga tttctaggcc     420 tcatgtataa ccagggtttt gaggataaag aactgtattt ttagaactat ctcatcatag    480
catatctgct ttggaataac tat                                             503

<210> SEQ ID NO 134
<211> LENGTH: 346
<212> TYPE: DNA
<213> ORGANISM: Homo sapiens

<400> SEQUENCE: 134
ttaccctcgt ggctaagcaa gtgtctgcag gagcagagat ggctggaagg ggcctctgca      60
cacggaagat ggcttgttca gcccattcac ctcctgagga tgtgggcagt ctcctccaag    120
aacacatgga gctgcttcct gatcccaagc aggtcattgc cactggaagg acatggcccc    180
ggtgatccat gcttcatgcc cacccagaaa cacacccctc agtgtgtgcc tcagtttact    240
ttggagatca gttgtcgttt ttagtgctcc tttaggctta ctaaaacagt tttggaaaca    300
```

```
aagctatttt gaagtattca agcagaggaa ttccctaaca ctgacc              346
```

<210> SEQ ID NO 135
<211> LENGTH: 506
<212> TYPE: DNA
<213> ORGANISM: Homo sapiens

<400> SEQUENCE: 135

```
gaccattttg cgagtgtagc cctgtttcac tcggatcagg ttggcacggc cgcctgcgtg   60
tctgtccacc tcatccctcc gtgtatctga gggagtaaag gtgaggtctt tattgcttca  120
ctgcctaatt ttctcaccca cattcgctga agcgatgag agtcgggggc cagtagccag  180
ccaaccccgt ggggaccggg gttgtctgtc atttatgtgg ctggaaagca cccaaagtgg  240
tggtcaggag ggtcgctgct gtggaagggg tctccgttct tggtgctgta tttgaaacgg  300
gtgtagagag aagcttgtgt ttttgtttgt aatggggaga agcgtggcca ggcagtggca  360
cgtggcatcg catggtgggc tcggcagcac cttgcctgtg tttctgtgag ggaggctgct  420
ttctgtgaaa tttctttata tttttctatt tttagtactg tatggatgtt actgagcact  480
acacatgatc cttctgtgct tgcttg                                       506
```

<210> SEQ ID NO 136
<211> LENGTH: 378
<212> TYPE: DNA
<213> ORGANISM: Homo sapiens

<400> SEQUENCE: 136

```
aaggaaggcc agagagccgc gcagttctct gcaggtgcag atgcaggcag tggaggtggc   60
ctgagcaggc agaaggacac caagcgccct atgttgcttg tcattcatga cgtggtcttg  120
gagcttctga ctagttcaga ctgccacgcc aaccccagaa ataccccac atgccagaaa   180
agtgaagtcc taggtgtttc catctatgtt tcaatctgtc catctaccag gcctcgcgat  240
aaaaacaaaa caaaaaaacg ctgccaggtt ttagaagcag ttctggtctc aaaaccatca  300
ggatcctgcc accagggttc ttttgaaata gtaccacatg taaaagggaa tttggctttc  360
acttcatcta atcactga                                                378
```

<210> SEQ ID NO 137
<211> LENGTH: 562
<212> TYPE: DNA
<213> ORGANISM: Homo sapiens

<400> SEQUENCE: 137

```
tcccggctac atgggagcgc ggtgtgagtt cccagtgcac cccgacggcg caagcgcctt   60
gcccgcggcc ccgccgggcc tcaggcccgg ggaccctcag cgctaccttt tgcctccggc  120
tctgggactg ctcgtggccg cgggcgtggc cggcgctgcg ctcttgctgg tccacgtgcg  180
ccgccgtggc cactcccagg atgctgggtc tcgcttgctg gctgggaccc cggagccgtc  240
agtccacgca ctcccggatg cactcaacaa cctaaggacg caggagggtt ccggggatgg  300
tccgagctcg tccgtagatt ggaatcgccc tgaagatgta gaccctcaag ggatttatgt  360
catatctgct ccttccatct acgctcggga ggtagcgacg ccccttttcc ccccgctaca  420
cactgggcgc gctgggcaga ggcagcacct gcttttttccc tacccttcct cgattctgtc  480
cgtgaaatga attgggtaga gtctctggaa ggttttaagc ccattttcag ttctaactta  540
ctttcatcct attttgcatc cc                                           562
```

```
<210> SEQ ID NO 138
<211> LENGTH: 528
<212> TYPE: DNA
<213> ORGANISM: Homo sapiens

<400> SEQUENCE: 138
tgaagaaaac cttcattacc cgcttctgct tattttgacc aaacatggat agaagattaa      60
gcttctcaaa gacgaagaaa cgtatcaagt gcatagggaa tatttttaca aaaacggaaa     120
tctgtaaggg gtataatcgc ctgcctgcgc cctttgcagc atttcacgtg tgggctatgg     180
actccacctg tcctcaccca cgttattccc cagctgccct ctccagctcc ctccccgcct     240 cttttttacac tctgcttgtt gctcgtcctg ccctaaacct tgtttgtct ttaaatgtgt      300 ataagctgcc tgtctgtgac ttgaatttga ctggtgaaca aactaaatat ttttccctgt     360
aattgagaca gaatttcttt tgatgatacc catccctcct tcatttttt ttttttttg       420 gtctttgttc tgttttggtg gtggtagttt ttaatcagta aacccagcaa atatcatgat     480
tctttcctgg ttagaaaaat aaataaagtg tatcttttta tctccctc                  528

<210> SEQ ID NO 139
<211> LENGTH: 371
<212> TYPE: DNA
<213> ORGANISM: Homo sapiens

<400> SEQUENCE: 139
tattcacaag ttttggaggg cttttttgttc tctgataga catgactgac ttttagctgt       60
cataatgtat taacctaaca gatgaaatat gttaaatatg tggttgctct ttatcccttt     120
gtacaagcat taaaaaaact gctgttttat aagaagactt tttgttgtac tatgtgcatg     180
catactacct atttctaaac tttgccatat tgaggccttt ataaactatt gatttatgta     240
atactagtgc aattttgctt gaacaatgtt atgcatatca taaacttttt caggttcttg     300
tttaagtaca ttttttaaat tgaacagtat ttttcatttt ggttataata tagtcatttt     360
gcctatgttt c                                                          371

<210> SEQ ID NO 140
<211> LENGTH: 324
<212> TYPE: DNA
<213> ORGANISM: Homo sapiens

<400> SEQUENCE: 140
ctcagcccct gtcaacagtg gggacccac caccaccatc ctggagtgat tccaactcaa        60
ctcaaaggac acccagagct gccatctggt atctgccagt ttttccaaat gacctgtacc     120
ctacccagta ccctgctccc cctttcccat aattcatgac atcaaaacac cagcttttca     180
ccttttcctt gagactcagg aggaccaaag cagcagcctt ttgcttttc tttttctc        240 cctcccctta tcaagggttg aaggaaggga gccatcctta ctgttcagag acagcaactc     300
cctcccgtaa ctcaggctga gaag                                            324

<210> SEQ ID NO 141
<211> LENGTH: 339
<212> TYPE: DNA
<213> ORGANISM: Homo sapiens

<400> SEQUENCE: 141
gtttctgtga ttcaggatcc tcttgggaga gtatattcaa taaaagcccg gaggtggtga      60
ctcctttgca gctccagtgt tgccagcgcc tagtggagct ttgtaaacag tgcctgctag     120
tggtttacaa atatgcaact gacaaaagag gatcactttc aggcattggt cctgactggg     180
```

```
gtaattccag gtatttacta ccagggagca cccaattctt cttgagaaca ccaacctaca    240
acttgaagta caattcacct ggaatgactc gctccaatgt tttgtttaca tccagatatg    300
gccatctgtg aaacagaagg gaagatcgcc attggttat                          339
```

<210> SEQ ID NO 142
<211> LENGTH: 414
<212> TYPE: DNA
<213> ORGANISM: Homo sapiens

<400> SEQUENCE: 142

```
ggaggtccca atatgtggt ctatcaccac tgaattcatg taatagataa gaaaaaaatt    60
agaggtggat gtcttgtttt gtgtcatgaa ttactaaaat ctcttagtag ttgtggtata    120
tttttgagta aaattaccat ttccagattt gagtttgaag gcttttata gttgtatttt    180 cctcctcact gttaataatc ataatccttt ttcagtattt tagtggcctt gaacaactgg    240
tttatctaca atctcaaatc ctaagtgtat aattatgtgc aatgttcaat acctcatata    300
atacttgctc aacagtatag tggtaccaat ggcattaaga tggtgttttt gttctacata    360
tttttcaata atttattctt tctaatgttg aaattatatc aggctttacc ggtt         414
```

<210> SEQ ID NO 143
<211> LENGTH: 524
<212> TYPE: DNA
<213> ORGANISM: Homo sapiens

<400> SEQUENCE: 143

```
gaagttgcaa cattcgtttg ataggaattc agaaaagga gagttatgag aatagggcag    60
aggacataat taagaaata attgatgaaa actttgcaga actaaagaaa ggttcaagtc    120
ttgagattgt cagtgcttgt cgagtaccta gtaaaattga tgaaagaga ctgactccta    180 gacacatctt ggtgaaattt tggaattcta gtgataaaga gaaataata agggcttcta    240 gagagagaag agaaattacc taccaaggaa caagaatcag gttgacagca gacttatcac    300
tggacacact ggatgctaga agtaaatgga gcaatgtctt caaagttctg ctggaaaaag    360
gctttaatcc tagaatccta tatccagcca aaatggcatt tgatttagg ggcaaaacaa    420 aggtatttct tagtattgaa gaatttagag attatgtttt gcatatgccc accttgagag    480
aattactggg gaataatata ccttagcacg ccagggtgac taca                   524
```

<210> SEQ ID NO 144
<211> LENGTH: 487
<212> TYPE: DNA
<213> ORGANISM: Homo sapiens

<400> SEQUENCE: 144

```
gttatacaga tgccatgctc cacaccacga gcagtgtaca aatctggctg cccgtttact    60
ttctgagcaa gcactggagt ccactccgac ctttttcttt gaacatgcat gctgctggaa    120
tatgtataaa tcagaactag cagaagtagc agagtgatgg gagcaaaata ggcactgaat    180
tcgtcaactc ttttttgtga gcctacttgt gaatattacc tcagatacct gttgtcactc    240
ttcacaggtt atttaagttc ttgaagctgg gaggaaaaag atggagtagc ttggaaagat    300
tccagcactg agccgtgagc cggtcatgag ccacgataaa aaatgccagt ttggcaaact    360
cagcactcct gttccctgct caggtatatg cgatctctac tgagaagcaa gcacaaaagt    420
agaccaaagt attaatgagt atttccttc tccataagtg caggactgtt actcactact    480
aaactct                                                            487
```

```
<210> SEQ ID NO 145
<211> LENGTH: 547
<212> TYPE: DNA
<213> ORGANISM: Homo sapiens

<400> SEQUENCE: 145
gaacgtcgta tgagatccta caatggaaga ataaaatcac ctcattcttc atttcagatc     60
tgaacattag cagtgatcta gattttttt tttttaaaca aaattaagtg tgcttagagt    120
catccctcta catgggctgt ggctgtcagc ccataggttt gtcagtttca catcaaaact    180
gtgggtataa actgttgaaa ccaatcacat aaaatattt agctgggcac agtggtgtgc    240
atctgtagtc ccagctactt gggaggctga ggcaggagga tcgcttaagc acaggagttg    300
gaatccagcc tgagcaacag agcaaaaccc cgtctctaaa atacaaataa aatatttgtg    360
tagtttttga ttaaaattga ctacagcggt cagtataaaa tacatgtcgc ttttaaggaa    420
gtgctcttta tgtatctaac agatggaagt ttttgcattg gtaagagcat ttatatatgc    480
tttgtttcag ggtttatgga tttgtattca tatattgtca aataggtttc atactctaat    540
tttactt                                                              547

<210> SEQ ID NO 146
<211> LENGTH: 514
<212> TYPE: DNA
<213> ORGANISM: Homo sapiens

<400> SEQUENCE: 146
agattatatc cctatcttct ttttcatgta aaccactggt cacaaatgaa ctgatctctg     60
tatcccatta ttactataag aggtgggaat cccaaaactg cttagattgc agtacatgag    120
tttacacaaa gacttcaaca attgcacatc ttcattctcc caactgagtg tagtatgtgg    180
agcataaaac agcatattct tagtatttca tgaatatcag atggtcttta aatgtctctt    240
tatggatgta ttgttcacat tatggcttta aaataatgaa tatgtaaaag tgaggtagtg    300
aacatcctaa atttctacac tggaattact aaataatctt atttcataaa atgggaaata    360
tatgttaaat gacatcactg gatgaacttg aagatctttt acttgttaac aaaaaaatac    420
tatggacagc tttctgattg ttggggtaaa tagcaaatgt tcaaactttg caggcatttt    480
gacattcatc ataacaacac aattcctaga catt                                514

<210> SEQ ID NO 147
<211> LENGTH: 478
<212> TYPE: DNA
<213> ORGANISM: Homo sapiens

<400> SEQUENCE: 147
ttaggcagtc tgtggtgctc agtcacctct gtcttcgatg agaaacagca gtggaaattc     60
tgtgaaacga atgagtatgg gggaaattct ctcaggaagc cctgcatctt cccctccatc    120
tacagaaata atgtggtctc tgattgcatg gaggatgaaa gcaacaagct ctggtgccca    180
accacagaga acatggataa ggatggaaag tggagtttct gtgccgacac cagaattttcc    240
gcgttggtcc ctggctttcc ttgtcacttt ccgttcaact ataaaacaa gaattatttt    300
aactgcacta acaaaggatc aaaggagaac cttgtgtggt gtgcaacttc ttacaactac    360
gaccaagacc acacctgggt gtattgctga tgctgaggaa aggagaaata tcttcagagg    420
aagactgccg ccatactgag gctgagcaca gatttgtctt tttcattgca tctgtcaa      478
```

<210> SEQ ID NO 148
<211> LENGTH: 426
<212> TYPE: DNA
<213> ORGANISM: Homo sapiens

<400> SEQUENCE: 148

```
gtgtggcagt gggactggtc agtattagag gtgtggacag tggtctctat cttggaatga      60
atgacaaagg agaactctat ggatcagaga aacttacttc cgaatgcatc tttagggagc     120
agtttgaaga gaactggtat aacacctatt catctaacat atataaacat ggagacactg     180
gccgcaggta ttttgtggca cttaacaaag acggaactcc aagagatggc gccaggtcca     240
agaggcatca gaaatttaca catttcttac ctagaccagt ggatccagaa agagttccag     300
aattgtacaa ggacctactg atgtacactt gaagtgcgat agtgacatta tggaagagtc     360
aaaccacaac cattctttct tgtcatagtt cccatcataa ataatgacc caagcagacg      420
ttcaaa                                                                426
```

<210> SEQ ID NO 149
<211> LENGTH: 503
<212> TYPE: DNA
<213> ORGANISM: Homo sapiens

<400> SEQUENCE: 149

```
tatgcattt ttaccacaat ttttaaaaag tttgaataga aatttttaat gtctttgagt       60
ggatttttgtt ttttgaacag ttggatagac ttctgcgtaa gaaagctgga ttgactgttg    120
ttccttcata taatgccttg agaaattctg aatatcaaag gcagtttgtt tggaagactt     180
ctaaagaaac tgctccagct tttgcagcca atcaggtagc ttaatggatg taatacattt     240
ctgagtacca ttatcttatc tagtaatgta gatttacata gaattaagag ttgaaagaaa    300
ttaagtactt aagtagcctg gaggtaggtt ctagaaaacc aaaatgagag ttttgctaaa    360
atcatcctat tacttatgat ttatggtagt aatattatac tgtcctaggc ttctgatgat    420
cattgttgcc agatgcagca catatactaa atatgagaca gggtaatgaa aacttgggga    480
actggtaagt ttttgcatgc tac                                            503
```

<210> SEQ ID NO 150
<211> LENGTH: 541
<212> TYPE: DNA
<213> ORGANISM: Homo sapiens

<400> SEQUENCE: 150

```
tgacccctttt gatattccag caagtgcaga atggagatgc agacatcaag gtttctttct      60
ggcagtgggc ccatgaagat ggttggccct tgatgggcc aggtggtatc ttaggccatg      120
cctttttacc aaattctgga atcctggag ttgtccattt tgacaagaat gaacactggt      180
cagcttcaga cactggatat aatctgttcc tggttgcaac tcatgagatt gggcattctt    240
tgggcctgca gcactctggg aatcagagct ccataatgta cccccacttac tggtatcacg    300
acccctagaac cttccagctc agtgccgatg atatccaaag gatccagcat tgtatggag    360
aaaaatgttc atctgacata ccttaatgtt agcacagagg acttattcaa cctgtccttt    420
cagggagttt attggaggat caagaactg aaagcactag agcagccttg gggactgcta    480
ggatgaagcc ctaagaatg caacctagtc aggttagctg aaccgacact caaaacgcta    540
c                                                                     541
```

<210> SEQ ID NO 151
<211> LENGTH: 511

<212> TYPE: DNA
<213> ORGANISM: Homo sapiens

<400> SEQUENCE: 151

```
aaggtagaaa gccttccgtc cagtgtgcga atctctgtga acgtgtaaga attcacagtc    60
aggaggacta ctttgaatgt tttcagtgcg gcaaagcttt tctccagaat gtgcatcttc   120
ttcaacatct caaagcccat gaggcagcaa gagtccttcc tcctgggttg tcccacagca   180
agacatactt aattcgttat cagcggaaac atgactacgt tggagagaga gcctgccagt   240
gttgtgactg tggcagagtc ttcagtcgga attcatatct cattcagcat tatagaactc   300
acactcaaga gaggccttac cagtgtcagc tatgtgggaa atgtttcggc cgaccctcat   360
acctcactca acattatcaa ctccattctc aagagaaaac tgttgagtgc gatcactgtt   420
gagaaacctt tagtcacagc acacactttt ctcaacatta ttggcttcct cctagagtgt   480
tgtgagtgtg agaaggcctt tcactagccc c                                  511
```

<210> SEQ ID NO 152
<211> LENGTH: 505
<212> TYPE: DNA
<213> ORGANISM: Homo sapiens

<400> SEQUENCE: 152

```
atgttactac aaacttgatt aaacttctgg tggaaattcc atcacatttt atgcaatttt    60
caatttattt ctccaattta tttttaatgc cacatggaca ttatattcct taaccattct   120
tttgcatgtg attaacattt gtgaaattaa ccacttaagc aagtgttttt gctttgatga   180
aagaaaaatg tttaaaatcc tactggatat gaaactgaaa gtaatgtttt gtgttttttg   240
tttcaaatga aagtgtaaat taagaatttg ttggcagggc gtggtggctc atgcctgtaa   300
tcccagcact ttgggaggcc gaggtgggca gatcacctga ggtcagcagt ccaagaccac   360
cctggccaac atggtgaagt cccgtctcta ctaaaaatac aaaaatcagc tgggcatggt   420
ggcgggcact tgtagtccca gctactcagg aggctgaagc aggagaatca cttgaactca   480
ggaggcagaa gttgcggtta gccga                                         505
```

<210> SEQ ID NO 153
<211> LENGTH: 477
<212> TYPE: DNA
<213> ORGANISM: Homo sapiens

<400> SEQUENCE: 153

```
cctctctcca ctctctagaa atattaaggc taggctgctg ctgtatgtca gggctagtcc    60
cctcttctat gaatccagaa taactctgaa gaagccgagt aacaggcatg aagtgaagag   120
aaatcgctgt aacaggaaga cagcaaagca gatgctaatg accacactat ttaacgaact   180
ggaaccaacg agaaaatacg gtattactga agactgcact tccttgaaca gagtgctctt   240
ctcagcaaat cggaaatgcc tacacaaatc gctttacaag aaagactgtt tcaaagcagc   300
acctttctca atgttctcgt tcaggtgaca attcttcttg gtctcagctc caattttatt   360
gtcattttca tcaataagga tacacatctc tgccaggagt tgaacctgtt gcttgtcgag   420
gtggttagtg tttatttcag gcatcattac aaaatgtctg atctgttcta gaaccct      477
```

<210> SEQ ID NO 154
<211> LENGTH: 332
<212> TYPE: DNA
<213> ORGANISM: Homo sapiens

<400> SEQUENCE: 154

```
aagtatctcc atacaaaata cggttgaatt acaaaaagaa aattgtaaca ttagcatgga      60
caaacctggc aggtactcct taactctcct aagtaataaa aactgtaaaa tgcaaataag     120
ccttcgatga catttactaa cctttactaa agtatcaatg atgacttggt tgtttaaaca     180
gctgacattt gggcaatttg agtatgtcaa actcaataat actggttttc atttgcaaga     240
tccacttaaa acttaaggag gccaaaaaac atcatttaaa ataccctata aattataatc     300
atacatatga tacgaaaaat atcctacttc ag                                   332

<210> SEQ ID NO 155
<211> LENGTH: 195
<212> TYPE: DNA
<213> ORGANISM: Homo sapiens

<400> SEQUENCE: 155
catacacata cgtattttcc gtagtgctct gggtggggga aaatgtttaa attgtattag      60
caaatgctaa cttacacttt atagcattta tcagctgtgg catattacct gtaacatgtt    120
taaattaagg caaaggcaat caaaaacctt tttgttttgt agcctgctttt tgctttcaca   180 atttgtctta caatt                                                     195

<210> SEQ ID NO 156
<211> LENGTH: 487
<212> TYPE: DNA
<213> ORGANISM: Homo sapiens

<400> SEQUENCE: 156
gctggccaag actactgggc cgtgctttct ggaaaaggca tttcagccac gctgatgatc      60
ttctccctct tggagttctt cgtagcttgt gccacagccc attttgccaa ccaagcaaac    120
accacaacca atatgtctgt cctggttatt ccaaatatgt atgaaagcaa ccctgtgaca    180
ccagcgtctt cttcagctcc tcccagatgc aacaactact cagctaatgc ccctaaatag    240
taaaagaaaa aggggtatca gtctaatctc atggagaaaa actacttgca aaaacttctt    300
aagaagatgt cttttattgt ctacaatgat ttcagtctt taaaaactgt gtttgagatt     360
tgtttttagg ttggtcgcta atgatggctg tatctcccct cactgtctct tcctacatta    420
ccactactac atgctggcaa aggtgaagga tcagaggact gaaaaatgat tctgcaactc    480
tcttaaa                                                              487

<210> SEQ ID NO 157
<211> LENGTH: 391
<212> TYPE: DNA
<213> ORGANISM: Homo sapiens

<400> SEQUENCE: 157
tgacatgcac cagagggtcc acaggggaga gcgaccctat aattgtaagg aatgtggaaa      60
gagctttggc tgggcttcat gtcttttgaa acatcagaga ctccacagtg gagaaaagcc    120
attgaaatct ggagtgtggg aagagatcta ctcagaattc acagcttcat ttacatcagt    180
aagtctatgt gggagaaaag ccatataaat gtgaagagtg tgggaagggc tttggctggg    240
cctcaactca tctgacccat caattctcca cagcagagaa aaaccattca aatatgagaa    300
ctgtgggaag agctttgtac atagatcata tctttttttt tttttttgag acagagtctc    360 actcttttcac ccaagcctga ctgcagtggc g                                  391

<210> SEQ ID NO 158
<211> LENGTH: 472
```

<212> TYPE: DNA
<213> ORGANISM: Homo sapiens

<400> SEQUENCE: 158

```
gaaaagcgcc ctgtgctgag taaagcagcc agtcttctct tgtcacagta aaaggctggg      60
agtaaaattt cccataaaca caggggaaac ctacatttac tcacatgcca aggaaaatgg     120
cacggaagac ccacgtgtag ccacagcaga gtctatgcag agggcctgca aatgcctggg     180
gtgcgagtga atgcctggag gggcggagtt tccaagataa cagctattgt gttttctttt     240
tcacacttca gaagagaatc ctaaggacta gactccgctc agtgcattcc ttttcatac      300
actgatctca agtacaatca cataattttg aaaatccatg tagtcctccc taaataaaat     360
tataaggata ggtttctatt tccttccgat tacctagata cctccgtctt ctggaaaacc     420
ccaaaaagac cagtagacga atcaggaagg tcctaggagt gattcctcca at             472
```

<210> SEQ ID NO 159
<211> LENGTH: 317
<212> TYPE: DNA
<213> ORGANISM: Homo sapiens

<400> SEQUENCE: 159

```
tgcccccaca gagcaataca ctgaagccta acatctatc tggtgttttt aaaaagttaa      60
aagaaaaata gattttttt cacaaggtga caatagtgat ttttaccatc tggatacagc     120
ctggtgtaag cagacgtcca ttaccaccct cacccacatt tcaggtgtc tacatcagcc      180
ttagtcatta tggatagtaa atcgaccttt aagaattcct ggggtggact ttgcaaacac     240
attctacaac ctgatggttt ttactgctca aactgtcacc atcatctttt gcaatgtgtt     300
gctcactgtt gtcaata                                                    317
```

<210> SEQ ID NO 160
<211> LENGTH: 476
<212> TYPE: DNA
<213> ORGANISM: Homo sapiens

<400> SEQUENCE: 160

```
ggacagtctc agggttctgt tctcgccttc acccggacct tcattgctac ccctggcagc      60
agttccagtc tgtgcatcgt gaatgacgag ctgtttgtga gggatgccag ccccaagag     120
actcagagtg ccttctccat cccagtgtcc acactctcct ccagctctga gccctccctc     180
tcccaggagc agcaggaaat ggtgcaggct ttctctgccc agtctgggat gaaactggag     240
tggtctcaga agtgccttca ggacaatgag tggaactaca ctagagctgg ccaggccttc     300
actatgctcc agaccgaggg caagatcccc gcagaggcct tcaagcaaat ctcctaaaag     360
gagccctccg atgtcttctt tgtcttcgtt cacatcctct ttgtttcctc ttttcaccag     420
cctaaggcct ggctgaccag gaagccaacg ttaacttgca ggccacgtga cataac         476
```

<210> SEQ ID NO 161
<211> LENGTH: 528
<212> TYPE: DNA
<213> ORGANISM: Homo sapiens

<400> SEQUENCE: 161

```
aagtctgcat tgaatccgct gatctactac tggaggatta agaaattcca tgatgcttgc      60
ctggacatga tgcctaagtc cttcaagttt ttgccgcagc tccctggtca cacaaagcga     120
cggatacgtc ctagtgctgt ctatgtgtgt ggggaacatc ggacggtggt gtgaatattg     180
gaactggctg acattttggg tgatgcttgt tctttattga cattgaattc tctttctcat     240
```

```
agcctctcca ctttattttt ttttataggg tttgtgtatg tatgtgtgtg agcagtgtaa    300
agaaagaatg gtaattatag ttctgttacc aagaataaat aataggaaag tgattacaaa    360
tattacctcc agggttcaat agaaatcctc aatttagggt gaggagactt ttttttggtt    420
ttggggtttt tccttgattg attttgtttt catagtggga atcaggattg tgctttattg    480
agcctgcagt tacattgaat tgtaggtgtt tcgtgtgctg ctaaggta                 528
```

<210> SEQ ID NO 162
<211> LENGTH: 477
<212> TYPE: DNA
<213> ORGANISM: Homo sapiens

<400> SEQUENCE: 162

```
gggactgtcg atgtagctga taagctagtg acatttggtc tggcaaaaaa catcacacct     60
caaaggcaga gtgctttaaa tacagaaaag atgtatagga cgaattgctg ctgcacagag    120
ttacagaaac aagttgaaaa acatgaacat attcttctct tcctcttaaa caattcaacc    180
aatcaaaata aatttattga atgaaaaaa ctggtaaaaa gttaagtaag ttaaatcgta     240
tgttttcgcc tcttctgtga tcaccaatag gacatcttca ggcatattgg caggatagag    300
ctaatggagt gaaacctatt gtaaggctgt actttcgtga tttaatgacc tgaggtttgg    360
tcataatgct tctgctgttt ttgtaggttt atctgatcgt tttcctttgc tactgctaat    420
ggaactgaac ccccaggggt attccagttg taatagcctt tccttactgt tgtttgg       477
```

<210> SEQ ID NO 163
<211> LENGTH: 435
<212> TYPE: DNA
<213> ORGANISM: Homo sapiens

<400> SEQUENCE: 163

```
gttgagttga aattctgccg cttactcaat ggccttgggt gatgatgctg taccctaatt     60
ctaaaggaag caatgaaccc ccttttcagc taccttactg ataagcactt atgttctgcc    120
ttctgctatc ctgatggttc gggttgtctg tcttactatc tacttcttga gtagagagac    180
cacattaaat ttattgctgt atctcacagg gcatcttgct agtgtgcaca ggctcgcctc    240
cctacctctg ccccgatggt gtgaagggga gagggcgagg ttccttagtg gcagggcttt    300
gctgttcttc actctcagcc ccctgaaagc agttcttcct gcctctgagc ctgtctttcc    360
ttctgctgtt aacttctttc ctactttcct tgcatccctc tcccttcctt ttcctgccgt    420
ctttcttgta gacat                                                     435
```

<210> SEQ ID NO 164
<211> LENGTH: 264
<212> TYPE: DNA
<213> ORGANISM: Homo sapiens

<400> SEQUENCE: 164

```
aaaaggacta actcacatgg ctgcagtaag tgctggctgt tagctggaag cacaaccaag     60
gctgttaaca ggtgtgccctt ggttctcttc catatggctt ctcttttgtt ttcagtactc    120
tgcagtttaa ttatgatgca tgcaggtgtg aatttctgtt tattctgctt gggatgtgtt    180
ttccttctgg gatctgtgaa tcggtttctc attattttg taaaacctga agccagttat    240
ctcttaaaat accagctctc cttg                                            264
```

<210> SEQ ID NO 165
<211> LENGTH: 523

<212> TYPE: DNA
<213> ORGANISM: Homo sapiens

<400> SEQUENCE: 165

```
ctggacttct tggatgagct caccctgaac cgcccaggcg gtctgctctt ggtgttcaga    60
atcacatcaa tgcgaacgtc acagcgcctt cgagggcgca gattttaact gccacgtatt   120
tttaagttgt acttttctgt ggaggaaatt gtgccttttg aaacgacgtt ttgtgtgtgt   180
atttcacgtt agcatttcat tgcataggca aaacactagt cacaattggg tagatgtgac   240
atccatatac ttgtttacat tttatctgtt ctcatgtcaa agactactcc ttgccccatt   300
gaatatatag tggtagcagg tgtacaaatt ggtcaagttg caattattta tgagagaata   360
atgataaatg taaatatct aaagcatgaa tctaagagca cgcaatatat aattttaaag    420
aaaatattct atttggtaga atacaaatgt ggtgtgtgtt gttttataat gactgctgta   480
cagtgggtat agtattttgg ttttggttcc agattgtgca atc                     523
```

<210> SEQ ID NO 166
<211> LENGTH: 518
<212> TYPE: DNA
<213> ORGANISM: Homo sapiens

<400> SEQUENCE: 166

```
gtgaagacat caagagctcg aagtgtaaat tacccgaaca agaatcacta ccaaatgata    60
acaaagacat tttacaacgg cttgatcctt cttcattctc aactaagcat tctatgcctg   120
taccaagcat ggtgccatcc tacatggcaa tgactactgc tgccaaaagg aaacggaaat   180
taacaagttc tacatcaaac agttcgttaa ctgcagacgt aaattctgga tttgccaaac   240
gtgttcgaca agataattca agtgagaagc acttacaaga aaacaaacca acaatggaac   300
ataaaagaaa catctgtaaa ataaatccaa gcatggttag aaaatttgga agaaatattt   360
caaaaggaaa tctaagataa atcacttcaa aaccaagcaa aatgaagttg atcaaatctg   420
ctttccaaag tttatcaata ccctttcaaa aatatattta aaatctttga agaagacccc   480
atcttaaagc taagtttacc caagtacttt cagcaagc                           518
```

<210> SEQ ID NO 167
<211> LENGTH: 177
<212> TYPE: DNA
<213> ORGANISM: Homo sapiens

<400> SEQUENCE: 167

```
cgggagcctg tctcagaact atcagtacga ggtgtgcctg gcaggaggct cagggacgaa    60
tgagttccag ttcctgaaac cagtattacc taatattcag ggccattctt ttgggccaga   120
aatggaacaa aactctaact ttaggaatgg ctttggtttc agccttcagt taaagta      177
```

<210> SEQ ID NO 168
<211> LENGTH: 576
<212> TYPE: DNA
<213> ORGANISM: Homo sapiens

<400> SEQUENCE: 168

```
gaactccacc ataaagcaac tgctggcatt ttgctggtca gttcctgctc tttttttctt   60
tggtttagtt ctatctgagg ccgatgtttc cggtatgcag agctataaga tacttgttgc   120
ttgcttcaat ttctgtgccc ttactttcaa caaattctgg gggacaatat tgttcactac   180
atgtttcttt acccctggct ccatcatggt tggtatttat ggcaaaatct ttatcgtttc   240
caaacagcat gctcgagtca tcagccatgt gcctgaaaac acaaggggg cagtgaaaaa    300
```

```
acacctatcc aagaaaaagg acaggaaagc agcgaagaca ctgggtatag taatgggggt    360
gtttctggct tgctggttgc cttgttttct tgctgttctg attgacccat acctagacta    420
ctccactccc atactaatat tggatctttt agtgtggctc cggtacttca actctacttg    480
caaccctctt attcatggct tttttaatcc atggtttcag aaagcattca agtacatagt    540
gtcaggaaaa atatttagct cccattcaga aactgc                              576
```

<210> SEQ ID NO 169
<211> LENGTH: 526
<212> TYPE: DNA
<213> ORGANISM: Homo sapiens

<400> SEQUENCE: 169

```
cacatctgga cccatcagtg actgcctgcc atagcctgag agtgtcttgg ggagaccttg     60
cagaggggga gaattgttcc ttctgctttc ctaggggact cttgagctta gaaactcatc    120
gtacacttga ccttgagcct tctatttgcc tcatctataa catgaagtgc tagcatcaga    180
tatttgagag ctcttagctc tgtacccggg tgcctggttt ttggggagtc atccgcagag    240
tcactcaccc actgtgtttc tggtgccaag gctcttgagg ccccactct catccctcct     300 ttccctacca gggactcgga ggaaggcata ggagatattt ccaggcttac gaccctgggc    360
tcacgggtac ctatttatat gctcagtgca gagcactgtg gatgtgccag gaggggtagc    420
cctgttcaag agcaatttct gcccttgta aattatttaa gaaacctgct ttgtcatttt     480
attagaaaga aaccagcgtg tgactttcct agataacact gctttc                   526
```

<210> SEQ ID NO 170
<211> LENGTH: 447
<212> TYPE: DNA
<213> ORGANISM: Homo sapiens

<400> SEQUENCE: 170

```
ccgccaggag agcgtgcagc tcgaagagaa ctgcctgtgc cgcttccact ggtgctgcgt     60
agtacagtgc caccgttgcc gtgtgcgcaa ggagctcagc ctctgcctgt gacccgccgc    120
ccggccgcta gactgacttc gcgcagcggt ggctcgcacc tgtgggacct cagggcaccg    180
gcaccgggcg cctctcgccg ctcgagccca gcctctccct gccaaagccc aactcccagg    240
gctctggaaa tggtgaggcg aggggcttga gaggaacgcc cacccacgaa ggcccagggc    300
gccagacggc cccgaaaagg cgctcgggga gcgtttaaag gacactgtac aggccctccc    360
tccccttggc ctctaggagg aaacagtttt ttagactgga aaaagccag tctaaaggcc     420 tctggatact gggctcccca gaactgc                                        447
```

<210> SEQ ID NO 171
<211> LENGTH: 394
<212> TYPE: DNA
<213> ORGANISM: Homo sapiens

<400> SEQUENCE: 171

```
gcgatgcaga aatgaaccac cggagttcaa tgcgagttct tggggatgtt gtcaggagac     60
ctcccattca taggagaagt ttcagtctag aaggcttgac aggaggagct ggtgtcggaa    120
acaagccatc ctcatctcta gaagtaagct ctgcaaatgc cgaagagctc agacacccat    180
tcagtggtga ggaacgggtt gactctttgg tgtcactttc agaagaggat ctggagtcag    240
accagagaga acataggatg tttgatcagc agatatgtca cagatctaag cagcagggat    300
ttaattactg tacatcagcc atttcctctc cattgacaaa atccatctca ttaatgacaa    360
```
tcagccatcc tggattggac aattcacggc cctt                              394

<210> SEQ ID NO 172
<211> LENGTH: 480
<212> TYPE: DNA
<213> ORGANISM: Homo sapiens
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t

<400> SEQUENCE: 172
gtaggctcag cgatagtggt cctcttacag agaaacgggg agcaggacga cgggggngct    60
ggggntggcg ggggagggtg cccacaaaaa gaatcaggac ttgtactggg aaaaaaaccc   120
ctaaattaat tatatttctt ggacattccc tttcctaaca tcctgaggct taaaaccctg   180
atgcaaactt ctcctttcag tggttggaga aattggccga gttcaaccat tcactgcaat   240
gcctattcca aactttaaat ctatctattg caaaacctga aggactgtag ttagcgggga   300
tgatgttaag tgtggccaag cgcacggcgg caagttttca agcactgagt ttctattcca   360
agatcataga cttactaaag agagtgacaa atgcttcctt aatgtcttct ataccagaat   420
gtaaatattt ttgtgttttg tgttaatttg ttagaattct aacacactat atacttccaa   480

<210> SEQ ID NO 173
<211> LENGTH: 24
<212> TYPE: DNA
<213> ORGANISM: Homo sapiens

<400> SEQUENCE: 173
agtcactcac ccactgtgtt tctg                                         24

<210> SEQ ID NO 174
<211> LENGTH: 22
<212> TYPE: DNA
<213> ORGANISM: Homo sapiens

<400> SEQUENCE: 174
ctgtgttctg catggtttgg at                                           22

<210> SEQ ID NO 175
<211> LENGTH: 20
<212> TYPE: DNA
<213> ORGANISM: Homo sapiens

<400> SEQUENCE: 175
atttgagtgg gtgtccaggg                                              20

<210> SEQ ID NO 176
<211> LENGTH: 20
<212> TYPE: DNA
<213> ORGANISM: Homo sapiens

<400> SEQUENCE: 176
aaaggaccgc atcagtgagc                                              20

<210> SEQ ID NO 177
<211> LENGTH: 21
<212> TYPE: DNA
<213> ORGANISM: Homo sapiens

```
<400> SEQUENCE: 177
aagaagattg ggcagttggg t                                          21

<210> SEQ ID NO 178
<211> LENGTH: 22
<212> TYPE: DNA
<213> ORGANISM: Homo sapiens

<400> SEQUENCE: 178
aagataaaca gccccaggaa cc                                         22

<210> SEQ ID NO 179
<211> LENGTH: 24
<212> TYPE: DNA
<213> ORGANISM: Homo sapiens

<400> SEQUENCE: 179
gtaggaaaaa tgcaagccat ctct                                       24

<210> SEQ ID NO 180
<211> LENGTH: 23
<212> TYPE: DNA
<213> ORGANISM: Homo sapiens

<400> SEQUENCE: 180
aaaggaaaga ttggttctcc cag                                        23

<210> SEQ ID NO 181
<211> LENGTH: 20
<212> TYPE: DNA
<213> ORGANISM: Homo sapiens

<400> SEQUENCE: 181
tcacagctcc ctccagaagc                                            20

<210> SEQ ID NO 182
<211> LENGTH: 23
<212> TYPE: DNA
<213> ORGANISM: Homo sapiens

<400> SEQUENCE: 182
caggcttttg agctgatctt gaa                                        23

<210> SEQ ID NO 183
<211> LENGTH: 23
<212> TYPE: DNA
<213> ORGANISM: Homo sapiens

<400> SEQUENCE: 183
gccaacagta caatagccca caa                                        23

<210> SEQ ID NO 184
<211> LENGTH: 25
<212> TYPE: DNA
<213> ORGANISM: Homo sapiens

<400> SEQUENCE: 184
agttggaaat gtggagtatt ttgga                                      25

<210> SEQ ID NO 185
<211> LENGTH: 20
<212> TYPE: DNA
<213> ORGANISM: Homo sapiens
```

```
<400> SEQUENCE: 185
ctgaccgaga acgaactgca                                              20

<210> SEQ ID NO 186
<211> LENGTH: 21
<212> TYPE: DNA
<213> ORGANISM: Homo sapiens

<400> SEQUENCE: 186
agcgattcac gtaggatctg c                                            21

<210> SEQ ID NO 187
<211> LENGTH: 20
<212> TYPE: DNA
<213> ORGANISM: Homo sapiens

<400> SEQUENCE: 187
tgccccttaa tgccattgaa                                              20

<210> SEQ ID NO 188
<211> LENGTH: 22
<212> TYPE: DNA
<213> ORGANISM: Homo sapiens

<400> SEQUENCE: 188
ggtagggaaa ggagggatga ga                                           22

<210> SEQ ID NO 189
<211> LENGTH: 21
<212> TYPE: DNA
<213> ORGANISM: Homo sapiens

<400> SEQUENCE: 189
ggttggaaga agttcggttg g                                            21

<210> SEQ ID NO 190
<211> LENGTH: 20
<212> TYPE: DNA
<213> ORGANISM: Homo sapiens

<400> SEQUENCE: 190
ggtcaaggcc aatgctctgt                                              20

<210> SEQ ID NO 191
<211> LENGTH: 18
<212> TYPE: DNA
<213> ORGANISM: Homo sapiens

<400> SEQUENCE: 191
agcagttggc gtgcttgg                                                18

<210> SEQ ID NO 192
<211> LENGTH: 22
<212> TYPE: DNA
<213> ORGANISM: Homo sapiens

<400> SEQUENCE: 192
tcctgctact cctggctcat tc                                           22

<210> SEQ ID NO 193
<211> LENGTH: 22
<212> TYPE: DNA
<213> ORGANISM: Homo sapiens
```

<400> SEQUENCE: 193
ccactgagga gctgtctgct tt                                           22

<210> SEQ ID NO 194
<211> LENGTH: 24
<212> TYPE: DNA
<213> ORGANISM: Homo sapiens

<400> SEQUENCE: 194
catgattagt actgctagcg gacc                                         24

<210> SEQ ID NO 195
<211> LENGTH: 24
<212> TYPE: DNA
<213> ORGANISM: Homo sapiens

<400> SEQUENCE: 195
agtagaccaa gcacaggcat acag                                         24

<210> SEQ ID NO 196
<211> LENGTH: 21
<212> TYPE: DNA
<213> ORGANISM: Homo sapiens

<400> SEQUENCE: 196
gatgaggact gggagagggt t                                            21

<210> SEQ ID NO 197
<211> LENGTH: 23
<212> TYPE: DNA
<213> ORGANISM: Homo sapiens

<400> SEQUENCE: 197
tttggagaag ctaaagttcg tgg                                          23

<210> SEQ ID NO 198
<211> LENGTH: 24
<212> TYPE: DNA
<213> ORGANISM: Homo sapiens

<400> SEQUENCE: 198
ccacgaccta caatgatgat atcg                                         24

<210> SEQ ID NO 199
<211> LENGTH: 27
<212> TYPE: DNA
<213> ORGANISM: Homo sapiens

<400> SEQUENCE: 199
catagtacgg ataatactgc agaggaa                                      27

<210> SEQ ID NO 200
<211> LENGTH: 18
<212> TYPE: DNA
<213> ORGANISM: Homo sapiens

<400> SEQUENCE: 200
agtccccttt gccccctc                                                18

<210> SEQ ID NO 201
<211> LENGTH: 21
<212> TYPE: DNA
<213> ORGANISM: Homo sapiens

```
<400> SEQUENCE: 201
atcaccagtg ttggaagtgg g                                              21

<210> SEQ ID NO 202
<211> LENGTH: 19
<212> TYPE: DNA
<213> ORGANISM: Homo sapiens

<400> SEQUENCE: 202
ttttgccatg gacaatgca                                                 19
```